(12) United States Patent
Kao et al.

(10) Patent No.: US 9,394,359 B2
(45) Date of Patent: *Jul. 19, 2016

(54) METHODS AND AGENTS FOR THE DIAGNOSIS AND TREATMENT OF HEPATOCELLULAR CARCINOMA

(71) Applicant: China Synthetic Rubber Corporation, Taipei (TW)

(72) Inventors: Kuo-Jang Kao, Gainesville, FL (US); Andrew T. Huang, Durham, NC (US)

(73) Assignee: CHINA SYNTHETIC RUBBER CORPORATION, Taipei (TW)

( * ) Notice: Subject to any disclaimer, the term of this patent is extended or adjusted under 35 U.S.C. 154(b) by 88 days.

This patent is subject to a terminal disclaimer.

(21) Appl. No.: 14/336,441

(22) Filed: Jul. 21, 2014

(65) Prior Publication Data

US 2015/0017171 A1    Jan. 15, 2015

Related U.S. Application Data

(63) Continuation of application No. 13/126,734, filed as application No. PCT/US2009/056382 on Sep. 9, 2009, now Pat. No. 8,821,880.

(60) Provisional application No. 61/197,650, filed on Oct. 29, 2008.

(51) Int. Cl.
| | |
|---|---|
| A61K 39/00 | (2006.01) |
| C07K 16/18 | (2006.01) |
| C07K 16/30 | (2006.01) |
| A61K 39/395 | (2006.01) |
| A61K 45/06 | (2006.01) |
| A61K 47/48 | (2006.01) |
| A61K 38/00 | (2006.01) |

(52) U.S. Cl.
CPC ........... *C07K 16/18* (2013.01); *A61K 39/39558* (2013.01); *A61K 45/06* (2013.01); *A61K 47/48607* (2013.01); *C07K 16/303* (2013.01); *A61K 38/00* (2013.01); *A61K 2039/505* (2013.01); *C07K 2317/24* (2013.01); *C07K 2317/34* (2013.01); *C07K 2317/51* (2013.01); *C07K 2317/515* (2013.01); *C07K 2317/76* (2013.01)

(58) Field of Classification Search
CPC ............ A61K 38/00; A61K 39/39558; A61K 2039/505
USPC ................. 536/23.5; 435/69.1, 325; 530/350, 530/387.1

See application file for complete search history.

(56) References Cited

U.S. PATENT DOCUMENTS

| | | | |
|---|---|---|---|
| 6,875,570 B2 | 4/2005 | Gerlach et al. | |
| 8,815,240 B2 | 8/2014 | Kao | |
| 8,821,880 B2 | 9/2014 | Kao | |
| 2008/0233117 A1 | 9/2008 | Roberts et al. | |
| 2011/0085973 A1 | 4/2011 | Kao et al. | |
| 2011/0159498 A1 | 6/2011 | Kao et al. | |
| 2011/0262349 A1 | 10/2011 | Kao et al. | |
| 2014/0322131 A1 | 10/2014 | Kao et al. | |

FOREIGN PATENT DOCUMENTS

| | | |
|---|---|---|
| WO | WO 03/010336 A2 | 2/2003 |
| WO | WO 03/023008 A2 | 3/2003 |
| WO | WO 03/024392 A2 | 3/2003 |
| WO | WO 2006/105361 A2 | 10/2006 |
| WO | WO 2006/110593 A2 | 10/2006 |
| WO | WO 2008/091781 A1 | 7/2008 |
| WO | WO 2009/117096 A1 | 9/2009 |
| WO | WO 2009/126271 A1 | 10/2009 |
| WO | WO 2010/051105 A1 | 5/2010 |

OTHER PUBLICATIONS

"*Homo sapiens* plasmalemma vesicle associated protein (PLVAP), mRNA." GenBank [online] [retreived on Jan. 26, 2011]. Retrieved from the Internet URL: http://www.ncbi.nlm.nih.gov/nuccore/13775237?sat=OLD06&satkey=7209055.

Bergers, G., and Coussens, L. M., "Extrinsic regulators of epithelial tumor progression: metalloproteinases," *Current Opinion in Genetics & Development*, 10: 120-127 (2000).

Bernard, A., et al., "A Unique Epitope on the CD2 Molecule Defined by the Monoclonal Antibody 9-1: Epitope-Specific Modulation of the E-Rosette Receptor and Effects on T-Cell Functions," *Human Immunology*, 17: 388-405 (1986).

Caldas, C., et al., "Humanization of the anti-CD18 antibody 6.7: an unexpected effect of a framework residue in binding to antigen," *Molecular Immunology*, 39: 941-952 (2003).

Carson-Walter, E. B., et al., "Plasmalemmal Vesicle Associated Protein-1 Is a Novel Marker Implicated in Brain Tumor Angiogenesis," *Clin. Cancer Res.*, 11(21): 7643-7650 (2005).

Casset, F., et al., "A peptide mimetic of an anti-CD4 monoclonal antibody by rational design," *Biochemical and Biophysical Research Communications*, 307: 198-205 (2003).

Chien, N. C., et al., "Significant structural and functional change of an antigen-binding site by a distant amino acid substitution: Proposal of a structural mechanism," Proc. Natl. Acad. Sci. USA, 86: 5532-5536 (1989).

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169: 3076-3084 (2002).

(Continued)

*Primary Examiner* — Stephen Rawlings
(74) *Attorney, Agent, or Firm* — Hamilton, Brook, Smith & Reynolds, P.C.

(57) ABSTRACT

The present invention relates to methods of diagnosing, and methods of treating, hepatocellular carcinoma in a subject. The invention also relates to polypeptide antagonists of PLVAP proteins, including humanized and chimeric antibodies that specifically bind PLVAP proteins, as well as compositions and kits comprising such polypeptide antagonists.

20 Claims, 153 Drawing Sheets

(56) References Cited

OTHER PUBLICATIONS

Dennis, C., "Off by a whisker," *Nature*, 442: 739-741 (2006).
Giusti, A. M., et al., "Somatic diversification of S107 from an antiphosphocholine to an anti-DNA autoantibody is due to a single base change in its heavy chain variable region," *Proc. Natl. Acad. Sci. USA*, 84: 2926-2930 (1987).
Gotoh, K., et al., "Apg-2 has a chaperone-like activity similar to Hsp110 and is overexpressed in hepatocellular carcinomas," *FEBS Letters*, 560: 19-24 (2004).
Gray, D., et al., "Maternal Embryonic Leucine Zipper Kinase/Murine Protein Serine-Threonine Kinase 38 Is a Promising Therapeutic Target for Multiple Cancers," *Cancer Res.*, 65(21): 9751-9761 (2005).
Gura, T., "Systems for Identifying New Drugs Are Often Faulty," *Science*, 278: 1041-1042 (1997).
Güssow, D., and Seemann, G., "Humanization of Monoclonal Antibodies," *Methods in Enzymology*, 203: 99-121 (1991).
Hayward, D. G., et al., "The Centrosomal Kinase Nek2 Displays Elevated Levels of Protein Expression in Human Breast Cancer," *Cancer Research*, 64: 7370-7376 (2004).
Hegmans, J. P. J. J., et al., "Proteomic Analysis of Exosomes Secreted by Human Mesothelioma Cells," *Am. J. Pathol.*, 164(5): 1807-1815 (2004).
Henry, M. D., et al., "A Prostate-Specific Membrane Antigen-Targeted Monoclonal Antibody-Chemotherapeutic Cojugate Designed for the Treatment of Prostate Cancer," *Cancer Research*, 64: 7995-8001 (2004).
Ho, S., et al., "Internal Radiation Therapy for Patients with Primary or Metastatic Hepatic Cancer," *Cancer*, 83: 1894-1907 (1998).
Holm, P., et al., "Functional mapping and single chain construction of the anti-cytokeratin 8 monoclonal antibody TS1," *Molecular Immunology*, 44: 1075-1084 (2007).
Jiang, B., et al., "A Novel Peptide Isolated from a Phage Display Peptide Library with Trastuzumab Can Mimic Antigen Epitope of HER-2," *J. Biol. Chem.*, 280(6): 4656-4662 (2005).
Kelland, L. R., "'Of mice and men': values and liabilities of the athymic nude mouse model in anticancer drug development," *Eur. J. Cancer*, 40: 827-836 (2004).
Keuschnigg, J., et al., "The prototype endothelial marker PAL-E is a leukocyte trafficking molecule," *Blood*, 114: 478-484 (2009).
Lee, J.-S., et al., "Classification and Prediction of Survival in Hepatocellular Carcinoma by Gene Expression Profiling," *Hepatology*, 40: 667-676 (2004).
Lin, M.-L., et al., "Involvement of maternal embryonic leucine zipper kinase (MELK) in mammmary carcinogenesis through interaction with Bcl-G, a pro-apoptotic member of the Bcl-2 family," *Breast Cancer Research*, 9: R17 (2007).
Liu, Z., et al., "Fine mapping of the antigen-antibody interaction of scFv215, a recombinant antibody inhibiting RNA polymerase II from *Drosophila melanogaster*," *J. Mol. Recognit.*, 12: 103-111 (1999).
MacCallum, R. M., et al., "Antibody-antigen Interactions: Contact Analysis and Binding Site Topography," *J. Mol. Biol.*, 262: 732-745 (1996).
Mariuzza, R. A., et al., "The Structural Basis of Antigen-Antibody Recognition," *Ann. Rev. Biophys. Biophys. Chem.*, 16: 139-159 (1987).
McDevitt, M. R., et al., "An α-Particle Emitting Antibody ($[^{213}Bi]J591$) for Radioimmunotherapy of Prostate Cancer," *Cancer Research*, 60: 6095-6100 (2000).
Nuyten, D. S. A., et al., "Using Microarray Analysis as a Prognostic and Predictive Tool in Oncology: Focus on Breast Cancer and Normal Tissue Toxicity," *Seminars in Radiation Oncology*, 18: 105-114 (2008).
Ørntoft, T. F., et al., "Genome-wide Study of Gene Copy Numbers, Transcripts, and Protein Levels in Pairs of Non-invasive and Invasive Human Transitional Cell Carconomas," *Molecular & Cellular Proteomics*, 1: 37-45 (2002).
Pettersen, R. D., et al., "CD47 Signals T Cell Death," *J. Immunol.*, 162: 7031-7040 (1999).
Rhodes, D. R., et al., "Large-scale meta-analysis of cancer microarray data identifies common transcriptional profiles of neoplastic transformation and progression," *PNAS*, 101(25): 9309-9314 (2004).
Rudikoff, S., et al., "Single amino acid substitution altering antigen-binding specificity," *Proc. Natl. Acad. Sci. USA*, 79: 1979-1983 (1982).
Saijo, N., "What are the reasons for negative phase III trials of molecular-target-based drugs?" *Cancer Sci.*, 95: 772-776 (2004).
Schier, R., et al., "Isolation of Picomolar Affinity Anti-c-erbB-2 Single-chain Fv by Molecular Evolution of the Complementarity Determining Regions in the Center of the Antibody Binding Site," *J. Mol. Biol.*, 263: 551-567 (1996).
Stan, R.-V., et al., "Immunoisolation and Partial Characterization of Endothelial Plasmalemmal Vesicles (Cavcolac)," *Molecular Biology of the Cell*, 8: 595-605 (1997).
Stan, R. V., et al., "PV1 Is a Key Structural Component for the Formation of the Stomatal and Fenestral Diaphragms," *Molecular Biology of the Cell*, 15: 3615-3630 (2004).
Stancovski, I., et al., "Mechanistic aspects of the opposing effects of monoclonal antibodies to the ERBB2 receptor on tumor growth," *Proc. Natl. Acad. Sci. USA*, 88: 8691-8695 (1991).
Strickland, L. A., et al., "Plasmalemmal vesicle-associated protein (PLVAP) is expressed by tumour endothelium and is upregulated by vascular endothelial growth factor-A (VEGF)," *J. Pathol.*, 206: 466-475 (2005).
Thorgeirsson, S. S., et al., "Molecular prognostication of liver cancer: End of the beginning," *Journal of Hepatology*, 44: 798-805 (2006).
Vajdos, F. F., et al., "Comprehensive Functional Maps of the Antigen-binding Site of an Anti-ErbB2 Antibody Obtained with Shotgun Scanning Mutagenesis," *J. Mol. Biol.*, 320: 415-428 (2002).
van 't Veer, L. J., et al., "Gene expression profiling predicts clinical outcome of breast cancer," *Nature*, 415: 530-536 (2002).
Winkler, K., et al., "Changing the Antigen Binding Specificity by Single Point Mutations of an Anti-p24 (HIV-1) Antibody," *J. Immunol.*, 165: 4505-4514 (2000).
Wolff, A. C., et al., "American Society of Clinical Oncology/College of American Pathologists Guideline Recommendations for Human Epidermal Growth Factor Receptor 2 Testing in Breast Cancer," *Arch. Pathol. Lab. Med.*, 131: 18-43 (2007).
Wu, H., et al., "Humanization of a Murine Monoclonal Antibody by Simultaneous Optimization of Framework and CDR Residues," *J. Mol. Biol.*, 294(1): 151-162 (1999).
International Search Report and Written Opinion of the International Searching Authority from International Application No. PCT/US2009/001689, "Methods and Agents for the Diagnosis and Treatment of Hepatocellular Carcinoma," mailed Jul. 23, 2009.
International Search Report and Written Opinion of the International Searching Authority from International Application No. PCT/US2009/002196, "Methods, Agents and Kits for the Detection of Cancer," mailed Jul. 24, 2009.
International Search Report and Written Opinion of the International Searching Authority from International Application No. PCT/US2009/056382, "Methods and Agents for the Diagnosis and Treatment of Hepatocellular Carcinoma," mailed Dec. 21, 2009.
International Preliminary Report on Patentability from International Application No. PCT/US2009/001689, "Methods and Agents for the Diagnosis and Treatment of Hepatocellular Carcinoma," mailed Sep. 30, 2010.
International Preliminary Report on Patentability from International Application No. PCT/US2009/002196, "Methods, Agents and Kits for the Detection of Cancer," dated Oct. 12, 2010.
Invitation to Correct Deficiencies from European Application No. 09723224.3, "Methods and Agents for the Diagnosis and Treatment of Hepatocellular Carcinoma," mailed Nov. 3, 2010.
Invitation to Correct Deficiencies from European Application No. 09729296.5, "Methods, Agents and Kits for the Detection of Cancer," mailed Nov. 18, 2010.
Reply from European Application No. 09723224.3, "Methods and Agents for the Diagnosis and Treatment of Hapatocellular Carcinoma," filed Dec. 7, 2010.
Reply from European Application No. 09729296.5, "Methods, Agents and Kits for the Detection of Cancer," filed Dec. 14, 2010.

(56) References Cited

OTHER PUBLICATIONS

Office Action from New Zealand Application No. 588587, "Methods and Agents for the Diagnosis and Treatment of Hepatocellular Carcinoma," mailed Mar. 8, 2011.
Office Action from New Zealand Application No. 588548, "Methods, Agents and Kits for the Detection of Cancer," mailed Mar. 18, 2011.
Office Action from European Application No. 09723224.3, "Methods and Agents for the Diagnosis and Treatment of Hepatocellular Carcinoma," mailed May 2, 2011.
International Preliminary Report on Patentability from International Application No. PCT/US2009/056382, "Methods and Agents for the Diagnosis and Treatment of Hepatocellular Carcinoma," mailed May 12, 2011.
Reply from European Application No. 09723224.3, "Methods and Agents for the Diagnosis and Treatment of Hepatocellular Carcinoma," filed Aug. 30, 2011.
Office Action from European Application No. 09723224.3, "Methods and Agents for the Diagnosis and Treatment of Hepatocellular Carcinoma," mailed Dec. 8, 2011.
Office Action from Australian Application No. 2009226152, "Methods and Agents for the Diagnosis and Treatment of Hepatocellular Carcinoma," mailed Dec. 13, 2011.
Office Action from Australian Application No. 2009/234444, "Methods, Agents and Kits for the Detection of Cancer," mailed Jan. 19, 2012.
Reply from Australian Application No. 2009226152, "Methods and Agents for the Diagnosis and Treatment of Hepatocellular Carcinoma," filed Apr. 26, 2012.
Reply from New Zealand Application No. 588587, "Methods and Agents for the Diagnosis and Treatment of Hepatocellular Carcinoma," filed May 18, 2012.
Reply from European Application No. 09723224.3, "Methods and Agents for the Diagnosis and Treatment of Hepatocellular Carcinoma," filed May 24, 2012.
Office Action from Australian Application No. 2009226152, "Methods and Agents for the Diagnosis and Treatment of Hepatocellular Carcinoma," mailed May 31, 2012.
Office Action from New Zealand Application No. 588587, "Methods and Agents for the Diagnosis and Treatment of Hepatocellular Carcinoma," mailed Jun. 11, 2012.
Office Action from Chinese Application No. 200980118081.2, "Methods and Agents for the Diagnosis and Treatment of Hepatocellular Carcinoma," dated Aug. 30, 2012.
Reply from New Zealand Application No. 588587, "Methods and Agents for the Diagnosis and Treatment of Hepatocellular Carcinoma," filed Sep. 27, 2012.
Office Action from New Zealand Application No. 588587, "Methods and Agents for the Diagnosis and Treatment of Hepatocellular Carcinoma," mailed Oct. 11, 2012.
Restriction Requirement from U.S. Appl. No. 12/933,248, mailed Nov. 5, 2012.
Reply from New Zealand Application No. 588587, "Methods and Agents for the Diagnosis and Treatment of Hepatocellular Carcinoma," filed Nov. 9, 2012.
Office Action from New Zealand Application No. 588587, "Methods and Agents for the Diagnosis and Treatment of Hepatocellular Carcinoma," mailed Nov. 22, 2012.
Reply from New Zealand Application No. 588587, "Methods and Agents for the Diagnosis and Treatment of Hepatocellular Carcinoma," filed Dec. 14, 2012.
Office Action from European Application No. 09723224.3, "Methods and Agents for the Diagnosis and Treatment of Hepatocellular Carcinoma," mailed Jan. 7, 2013.
Reply from U.S. Appl. No. 12/933,248, filed Jan. 14, 2013.
Reply from Chinese Application No. 200980118081.2, "Methods and Agents for the Diagnosis and Treatment of Hepatocellular Carcinoma," filed on or before Feb. 12, 2013.
Office Action from U.S. Appl. No. 12/933,248, mailed May 21, 2013.
Office Action from Chinese Application No. 200980118081.2, "Methods and Agents for the Diagnosis and Treatment of Hepatocellular Carcinoma," mailed May 30, 2013.
Reply from European Application No. 09723224.3, "Methods and Agents for the Diagnosis and Treatment of Hepatocellular Carcinoma," filed Jul. 12, 2013.
Office Action from Taiwanese Application No. 098108921, "Methods and Agents for the Diagnosis and Treatment of Hepatocellular Carcinoma," mailed Aug. 15, 2013.
Office Action from Japanese Application No. 2011-500800, "Methods and Agents for the Diagnosis and Treatment of Hepatocellular Carcinoma," mailed Aug. 21, 2013.
Office Action from U.S. Appl. No. 13/126,734, mailed Aug. 28, 2013.
Final Office Action from U.S. Appl. No. 12/933,248, mailed Nov. 22, 2013.
Notice of Allowance from U.S. Appl. No. 12/933,248, mailed Feb. 14, 2014.
Notice of Allowance from U.S. Appl. No. 13/126,734, mailed Mar. 12, 2014.
Corrected Notice of Allowance from U.S. Appl. No. 13/126,734, mailed Apr. 8, 2014.
Notice of Intention to Grant from European Application No. 09723224.3, "Methods and Agents for the Diagnosis and Treatment of Hepatocellular Carcinoma," mailed Apr. 11, 2014.
Office Action from Taiwanese Application No. 098131450, "Methods and Agents for the Diagnosis and Treatment of Hepatocellular Carcinoma," mailed Apr. 28, 2014.
Office Action from Taiwanese Application No. 098108921, "Methods and Agents for the Diagnosis and Treatment of Hepatocellular Carcinoma," mailed Jun. 17, 2014.
Decision of Rejection from Japanese Application No. 2011-500800, "Methods and Agents for the Diagnosis and Treatment of Hepatocellular Carcinoma," mailed Jul. 7, 2014.

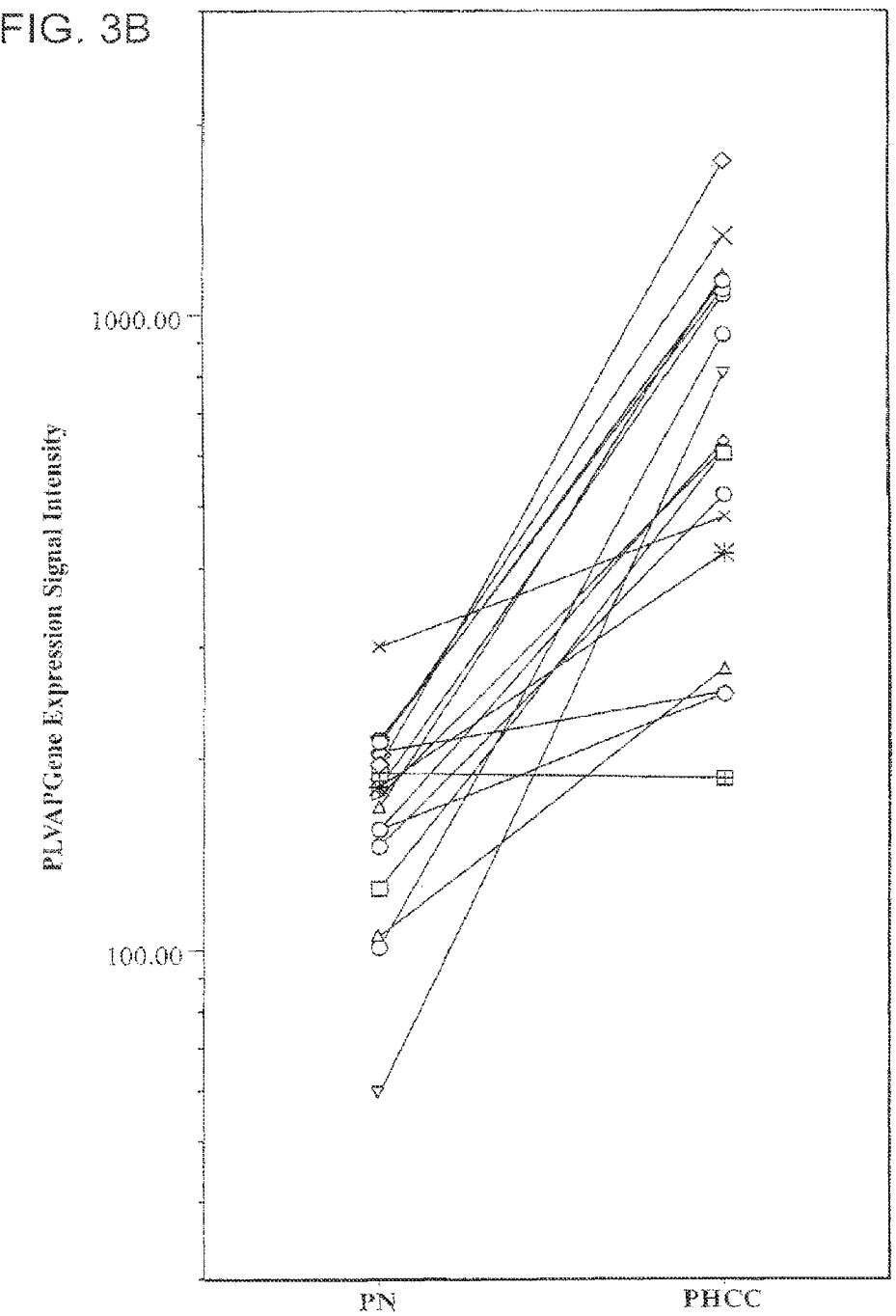

```
  1 atgggcagcagccatcatcatcatcatcacagcagcggcctggtg
    M  G  S  S  H  H  H  H  H  H  S  S  G  L  V
 46 ccgcgcggcagccatatgaacgtgcacgtgagcacagagtccaac
    P  R  G  S  H  M  N  V  H  V  S  T  E  S  N
 91 ctgcaggccaccgagcgccgagccgagggcctatacagtcagctc
    L  Q  A  T  E  R  R  A  E  G  L  Y  S  Q  L
136 ctagggctcacggcctccagtccaacttgaccaaggagctcaac
    L  G  L  T  A  S  Q  S  N  L  T  K  E  L  N
181 ttcaccacccgcgccaaggatgccatcatgcagatgtggctgaat
    F  T  T  R  A  K  D  A  I  M  Q  M  W  L  N
226 gctcgccgcgacctggaccgcatcaatgccagcttccgccagtgc
    A  R  R  D  L  D  R  I  N  A  S  F  R  Q  C
271 cagggtgaccgggtcatctacacgaacaatcagaggtacatggct
    Q  G  D  R  V  I  Y  T  N  N  Q  R  Y  M  A
316 gccatcatcttgagtgagaagcaatgcagagatcaattcaaggac
    A  I  I  L  S  E  K  Q  C  R  D  Q  F  K  D
361 atgaacaagagctgcgatgccttgctcttcatgctgaatcagaag
    M  N  K  S  C  D  A  L  L  F  M  L  N  Q  K
406 gtgaagacgctggaggtggagatagccaaggagaagaccatttgc
    V  K  T  L  E  V  E  I  A  K  E  K  T  I  C
451 actaaggataaggaaagcgtgctgctgaacaaacgcgtggcggag
    T  K  D  K  E  S  V  L  L  N  K  R  V  A  E
496 gaacagctggttgaatgcgtgaaaacccgggagctgcagcaccaa
    E  Q  L  V  E  C  V  K  T  R  E  L  Q  H  Q
541 gagcgccagctggccaaggagcaactgcaaaaggtgcaagccctc
    E  R  Q  L  A  K  E  Q  L  Q  K  V  Q  A  L
586 tgcctgcccctggacaaggacaagtttgagatggaccttcgtaac
    C  L  P  L  D  K  D  K  F  E  M  D  L  R  N
631 ctgtggagggactccattatcccacgcagcctggacaacctgggt
    L  W  R  D  S  I  I  P  R  S  L  D  N  L  G
676 tacaacctctaccatcccctgggctcggaattggcctccatccgc
    Y  N  L  Y  H  P  L  G  S  E  L  A  S  I  R
721 agagcctgcgaccacatgcccagctcatgagctccaaggtggag
    R  A  C  D  H  M  P  S  L  M  S  S  K  V  E
766 gagctggcccggagcctccggcgggatatcgaacgcgtggcccgc
    E  L  A  R  S  L  R  A  D  I  E  R  V  A  R
811 gagaactcagacctccaacgccagaagctggaagcccagcagggc
    E  N  S  D  L  Q  R  Q  K  L  E  A  Q  Q  G
856 ctgcgggccagtcaggaggcgaaacagaaggtggagaaggaggct
    L  R  A  S  Q  E  A  K  Q  K  V  E  K  E  A
901 caggcccggggaggccaagctccaagctgaatgctcccggcagacc
    Q  A  R  E  A  K  L  Q  A  E  C  S  R  Q  T
```

FIG. 4A

```
 946 cagctagcgctggaggagaaggcggtgctgcggaaggaacgagac
     Q  L  A  L  E  E  K  A  V  L  R  K  E  R  D
 991 aacctggccaaggagctggaagagaagaagagggaggcggagcag
     N  L  A  K  E  L  E  E  K  K  R  E  A  E  Q
1036 ctcaggatggagctggccatcagaaactcagccctggacacctgc
     L  R  M  E  L  A  I  R  N  S  A  L  D  T  C
1081 atcaagaccaagtcgcagccgatgatgccagtgtcaaggcccatg
     I  K  T  K  S  Q  P  M  M  P  V  S  R  P  M
1126 ggccctgtccccaaccccagcccatcgacccagctagcctggag
     G  P  V  P  N  P  Q  P  I  D  P  A  S  L  E
1171 gagttcaagaggaagatcctggagtcccagaggccccctgcaggc
     E  F  K  R  K  I  L  E  S  Q  R  P  P  A  G
1216 atccctgtagccccatccagtggctga
     I  P  V  A  P  S  S  G  *  (SEQ ID NO:2)
     ggaggctccaggcctgaggaccaagggatggcccgactcggcggt ttgcggaggatgcagggatatgctcacagggattc (SEQ ID NO:1)
```

FIG. 4B

HCC tissue in dashed line

Adjacent non-tumorous tissue outside dashed line

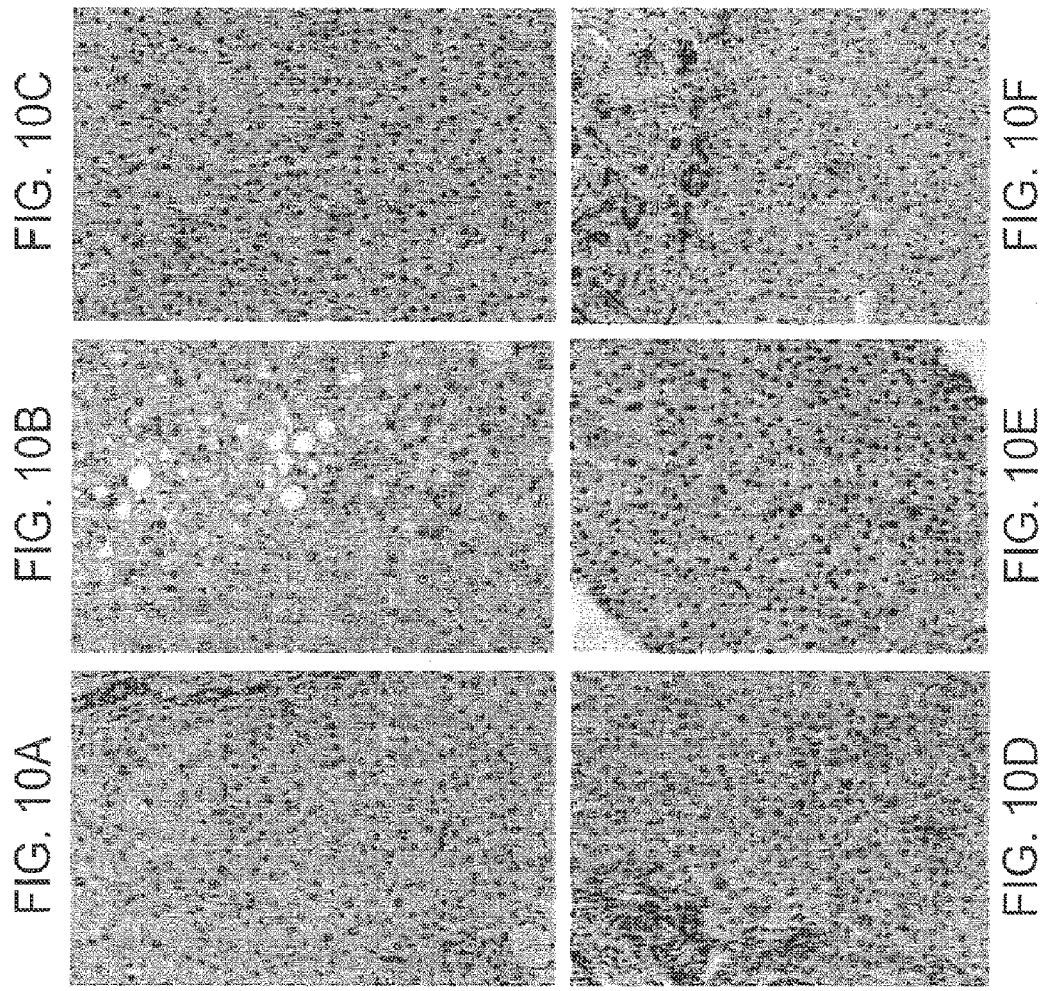

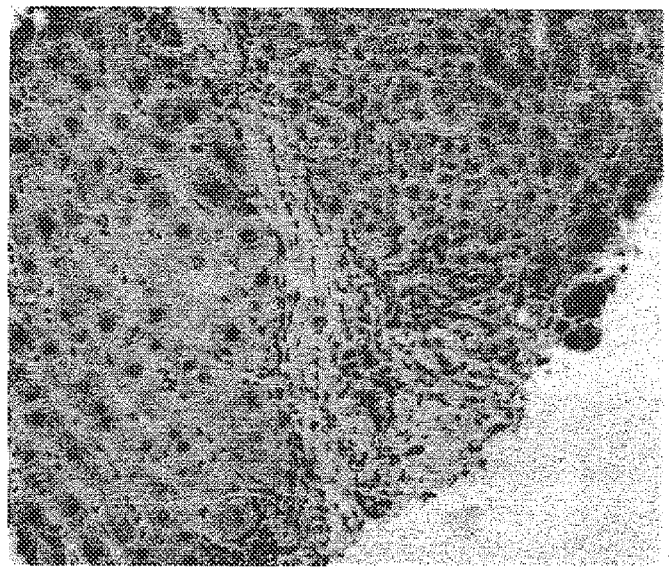
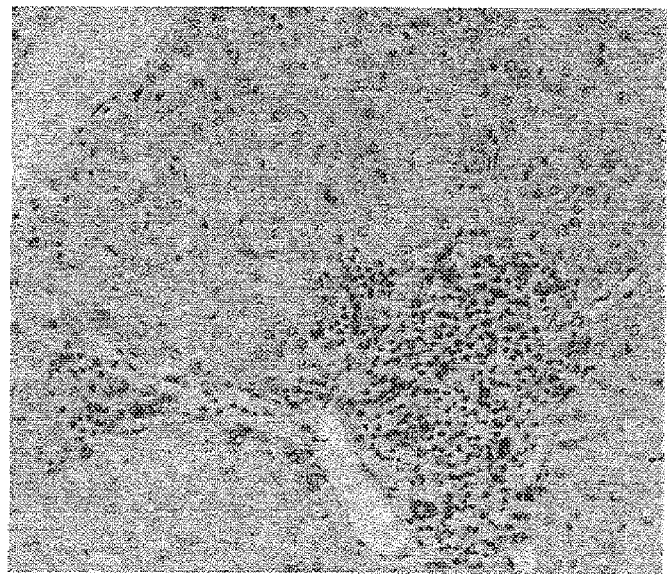

GAGGTTCAGCTGCAGCAGTCTGGGGCAGAGTTTGTGAGGTCAAGGGCCTTCAGTCAAGTTGTCCTGCACAGTTCTGGCTTCAACATTAAA 90
GACTACTATATACACTGGGTGAAGCAGAGGCCTGAACAGGGCCTGGAGTGGATTGGATGGATTGATCCTGAGAATGGTGATATTGAATAT 180
GCCCCGAAGTTCCAGGGCAAGGCCACTATGACTGCAGACACATCCTCCAATACAGCCTACCTGCAGTTCAGCAGCCTGACATCTGAGGAC 270
ACTGCGGTCTATTACTGTGTCTCTACCAAGAAGGCTCCTGGGCCAAGGCACCACTCTCACAGTCTCCTCAGCC 342 (SEQ ID NO:3)

E V Q L Q Q S G A E F V R S G A S V K L S C T A S G F N I K
D Y Y I H W V K Q R P E Q G L E W I G W I D P E N G D I E Y
              CDR1                              CDR2
A P K F Q G K A T M T A D T S S N T A Y L Q F S S L T S E D
T A V Y Y C V S T K K A P G P R H H S H S L Q S P P Q P (SEQ ID NO:4)
              CDR3

CDR1: D Y Y I H (SEQ ID NO:5)
CDR2: W I D P E N G D I E Y A P K F Q G (SEQ ID NO:6)
CDR3: Q E G S (SEQ ID NO:7)

FIG. 15A

GATGTTGTGATGACCCAGACTCCACTCACTTTGTCGGTTACCATTGGACAACCAGCCTCCATCTCTTGCAAGTCAAGTCAGAGCCTCTTA 90
AATAGTGATGGAAAGACATATTTGAATTGGTTGTTACAGAGGCCAGGCCAGTCTCCAAAGCGCCTAATCTATCTGGTGTCTAAATTGGAC 180
TCTGGAGTCCCTGACAGGTTCACTGGCAGTGGATCAGGGACAGATTTCACACTGAAAATCAGCAGAGTGGAGGCTGAGGATTTGGGAGTT 270
TATTATTGCTGGCAAGGTACACATTTTCCGTTCACGTTCGGAGGGGGGACCAAGCTGGAATAAAA 336 (SEQ ID NO:8)

```
D  V  V  M  T  Q  T  P  L  T  L  S  V  T  I  G  Q  P  A  S  I  S  C  K  S  S  Q  S  L  L
N  S  D  G  K  T  Y  L  N  W  L  L  Q  R  P  G  Q  S  P  K  R  L  I  Y  L  V  S  K  L  D
       CDR1                                                         CDR2
S  G  V  P  D  R  F  T  G  S  G  S  G  T  D  F  T  L  K  I  S  R  V  E  A  E  D  L  G  V
Y  Y  C  W  Q  G  T  H  F  P  F  T  F  G  G  G  T  K  L  E  I  K    (SEQ ID NO:9)
                    CDR3
```

CDR1: K S S Q S L L N S D G K T Y L N (SEQ ID NO:10)
CDR2: L V S K L D S (SEQ ID NO:11)
CDR3: W Q G T H F P F T (SEQ ID NO:12)

FIG. 15B

CAGGTCCAACTGCAGCAGCCTGGGGCTGAGCTGGTGAGGCCTGGGGCCTTCAGTGAAGCTGTCCTGCAAGGCTTCTGGCTACACCTTCAC
C 90
AGCAACTACATAAACTGGGTGAAACAGAGGCCTGGACAGGGCCTTGAGTGGATCGGAAATATTTATCCTTCTGATGGTTTTACTAACTA
C 180
AATCAAAAGTTCAAGGACAGGGCCACATTGACTGTAGACAAATCCTCCAGCACAGCCTACATGCAGCTCAGCAGCCCGACAATCTGAGGA
C 270
TCTGCGGTCTATTACTGTACAAGAAACTTCGATGTCTGGGGCGCAGGGACCACGGTCACCGTCTCCTCAGCC 342 (SEQ ID NO:13)

Q V Q L Q Q P G A E L V R P G A S V K L S C K A S G Y T F T
S N Y I N W V K Q R P G Q G L E W I G N I Y P S D G F T N Y
  ‾‾CDR1‾‾                              ‾‾‾‾‾‾‾CDR2‾‾‾‾‾‾‾
N Q K F K D R A T L T V D K S S S T A Y M Q L S S P T S E D
S A V Y Y C T R N F D V W G A G T T V T V S S A (SEQ ID NO:14)
              ‾CDR3‾

CDR1: S N Y I N (SEQ ID NO:15)
CDR2: N I Y P S D G F T N Y N Q K F K D (SEQ ID NO:16)
CDR3: N F D V (SEQ ID NO:17)

FIG. 16A

```
GATGTTGTGATGACCCAAACTCCACTCTCCCTGCCTGTCAGTCTTGGAGATCAAGCCTCCATCTCTTGCAGATCTAGTCAGAGCCTTGT
C         90
CACAGTAATGGAAACACCTATTTACAGTGGTACCTGCAGAAGCCAGGCCAGTCTCCAAAGCTCCTGATCTACACAGTTTCCAACCGATT
T         180
TCTGGGGTCCCAGACAGATTCAGTGGCAGTGGATCAGGGACAGATTTCACACTCAAGATCAGCAGAGTGGAGGCTGAGGATCTGGGAGT
T         270
TATTTCTGCTCTCAAAGTACACATGTTCCTTCACGTTCGGCTCGGGGACAAAGTTGGAAATAAAA  336 (SEQ ID NO:18)
```

```
D  V  V  M  T  Q  T  P  L  S  L  P  V  S  L  G  D  Q  A  S  I  S  C  R  S  S  Q  S  L  V
                                                                    ─────────────────────
                                                                            CDR1
H  S  N  G  N  T  Y  L  Q  W  Y  L  Q  K  P  G  Q  S  P  K  L  L  I  Y  T  V  S  N  R  F
                                                                        ──────────────────
                                                                                CDR2
S  G  V  P  D  R  F  S  G  S  G  S  G  P  D  F  T  L  K  I  S  R  V  E  A  E  D  L  G  V
Y  F  C  S  Q  S  T  H  V  P  F  T  F  G  S  G  T  K  L  E  I  K    (SEQ ID NO:19)
─────────────────────
        CDR3
```

CDR1:  R  S  S  Q  S  L  V  H  S  N  G  N  T  Y  L  Q  (SEQ ID NO:20)
CDR2:  T  V  S  N  R  F  S  (SEQ ID NO:21)
CDR3:  S  Q  S  T  H  V  P  F  T  (SEQ ID NO:22)

FIG. 16B

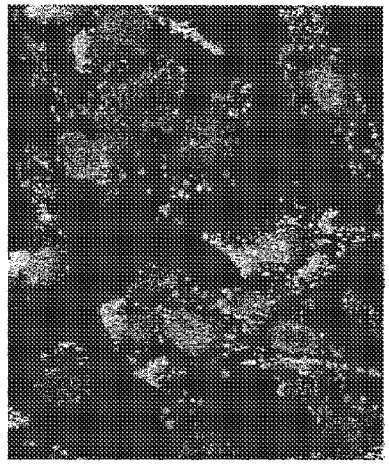
FIG. 20A / FIG. 20B  Mouse IgG / Mouse vWF
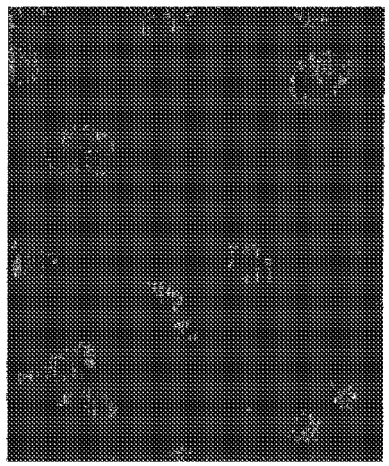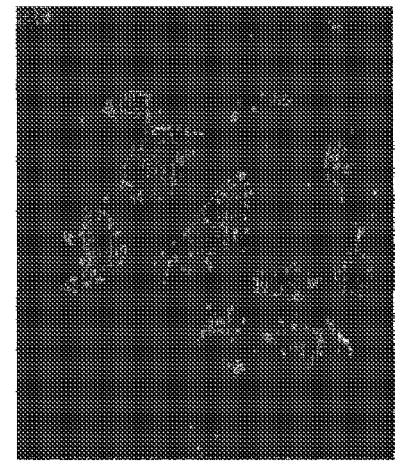
FIG. 20C / FIG. 20D  KFCC-GY4 / KFCC-GY5

```
  1  mglamehggs yaraggssrg cwyylryffl fvsliqflii lglvlfmvyg nvhvstesnl
 61  qaterraegl ysqllqltas qsnltkelnf ctrakdalmq mwlnarrdld rinasfrccq
121  gdrviytnnq rymaaiilse kqcrdqfkdm nkscdallfm lnqkvktlev eiakektict
181  kdkesvllnk rvaeeqlvec vktrelqhqe rqlakeqlqk vqaldlpldk dkfemdlrnl
241  wrdsiiprsl dnlgynlyhp lgselasirr acdhmpslms skveelarsl radiervare
301  nsdlqrqkle aqqglrasqs akqkvekeaq areaklqsec srqtqlalee kavlrkerdn
361  lakeleekkr eaeqlrmela irnsaldtci ktksqpmmpv srpmgpvpnp qpidpaslee
421  fkrkilesqr ppagipvaps sg   (SEQ ID NO:23)
```

FIG. 24

```
1    cggacgcgtg ggtgagcagg gacggtgcac cggacggcgg gatcgagcaa atgggtctgg
61   ccatggagca cggagggtcc tacgctcggg cggggggcag ctctggggc tgctggtatt
121  acctgcgcta cttcttcctc ttcgtctccc tcatccaatt cctcatcatc ctgggctcg
181  tgctcttcat ggtctatgc aacgtgcacg tgagcacaga gtccaactg caggccaccg
241  agcgccgagc cgagggccta tacagtcagc tcctagggct cacggcctcc cagtccaact
301  tgaccaagga gctcaacttc accaccgcg ccaaggatgc catcatgcag atgtggctga
361  atgctcgccg cgacctggac cgcatcaatg ccagcttccg ccagtgccag ggtgaccggg
421  tcatctacac gaacaatcag aggtacatgg ctgccatcat cttgagtgag aagcaatgca
481  gacatcaatt caaggacatg aacaagagct gcgatgcctt gctcttcatg ctgaatcaga
541  aggtgaagac gctggaggtg gagatagcca aggagaagac catttgcact aaggataagg
601  aaagcgtgct gctgaacaaa cgcgtggtgg aggaacagct ggttgaatgc gtgaaaaccc
661  gggagctgca gcaccaagag cgccagctgg ccaaggagca actgcaaaag ctgcaagccc
721  tctgctgcc cctggacaag gacaagtttt agatggacct tgtaacctg tggagcgact
781  ccattatccc acgcagcctg gacaacctgg gttacaacct ctaccatccc ctgggctcgg
841  aattggcctc catccgcaga gcctgcgatc acatgccag cctcatgagc tccaaggtgg
901  aggagctggc ccggagcctc cgggcggata tcgaacgcgt ggcccgcgag aactcagacc
961  tccaacgcca gaagctggaa gcccagcagg cctgcgggc cagtcaggag gcgaaaacaga
1021 aggtggagaa ggaggctcag gccgggagg ccaagctcca agctgaatgc tcccggcaga
1081 cccagctagc gctggaggac aaggcggtgc tgcggaagga acgagacaac ctggccaagg
1141 agctggaaga gaagaagagg gaggcggagc agtcaggat ggagctggcc atcagaaact
1201 cagccctgga cacctgcatc aagaccaagt cgcagccgat gatgccagtg tcaaggccca
1261 tgggccctgt cccaacccc cagcccatcg acccagctag cctggaggag ttcaagagga
1321 agatcctgga gtcccagagg ccccctgcag gcatccctgt agccccatcc agtggctgag
1381 gaggctccag gcctgaggac caagggatgg ccgactcgg cggtttgcgg aggatgcagg
1441 gatatgttca cagcgccga cacaaccccc tcccgccgcc cccaaccacc cagggccacc
1501 atcagacaac tccctgcatg caaaccccta gtaccctctc acaccgcac ccgcgcctca
```

FIG. 25A

```
1561 cgatcctca cccagagcac acggccgcgg agatgacgtc acgcaagcaa cggcgctgac
1621 gtcacatatc accgtggtga tggcgtcacg tggccatgta gacgtcacga agagatatag
1681 cgatggcgtc gtgcagatgc agcacgtcgc acacagacat ggggaacttc gcatgacgtc
1741 acaccgagat gcagcaacga cgtcacgggc catgtcgacg tcacacatat taatgtcaca
1801 cagacgcggc gatggcatca cacagacggt gatgatgtca cacacagaca cagtgacaac
1861 acacaccatg acaacgacac ctatagatat ggcaccaaca tcacatgcac gcatgcccct
1921 tcacacacac tttctaccca attctcacct agtgtcacgt tccccgacc ctggcacacg
1981 ggcaaggtc cccacaggat cccatcccct cccgcacagc cctggcccc agcacctccc
2041 ctcctccagc ttcctggcct cccagccact tcctcaccc cagtgcctgg accggaggt
2101 gagaacagga agccattcac ctccgctcct tgagcgtgag tgtttccagg accccctcgg
2161 ggccctgagc cggggtgag ggtcacctgt tgtcgggagg ggagccactc ctttctccc
2221 aactcccagc cctgcctgtg gcccgttgaa atgttggtgg cacttaataa atattagtaa
2281 atccttaaaa aaaaaaaaaa aaaaaaaaaa aaaaaaa   (SEQ ID NO:24)
```

FIG. 25B

| Normal Tissue | Human normal tissue | | Cy-Monkey | Rh-Monkey |
|---|---|---|---|---|
| | PLVAP positivity by GY4 | PLVAP positivity by GY5 | PLVAP positivity by GY4 or GY5 | PLVAP positivity by GY4 or GY5 |
| Bone marrow | − | − | − | − |
| Cerebellum | − | − | − | − |
| Cerebrum | − | − | − | − |
| Liver (except small vessels of portal tract) | − | − | − | − |
| Nerve (except intrstitial tissue) | − | − | − | − |
| Ovary | − | − | − | − |
| Spleen- white pulp | − | − | − | − |
| Skeletal muscle | − | +/−* | − | − |
| Testis | +w | +w | − | − |
| Parathyroid | +w | +w | ** | ** |
| prostate | + | +w | + | + |
| Salivary gland | + | + | + | + |
| Kidney | +w | + | + | + |
| Adrenal-Cortex | + | + | + | + |
| Breast | + | + | + | + |
| Colon | + | + | + | + |
| Esophagus | + | + | + | + |
| Heart | + | + | − | − |
| Intestine | + | + | + | + |
| Lung | + | + | + | +w |
| Mesothelium | + | + | + | + |
| Pancreas | + | + | + | + |
| Pituitary | + | + | + | + |
| Skin | − | + | + | + |
| Spleen-red pulp | + | + | + | + |
| Thymus | + | + | + | + |
| Thyroid | + | + | + | + |
| Tonsil | + | + | + | + |
| Uterine cervix | + | + | + | + |
| Uterus | + | + | + | + |
| Stomach | + | + | + | + |

*: Small vessel + Large vessel −

**: no parathyroid tissue

All positivity was confined in vascular endothelial cells

FIG. 26

FIG. 27A2 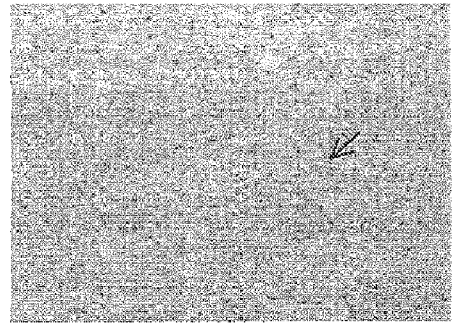
FIG. 27B2 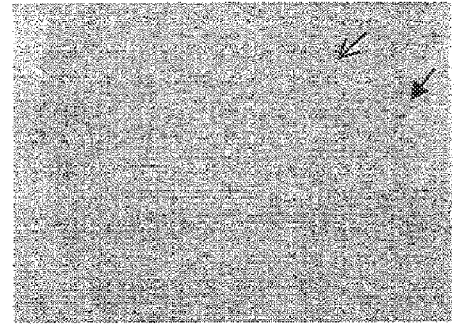
FIG. 27C2 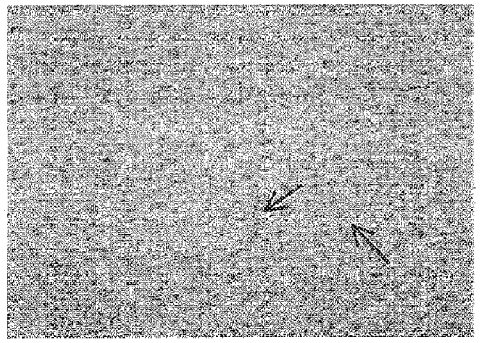
FIG. 27D2 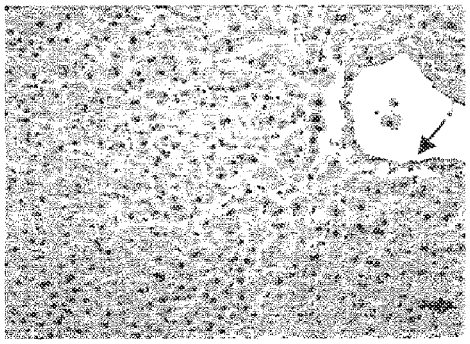

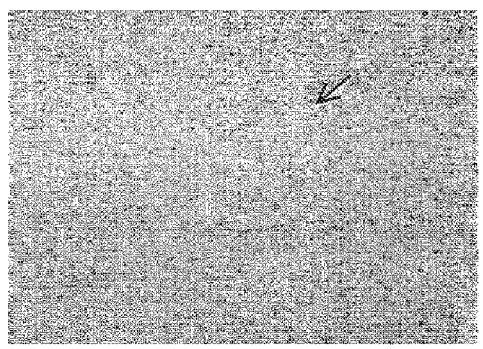
FIG. 27E2
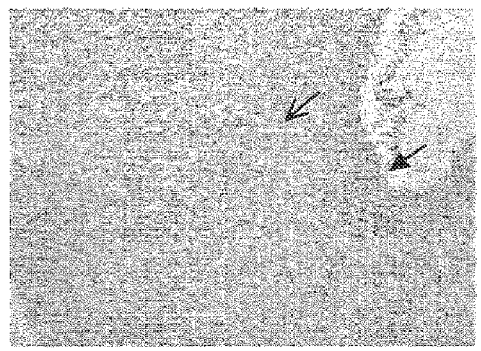
FIG. 27F2

FIG. 32A-1
GY4 VH Chimera (pANT12)

```
ACTAGTTATTAATAGTAATCAATTACGGGGTCATTAGTTCATAGCCCATATATGGAGTTCCGCGTTACATAACTT
————————+————————+————————+————————+————————+————————+————————+————————+
TGATCAATAATTATCATTAGTTAATGCCCCAGTAATCAAGTATCGGGTATATACCTCAAGGCGCAATGTATTGAA
                                          —————————— CMV Promoter ACGGTAAATGGCCCGCCTGGCTGACCGCCCAACGACCCCCGCCCATTGACGTCAATAATGACGTATGTTCCCATA                 150
————————+————————+————————+————————+————————+————————+————————+————————+
TGCCATTTACCGGGCGGACCGACTGGCGGGTTGCTGGGGGCGGGTAACTGCAGTTATTACTGCATACAAGGGTAT
—————————— CMV Promoter ——————————

GTAACGCCAATAGGGACTTTCCATTGACGTCAATGGGTGGAGTATTTACGGTAAACTGCCCACTTGGCAGTACAT
————————+————————+————————+————————+————————+————————+————————+————————+
CATTGCGGTTATCCCTGAAAGGTAACTGCAGTTACCCACCTCATAAATGCCATTTGACGGGTGAACCGTCATGTA
                 —————————— CMV Promoter ——————————

CAAGTGTATCATATGCCAAGTACGCCCCCTATTGACGTCAATGACGGTAAATGGCCCGCCTGGCATTATGCCCAG                 300
————————+————————+————————+————————+————————+————————+————————+————————+
GTTCACATAGTATACGGTTCATGCGGGGGATAACTGCAGTTACTGCCATTTACCGGGCGGACCGTAATACGGGTC
—————————— CMV Promoter
```

FIG. 32A-3

GCTGGACTCACAAGTCTTTCTCTTCAGTGACAAACACAGAAATAGAGCCGCCACCATGGGTTGGAGCCTCATCTT
CGACCTGAGTGTTCAGAAAGAGAAGTCACTGTTTGTGTCTTTTATCTCGGCGGTGGTACCCAACCTCGGAGTAGAA
                                                        M  G  W  S  L  I  L
                                                           Signal Sequence GCTCTTCCTTGTGCTGTTGCTACGCGTGTCCACTCCGAGGTTCAGCTGCAGCAGTCTGGGGCAGAGTTTGTGAG
CGAGAAGGAACAGCACAACGATGCGCACAGGTGAGGCTCCAAGTCGACGTCTCAGACCCCGTCTCAAACACTC
 L  F  L  V  A  T  R  V  H  S  E  V  Q  L  Q  Q  S  G  A  E  F  V  R
    Signal Sequence          |              GY4VH
                    MluI GTCAGGGGGCCTCAGTCAAGTTGTCCTGCACAGCTTCTGGCTTCAACATTAAAGACTACTATATACACTGGGTGAA
CAGTCCCCCGGAGTCAGTTCAACAGGACGTGTCGAAGACCGAAGTTGTAATTTCTGATGATATATGTGACCCACTT
 S  G  A  S  V  K  L  S  C  T  A  S  G  F  N  I  K  D  Y  Y  I  H  W  V  K
                                GY4VH GCAGAGGCCTGAACAGGCCTGGAGTGGATTGGATGGATTGATCCTGAGAATGGTGATATTGAATATGCCCCGAA
CGTCTCCGGACTTGTCCCGGACCTCACCTAACCTACCTAACTAGGACTCTTACCACTATAACTTATACGGGCTT
 Q  R  P  E  Q  G  L  E  W  I  G  W  I  D  P  E  N  G  D  I  E  Y  A  P  K
   GY4VH

FIG. 32A-4

```
GTTCCAGGGCAAGGCCACTATGACTGCAGACACATCCTCCAATACAGCCTACCTGCAGTTCAGCAGCCTGACATC
     +         +         +         +         +         +         +
CAAGGTCCCGTTCCGGTGATACTGACGTCTGTGTAGGAGGTTATGTCGGATGGACGTCAAGTCGTCGGACTGTAG
 F  Q  G  K  A  T  M  T  A  D  T  S  S  N  T  A  Y  L  Q  F  S  S  L  T  S
                                                                    ─────────
                                                                      GY4VH

1050
TGAGGACACTGCCGTCTATTACTGTCTCTACCAAGAAGGCTCCTGGGGCCAAGGCACCACTCTCACAGTCTCCTC
     +         +         +         +         +         +         +
ACTCCTGTGACGGCAGATAATGACAGAGATGGTTCTTCCGAGGACCCCGGTTCCGTGGTGAGAGTGTCAGAGGAG
 E  D  T  A  V  Y  Y  C  L  Y  Q  E  G  S  W  G  Q  G  T  T  L  T  V  S  S
─────────────────────────                        ─────────────────────────────
         GY4VH                                              GY4VH (SEQ ID NO:45)
```

FIG. 32B-1

Hind III

AGGTAAGCTTTCTGGGGCAGGCCGGGCCTGACTTTGGCTTGGGGCAGGGAGGGGCTAAGGTGACGCAGGTGGCG
TCCATTCGAAAGACCCCGTCCGGCCCGGACTGAAACCGACCCCGCTCCCCGATTCCACTGGGTCCACCGC

CCAGCCAGGTGCACACCCAATGAGCCCAGACACTGGACCCTGCATGGACCATCGCGGATAGACAAGAAC 1200
GGTGGGTCCAGCTGTGGGTTAGGGTCTGTGACCTGGGAGGTACCTGTGGTAGCGCCTATCTGTTCTTG

CGAGGGGCCCTGCGCCCTGGGCCCCAGCTCTGTGTCCCACACCGCGGTCACATGCACCACCTCTCTCTTGCAGCTTCC
GCTCCCCGAGAACGCGGGACACCCGGTGTCGAGACACAGGTGTGGCCGCCAGTGTACCGTGTGGAGAGAACGTCGAAGG
                                                          A  S
                                                          _____ 1350

ACCAAGGGCCCATCCGTCTTCCCCCTGGCGCCCTGCTCCAGGAGCACCTCCGAGAGCACAGCCGCCCTGGGCTGC
TGGTTCCCGGGTAGCCAGAAGGGGGACCGCGGGACGAGGTCCTCGTGGAGGCTCTCGTGTCGGCGGGACCCGACG
    T  K  G  P  S  Y  F  P  L  A  P  C  S  R  S  T  S  E  S  T  A  A  L  G  C
                      IgG4 CH1

CTGGTCAAGGACTACTTCCCCGAACCGGTGACGGTGTCGTGGAACTCAGGCGCCCTGACCAGCGGCGTGCACACC
GACCAGTTCCTGATGAAGGGGCTTGGCCACTGCCACAGCACCTTGAGTCCGCGGGACTGGTCGCCGCACGTGTGG
    L  V  K  D  Y  F  P  E  P  V  T  V  S  W  N  S  G  A  L  T  S  G  V  H  T
                                                              IgG4 CH1

FIG. 32B-2

```
TTCCCGGCTGTCCTACAGTCCTCAGGACTCTCTACTCCCTCAGCAGGCTGTGCTGCAGTCCTCAGGACTCTCTACTCCCTCAGCAGCTTGGGC
                                                                                          1500
AAGGGCCGACAGAGTGTCAGGAGTCCTGAGATGAGGGAGTCGTGCACCACTGGCACGGGAGGTCGTGAACCCG
        F  P  A  V  L  Q  S  S  G  L  Y  S  L  S  S  V  V  T  V  P  S  S  S  L  G
                                                                        IgG4 CH1

ACGAAGACCTACACCTGCAATGTAGATCACAAGCCCAGCAACACCAAGGTGGACAAGAGAGTTGGTGAGAGGCCA
                                                                                          1650
TGCTTCTGGATGTGGACGTTACATCTAGTGTTCGGGTCGTTGTGGTTCCACCTGTTCTCTCAACCACTCTCCGT    (SEQ ID NO:46)
  T  K  T  Y  T  C  N  V  D  H  K  P  S  N  T  K  V  D  K  R  V
                            IgG4 CH1

GCACAGGAGGAGGGTGTCTGCTGAAGCCAGGCCTCAGCCCTCCTGACGCCACCCCGGCTGTGCAGCCCC
CGTGTCCCTCCCCACAGACGACTTCGGTCCGGAGTCGGGAGGACTGCGGTGGGGCCGACACGTCGGGG

AGCCCAGGGCAGGCCAGCAAGACTCGTCCTCCTCACCTGAGGCCTCGACTGGACTGTGGGTGAGAGA
TCGGGTCCCGTCGTTCGTCCGGGTAGACAGAGGAGTGGACCTCCGGAGACTGGTGAGTACGAGTCCCT

GAGGGTCTTCTGGATTTTCCACCAGGTCCGGGCAGCCACACAGGCTGATGCCCCTACCCAGGCCCTGCCATA
                                                                                          1800
CTCCCAGAAGACCTAAAAGGTGTCCAGGCCCGTCGGTTCCGACCTACGGGGATGGGTCCGGGACGCGTAT
```

FIG. 32B-3

```
CAGGGGCAGTGCTGCGCTCAGAGACCTGCCAAGAGCCCATATCCGGGAGGACCCCTGCCCCTGACCTAAGCCCACCCC
----------------+---------+---------+---------+---------+---------+---------+
GTCCCCGTCACGACGCGAGTCTGGACGGTTCTCGGTATAGGCCCTCCTGGGGACGGGGACTGGATTCGGTGGGG

AAAGGCCAAACTCTCCACTCCCTCAGCTCAGACACCTTCTCTCCTCCCAGATCTGAGTAACTCCCAATCTTCTCT 1950
----------------+---------+---------+---------+---------+---------+---------+
TTTCCGGTTTGAGAGGTGAGGGAGTCGAGTCTGTGGAAGAGAGAGGGTCTAGACTCATTGAGGGTTAGAAGAGA

CTGCAGAGTCCAAATATGGTCCCCCATGCCCATCATGCCCAGGTAAGCCAACCCAGGCCTCGCCCTCCAGCTCAA
----------------+---------+---------+---------+---------+---------+---------+
GACGTCTCAGGTTTATACCAGGGGTACGGGTAGTACGGGTCCATTCGGTTGGGTCCGGAGCGGGAGGTCGAGTT
      E  S  K  Y  G  P  P  C  P  P  S  C  P
      └─── IgG4 Hinge ───┘

GGCGGGACAGGTGCCCTAGAGTAGCCTGCATCCAGGACAGGCCCCAGCCGGGTGCTGACCGCCATCCACCTCCATC 2100
----------------+---------+---------+---------+---------+---------+---------+
CCGCCCTGTCCACGGGATCTCATCGGACGTAGGTCCTGTCCGGGGTCGGCCCACGACTGGCGGTAGGTGGAGGTAG (SEQ ID NO:47)
```

FIG. 32C-1

```
TCTTCCTCAGCACCTGAGTTCCTGGGGGGACCATCAGTCTTCCTGTTCCCCCCAAAACCCAAGGACACTCTCATG
----+----+----+----+----+----+----+----+----+----+----+----+----+----+
AGAAGGAGTCGTGGACTCAAGGACCCCCCTGGTAGTCAGAAGGACAAGGGGGGTTTTGGGTTCCTGTGAGAGTAC
         A  P  E  F  L  G  G  P  S  V  F  L  F  P  P  K  P  K  D  T  L  M
                                                                    IgG4 CH2
                                                                            2250
ATCTCCCGGACCCCCTGAGGTCACGTGCGTGGTGGTGGACGTGAGCCAGGAAGACCCCGAGGTCCAGTTCAACTGG
----+----+----+----+----+----+----+----+----+----+----+----+----+----+
TAGAGGGCCTGGGGGACTCCAGTGCACGCACCACCACCTGCACTCGGTCCTTCTGGGGCTCCAGGTCAAGTTGACC
    I  S  R  T  P  E  V  T  C  V  V  V  D  V  S  Q  E  D  P  E  V  Q  F  N  W
                     IgG4 CH2

TACGTGGATGGCGTGGAGGTGCATAATGCCAAGACAAAGCCGCGGGAGGAGCAGTTCAACACAGCACGTAGCGTGTG
----+----+----+----+----+----+----+----+----+----+----+----+----+----+
ATGCACCTACCGCACCTCCACGTATTACGGTTCTGTTTCGGCGCCCTCCTCGTCAAGTTGTGTCGTGCATCGCACAC
    Y  V  D  G  V  E  V  H  N  A  K  T  K  P  R  E  E  Q  F  N  S  T  Y  R  V
                             IgG4 CH2
```

FIG. 32C-2

```
GTCAGGCGTCCTCACCGTCCTGCACCAGGACTGGCTGAACGGCAAGGAGTACAAGTGCAAGGTCTCCAACAAAGGC
       ----+----+----+----+----+----+----+----+----+----+----+----+----+----+----     2400
CAGTCGCAGGAGTGGCAGGACGTGGTCCTGACCGACTTGCCGTTCCTCATGTTCACGTTCCAGAGGTTGTTTCCG

V  S  V  L  T  V  L  H  Q  D  W  L  N  G  K  E  Y  K  C  K  V  S  N  K  G
  └─────────────────── IgG4 CH2

CTCCCCGTCCTCCATCGAGAAAACCATCTCCAAAGCCAAAGGTGGGACCCACGGGGTGCGAGGGCCACATGACAG
       ----+----+----+----+----+----+----+----+----+----+----+----+----+----+----
GAGGGGCAGGAGTAGCTCTTTTGGTAGAGGTTTCGGTTTCCACCCTGGGTGCCCCACGCTCCCGGTGTACCTGTC

L  P  S  S  I  E  K  T  I  S  K  A  K   (SEQ ID NO:48)
──── IgG4 CH2 ────────────────────┘

AGGTCAGCTCGGCCCACCCTCTCTGCCCCTGGGAGTGACCGCTGTGCCAACCTCTGTCCCTACAGGGCAGCCCCGAGA
       ----+----+----+----+----+----+----+----+----+----+----+----+----+----+----     2550
TCCAGTCGAGCCGGGTGGGAGACGGGGACCCTCACTGGCGACACGGTTGGAGACAGGGATGTCCCGTCGGGGCTCT

G  Q  P  R  E
                                                         └── IgG4 CH3
```

FIG. 32C-3

```
GAATGTCTTCTCATGCTCCGTGATGGAGGATGTGCTGCACAACCACTACACAGAAGAGCCTCTCCCTGTCTCT
                                                                              2850
CTTACAGAAGAGTACGAGGCACTACTCCGAGACGTGTTGGTGATGTGTCTTCTCGGAGAGGGACAGAGA
 N  Y  F  S  C  S  Y  H  H  E  A  L  H  N  H  Y  T  Q  K  S  L  S  L  L
                                    IgG4 CH3

GGGTAAAATGAGTCCAGGGCCGGCAAGCCCCGCTCCCCGGGCTCTCGGGGTCGCGGAGGATGCTTGGCACGTA
CCCATTTACTCAGGTCCCGGCCGTTCGGGGCGAGGGGCCCGAGAGCCCCAGCGCCTCCTACGAACCGTGCAT
 G  K                                                                   poly A
   IgG4 CH3            (SEQ ID NO:49)
```

FIG. 32D-1

TGATGGTTCTTTCCACGGGTCAGGCCGAGTCTGAGGCCTGAGTGACATGAGGAGGCAGAGAGGCGGTCCCACTGTC
ACTACCAAGAAAGTGCCCAGTCCGGCTCAGATCCGGCTCAGACTCACTGTACTCCCTCCGTCCGCCCAGGTGACAG
— poly A — 3150

CCCACACTGGCCCCAGGCTGTGCAGGTGCCTGGGCCACCTAGGGTGCCTCAGCCAGGGGCTGCCCTCGGCAG
GGGTGTGACGGGTCCGACAGTCCCACACGGACCCGGTGATCCCACCCCGAGTCGGTCCCCGACGGGAGCCGTC
— poly A —

GGTGGGGATTTGCCAGCGTGGCCCCTCCCCTCCAGCAGACATGTGAGCAAAAGGCCAGGAACCGT
CCACCCCCTAAACGGTCGCACCGGGAGGAGGTCGTCTGTACACTCGTTTTCCGGTCGTTCCTTGGCA
— poly A —

FIG. 32D-2

```
AAAAAGGCCGCGTTGCTGGCGTTTTTCCATAGGCTCCGCCCCCTGACGAGCATCACAAAAATCGACGCTCAAGT
      ++++++++++++++++++++++++++++++++++++++++++++++++++++++++++++++++++++++++  3300
TTTTTCCGGCGCAACGACCGCAAAAAGGTATCCGAGGCGGGGGACTGCTCGTAGTGTTTTTAGCTGCGAGTTCA

CAGAGGTGGCGAAACCCGACACAGGACTATAAAGATACCAGGCGTTTCCCCCTGGAAGCTCCCTCGTGCGCTCTCCT
      ++++++++++++++++++++++++++++++++++++++++++++++++++++++++++++++++++++++++
GTCTCCACCGCTTTGGGCTGTGTCCTGATATTTCTATGGTCCGCAAAGGGGACCTTCGAGGGAGCACGCGAGAGGA

GTTCCGACCCCTGCCGCTTACCGGATACCCTGTCCGCCTTTCTCCCCTTCGGGAAGCGTGGCGCTTTCTCATAGCTCA
      ++++++++++++++++++++++++++++++++++++++++++++++++++++++++++++++++++++++++  3450
CAAGGCTGGGACGGCGAATGGCCTATGGACAGGCCGGAAAGAGGGAAGCCCTTCGCACCGCGAAAGAGTATCGAGT

CGCTGTAGGTATCTCAGTTCGGTGTAGGTCGTTCGCTCCAAGCTGGGCTGTGTGCACGAACCCCCGTTCAGCCC
      ++++++++++++++++++++++++++++++++++++++++++++++++++++++++++++++++++++++++
GCGACATCCATAGAGTCAAGCCACATCCAGCAAGCGAGGTTCGACCCGACACACGTGCTTGGGGGCAAGTCGGG

GACCGCTCGCCCTTATCCGGTAACTATCGTCTTGAGTCCAACCCGGTAAGACACGACTTATCGCCACTGGCAGCA
      ++++++++++++++++++++++++++++++++++++++++++++++++++++++++++++++++++++++++  3600
CTGGCGACGCGGAATAGGCCATTGATAGCAGAACTCAGGTTGGGCCATTCTGTGCTGAATAGCGGGTGACCGTCGT
```

FIG. 32D-3

```
GCCACTGGTAACAGGATTAGCAGAGCGAGGTATGTAGGCGGTGCTACAGAGTTCTTGAAGTGGTGGCCTAACTAC
CGGTGACCATTGTCCTAATCGTCTCGCTCCATACATCCGCCACGATGTCTCAAGAACTTCACCACCGGATTGATG

GGCTACACTAGAAGGACAGTATTTGGTATCTGCGCTCTGCTGAAGCCAGTTACCTTCGGAAAAAGAGTTGGTAGC     3750
CCGATGTGATCTTCCTGTCATAAACCATAGACGCGAGACGACTTCGGTCAATGGAAGCCTTTTTCTCAACCATCG

TCTTGATCCGGCAAACAAACCACCGCTGGTAGCGGTGGTTTTTTTGTTGCAAGCAGCAGATTACGCGCAGAAAA
AGAACTAGGCCGTTTGTTTGGTGGCGACCATCGCCACCAAAAAAACAACGTTCGTCGTCTAATGCGCGTCTTTT

AAAGGATCTCAAGAAGATCCTTTGATCTTTTTCTACGGGGTCTGACGCTCAGTGGAACGAAAACTCACGTTAAGG     3900
TTTCCTAGAGTTCTTCTAGGAAACTAGAAAAAGATGCCCCAGACTGCGAGTCACCTTGCTTTGAGTGCAATTCCC

ATTTTGGTCATGAGATTATCAAAAAGGATCTTCACCTAGATCCTTTTAAATTAAAAATGAAGTTTTAAATCAATC
TAAAACCAGTACTCTAATAGTTTTTCCTAGAAGTGGATCTAGGAAAATTTAATTTTTACTTCAAAATTTAGTTAG
```

FIG. 32D-4

```
TAAAGTATATATGAGTAAACTTGGTGTGACAGTTACCAATGCTTAATCAGTGAGGCACCTATCTCAGCGATCTGT
----+----+----+----+----+----+----+----+----+----+----+----+----+----+   4050
ATTTCATATATACTCATTTGAACCACAGACTGTCAATGGTTACGAATTAGTCACTCCGTGGATAGAGTCGCTAGACA
                                                        ──────────▶
                                                          Ampicillin CTATTTCGTTCATCCATAGTTGCCTGACTCCCCGTCGTGTAGATAACTACGATACGGGAGGGCTTACCATCTGGC
----+----+----+----+----+----+----+----+----+----+----+----+----+----+   4200
GATAAAGCAAGTAGGTATCAACGGACTGAGGGGCAGCACATCTATTGATGCTATGCCCTCCGAATGGTAGACCG
                              ──────────
                                Ampicillin CCCAGTGCTGCAATGATACCGCGAGACCCACGCTCACCGGCTCCAGATTTATCAGCAATAAACCAGCCAGCCGGA
----+----+----+----+----+----+----+----+----+----+----+----+----+----+
GGGTCACGACGTTACTATGGCGCTCTGGGTGCGAGTGGCCGAGGTCTAAATAGTCGTTATTTGGTCGGTCGGCCT
                                                      ──────────────
                                                         Ampicillin AGGGCCGAGCGCAGAAGTGGTCCTGCAACTTTATCCGCCTCCATCCAGTCTATTAATTGTTGCCGGGAAGCTAGA
----+----+----+----+----+----+----+----+----+----+----+----+----+----+
TCCCGGCTCGCGTCTTCACCAGGACGTTGAAATAGGCGGAGGTAGGTCAGATAATTAACAACGGCCCTTCGATCT
                                        ─────────────────────────
                                                Ampicillin
```

FIG. 32D-5

```
GTAAGTACTTCGCCAGTTAATAGTTTGCGCAACGTTGTTGCCATTGCTACAGGCATCGTGGTGTCACGCTCGTCG
                                                                              4350
CATTCATCAGCGGTCAATTATCAAACGCGTTGCAACAACGTTGCAACGATGTCCGTAGCACCACAGTGCGAGCAGC
                              —— Ampicillin ——

TTTGGTATGGCTTCATTCAGCTCCGGTTCCCAACGATCAAGGCGAGTTACATGATCCCCCATGTTGTGCAAAAAA
AAACCATACCGAAGTAAGTCGAGGCCAAGGGTTGCTAGTTCCGCTCAATGTACTAGGGGGTACAACACGTTTTTT
                              —— Ampicillin ——

GCGGGTTAGCTCCTTCGGTCCTCCGATCGTTGTCAGAAGTAAGTTGGCCGCAGTGTTATCACTCATGGTTATGGCA
                                                                              4500
CGCCAATCGAGGAAGCCAGGAGGCTAGCAACAGTCTTCATTCAACCGGCGTCACAATAGTGAGTACCAATACCGT
   —— Ampicillin
```

FIG. 32E-1

```
GCACTGCATAATTCTCTTACTGTCATGCCATCCGTAAGATGCTTTTCTGTGACTGGTGAGTACTCAACCAAGTCA
     ----+----+----+----+----+----+----+----+----+----+----+----+----+----+
CGTGACGTATTAAGAGAATGACAGTAGGCATTCTACGAAAAGACACTGACCACTCATGAGTTGGTTCAGT
                              ━━━━━ Ampicillin ━━━━━

4650
TTCTGAGAATAGTGTATGCGGCGACCGAGTTGCTCTTGCCCGGCGTCAATACGGGATAATACCGCGCCACATAGC
     ----+----+----+----+----+----+----+----+----+----+----+----+----+----+
AAGACTCTTATCACATACGCCGCTGGCTCAACGAGAACGGGCCGCAGTTATGCCCTATTATGGCGCGGTGTATCG
                              ━━━━━ Ampicillin ━━━━━

AGAACTTTAAAAGTGCTCATCATTGGAAAACGTTCTTCGGGGCGAAAACTCTCAAGGATCTTACCGCTGTTGAGA
     ----+----+----+----+----+----+----+----+----+----+----+----+----+----+
TCTTGAAATTTTCACGAGTAGTAACCTTTTGCAAGAAGCCCCGCTTTTGAGAGTTCCTAGAATGGCGACAACTCT
                              ━━━━━ Ampicillin ━━━━━

4800
TCCAGTTCAATGTAACCCACTCGTGACCCAACTGATCTTCAGGCATCTTTTACTTTCACCAGCGTTTCTGGGTGA
     ----+----+----+----+----+----+----+----+----+----+----+----+----+----+
AGGTCAAGTTACATTGGGTGAGCACTGGGTTGACTAGAAGTCGTAGAAAATGAAAGTGGTCGCAAAGACCCACT
                              ━━━━━ Ampicillin ━━━━━
```

FIG. 32E-2

```
GCAAAAACAGGAAGGCAAAATGCCGCAAAAAAGGGAATAAGGGCGACACGGAAATGTTGAATACTCATACTCTTC
----+----+----+----+----+----+----+----+----+----+----+----+----+----+
CGTTTTTGTCCTTCCGTTTTACGGCGTTTTTTCCCTTATTCCCGCTGTGCCTTTACAACTTATGAGTATGAGAAG
                                                ━━━━━━━━━━━━━━━━━
                                                    Amp Promoter CTTTTTTCAATATTATTGAAGCATTTATCAGGGTTATTGTCTCATGAGCGGATACATATTTGAATGTATTTAGAAA  4950
----+----+----+----+----+----+----+----+----+----+----+----+----+----+
GAAAAAGTTATAATAACTTCGTAAATAGTCCCAATACAGAGTACTCGCCTATGTATAAACTTACATAAATCTTT
━━━━━━━━━
 Ampicillin AATAAACAAATAGGGGTTCCGCGCACATTTCCCCGAAAAAGTGCCACCTGACGTCTAAGAAACCATTATTATCAT
----+----+----+----+----+----+----+----+----+----+----+----+----+----+
TTATTTGTTTATCCCCAAGGCGCGTGTAAAGGGGCTTTTCACGGTGGACTGCAGATTCTTTGGTAATAATAGTAC
━━━━━━━━━━━
 Amp Promoter GACATTAACCTATAAAAATAGGCGTATCACGAGGCCCTATTGATTATTGATAGTGTGGAATGTGTCAGTTAGG  5100
----+----+----+----+----+----+----+----+----+----+----+----+----+----+
TGTAATTGGATATTTTTATCCGCATAGTGCTCCGGGATAACTAATAACTGATCACACCTTACACACAGTCAATCC
                                                     ━━━━━━━━━━
                                                      SV40 Promoter GTGTGGAAAGTCCCCAGGCTCCCCAGCAGGCAGAAGTATGCAAAGCATGCATCTCAATTAGTCAGCAACCAGGTG
----+----+----+----+----+----+----+----+----+----+----+----+----+----+
CACACCTTTCAGGGGTCCGAGGGGTCGTCCGTCTTCATACGTTTCGTACGTAGAGTTAATCAGTCGTTGGTCCAC
                       ━━━━━━━━━━━━━━
                         SV40 Promoter
```

FIG. 32E-3

```
TGGAAAGTCCCCAGCTCCCCAGCAGGCAGAAGTATGCAAAGCATGCATCTCAATTAGTCAGCAACCATAGTCCC
     +         +         +         +         +         +         +     5250
ACCTTTCAGGGGTCGAGGGGTCGTCCGTCTTCATACGTTTCGTAGTAGAGTTAATCAGTCGTTGGTATCAGGG
                                      ━━━━━━━━━━━ SV40 Promoter ━━━━━━━━━━━

GCCCCTAACTCCGCCCATCCCGCCCCCTAACTCCGCCCAGTTCCGCCCATTCTCCGCCCCATGGCTGACTAATTTT
     +         +         +         +         +         +         +
CGGGGATTGAGGCGGGTAGGGCGGGGATTGAGGCGGGTCAAGGCGGGTAAGAGGCGGGGTACCGACTGATTAAAA
                           ━━━━━━━━━ SV40 Promoter ━━━━━━━━━

TTTTATTTATGCAGAGGCCGAGGCCGCCTCGGCCCTCTGAGCTATTCCAGAAGTAGTGAGGAGGCTTTTTTGGAGG
     +         +         +         +         +         +         +     5400
AAAATAAATACGTCTCCGGCTCCGGCGGAGCCGGGAGACTCGATAAGGTCTTCATCACTCCTCCGAAAAAACCTCC
━━━━━━━━━ SV40 Promoter ━━━━━━━━━
```

FIG. 32F-2

```
TTCTTGCCAAAAGTTTGGATGATGCCTTAAGACTTATTGAACAACCGGAATTGGCAAGTAAAGTAGACATGGTTT
----+----+----+----+----+----+----+----+----+----+----+----+----+----+----  5850
AAGAACGGTTTTCAAACCTACTACGGAATTCTGAATAACTTGTTGGCCTTAACCGTTCATTTCATCTGTACCAAA
 F  L  A  K  S  L  D  D  A  L  R  L  I  E  Q  P  E  L  A  S  K  V  D  M  V
                                      ─────────── DHFR ───────────

GGATAGTCGGAGGCAGTTCTGTTTACCAGGAAGCCATGAATCAACCAGGCCACCTCAGACTCTTTGTGACAAGGA
----+----+----+----+----+----+----+----+----+----+----+----+----+----+----
CCTATCAGCCTCCGTCAAGACAAATGGTCCTTCGGTACTTAGTTGGTCCGGTGAGTCTGAGAAACACTGTTCCT
 W  I  V  G  G  S  S  V  Y  Q  E  A  M  N  Q  P  G  H  L  R  L  F  V  T  R
                                      ─────────── DHFR ───────────

TCATGCAGGAATTTGAAAGTGACACGTTTTTCCCAGAAATTGATTTGGGGAAATATAAACTTCTCCCAGAATACC
----+----+----+----+----+----+----+----+----+----+----+----+----+----+----  6000
AGTACGTCCTTAAACTTTCACTGTGCAAAAAGGGTCTTTAACTAAACCCCTTTATATTTGAAGAGGTCTTATGG
 I  M  Q  E  F  E  S  D  T  F  F  P  E  I  D  L  G  K  Y  K  L  L  P  E  Y
                                      ─────────── DHFR ───────────

CAGGCGTCCTCTCTGAGGTCCAGGAGGAAAAAGGCCATCAAGTATAAGTTTGAAGTCTACGAGAAGAAAGACTAAC
----+----+----+----+----+----+----+----+----+----+----+----+----+----+----
GTCCGCAGGAGAGACTCCAGGTCCTCCTTTTTCCGGTAGTTCATATTCAAACTTCAGATGCTCTTCTTTCTGATTG
 P  G  V  L  S  E  V  Q  E  E  K  G  I  K  Y  K  F  E  V  Y  E  K  K  D
 ─── DHFR ───                                                 (SEQ ID NO:50)
```

FIG. 33A-1

GY4 VK Chimera (pANT13)

ACTAGTTATTAATAGTAATCAATTACGGGGTCATTAGTTCATAGCCCATATATGGAGTTCCGCGTTACATAACTT
TGATCAATAATTATCATTAGTTAATGCCCCAGTAATCAAGTATCGGGTATATACCTCAAGGCGCAATGTATTGAA
CMV Promoter ACGGTAAATGGCCCGCCTGGCTGACCGCCCAACGACCCCCGCCCATTGACGTCAATAATGACGTATGTTCCCATA
TGCCATTTACCGGGGCGGACCGACTGGCGGGTTGCTGGGGGCGGGTAACTGCAGTTATTACTGCATACAAGGTAT
CMV Promoter                                                                    150

GTAACGCCAATAGGGACTTTCCATTGACGTCAATGGGTGGAGTATTTACGGTAAACTGCCCACTTGGCAGTACAT
CATTGCGGTTATCCCTGAAAGGTAACTGCAGTTACCCACCTCATAAATGCCATTTGACGGGTGAACCGTCATGTA
CMV Promoter ATGGGCGGTAGCGTGTACGGTGGGAGGTCTATATAAGCAGAGCTCGTTTAGTGAACCGTCAGATCTGGCACGAG
TACCCGCCATCCGCACATGCCACCCTCCAGATATATTCGTCTCGAGCAAATCACTTGGCAGTCTAGACCGTGCTC
CMV Promoter                                                                    300

FIG. 33A-3

```
                                                                                    BssH II
GGTCTCCTCAGGTTGCCGCCACCATGAGGGTTCCCCGCTCCTCAGCTCTTGGGGCTCCTGCTCTGCTCTGGCTCCCAGGCG
                                                                                    -------
CCAGAGGAGTCCAACGGCGGTGTACTCCCAGGGGCGAGTCGAGAGGCCGAGTGAGAGACCCGAGGAGACGAGACCGAGGTCCGC
                    M  R  V  P  A  Q  L  L  G  L  L  L  L  W  L  P  G
                                          Signal Sequence CGGCGATGTGATGTTGTGATGACCCAGACTCCACTCTCACTTTGTCGGTTACCATTGGACAACCAGCCTCCATCTCTT     750
GCGCTACACTACAACACTACTGGGTCTGAGGTGAGTGAAACAGCCAATGGTAACCTGTTGGTCGGAGGTAGAGAA
 A  R  C  D  V  V  M  T  Q  T  P  L  T  L  S  V  T  I  G  Q  P  A  S  I  S
                                                                        GY4VK GCAAGTCAAGTCAGAGAGCCCTCTTAAAATAGTGATGAAAGACATATTTGAATTGGTTGTTACAGAGGCCAGGCCAGT
CGTTCAGTTCAGTCGTCTCGGAGAATTTATCACTACCTTTCTGTATAAACTTAACCACAATGTCTCCGGTCCGGTCA
 C  K  S  S  Q  S  L  L  N  S  D  G  K  T  Y  L  N  W  L  L  Q  R  P  D  Q
                                                                      GY4VK CTCCAAAGCGCCTAATCTATCTGGTGTCTAAACTGGACTCTGGAGTCCCTGACAGTTCACTGGCAGTGGATCAG         900
GAGGTTTCGCGGATTAGATAGACCACAGATTTGACCTGAGACCTCAGGGACTGTCCAAGTGACCGTCACCTAGTC
 S  P  K  R  L  I  Y  L  V  S  K  L  D  S  G  V  P  D  R  F  T  G  S  G  S
                             GY4VK
```

FIG. 33A-4

```
GGACAGATTTCACACTGAAAATCAGCAGAGTGTGGAGGCTGAGGATTTGGGAGTTTATTATTGCTGGCAAGGTACAC
          +         +         +         +         +         +         +
CCTGTCTAAAGTGTGACTTTTAGTCGTCTCACCTCCGACTCCTAAACCCTCAAATAATAACGACCGTTCCATGTG
 G  T  D  F  T  L  K  I  S  R  V  E  A  E  D  L  G  V  Y  Y  C  W  Q  G  T
                                                              GY4VK

ATTTTCCGTTCACGTTCGGAGGGGGGACCAAGCTGGAAATAAAACGTGAGTAGAATTTAAACTTTGCTTCCTCAG
          +         +         +         +         +         +         + 1050
TAAAAGGCAAGTGCAAGCCTCCCCCCTGGTTCGACCTTTATTTTGCACTCATCTTAAATTTGAAACGAAGGAGTC
 H  F  P  F  T  F  G  G  G  T  K  L  E  I  K  R  (SEQ ID NO:52)
              GY4VK
```

FIG. 33B-1

```
     BamH I
TTGGATCCCGCAATTCTAAACTCTGAGGGGTCGGATGACGTGGCCATTCTTTGCCTAAAGCATTGAGTTTACTG
     +---------+---------+---------+---------+---------+---------+---------+
AACCTAGGGCGTTAAGATTTGAGACTCCCCAGCCTACTGCACCGGTAAGAAACGGATTCGTAACTCAAATGAC
                                                                        1200

CAAGGTCAGAAAGCATGCAAAGCCCTCAGAATGGCTGCAAAGAGCTCCAACAAACAATTTAGAACTTTATTAA
     +---------+---------+---------+---------+---------+---------+---------+
GTTCCAGTCTTTCGTACGTTTCGGGAGTCTTACCGACGTTTCTCGAGGTTGTTTAAATCTTGAAATAATT

GGAATAGGGGAAGCTAGGAAGAAACTCAAAACATCAAGATTTAAATACGCTTCTTGGTCTCCCTTGCTATAATT
     +---------+---------+---------+---------+---------+---------+---------+
CCTTATCCCCTTCGATCCTTCTTTGAGTTTTGTAGTTCTAAAATTTATGCGAAGAACCAGAGGAACGATATTAA
                                                                        1350

ATCTGGGATAAGCATGCTGTTTCTGTCCCTAACATGCCCTGTGATTATCCGCAAACAACACACCCAAGGG
     +---------+---------+---------+---------+---------+---------+---------+
TAGACCCTATTCGTACGACAAAGACAGGATTGTACGGACACTAATAGGCGTTTGTTGTGTGGGTTCCC

CAGAACTTTGTTACTTAAACACCATCCTGTTGCTTCTTCCTCAGGAACTGTGGCTGCACCATCTGTCTTCATC
     +---------+---------+---------+---------+---------+---------+---------+
GTCTTGAAACAATGAATTGTGTAGGACAAACGAAGAAAGGAGTCCTTGACACCGACGTGGTAGACAGAAGTAG
                   T   V   A   A   P   S   V   F   I
                                                    Ck
```

FIG. 33B-2

```
TTCCCGCCATCTGATGAGCAGTTGAAATCTGGAACTGCCTCTGTTGTGCCTGCTGAATAACTTCTATCCCAGA
                                                                        1500
AAGGGCGGTAGACTACTCGTCAACTTTAGACCTTGACGGAGACAACACGGACGACTTATTGAAGATAGGGTCT
 F  P  P  S  D  E  Q  L  K  S  G  T  A  S  V  V  G  L  L  N  N  F  Y  P  R
                                        Ck

GAGGCCAAAGTACAGTGGAAGGTGGATAACGCCCTCCAATCGGGTAACTCCCAGGAGAGTGTCACAGAGCAGGAC
CTCCGGTTTCATGTCACCTTCCACCTATTGCGGGAGGTTAGCCCATTGAGGGTCCTCTCACAGTGTCTCGTCCTG
 E  A  K  V  Q  W  K  V  D  N  A  L  Q  S  G  H  S  Q  E  S  V  T  E  Q  D
                                        Ck

AGCAAGGACAGCACCTACAGCCTCAGCAGCACCCTGACGCTGAGCAAAGCAGACTACGAGAAACACAAAGTCTAC
                                                                        1650
TCGTTCCTGTCGTGGATGTCGGAGTCGTCGTGGGACTGCGACTCGTTCGTCTGATGCTCTTTGTGTTTCAGATG
 S  K  D  S  T  Y  S  L  S  S  T  L  T  L  S  K  A  D  Y  E  K  H  K  V  Y
                                        Ck
```

FIG. 33B-3

```
GCCTGCGAAGTCACCCATCAGGGGCCTGAGCTCGCCCGTCACAAAGAGCTTCAACAGGGAGAGTGTTAGAGGGAG
   ----+----+----+----+----+----+----+----+----+----+----+----+----+----+
CGGACGCTTCAGTGGGTAGTCCCGGACTCGAGCGGGCAGTGTTTCTCGAAGTTGTCCCTCTCACAATCTCCCTC
 A  C  E  V  T  H  G  G  L  S  S  P  V  T  K  S  F  N  R  G  E  C  .
 ──────Ck──────────────────────────────────────────────────────  ┘ polyA ■
                                                                (SEQ ID NO:53)

AAGTGCCCCCCACCTGCTCCTCAGTTCCAGCCTGACCCCTCCCATCCTTTGGCCTCTGACCCTTTTCCACAGGG
   ----+----+----+----+----+----+----+----+----+----+----+----+----+----+ 1800
TTCACGGGGTGGACGAGGAGTCAAGGTCGGACTGGGGAGGGTAGGAAACCGGAGACTGGGAAAAGGTGTCCC
──────────────────────────────────────────────────────────────────── polyA
```

FIG. 33C-1

```
GACCTACCCCTATTGCGGTCCTCCAGCTCATCTTTCACCTCACCCCCCTCCTCCTTGGCTTTAATTATGCTA
CTGGATGGGATAACGCCAGGAGGTCGAGTAGAAAGTGAATGGGGGAGGAGGAGAACCGAAATTAATACGAT
                                    ━━━━ poly A ━━━━

ATGTTGGAGGAGAATGAATAAATAAAGTGAATCTTTGCACCTGTGGTTTCTCTCTTTCCTCAATTAATAATTAT   1950
TACAACCTCCTCCTTACTTATTTATTTCACTTAGAAACGTGACACCAAAGAGAGAAAGGAGTAAATTATTAATA
                                    ━━━━ poly A ━━━━

TATCTGTTGTTTACCAACTACTCAATTTCTCTCTTATAAGGGACTAAAATATGTAGTCATCCTAAGGCGCATAACCAT
ATAGACAACAAATGGTTGATGAGTTAAAGAGAATATTCCCTGATTTATACATCAGTAGGATTCCGCGTATTGGTA
                                    ━━━━ poly A ━━━━
```

FIG. 33C-2

```
TTATAAAATCATCCTTCATTCTATTTTACCCTATCATCCTCTGCAAGACAGTCCTCCCTCAAACCCACAAGCCT
                                                                              2100
AATATTTTAGTAGGAAGTAAGATAAATGGGATAGTAGGAGACGTTCTGTCAGGAGGAGTTTGGGTGTTCGGA
                        ───── poly A TCTGTCCTCACAGTCCCCTGGGCCATGGTAGGAGAGACTTGCTTCCTTGTTTCCCCTCCTCAGCAAGCCCTCAT
                                                                              2250
AGACAGGAGTGTCAGGGGACCCGGTACCACCATCCTCTCTGAACGAAGGAACAAAAGGGGAGGAGTCGTTCGGGAGTA
                                                                    ───── poly A AGTCCTTTTAAGGGTGACAGGTCTTACGGTCATATATCCTTTGATTCAATTCCCTGGAATCAACCAAGGCAAA
TCAGGAAAAATTCCCACTGTCCAGAATGCCAGTATATAGGAAACTAAGTTAAGGGACCCTTAGTTGGTTCCGTTT
                                                        ───── poly A TTTTTCAAAAGAAGAAACCTGCTATAAAGAGAATCATTCATTGCAACATGATATAAAATAACAACACAATAAAAG
AAAAGTTTTCTTCTTTGGACGATATTTCTCTTAGTAAGTAACGTTGTACTATATTTATTGTGTTATTTTC
                                                ───── poly A
```

FIG. 33C-3

```
CAATTAAATAAACAAACAATAGGGAATGTTTAAGTTCATCATGGTACTTAGACTTAATGGAATGTCATGCCTTA
   +         +         +         +         +         +         +          2400
GTTAATTTATTTGTTGTTATCCCTTTACAAATTCAAGTAGTACCATGAATCTGAATTACCTTACAGTACGGAAT
                                    ────── poly A ──────

TTTACATTTTTAAACAGGTACTGAGGGACTCCTGTCTGCCAAGGGCCGTATTGAGTACTTTCCACAACCTAATTT
   +         +         +         +         +         +         +
AAATGTAAAAATTTGTCCATGACTCCCTGAGGACAGACGGTTCCCGGCATAACTCATGAAAGGTGTTGGATTAAA
                                                         ────── poly A ──────

AATCCACACTATACTGTGAGATTAAAAACATTCATTAAAATGTTGCAAAGGTTCTATAAAGCTGAGAGACAAATA
   +         +         +         +         +         +         +          2550
TTAGGTGTGATATGACACTCTAATTTTTGTAAGTAATTTTACAACGTTTCCAAGATATTTCGACTCTCTGTTTAT
                                    ────── poly A ──────

TATTCTATAACTCAGCAATCCCACTACATGTGAGCAAAAGGCCAGCAAAAGGCCAGGAACCGTAAAAAGGCCGCG
   +         +         +         +         +         +         +
ATAAGATATTGAGTCGTTAGGGTGATGTACACTCGTTTTCCGGTCGTTTTCCGGTCCTTGGCATTTTTCCGGCGC
   ────── poly A
```

FIG 33C-4

```
TTGCTGGCGTTTTTCCATAGGCTCTCCGCCCCCTGACGAGCATCACAAAAATCGACGCTCAAGTCAGAGGTGGCGA
AACGACCGCAAAAAGGTATCCGAGGCGGGGACTGCTCGTAGTGTTTTTAGCTGCGAGTTCAGTCTCCACCGCT    2700
AACCCGACAGGACTATAAAGATACCAGGCGTTTCCCCCTGGAAGCTCCCTCGTGCGCTCTCCTGTTCCGACCCTG
TTGGGCTGTCCTGATATTTCTATGGTCCGCAAAGGGGACCCTTCGAGGGAGCACGCGAGAGGACAAGGCTGGGAC
CCGCTTACCGGATACCTGTCCGCCTTTCTCCCTTCGGGAAGCGTGGCGCTTTCTCATAGCTCACGCTGTAGGTAT    2850
GGCGAATGGCCTATGGACAGGCGGAAAGAGGGAAGCCCTTCGCACCGCGAAAGAGTATGAGTGCGACATCCATA
CTCAGTTCGGGTGTAGTCGTTCGCTCCAAGCTGGGCTGTGTGCACGAACCCCCGTTCAGCCGACCGCTGCGCC
GAGTCAAGCCACACATCCAGCAAGCGAGGTTCGACCCGACACACGTGCTTGGGGGCAAGTCGGGCTGGCGACGCGG
TTATCCGGTAACTATCGTCTTGAGTCCAACCCGGTAAGAGACGACTTATCGCCACTGGCAGCAGCCACTGGTAAC
AATAGGCCATTGATAGCAGAACTCAGGTTGGGCCATTCTGTGCTGAATAGCGGTGACCGTCGTCGGTGACCATTG    3000
AGGATTAGCAGAGCGAGGTATGTAGGCGGTGCTACAGAGTTCTTGAAGTGGTGGCCTAACTACGGCTACACTAGA
TCCTAATCGTCTCGCTCCATACATCCGCCACGATGCTCAAGAACTTCACCACCGGATTGATGCCGATGTGATCT
```

FIG. 33C-5

```
AGGACAGTATTTGGTATCTGCGCTCTGCTGAAGCCAGTTACCTTCGGAAAAAGAGTTGGTAGCTCTTGATCCGGC
                                                                         3150
TCCTGTCATAAACCATAGACGCGAGACGACTTCGGTCAATGGAAGCCCTTTTTCTCAACCATCGAGAACTAGGCCG

AAACAAACCACCGCTGGTAGCGGTGGTTTTTTTGTTTGCAAGCAGCAGATTACGCGCAGAAAAAAGGATCTCAA

TTTGTTTGGTGGCCGACCATCGCCACCAAAAAACAAAACAACGTTCGTCGTCTAATGCGGTCTTTTTTCCTAGAGTT

GAAGATCCTTTTGATCTTTTCTACGGGGTCTGACGCTCAGTGGAACGAAAACTCACGTTAAGGGATTTTGGTCATG
                                                                         3300
CTTCTAGGAAAACTAGAGAAAAGATGCCCCAGACTGCGAGTCACCTTGCTTTTGAGTGCAATTCCCTAAAACCAGTAC
```

```
CCAGTTAATAGTTTGCGCAACGTTGTTGCCATTGCTACAGGCATCGTGGTGTCACGGCTCGTCGTTTGGTATGGCT
         +         +         +         +         +         +         +    3750
GGTCAATTATCAAACGCGTTGCAACAACGGTAACGATGTCCGTAGCACCACAGTGCCGAGCAGCAAACCATACCGA
━━━━━━━━━━━━━━━━━━━━━━━━━━━
        Ampicillin TCATTCAGCTCCGGTTCCCAACGATCAAGGCGAGTTACATGATCCCCCATGTTGTGCAAAAAAGCGGTTAGCTCC
         +         +         +         +         +         +         +
AGTAAGTCGAGGCCAAGGGTTGCTAGTTCCGCTCAATGTACTAGGGGGTACAACACGTTTTTTCGCCAATCGAGG
━━━━━━━━━━━━━━━━━━━━━━━━━━━━━━━━━━━━━━━━━━━━━━━━━━
                              Ampicillin TTCGGTCCTCCGATCGTTGTCAGAAGTAAGTTGGCCGCAGTGTTATCACTCATGGTTATGGCAGCACTGCATAAT
         +         +         +         +         +         +         +    3900
AAGCCAGGAGGCTAGCAACAGTCTTCATTCAACCGGCGTCACAATAGTGAGTACCAATACCGTCGTGACGTATTA
━━━━━━━━━━━━━━━━━━━━━━━━━━━━━━━━━━━━━━━━━━━━━━━━━━━━━━━━━━━━━━━━━━
                              Ampicillin TCTCTCTTACTGTCATGCCATCCGTAAGATGCTTTTCTGTGACTGGTGAGTACTCAACCAAGTCATTCTGAGAATAG
         +         +         +         +         +         +         +
AGAGAATGACAGTACGGTAGGCATTCTACGAAAAGACACTGACCACTGAGTTGGTTCAGTAAGACTCTTATC
━━━━━━━━━━━━━━━━━━━━━━━━━━━━━━━━━━━━━━━━━━━━━━━━━━━━━━━━━━━━━━━━━━━━━
                              Ampicillin
```

FIG. 33D-3

```
TGTATGCGGCGACCGAGTTGCTCTGCCCGGCGTCAATACGGGATAATACCGCGCCACATAGCAGAACTTTAAAA
   ||||||||||||||||||||||||||||||||||||||||||||||||||||||||||||||||||||||||||   4050
ACATACGCCGCTGGCTCAACGAGACGAACGGGCCGCAGTTATGCCCTATTATGGCCGCGGTGTATCGTCTTGAAATTTT
                        ▬▬▬▬▬▬▬ Ampicillin GTGCTCATCATTGGAAAACGTTCTTCTCGGGGCGAAAACTCTCAAGGATCTTACCGCTGTTGAGATCCAGTTCGATG
   ||||||||||||||||||||||||||||||||||||||||||||||||||||||||||||||||||||||||||
CACGAGTAGTAACCTTTTGCAAGAAGAGCCCCGCTTTTGAGAGTTCCTAGAATGGCGACAACTCTAGGTCAAGCTAC
 ▬▬▬▬▬▬▬▬▬▬▬▬▬▬▬▬▬▬▬▬▬▬▬▬▬▬▬▬ Ampicillin TAACCCACTCGTGCACCCAACTGATCTTCAGCATCTTTTACTTTCACCAGCGTTTCTGGGTGAGCAAAAACAGGA
   ||||||||||||||||||||||||||||||||||||||||||||||||||||||||||||||||||||||||||   4200
ATTGGGTGAGCACGTGGTTGACTAGAAGTCGTAGAAAATGAAAGTGGTCGCAAAGACCCACTCGTTTTTGTCCT
 ▬▬▬▬▬▬▬▬▬▬▬▬▬▬▬▬▬▬▬▬▬▬▬▬▬▬▬▬ Ampicillin AGGCAAAATGCCGCAAAAAAGGGAATAAGGGCGACACGGAAATGTTGAATACTCATACTCTTCCTTTTTCAATAT
   ||||||||||||||||||||||||||||||||||||||||||||||||||||||||||||||||||||||||||
TCCGTTTTACGGCGTTTTTTCCCTTATTCCCGCTGTGCCTTTACAACTTATGAGTATGAGAAGGAAAAGTTATA
 ▬▬▬▬▬▬▬▬▬▬▬▬▬▬▬▬▬▬▬▬▬▬▬ Ampicillin                      ▬▬▬▬▬▬ Amp Promoter TATTGAAGCATTTATCAGGGTTATTGTCTCATGAGCGGATACATATTTGAATGTATTTAGAAAAATAAACAAATA
   ||||||||||||||||||||||||||||||||||||||||||||||||||||||||||||||||||||||||||   4350
ATAACTTCGTAAATAGTCCCAATAACAGAGTACTCGCCTATGTATAAACTTACATAAATCTTTTTATTTGTTTAT ▬▬▬▬▬ Amp Promoter
```

FIG. 33D-4

```
GGGGTTCCGCGCACATTTCCCGAAAAGTGCCACCTGACGTCTAACAAACCATTATTATCATGACATTAACCTAT
----+----+----+----+----+----+----+----+----+----+----+----+----+----+
CCCCAAGGCGCGTGTAAAGGGCTTTTCACGGTGGACTGCAGATTCTTTGGTAATAATAGTACTGTAATTGGATA

AAAAATAGGGCGTATCACGAGGCCCTATTGATTATTG   (SEQ ID NO:54)
----+----+----+----+----+----+----→ 4461
TTTTTATCCGCATAGTGCTCCGGGATAACTAATAAC
```

FIG. 34A-1

GY5 VH Chimera (pANT12)

```
ACTAGTTATTAATAGTAATCAATTACGGGGTCATTAGTTCATAGCCCATATATGGAGTTCCGCGTTACATAACTT
||||||||||||||||||||||||||||||||||||||||||||||||||||||||||||||||||||||||||
TGATCAATAATTATCATTAGTTAATGCCCCAGTAATCAAGTATCGGGTATATACCTCAAGGCGCAATGTATTGAA
                                       ─── CMV Promoter ───                                         150

ACGGTAAATGGCCCGCCTGGCTGACCGCCCAACGACCCCGCCCATTGACGTCAATAATGACGTATGTTCCCATA
||||||||||||||||||||||||||||||||||||||||||||||||||||||||||||||||||||||||||
TGCCATTTACCGGGTCGGACCGACTGGCGGGTTGCTGGGGCGGGTAACTGCAGTCAGTTATTACTGCATACAAGGGTAT
                                       ─── CMV Promoter ───

GTAACGCCAATAGGGACTTTCCATTGACGTCAATGGGTGGAGTATTTACGGTAAACTGCCCACTTGGCAGTACAT
||||||||||||||||||||||||||||||||||||||||||||||||||||||||||||||||||||||||||
CATTGCGGTTATCCCTGAAAGGTAACTGCAGTTACCCACCTCATAAATGCCATTTGACGGGTGAACCGTCATGTA
                                       ─── CMV Promoter ───                                         300

CAAGTGTATCATATGCCAAGTACGCCCCCTATTGACGTCAATGACGGTAAATGCCCGCCTGGCATTATGCCCAG
||||||||||||||||||||||||||||||||||||||||||||||||||||||||||||||||||||||||||
GTTCACATAGTATACGGTTCATGCGGGGGATAACTGCAGTTACTGCCATTTACCGGCGGACCGTAATACGGGTC
                                       ─── CMV Promoter ───
```

FIG. 34A-3

```
                                                          M  G  W  S  L  I  L
                                                              Signal Sequence
                                    Mlu I                                                                     750
GCTCTTCCTTGTGTCGCTGTTGCTACGCGTGTCCACTCCCAGGTCCAGCAGCCTGGGGCTGAGCTGGTGAG
CGAGAAGGAACAGCGACAACGATGCGCACAGGTGAGGGTCCAGGTTGACGTCGTCGGACCCCGACTCGACCACTC
 L  F  L  V  A  V  A  T  R  V  H  S  Q  V  Q  L  Q  Q  P  G  A  E  L  V  R
    Signal Sequence                                                 GY5VH GCCTGGGGCTTCAGTGAAGCTGTCCTGCAAGGCTTCTGGCTACACCTTCACCAGCAACTACATAAACTGGGTGAA
CGGACCCCGAAGTCACTTCGACAGTTCCGAAGACCGATGTGGAAGTGGTCGTTGATGTATTTGACCCACTT
 P  G  A  S  V  K  L  S  C  K  A  S  G  Y  T  F  T  S  N  Y  I  N  W  V  K
                                                                 GY5VH ACAGAGGCCTGGACAGGGCCTTGAGTGGATCGGAAATATTTATCCTTCTGATGGTTTTACTAACTACAATCAAAA
TGTCTCCGGACCTGTCCCGGAACTCACCTAGCCTTATAAATAGGAAGACTACCAAAATGATTGATGTTAGTTTT
 Q  R  P  G  Q  G  L  E  W  I  G  N  I  Y  P  S  D  G  F  T  N  Y  N  Q  K
                                                        GY5VH                                                 900

GTTCAAGGACAGGGCCACATTGACTGTAGACAAATCCTCCAGCACACCTACATGCAGCTCAGCAGCCCGACATC
CAAGTTCCTGTCCCGGTGTAACTGACATCTGTTTAGGAGGTCGTGTGGATGTACGTCGAGTCGTCGGGCTGTAG
 F  K  D  R  A  T  L  T  V  D  K  S  S  S  T  A  Y  M  Q  L  S  S  P  T  S
                                  GY5VH
```

FIG. 34A-4

TGAGGACTCTGCGGTCTATTACTGTACAAGAAACTTCGATGTCTGGGGCGCAGGGACCACGGTCACCGTCTCCTC
                                                                    1050
ACTCCTGAGACGCCAGATAATGACATGTTCTTTGAAGCTACAGACCCCGTCCCTGTGCCAGTGGCAGAGGAG

E  D  S  A  V  Y  Y  C  T  R  N  F  D  V  W  G  A  G  T  T  V  T  V  S  S
                              —————————— GY5VH ——————————

(SEQ ID NO:55)

FIG. 34B-1

Hind III

AGGTAAGCTTTCTGGGGCAGGCCGGGCCTGACTTTGGCTGGGGCAGGAGGGGCTAAGGTGACGCAGGTGGCG

TCCATTCGAAAGACCCCGTCCGGCCCCGGACTGAAACCGACCCCGTCCCCTCCCCCGATTCCACTGCCACCGC

GY5VH

CCAGCCAGGTGCACACCCAATGAGCCCATGAGACCCTGCATGGACCATCGCGGATAGACAAGAAC — 1200

GGTCGGTCCACGTGTGGGTTACGGGTACTCGGGTCTGTGACCTGGACGTACCTGGCCTATCTGTTCTTG

CGAGGGGCCTCTGCGCCCTGGGCCCAGCTCTGTCCCCACACCGGTCACATGGCCACCACCTCTCTTGCAGCTTCC

GCTCCCCGGAGACGCCGGTGGCGCCGGTGCGAGACCAGGGTGTGGCGCCAGTGTACCGTGGTGGAGAACGTCGAAGG

IgG4 CH1   A   S

ACCAAGGGCCCATCCGTCTTCCCCCTGGCGCCCTGCTCCTCCAGGAGCACCTCCGAGAGCACAGCCGCCCTGGGCTGC — 1350

TGGTTCCCGGTAGGCAGAAGGGGACCGCGGGACGAGGTCCTCGTGGAGGCTCTCGTGTCGGCGGGACCCGACG

T   K   G   P   S   V   F   P   L   A   P   C   S   R   S   T   S   E   S   T   A   A   L   G   C
                                                            IgG4 CH1

FIG. 34B-2

```
CTGGTCAAGGACTACTTCCCCGAACTGGTGACGGTGTCGTGGAACTCAGGCGCCCTGACCAGCGGCGTGCACACC
    L  V  K  D  Y  F  P  E  P  V  T  V  S  W  N  S  G  A  L  T  S  G  V  H  T
                                                       IgG4 CH1

GACCAGTTCCTGATGAAGGGCTTGGCCACTGGCCACAGCACCTTGAGTGTCCGGGACTCCGGCGTCGCCGCGTGTGG
                                                                              1500

TTCCCGGCGTGTCCTACAGTCCTCAGGACTCTACTCCCTCAGCAGCGTGGTGACCGTGCCCTCCAGCAGCTTGGGC
    F  P  A  V  L  Q  S  S  G  L  Y  S  L  S  S  V  V  T  V  P  S  S  S  L  G
        IgG4 CH1

AAGGGCGACAGAGATGTCAGGAGTCCTGAGATGAGGAGTCGTGCCACCAAGGCCAAGCGGAGGTCGTCGAACCCG

ACGAAGACCTACACCTGCAATGTAGATCACAAGCCCAGCAACACCAAGGTGGACAAGAGAGTTGGTGAGAGGCCA

TGCTTCTGGATGTGGACGTTACATCTAGTGTTCGGGTCGTTGTGGTTCCACCTGTTCTCTCAACCACTCTCCGGT
    T  K  T  Y  T  C  N  V  D  H  K  P  S  N  T  K  V  D  K  R  V   (SEQ ID NO:46)
        IgG4 CH1

GCACAGGAGGGAGGGTGTCTGCTGGAAGCCAGGCTCAGCTCCCTGCCTGACGCACCCGGTCTGTGCAGCCCC
                                                                              1650

CGTGTCCCTCCCCTCCCCACAGACCTTCGGTCCGAGTCGGACCGACCTTCGGTCGGGGAGGACGACGTCGGGG

AGCCCAGGGCAGCAAGGCAGGCCCCATCTGTCCTCACCTGAGGCCTCTGACCACCCACTCATGCTCAGGGA

TCGGGTCCCGTCGTTCCGTCCGGGTAGACAGGAGTGGACCTCCGGAGACTGAGGTGGGGTGAGTACGAGTCCCT
```

FIG. 34B-3

```
GAGGGTCTTCTGGATTTTTCCACCAGGCTCCGGGCAGCCACAGGCTGGATGCCCCTACCCCAGGCCCTGCGCATA
----+----+----+----+----+----+----+----+----+----+----+----+----+----+  1800
CTCCCAGAAGAGACCTAAAAAAGTGTCCGAGGCCCGTCGGTTGCCGACCTACGGGGATGGGGTCCGGACGCGTAT

CAGGGCAGGTGCTGCGCTCAGAGACCTGCCAAGAGCCATATCCGGAGGACCCTGCCCCTGACCTAAGCCCACCC
----+----+----+----+----+----+----+----+----+----+----+----+----+----+
GTCCCCGTCCACGACGAGTCTGGACGGTTCTCTGGTATAGGCCCTCCTGGGACTGGATTCGGGTGGGG

AAAGGCCAAACTCTCCACTCCCTCAGCTCCAGACACCTTCTCTCCTCCCAGATCTGAGTAACTCCCAATCTTCTCT
----+----+----+----+----+----+----+----+----+----+----+----+----+----+  1950
TTTCCGGTTTGAGAGGTGAGGGAGTCGAGTCTGTGGAAGAGAGGAGGGTCTAGACTCATTGAGGGTTAGAAGAGA

CTGCAGAGTCCAAATATGGTCCCCATGCCCATCATGCCCCAGGTAAGCCAACCCAGGCCTCGCCCTCCAGCTCAA
----+----+----+----+----+----+----+----+----+----+----+----+----+----+
GACGTCTCAGGTTTATACCAGGGGTACGGGTAGTACGGGGTCCATTCGGTTGGGTCCGGAGCGGGAGGTCGAGTT
          E  S  K  Y  G  P  P  C  P  P  C  P
                    └─── IgG4 Hinge ───────┘        (SEQ ID NO:47)

GGCGGGACAGGTGCCCTAGAGTAGCCTTGCATCCAGGGACACAGGCCCAGCCGGTGCTGACGCATCCACCTCCATC
----+----+----+----+----+----+----+----+----+----+----+----+----+----+  2100
CCGCCCTGTCCACGGGATCTCATCGGAACGTAGGTCCCTGTGTCCGGGTCGGCCACGACTGCGTAGGTGGAGGTAG
```

FIG. 34C-1

```
TCTTCCTCAGCACCTGAGTTCCTGGGGGGACCATCAGTCTTCCTGTTCCCCCCAAAACCCAAGGACACTCTCATG
----+----+----+----+----+----+----+----+----+----+----+----+----+----+
AGAAGGAGTCGTGGACTCAAGGACCCCCCTGGTAGTCAGAAGGACAAGGGGGGTTTTGGGTTCCTGTGAGAGTAC
   A  P  E  F  L  G  G  P  S  V  F  L  F  P  P  K  P  K  D  T  L  M
                                                            IgG4 CH2

2250
ATCTCCCGGACCCCTGAGGTCACGTGCGTGGTGGTGGACGTGAGCCAGGAAGACCCCGAGTCCAGTTCAACTGG
----+----+----+----+----+----+----+----+----+----+----+----+----+----+
TAGAGGGCCTGGGGACTCCAGTGCACGCACCACCACCTGCACTCGGTCCTTCTGGGGCTCCAGGTCAAGTTGACC
   I  S  R  T  P  E  V  T  C  V  V  V  D  V  S  Q  E  D  P  E  V  Q  F  N  W
                                                 IgG4 CH2

TACGTGGATGGCGTGGAGGTGCATAATGCCAAGACAAAGCCGGGAGGAGCAGTTCAACAGCACGTACCGTGTG
----+----+----+----+----+----+----+----+----+----+----+----+----+----+
ATGCACCTACCGCACCTCCACGTATTACGGTTCTGTTTCGGCCCTCCTCGTCAAGTTGTCGTGCATGGCACAC
   Y  V  D  G  V  E  V  H  N  A  K  T  K  P  R  E  E  Q  F  N  S  T  Y  R  V
                                            IgG4 CH2
```

FIG. 34C-2

```
GTCAGCGTCCTCCACCGTCCTGCACCAGGACTGGCTGAACGGCAAGGAGTACAAGTGCAAGGTCTCCAACAAAGGC
----+----+----+----+----+----+----+----+----+----+----+----+----+----+----+    2400
CAGTCGCAGGAGGTGGCAGGACGTGGTCCTGACCGACTTGCCGTTCCTCATGTTCACGTTCCAGAGGTTGTTTCCG

V  S  V  L  T  V  L  H  Q  D  W  L  N  G  K  E  Y  K  C  K  V  S  N  K  G
 ─────────────────────────────────────────────────────────────────────────
   IgG4 CH2

CTCCCGTCCTCCATCGAGAAAACCATCTCCAAAGCCAAAGGTGGGACCCACGGGGTGCGAGGGCCACATGACAG
----+----+----+----+----+----+----+----+----+----+----+----+----+----+----+    2550
GAGGGCAGGAGGTAGCTCTTTTGGTAGAGGTTTCGGTTTCCACCCTGGGTGCCCCACGCTCCCGGTGTACTGTC

L  P  S  S  I  E  K  T  I  S  K  A  K  │(SEQ ID NO:48)
 ─────────────────────────────────────────
   IgG4 CH2

AGGTCAGCTCGGCCCCACCCTCTGCCCTGGGAGTGACCGCGTGTGCCAACCTCTGTCCCTACAGGGCAGCCCCGAGA
----+----+----+----+----+----+----+----+----+----+----+----+----+----+----+
TCCAGTCGAGCCGGGGTGGGAGACGGGACCCTCACTGGCGCACACGGTTGGAGACAGGGATGTCCCGTCGGGCTCT

G  Q  P  R  E
                                                              ──────────────
                                                                IgG4 CH3

GCCACAGGTGTACACCCTGCCCCCATCCCAGGAGGAGATGACCAAGAACCAGGTCAGCCTGACCTGCCTGGTCAA
----+----+----+----+----+----+----+----+----+----+----+----+----+----+----+
CGGTGTCCACATGTGGGACGGGGGTAGGGTCCTCCTCTACTGGTTCTTGGTCCAGTCGGACTGGACGGACCAGTT

P  Q  Y  Y  T  L  P  P  S  Q  E  E  M  T  K  N  Q  V  S  L  T  C  L  V  K
 ─────────────────────────────────────────────────────────────────────────
                                                IgG4 CH3
```

FIG. 34C-3

```
AGGCTTCTACCCCAGGCGACATCGCCGTGGAGTGGGAGAGCAATGGGCAGCCGGAGAACAACTACAAGACCACGCC
----+----+----+----+----+----+----+----+----+----+----+----+----+----+----  2700
TCCGAAGATGGGGTCCGCTGTAGCGGCACCTCACCCTCGTTACCCGTCGGCCTCTTGTTGATGTTCTGGTGCGG
  G  F  Y  P  S  D  I  A  V  E  W  E  S  N  G  Q  P  E  N  N  Y  K  T  P
                                              ─── IgG4 CH3

TCCCGTGCTGGACTCCGACGGCTCCTTCTTCCTCTACAGCAGGCTAACCGTGGACAAGAGCAGGTGGCAGGAGGG
----+----+----+----+----+----+----+----+----+----+----+----+----+----+----
AGGGCACGACCTGAGGCTGCCGAGGAAGAAGGAGATGTCGTCCGATTGGCACCTGTTCTCGTCCACCGTCCTCCC
  P  Y  L  D  S  D  G  S  F  F  L  Y  S  R  L  T  V  D  K  S  R  W  Q  E  G
                       ─── IgG4 CH3

GAATGTCTTCTCATGCTCCGTGATGCATGAGGCTCTGCACAACCACTACACACAGAAGAGCCTCTCCCTGTCTCT
----+----+----+----+----+----+----+----+----+----+----+----+----+----+----  2850
CTTACAGAAGAGTACGAGGCACTACGTACTCCGAGACGTGTTGGTGATGTGTCTTCTCGGAGAGGACAGAGA
  N  V  F  S  C  S  V  M  H  E  A  L  H  N  H  Y  T  Q  K  S  L  S  L
                   ─── IgG4 CH3
```

FIG. 34C-4

```
GGGTAAATGAGTGCCAGGCGCGGGCAAGCCCCGCTCCCGGCTCTCGGGTCGCGGAGGATGCTTGGCACGTA
CCCATTTACTCACGGTCCCGCCGGCCGTTCCCGGCGCCCCAGAGCCCCGAGAGCCCTACGAACCGTGCAT
    G  K
  IgG4 CH3 ┘ (SEQ ID NO:49)              ───── poly A ─────

CCCGTCTACATACTTCCCAGGCACCCAGCATGGAAATAAAGCACCACCACTGCCCCTGGCCCCTGTGAGACTG
                                                                      3000
GGGGCAGATGTATGAAGGGTCCGTGGTCGTACCTTTATTCGTGGTGACGGGACCCGGGGACACTCTGAC
    ═══════════════════════ poly A ═══════════════════════
```

FIG. 34D-1

```
TGATGGTTCTTTCCACGGGTCAGGCCTGAGTCTGAGTGACATGAGGAGGCAGAGCGGGTCCCACTGTC
ACTACCAAGAAAGTGCCCAGTCCGGCTCAGACTCCGGACTCACTGTACTCCCGTCGCCCAGGGTGACAG
                                    ━━━ polyA ━━━                            3150
CCCACACTGGCCCAGGCTGTGCAGGTGTGCCTAGGGTGCCTGGGCTCAGCCAGGGGCTGCCCTCGGCAG
GGGTGTGACCGGGTCCGACACGTCCACACGGACCCGTGGATCCCACCCCGAGTCGGTCCCGACGGAGCCGTC
                          ━━━ polyA ━━━
GGTGGGGGATTTGCCAGCGTGCTGCCCTCCCCTCCAGACAGACATGTGAGCAAAAGGCCAGCAAAACCGT
CCACCCCCTAAACGTCGCACCGGAGGAGTCGTCGTTTCCGGTCGTTTTCCGGTCGTTTTCCGGTCCTTGGCA
■ polyA
AAAAAGGCCGCGTTGCTGGCGTTTTTCCATAGGCTCCGCCCCCCCCTGACGAGCATCACAAAATCGACGCTCAAGT
                                                                          3300
TTTTTCCGGCGAAGCGACCGCAAAAAGGTATCCGAGGCGGGGACTGCTCGTAGTGTTTTTAGCTGCGAGTTCA
CAGAGGTGGGCGAAACCCGACAGGACTATAAAGATACCAGGCGTTTCCCCCTGGAAGCTCCCTCGTGCGCTCTCCT
GTCTCCACCGCTTTGGGCTGTCCTGATATTTCTATGGTCCGCAAAGGGGAGGTTCGAGGGAGGAGCACGCGAGAGGA
```

FIG. 34D-2

```
CAGAGGTGGCGGAAACCCGACACAGGACTATAAAGATACCAGGCGTTTCCCCCTGAAGCTCCCTCGTGCGCTCTCCT
GTCTCCACCGCTTTGGGCGTGTCCTGATATTTCTATGGTCCGCAAAGGGGGAGGTTCGAGGGAGCACGCGAGAGGA
                                                                        3450
GTTCCGACCCTGCCGCTTACCGGATACCTGTCCGCCTTTCTCCCTTCGGGAAGCGTGGCGCTTTCTCATAGCTCA
CAAGGCTGGGACGGCGAATGGCCTATGGACAGGCGGAAAGAGGGAAGCCCTTCGCACCGCGAAAGAGTATCGAGT

CGCTGTAGGTATCTCAGTTCGGTGTAGGTCGTTCGCTCCAAGCTGGGCTGTGTGCACGAACCCCCCGTTCAGCCC
GCGACATCCATAGAGTCAAGCCACACATCCAGCAAGCGAGGTTCGACCGACACACGTGCTTGGGGGCAAGTCGGG
                                                                        3600
GACCGGCTGCGCCTTATCCGGTAACTATCGTCTCTTGAGTCCAACCCGGTAAGACACGACTTATCGCCACTGGCAGCA
CTGGCGACGCGGAATAGGCCATTGATAGCAGAAGTGAGGTTGGGCCATTCTGTGCTGAATAGCGGTGACCGTCGT

GCCACTGGTAACAGGATTAGCAGAGCGGAGGTATGTAGGCGGTGCTACAGAGTTCTTGAAGTGGTGCCTAACTAC
CGGTGACCATTGTCCTAATCGTCTCCGCTCCATACATCCGCCACGATGTCTCAAGAACTTCACCACCGGATTGATG

GGCTACACTAGAAGGACAGTATTTGGTATCTGCGCTCTCTGCTGAAGCCAGTACCTTCGGAAAAAGAGTTGGTAGC
CCGATGTGATCTTCCTGTCATAAACCATAGACGCGAGACGACTTCGGTCAATGAAGCCTTTTTCTCAACCATCG
                                                                        3750
```

```
CCCAGTGCTGCAATGATACCGCGAGACCCACGCTCACCGGCTCCAGATTTATCAGCAATAAACCAGCCAGCCGGA
----+----+----+----+----+----+----+----+----+----+----+----+----+----+   4200
GGGTCACGACGTTACTATGGCGCTCTGGGTGCGAGTGGCCGAGGTCTAAATAGTCGTTATTTGGTCGGTCGGCCT
                                            ━━━━━━━━━━━━━
                                              Ampicillin AGGGCCGAGCGCAGAAGTGGTCCTGCAACTTTATCCGCCTCCATCCAGTCTATTAATTGTTGCCGGGAAGCTAGA
----+----+----+----+----+----+----+----+----+----+----+----+----+----+
TCCCGGCTCGCGTCTTCACCAGGACGTTGAAATAGGCGGAGGTAGGTCAGATAATTAACAACGGCCCTTCGATCT
━━━━━━━━━━━━━━━━━━━━━━━━━━━━━━━━━━━━━━
              Ampicillin GTAAGTAGTTCGCCAGTTAATAGTTTGCGCAACGTTGTTGCCATTGCTACAGGCATCGTGGTGTCACGCTCGTCG
----+----+----+----+----+----+----+----+----+----+----+----+----+----+   4350
CATTCATCAAGCGGTCAATTATCAAACGCGTTGCAACAACGGTAACGATGTCCGTAGCACCACAGTGCGAGCAGC
━━━━━━━━━━━━━━━━━━━━━━━━━━━━━━━━━━━━━━━━━━━━━━━━━━━━━━━━━━━━━━━━━━━━━━━━━━
                                Ampicillin TTTGGTATGGCTTCATTCAGCTCCGGTTCCCAACGATCAAGGCGAGTTACATGATCCCCGATGTTGTGCAAAAAA
----+----+----+----+----+----+----+----+----+----+----+----+----+----+
AAACCATACCGAAGTAAGTCGAGGCCAAGGGTTGCTAGTTCCGCTCAATGTACTAGGGGCTACAACACGTTTTTT
━━━━━━━━━━━━━━━━━━━━━━━━━━━━━━━━━━━━━━━━━━━━━━━━━━━━━━━━━━━━━━━━━━━━━━━━━━
                          Ampicillin
```

GCGGTTAGCTCCTTCGGTCCTCCGATCGTTGTCAGAAGTAAGTTGGCCGCAGTGTTATCACTGATGGTTATGGCA
CGCCAATCGAGGAAGCCAGGAGGCTAGCAACAGTCTTCATTCAACCGGCGTCACAATAGTGACTACCAATACCGT
                                                                    4500

■ Ampicillin

FIG. 34E-1

```
GCACTGCATAATTCTCTTACTGTCATGCCATCCGTAAGATGCTTTTCTGTGACTGGTGAGTACTCAACCAAGTCA
CGTGACGTATTAAGAGAATGACAGTACGGTAGGCATTCTACGAAAAGACACTGACCACTCATGAGTTGGTTCAGT
                                    ──── Ampicillin TTCTGAGAATAGTGTATGCGGCGACCGAGTTGCTCTTGCCCGGCGTCAATACGGGATAATACCGCGCCACATAGC  4650
AAGACTCTTATCACATACGCCGCTGCCTCAACGAGAACGGGCCGCAGTTATGCCCTATTATGGCGCGGTGTATCG
                                    ──── Ampicillin AGAACTTTAAAAGTGCTCATCATTGGAAAACGTTCTTCGGGGCGAAAACTCTCAAGGATCTTACCGCTGTTGAGA
TCTTGAAATTTTCACGAGTAGTAACCTTTTGCAAGAAGCCCCGCTTTTGAGAGTTCCTAGAATGGCGACAACTCT
                                    ──── Ampicillin TCCAGTTCGATGTAACCCACTCGTGCACCCAACTGATCTTCAGCATCTTTTACTTTCACCAGCGTTTGTGGTGA  4800
AGGTCAAGCTACATTGGGTGAGCACGTGGGTTGACTAGAAGTCGTAGAAAATGAAAGTGGTCGCAAAGACCCACT
                                    ──── Ampicillin
```

FIG. 34E-3

```
TGGAAAGTCCCCAGGCTCCCCAGCAGGCAGAAGTATGCAAAGCATGCATCTCAATTAGTCAGCAACCATAGTCCC
     +         +         +         +         +         +         +       5250
ACCTTTCAGGGGTCCGAGGGGTCGTCCGTCTTCATACGTTTCGTACGTAGAGTTAATCAGTCGTTGGTATCAGGG
                    ──── SV40 Promoter ────

GCCCCTAACTCCGCCCCATCCCGCCCCCTAGTTCCGCCCATTCTCCGCCCCCATGGCTGACTAATTTT
     +         +         +         +         +         +         +
CGGGGATTGAGGCGGGGTAGGGCGGGGATTGAGGCGGGTCAAGGCGGGTAAGAGGCGGGGTACCGACTGATTAAAA
                                     ──── SV40 Promoter ────

TTTTATTTATTTATGCAGAGGCCGAGGCCGCCTCGGCCTCTGAGCTATTCCAGAAGTAGTGAGGAGGCTTTTTTGGAGG
     +         +         +         +         +         +         +       5400
AAAATAAATAAATACGTCTCCGGCTCCGGCGGAGACCGGAGACTCGATAAGGTCTTCATCACTCCTCCGAAAAAACCTCC
                                                         ──── SV40 Promoter ────

CCTAGGCTTTTTGCAAAAAGCTAGCTTGGTGCCCTCATGTTCGACCATTGAACTGCATCGTCGCCTGTCCCAAA
     +         +         +         +         +         +         +
GGATCCGAAAAACGTTTTTCGATCGAACCACGGGAGTACCAAGCTGGTAACTTGACGTAGCAGGCGGCACAGGGTTT
──── SV40 Promoter ────             M  V  R  P  L  N  C  I  Y  A  Y  S  Q
                                   ──── DHFR ────
```

FIG. 34E-4

```
ATATGGGATTGGCAAGAATGGAGACCGACCCTGGCCTCCGCTCAGGAACGAGTTCAAGTACTTCCAAAGAATGA
                                                                        5550
TATACCCCTAACCGTTCTTGCCTCTGGCTGGGACCGGAGGCGAGTCCTTGCTCAAGTTCATGAAGGTTTCTTACT
 N  M  G  I  G  K  N  G  D  R  P  W  P  P  L  R  N  E  F  K  Y  F  Q  R  M
                                       DHFR
```

FIG. 34F-1

```
CCACAACCTCTTCAGTGGAAGGTAAACAGAATCTGGTGATTATGGGTAGGAAAACCTGGTTCTCCATTCCTGAGA
GGTGTTGGAGAAGTCACCTTCCATTTGTCTTAGACCACTACTAATACCCATCCTTTTGGACCAAGAGGTAAGGACTCT
  T  T  S  S  V  E  G  K  Q  N  L  V  I  M  G  R  K  T  W  F  S  I  P  E
                                        ——————————— DHFR ———————————

AGAATCGACCCTTTAAAGGACAGAATTAATATAGTTCTCAGTAGAGAACTCAAAGAACCACCAGGAGCTCATT —— 5700
TCTTAGCTGGGAAATTTCCTGTCTTAATTATATCAAGAGTCATCTCTTGAGTTTCTTGGTGTGCTCCTCGAGTAA
  K  N  R  P  L  K  D  R  I  N  V  L  S  R  E  L  K  E  P  P  R  G  A  H
                                        ——————————— DHFR ———————————

TTCTTGCCAAAAGTTTGGATGATGCCTTAAGACTTATTGAACAACCGGAATTGGCAAGTAAAGTAGACATGGTTT
AAGAACGGTTTTCAAACCTACTACGGAATTCTGAATAACTTGTTGGCCTTAACCGTTCATTTCATCTGTACCAAA
  F  L  A  K  S  L  D  D  A  L  R  L  I  E  Q  P  E  L  A  S  K  V  D  M  V
                                        ——————————— DHFR ———————————

GGATAGTCGGAGGCAGTTCTGTTTACCAGGAAGCCATGAATCAACCAGGCCACCTCAGACTCTTTGTGACAAGA —— 5850
CCTATCAGCCTCCGTCAAGACAAATGGTCCTTCGGTACTTAGTTGGTCCGGTGAGTCTGAGAAACACTGTTCCT
  W  I  V  G  G  S  S  V  Y  Q  E  A  M  N  Q  P  G  H  L  R  L  F  V  T  R
                                        ——————————— DHFR ———————————
```

FIG. 34F-2

```
TCATGCAGGAATTTGAAAGTGACACGTTTTTTCCCAGAAATTGATTTGGGGAAATATAAACTTCTCCCAGAATACC
----+----+----+----+----+----+----+----+----+----+----+----+----+----+----
AGTACGTCCTTAAACTTTCACTGTGCAAAAAAGGGTCTTTAACTAAACCCCTTTATATTTGAAGAGGGTCTTATGG
 I  M  Q  E  F  E  S  D  T  F  F  P  E  I  D  L  G  K  Y  K  L  L  P  E  Y
 ────────────────────────────── DHFR ──────────────────────────────────────

CAGGGCGTCCTCTCTGAGGTCCAGGAGGAGAAAAAGGCATCAAGTATAAGTTTGAAGTCTACGAGAAGAAAGACTAAC    6000
----+----+----+----+----+----+----+----+----+----+----+----+----+----+----
GTCCCGCAGGAGAGACTCCAGGTCCTCCTCTTTTTCCGTAGTTCATATTCAAACTTCAGATGCTCTTCTTTCTGATTG
 P  G  V  L  S  E  V  Q  E  E  K  G  I  K  Y  K  F  E  V  Y  E  K  K  D  .
 ─────────── DHFR ─────────────                              (SEQ ID NO:50)

AGGAAGATGCTTTCAAGTTCTCTGCTCCCCTCCTAAAGCTATGCATTTTTATAAGACCATGGGACTTTTGCTGGC
----+----+----+----+----+----+----+----+----+----+----+----+----+----+----
TCCTTCTACGAAAGTTCAAGAGACGAGGGAGGATTTCGATACGTAAAAAATATTCTGGTACCCTGAAAACGACCG
                                                              ▬▬▬ polyA ▬▬▬

TTTAGATCATAATCAGCCATACCACACATTTGTAGAGTTTTACTTGCTTTAAAAAACCTCCCACACTCCCCCTGA    6150
----+----+----+----+----+----+----+----+----+----+----+----+----+----+----
AAATCTAGTATTAGTCGGTATGGTGTGTAAACATCTCCAAAATGAACGAAATTTTTGGAGGGTGTGGAGGGGACT
▬▬▬▬▬▬▬▬▬▬ polyA ▬▬▬▬▬▬▬▬▬▬▬▬
```

FIG. 34F-3

```
ACCTGAAACATAAATGAATTGTTGTTGTTAACTTGTTTATTGCAGCTTCTAATGGTTACAAATAAAGCA
    ----+----+----+----+----+----+----+----+----+----+----+----+----+
TGGACTTTGTATTTTACTTAACGTTAACAACAATTGAACAATAACGTCGAAGATTACCAATGTTTATTTCGT
                                        ━━━ poly A ━━━

ATAGCATCACAAATTTCACAAATAAAGCATTTTTTTCACTGCATTCTAGTTGTGGTTTGTCCAAACTCATCAATG   6300
    ----+----+----+----+----+----+----+----+----+----+----+----+----+
TATCGTAGTGTTTAAAGTGTTTATTTCGTAAAAAAAGTGACGTAAGATCAACACCAAACAGGTTTGAGTAGTTAC
                             ━━━ poly A ━━━

TATCTTATCATGTCTGGATCGG   (SEQ ID NO:56)
    ----+----+----+---   6322
ATAGAATAGTACAGACCTAGCC
  ━━━ poly A ━━━
```

FIG. 35A-1

GY5 VK Chimera (pANT13)

```
ACTAGTTATTAATAGTAATCAATTACGGGGTCATTAGTTTCATAGCCCATATATGGAGTTCCGCGTTACATAACTT
TGATCAATAATTATCATTAGTTAATGCCCCAGTAATCAAGTATATACCCTCAAGGCGCAATGTATTGAA
                                    ━━━━ CMV Promoter ━━━━                      150

ACGGTAAAATGGCCCGCCTGGCTGACCGCCCAACGACCCCCGCCCATTGACGTCAATAATGACGTATGTTCCCATA
TGCCATTTACCGGGCGGACCGACTGGGCGGTTGCTGGGGGCGGACTGGTAACTGCAGTTATTACTGCATACAAGGGTAT
                                    ━━━━ CMV Promoter ━━━━

GTAACGCCAATAGGGACTTTCCATTGACGTCAATGGGTGGAGTATTTACGGTAAACTGCCCACTTGGCAGTACAT
CATTGCGGTTATCCCTGAAAGGTAACTGCAGTTACCCACCTCATAAATGCCATTTGACGGGTGAACCGTCATGTA    300
                                    ━━━━ CMV Promoter ━━━━

CAAGTGTATCATATGCCAAGTACGCCCCCTATTGACGTCAATGACGGTAAATGCCCGCCTGGCATTATGCCCAG
GTTCACATAGTATACGGTTCATGCGGGGGATAACTGCAGTTACTGCCATTTACCGGGCGGACCGTAATACGGGTC
                                    ━━━━ CMV Promoter ━━━━
```

FIG. 35A-2

TACATGACCTTATGGGACTTTCCTACTTGGCAGTACATCTACGTATTAGTCATCGCTATTACCATGGTGATGCGG
ATGTACTGGAATACCCTGAAAGGATGAACCGTCATGTAGATGCATAATCAGTAGCGATAATGGTACCACTACGCC
━━━━━ CMV Promoter 450
TTTTGGCAGTACATCAATGGGCGTGGATAGCGGTTTGACTCACGGGGATTTCCAAGTCTCCACCCCATTGACGTC
AAAACCGTCATGTAGTTACCCGCACCTATCGCCAAACTGAGTGCCCCTAAAGTTCAGAGGTGGGTAACTGCAG
━━━━━ CMV Promoter AATGGGAGTTTGTTTTGGCACCAAAATCAACGGGACTTTCCAAAATGTCGTAACAACTCCGCCCCATTGACGCAA
TTACCCTCAAACAAACCGTGGTTTTTAGTTGCCCTGAAAGGTTTTACAGCATTGTTGAGGCGGGGTAACTGCGTT
━━━━━ CMV Promoter 600
ATGGGCGGTAGGCGTGTACGGTGGGAGGTCTATATAAGCAGAGCTCGTTTAGTGAACCGTCAGATCTGGCACGAG
TACCCGCCATCCGCACATGCCACCCTCCAGATATATTCGTCTCGAGCAAATCACTTGGCAGTCTAGACCGTGCTC
━━━━━ CMV Promoter

FIG. 35A-3

```
                                                                BssH II
GGTCTCCTCAGGTTGCCGCCACCATGAGGGTCCCCGCTCCTCAGCTCCTGCTCTGGCTTCCAGGCGC
----+----+----+----+----+----+----+----+----+----+----+----+----+
CCAGAGGAGTCCAACGGCGGTGGTACTCCACAGGGCGAGGAGTCGAGGACGAGAGACCGAGGGTCCGC
                    M  R  V  P  A  Q  L  L  L  L  W  L  P  G
                                                   Signal Sequence 750
GCGATGTGTGATGACCCAAACTCCACTCTCCCTGCCTGTCAGTCTTGGAGATCAAGCCTCCATCTCTT
----+----+----+----+----+----+----+----+----+----+----+----+----+
CGCTACACACTACAACAGGACTTGGGTTTGAGGTGAGAGGGACGGACAGTCAGAACCTCTAGTTCGGAGGTAGAGAA
 A  R  C  D  V  V  M  T  Q  T  P  L  S  L  P  V  S  L  G  D  Q  A  S  I  S
 Signal                                                              GY5VK
 Sequence GCAGATCTAGTCAGAGCCTTGTCCACAGTAATGGAAACACCTATTTACAGTGGTACCTGCAGAAGCCAGGCCAGT
----+----+----+----+----+----+----+----+----+----+----+----+----+
CGTCTAGATCAGTCTCGGAACAGGTGTCATTACCTTTGTGGATAAATGTCACCATGGACGTCTTCGGTCCGGTCA
 C  R  S  S  Q  S  L  V  H  S  N  G  N  T  Y  L  Q  W  Y  L  Q  K  P  G  Q
                                                         GY5VK 900
CTCCAAAGCTCCTGATCTACACAGTTTCCAACCGATTTTCTGGGGTCCCAGACAGGTTCAGTGGCAGTGGATCAG
----+----+----+----+----+----+----+----+----+----+----+----+----+
GAGGTTTCGAGGACTAGATGTGTCAAAGGTTGGCTAAAAGACCCCAGGGTCTGTCCAAGTCACCGTCACCTAGTC
 S  P  K  L  L  I  Y  T  V  S  N  R  F  S  G  V  P  D  R  F  S  G  S  G  S
                          GY5VK
```

FIG. 35A-4

```
GGCCAGATTTCACACTCAAGATCAGCAGAGAGTGGAGGCTGAGGATCTGGGAGTTTATTTCTGCTCTCAAAGTACAC
     +         +         +         +         +         +         +
CCGGTCTAAAGTGTGAGTTCTAGTCGTCTCTCACCTCCGACTCCTAGACCCTCAAATAAAGACGAGAGTTTCATGTG
 G   P   D   F   T   L   K   I   S   R   V   E   A   E   D   L   G   V   Y   F   C   S   Q   S   T
                                     ──────GY5VK──────

ATGTTCCTTTCACGTTCGGCTCGGGGACAAAGTTGGAAATAAAACGTGAGTAGAATTTAAACTTTGCTTCCTCAG
     +         +         +         +         +         +         +──1050
TACAAGGAAAGTGCAAGCCGAGCCCCTGTTTCAACCTTTATTTTGCACTCATCTTAAATTTGAAACGAAGGAGTC
 H   V   P   F   T   F   G   S   G   T   K   L   E   I   K   R   (SEQ ID NO:57)
 ──────GY5VK──────
```

FIG. 35B-1

BamHI

TTGGATCCCGCAATTCTAAACTCTCTGAGGGGGTCGGATGACGTGGCCATTCTTTGCCTAAAGCATTGAGTTTACTG
AACCTAGGGCGTTAAGATTTGAGACTCCCCCAGCCTACTGCACCGGTAAGAAACGGATTTCGTAACTCAAATGAC

CAAGGTCAGAAAAGCATGCAAAGCCCTCAGAATGGCTGCAAAGAGCTCCAACAAAACAATTTAGAACTTTATTAA —— 1200
GTTCCAGTCTTTTCGTACGTTTCGGGAGTCTTACCGACGTTTCTCGAGGTGTTTTGTTAAATCTTGAAATAATT

GGAATAGGGGAAGCTAGGAAGAAACTCAAAACATCAAGATTTTAAATACGCTTCTTGGTCTCCTTGCTATAATT
CCTTATCCCCTTCGATCCTTCTTTGAGTTTTGTAGTTCTAAAATTTATGCGAAGAACCAGAGAACGATATTAA

ATCTGGGATAAGCATGCTGTTTTCTGTCGTCCCTAACATGCCCTGTGATTATCCGCAAACAACACCCAAGG —— 1350
TAGACCCTATTCGTACGACAAAAGACAGACAGGATTGTACGGGACACTAATAGGCGTTTGTTGTGTGGGTTCCC

CAGAACTTTGTTACTTAAACACCATCCCTGTTTGCTTCTTTCCCTCAGGAACTGTGGCTGCCACCATCTGTCTTCATC
GTCTTGAAACAATGAATTTGTGTAGGACATCCTTGACACCGACGTGGTAGACAGAAGTAG

```
TTCCCGCCATCTGATGAGCAGTTGAAATCTGGAACTGCCTCTGTTGTGTGCCTGCTGAATAACTTCTATCCCAGA
                                                                         1500
AAGGGCGGTAGACTACTCGTCAACTTTAGACCTTGACGGAGACAACACGGACGACCTATTGAAGATAGGGTCT
 F  P  P  S  D  E  Q  L  K  S  G  T  A  S  V  V  C  L  L  N  N  F  Y  P  R
                                  Ck

GAGGCCAAAGTACAGTGGAAGGTGGATAACGCCCTCCAATCGGGTAACTCCCAGGAGAGTGTCACAGAGCAGGAC
CTCCGGTTTCATGTCACCTTCCACCTATTGCGGGAGGTTAGCCCATTGAGGGTCCTCTCACAGTGTCTCGTCCTG
 E  A  K  V  Q  W  K  V  D  N  A  L  Q  S  G  N  S  Q  E  S  V  T  E  Q  D  S
                                  Ck

AGCAAGGACAGCACCTACAGCCTCAGCAGCACCCTGACGCTGAGCAAAGCAGACTACGAGAAACACAAAGTCTAC
                                                                         1650
TCGTTCCTGTCGTGGATGTCGGAGTCGTCGTGGGACTGCGACTCGTTCGTCTGATGCTCTTTGTGTTTCAGATG
 K  D  S  T  Y  S  L  S  S  T  L  T  L  S  K  A  D  Y  E  K  H  H  K  V  Y
                                  Ck

GCCTGCGAAGTCACCCATCAGGGCCTGAGCTCGCCCGTCACAAAGAGCTTCAACAGGGGAGAGTGTTAGAGGGAG
CGGACGCTTCAGTGGGTAGTCCCGGACTCGAGCGGGCAGTGTTTCTCGAAGTTGTCCCCTCTCACAATCTCCCTC
 A  C  E  V  T  H  Q  G  L  S  S  P  V  T  K  S  F  N  R  G  E  C  .       polyA
            Ck                                                      (SEQ ID NO:53)
```

FIG. 35B-3

```
AAGTGCCCCACCTGCTCCTCAGTTCCTCAGCCCTGACCCCTCCCATCCTTTGGCCTCTGACCCTTTTCCACAGGG
                                                                          1800
TTCACGGGGTGGACGAGGAGTCAAGGTCGGACTGGGGGAGGGTAGGAACCGAGAACTGGGAAAAGGTGTCCC
                                        ———— poly A ————

GACCTACCCCCTATTGCGGTCCTCCAGCTCATCTTTCACCTCACCCCCTCCTCCTTGGCTTTAATTATGCTA
                                                                          1950
CTGGATGGGGATAACGCCAGGAGGTCGAGTAGAAAGTGGAGTGGGGAGGAGGAGGAACCGAAATTAATACGATT
                                        ———— poly A ————

ATGTTGGAGGAGAATGAATAAATAAAGTGAATCTTTGCACCTGTGTTTCTCTCTTTCCTCAATTTAATAATTAT
TACAACCTCCTCTTACTTATTTATTTCACTTAGAAACGTGGACACCAAAGAGAGAAAGGAGTTAAATTATTAATA
                                        ———— poly A ————

TATCTGTTGTTTACCAACTACTCAATTTCTCTTATAAGGGACTAAATATGTAGTCATCCTAAGGCGCATAACCAT
ATAGACAACAAATGGTTGATGAGTTAAAGAGAATATTCCCTGATTTATACATCAGTAGGATTCCGCGTATTGGTA
                                        ———— poly A ————
```

FIG. 35B-4

TTATAAAATCATCCTTCATTCTATTTTACCCTATCATCCTCTGCAAGACAGTCCTCCCTCAAACCCACAAGCCT

AATATTTTAGTAGGAAGTAAGATAAAATGGGATAGTAGGAGACGTTCTGTCAGGAGGGAGTTTGGGTGTTCGGA

2100 poly A

FIG. 35C-1

```
TCTGTCCTCACAGTCCCCTGGGCCATGGTAGGAGAGACTTGCTTCCTTGTTTTCCCCTCCTCAGCAAGCCCTCAT
AGACAGGAGTGTCAGGGGACCCCGGTACCATCCCTCTCTGAACGAAGGAACAAAAGGGGAGGAGTCGTTCGGAGTA
                                                         ──── poly A ────
                                                                                2250
AGTCCTTTTTAAGGGTGACAGAGTGTCTTACGGTCTCATATATCCTTTGATTCAATTCCCTGGAATCAACCAAGGCAAA
TCAGGAAAAATTCCCACTGTCCAGAATGCCAGTATATAGGAAAACTAAGTTAAGGGACCCCTTAGTTGGTTCCGTTT
                                                                  ──── poly A ────

TTTTTCAAAAGAAGAAACCTGCTATAAAGAGAATCATTCATTGCAACATGATATAAAATAACACACAATAAAAG
AAAAAGTTTTCTTCTTTGGACGATATTTCTCCTTAGTAAGTAACGTTGTACTATATTTTATTGTTGTTATTTTC
                                            ──── poly A ────
                                                                                2400
CAATTAAATAAACAAACAATAGGGAAATGTTTAAGTTCATCATGGTACTTAGACTTAATGGAATGTCATGCCTTA
GTTAATTTATTTGTTTGTTTATCCCTTTACAAATTCAAGTAGTACCATGAATCTGAATTACCTTACAGTACGAAT
                                                    ──── poly A ────

TTTACATTTTTAAACAGGTACTGAGGGACTCCTGTCTGCCAAGGGCCGTATTGAGTACTTTCCACAACCTAATTT
AAATGTAAAAATTTGTCCATGACTCCCTGAGGACAGACGGTTCCCGGCATAACTCATGAAAGGTGTTGATTAAA
  ──── poly A ────
```

FIG. 35C-2

```
AATCCACACTATACTGTGAGATTAAAAACATTCATTAAAAATGTTGCAAAGGTTCTATAAAGCTGAGAGACAAATA
                                                                              2550
TTAGGTGTGATATGACACTCTAATTTTTGTAAGTAATTTTACAACGTTTCCAAGATATTTCGACTCTCTGTTTAT
                    ━━━ polyA TATTCTATAACTCAGCAATCCCACTACATGTGAGCAAAAGGCCAGCAAAAGGCCAGGAACCGTAAAAAGGCCGCG
ATAAGATATTGAGTCGTTAGGGTGATGTACACTCGTTTTCCGGTCGTTTTCCGGTCCTTGGCATTTTTCCGGCGC
      ━━━ polyA TTTGCTGGCGTTTTTCCATAGGCTCCGCCCCCCTGACGAGCATCACAAAAATCGACGCTCAAGTCAGAGGTGGCGA
                                                                              2700
AACGACCCGCAAAAGGTATCCGAGGCGGGGACTGCTCGTAGTGTTTTTAGCTGCGAGTTCAGTCTCCACCGCT AACCCGACAGGACTATAAAGATACCAGGCGTTTCCCCCTGGAAGCTCCCTCGTGCGCTCTCCTGTTCCGACCCTG
TTGGGCTGTCCTGATATTTCTATGGTCCGCAAAGGGGGACCTTCGAGGGAGCACGCGAGAGACAAGGCTGGGAC CCGCTTACCGGATACCCTGTCCGCCTTTCTCCCTTCGGGAAGCGTGGCGCTTTCTCATAGCTCACGCTGTAGGTAT
                                                                              2850
GGCGAATGGCCTATGGACAGGCGGGAAAGAGGGAAGCCCTTCGCACCGCGAAAGAGTATCGAGTGCGACATCCATA CTCAGTTCGGTGTAGGTCGTTCGCTCCAAGCTGGGCTGTGTGCACGAACCCCCGTTCAGCCCGACCGCTGCGCC
GAGTCAAGCCACATCCAGCAAGCGAGGTTCGACCCGACACGTGCTTGGGGGCAAGTCGGGCTGGCGACGCGG
```

FIG. 35C-3

```
TTATCCGGTAACTATCGTCTTGAGTCCAACCCGGTAAGACACGACTTATCGCCACTGGCAGCAGCCACTGGTAAC
----+----+----+----+----+----+----+----+----+----+----+----+----+----+   3000
AATAGGCCATTGATAGCAGAACTCAGGTTGGGCCATTCTGTGCTGAATAGCGGTGACCGTCGTCGGTGACCATTG

AGGATTAGCAGAGCGAGGTATGTAGGCGGTGCTGCTACAGAGTTCTTGAAGTGGTGGCCTAACTACGGCTACACTAGA
----+----+----+----+----+----+----+----+----+----+----+----+----+----+
TCCTAATCGTCTCGCTCCATACATCCGCCACGATGTCTCAAGAACTTCACCACCGGATTGATGCCGATGTGATCT

AGGACAGTATTTGGTATCTGCGCTCTGCTGAAGCCAGTTACCTTCGGAAAAGAGTTGGTAGCTCTCTTGATCCGGC
----+----+----+----+----+----+----+----+----+----+----+----+----+----+   3150
TCCTGTCATAAACCATAGACGCGAGACGACTTCGGTCAATGGAAGCCCTTTTTCTCAACCATCGAGAACTAGGCCG

AAACAAACCACCGCTGGTAGCGGTGGTTTTTTGTTTGCAAGCAGCAGATTACGCGCAGAAAAAAGGATCTCAA
----+----+----+----+----+----+----+----+----+----+----+----+----+----+
TTTGTTTGGTGGCGACCATCGCCACCAAAAAACAAACGTTCGTCGTCTAATGCGCGTCTTTTTTTCCTAGAGTT

GAAGATCCTTTGATCTTTTCTACGGGGTCTGACGCTCAGTGGAACGAAAACTCACGTTAAGGGATTTTGGTCATG
----+----+----+----+----+----+----+----+----+----+----+----+----+----+   3300
CTTCTAGGAAACTAGATGCCCCAGACTGCGAGTCACCTTGCTTTTGAGTGCAATTCCCTAAAACCAGTAC

AGATTATCAAAAAGGATCTTCACCTAGATCCTTTTAAATTAAAAATGAAGTTTTAAATCAATCTAAAGTATATAT
----+----+----+----+----+----+----+----+----+----+----+----+----+----+
TCTAATAGTTTTTCCTAGAAGTGGATCTAGGAAAATTTAATTTTACTTCAAAATTTAGTTAGATTTCATATATA
```

FIG. 35D-1

```
AGATTATCAAAAAGGATCTTCACCTAGATCCTTTTAAATTAAAAATGAAGTTTTAAATCAATCTAAAGTATATAT
 ----+----+----+----+----+----+----+----+----+----+----+----+----+----+----
TCTAATAGTTTTTCCTAGAAGTGGATCTAGGAAAATTTAATTTTTACTTCAAAATTTAGTTAGATTTCATATATA

GAGTAAACTTGGTCTGACAGTTACCAATGCTTAATCAGTGAGGCACCTATCTCAGGCTATCTGTCTATTTCGTTCA 3450
 ----+----+----+----+----+----+----+----+----+----+----+----+----+----+----
CTCATTTGAACCAGACTGTCAATGGTTACGAATTAGTCACTCCGTGGATAGAGTCGCTAGACAGATAAAGCAAGT
                                                    ──────────────▶
                                                       Ampicillin TCCATAGTTGCCTGACTCCCCGTCGTGTAGATAACTACGATACGGGAGGGCTTACCATCTGGCCCCAGTGCTGCA
 ----+----+----+----+----+----+----+----+----+----+----+----+----+----+----
AGGTATCAACGGACTGAGGGGCAGCACATCTATTGATGCTATGCCCTCCCGAATGGTAGACCGGGTCACGACGT
                                                                   Ampicillin ATGATACCGCGAGACCCACGCTCACCGGCTCCAGATTTATCAGCAATAAACCAGCCAGCCGGAAGGGCCGAGCGC 3600
 ----+----+----+----+----+----+----+----+----+----+----+----+----+----+----
TACTATGGCGCTCTGGGTGCGAGTGGCCGAGGTCTAAATAGTCGTTATTTGGTCGGTCGGCCTTCCCGGCTCGCG
                                                            Ampicillin AGAAGTGGTCCTGCAACTTTATCCGCCTCCAGTCTATTAATTGTTGCCGGGAAGCTAGAGTAAGTAGTTCG
 ----+----+----+----+----+----+----+----+----+----+----+----+----+----+----
TCTTCACCAGGACGTTGAAATAGGCGGAGGTCAGATAATTAACAACGGCCCTTCGATCTCATTCATTCAAGC
                                                                   Ampicillin
```

FIG. 35D-2

```
CCAGTTAATAGTTTGCGCAACGTTGTTGCCATTGCTACAGGCATCGTGGTGTCACGCTCGTCGTTTGGTATGGCT
     ----+----+----+----+----+----+----+----+----+----+----+----+----+----+    3750
GGTCAATTATCAAACGCGTTGCAACAACGGTAAGCATGTCCGTAGCACCACAGTGCGAGCAGCAAACCATACCGA
                                        ━━━━━━━━━━━━━ Ampicillin TCATTCAGCTCCGGTTCCCAACGATCAAGGCGAGTTACATGATCCCCATGTTGTGCAAAAAAGCGGTTAGCTCC
     ----+----+----+----+----+----+----+----+----+----+----+----+----+----+
AGTAAGTCGAGGCCAAGGGTTGCTAGTTCCGCTCAATGTACTAGGGGGTACAACACGTTTTTTCGCCAATCGAGG
                                        ━━━━━━━━━━━━━ Ampicillin TTCGGGTCCCTCCGATCGTTGTCAGAAGTAAGTTGGGCCGCAGTGTTATCACTCATGGTTATGGCAGCACTGCATAAT
     ----+----+----+----+----+----+----+----+----+----+----+----+----+----+    3900
AAGCCCAGGAGGCTAGCAACAGTCTTCATTCAACCGGCGTCACAATAGTGAGTACCAATACCGTCGTGACGTATTA
                                        ━━━━━━━━━━━━━ Ampicillin TCTCTTACTGTCATGCCATCCGTAAGATGCTTTTCTGTGACTGGTGAGTACTCAACCAAGTCATTCTGAGAATAG
     ----+----+----+----+----+----+----+----+----+----+----+----+----+----+
AGAGAATGACAGTACGGTAGGCATTCTACGAAAAGACACTGACCACTCATGAGTTGGTTCAGTAAGACTCTTATC
                                        ━━━━━━━━━━━━━ Ampicillin TGTATGCGGCGACCGAGTTGCTCTTGCCCGGCGTCAATACGGGATAATACCGCGCCACATAGCAGAACTTTAAAA
     ----+----+----+----+----+----+----+----+----+----+----+----+----+----+    4050
ACATACGCCGCTGGCTCAACGAGAACGGGCCGCAGTTATGCCCTATTATGGCGCGGTGTATCGTCTTGAAATTTT
                                        ━━━━━━━━━━━━━ Ampicillin
```

FIG. 35D-3

GTGCTCATCATTGGAAAACGTTCTTCGGGGCGAAAACTCTCAAGGATCTTACGCTGTTGAGATCCAGTTCGATG
CACGAGTAGTAACCTTTTGCAAGAAGCCCCGCTTTTGAGAGTTCCTAGAATGGCGACAACTCTAGGTCAAGCTAC
━━━ Ampicillin TAACCCACTCGTGCACCCAACTGATCTTCAGCATCTTTACTTTCACCAGCGTTTCTGGGTGAGCAAAAACAGGA — 4200
ATTGGGTGAGCACGTGGGTTGACTAGAAGTCGTAGAAATGAAAGTGGTCGCAAGACCCACTCGTGTTTTGTCCT
━━━ Ampicillin AGGCAAAATGCCGCAAAAAAGGGAATAAGGCGACACGGAAATGTTGAATACTCATACTCTTCCTTTTTCAATAT
TCCGTTTTACGGCGTTTTTTCCCTTATTCCCGCTGTGCCTTTACAACTTATGAGTATGAGAGGAAAAAGTTATA
━━━ Ampicillin TATTGAAGCATTTATCAGGGTTATTGTCTCATGAGCGGATACATATTTGAATGTATTTAGAAAAATAAACAAATA — 4350
ATAACTTCGTAAATAGTCCCAATAACAGAGTACTCGCCTATGTATAAACTTACATAAATCTTTTTATTTGTTTAT
▼ ━━━ Amp Promoter GGGGTTCCGGCGCACATTTCCCCGAAAAGTGCCACCTGACGCTTAAGAAACCATTATTATCATGACATTAACCTAT
CCCCAAGGCCGCGTGTAAAGGGGCTTTTCACGGTGGACTGCAGATTCTTTGGTAATAATAGTACTGTAATTGGATA
━━━ Amp Promoter

FIG. 35D-4

AAAAATAGGCGTATCACGAGGCCCTATTGATTATTG (SEQ ID NO:58)
                                    4461
TTTTTATCCGCATAGTGCTCCGGGATAACTAATAAC

CSR01-VK1 (kappa light chain)
ATGAGGGTCCCCGCTCAGCTCCTGGGGCTCCTGCTGCTCTGGCTCCCAGGGGCGCGA
 M  R  V  P  A  Q  L  L  G  L  L  L  L  W  L  P  G  A  R
TGTGATGTTGTGATGACCCAGTCTCCACTCTCCCTGCCCGTCACCCCTGGAGAGCCG
 C  D  V  V  M  T  Q  S  P  L  S  L  P  V  T  L  G  Q  P
GCCTCCATCTCTTGCAAGTCAAGTCAGAGCCTCTTAAATAGTGATGGAAAGACATAT
 A  S  I  S  C  K  S  S  Q  S  L  L  N  S  D  G  K  T  Y
TTGAATTGGTTGCAGCAGAGGCCAGGCCAGTCTCCAAGGCGCCTAATCTATCTGGTG
 L  N  W  L  Q  Q  R  P  G  Q  S  P  R  R  L  I  Y  L  V
TCTAAATTGGACTCTGGAGTCCCTGACAGGTTCACTGGCAGTGGATCAGGGACAGAT
 S  K  L  D  S  G  V  P  D  R  F  T  G  S  G  S  G  T  D
TTCACACTGAAAATCAGCAGAGTGGAGGCTGAGGATGTGGGAGTTTATTATTGCTGG
 F  T  L  K  I  S  R  V  E  A  E  D  V  G  V  Y  Y  C  W
CAAGGTACACACTTTCCGTTCACGTTCGGCGAGGGGACCAAGGTGGAAATAAAACGT (SEQ ID NO: 59)
 Q  G  T  H  F  P  F  T  F  G  G  G  T  K  V  E  I  K  R  (SEQ ID NO: 60)

FIG. 38A

CSR01-VK2 (kappa light chain)
ATGAGGGTCCCCGCTCAGCTCCTGGGGCTCCTGCTCTGCTCTGGCTCTCCAGGCGCCGA
 M  R  V  P  A  Q  L  L  G  L  L  L  L  W  L  P  G  A  R
TGTGATGTTGTGATGACCCAGTCTCCACTCAGCTTGCCTGTTACCCTGGGACAACCA
 C  D  V  V  M  T  Q  S  P  L  S  L  P  V  T  L  G  Q  P
GCCTCCATCTCTTGCAAGTCAAGTCAGAGCCTCTTAAATAGTGATGGAAAGACATAT
 A  S  I  S  C  K  S  S  Q  S  L  L  N  S  D  G  K  T  Y
TTGAATTGGTTGCAGCAGAGGCCAGGCCAGTCTCCAAGGCGCCTAATCTATCTGGTG
 L  N  W  L  Q  Q  R  P  G  Q  S  P  R  R  L  I  Y  L  V
TCTAAATTGGACTCTGGAGTCCCTGACAGGTTCACTGGCAGTGGATCAGGGACAGAT
 S  K  L  D  S  G  V  P  D  R  F  T  G  S  G  S  G  T  D
TTCACACTGAAAATCAGCAGAGTGGAGGCTGAGGATGTGGGAGTTTATTATTGCTGG
 F  T  L  K  I  S  R  V  E  A  E  D  V  G  V  Y  Y  C  W
CAAGGTACACATTTCCGTTCACGTTCGGAGGGGGGACCAAGGTGGAAATAAAACGT (SEQ ID NO: 61)
 Q  G  T  H  F  F  F  G  G  G  T  K  V  E  I  K  R  (SEQ ID NO: 62)

FIG. 38B

CSR01-VK3 (kappa light chain)
ATGAGGGTCCCCGTCAGCTCAGGGGCTCCTGGGGCTCCTGCTGCTCTGGCTTCCAGGGGCGCGCGA
 M  R  V  P  A  Q  L  L  G  L  L  L  L  W  L  P  G  A  R
TGTGATGTTGTGATGACCCAGTCTCCACTTCAGTCTGTTACCTGTGGGACAACCA
 C  D  V  V  M  T  Q  [S]  P  L  [P]  V  T  G  Q  P
GCCTCCATCTCTTGCAAGTCAAGTCAGAGCCTCTTAAATAGTGATGGAAAGACATAT
 A  S  I  S  C  K  S  S  Q  S  L  L  N  S  D  G  K  T  Y
TTGAATTGGTTGCAGCAGAGGCCAGGCCAGTCTCCAAGGCGCCTAATCTATCTGGTG
 L  N  W  L  Q  [Q]  R  P  G  Q  S  P  [R]  L  I  Y  L  V
TCTAAATTGGACTCTGGAGTCCCTGACAGGTTCTCTGGCAGTGGATCAGGGACAGAT
 S  K  L  D  S  G  V  P  D  R  F  [S]  G  S  G  S  G  T  D
TTCACACTGAAAATCAGCAGAGTGGAGGCTGAGGATGTGGGAGTTTATTATTGCTGG
 F  T  L  K  I  S  R  V  E  A  E  D  [V]  G  V  Y  Y  C  W
CAAGGTACACACATTTTCCGTTCACGTTCGGAGGGGGGACCAAGGTGGAAATAAAACGT (SEQ ID NO: 63)
 Q  G  T  H  F  P  F  T  F  G  G  G  T  K  [V]  E  I  K  R  (SEQ ID NO: 64)

FIG. 38C

CSR01-VH4 (Heavy chain)

```
ATGGGTTGGAGCTTGCATCTTCTTCCTTGTCGCTGTTGCTACGCGTGTCCACTCC
 M  G  W  S  L  I  L  F  L  V  A  V  A  T  R  V  H  S

GAGGTTCAGCTGGTGCAGTCTGGGGCAGAGGTGAAGAAGCCAGGGGCCTCAGTCAAG
 E  V  Q  L [V] Q  S  G  A  E [V  K  K  P] G  A  S  V  K

GTGTCCTGCACAGCTTCTGGCTTCAACATTAAAGACTACTATATACACTGGGTGAGG
[V] S  C  T  A  S  G  F  N  I  K  D  Y  Y  I  H  W  V [R]

CAGGCCCCTGGACAGGGCCTGGAGTGGATTGGATGGATTGATCCTGAGAATGGTGAT
 Q [A] P [G] Q  G  L  E  W  I  G  W  I  D  P  E  N  G  D

ATTGAATATGCCCCGAAGTTCCAGGGCAGCAGCCTGAGAGTTCAGCAGTTCAG
 I  E  Y  A  P  K  F  Q  G [R] A  T [H] T  A  D  T  S [H]

GATACAGCCTACATGGAGTTCAGCAGCCTGAGATCCAGCAGCCTGAGGACACTGCCGTCTATTAC
 D  T  A  Y  M [E] F  S  S  L [R] S  E  D  T  A  V  Y  Y

TGTCTCTACCAAGAAGGCTCCTGGGGCCAAGGCACCACTGTCACAGTCTCCTCA  (SEQ ID NO: 65)
 C  L  Y  Q  E  G  S  W  G  Q  G  T [M] T  V  S  S       (SEQ ID NO: 66)
```

FIG. 38D

CSR01-VH5 (Heavy chain)
ATGGGTTGGAGCCTCATCTTGCTTCTCCTTGTCGCTGTTGCTACGGCGTGTCCACTCC
M G W S L I L L L F L V A V A T R V S
GAGGTTCAGCTGGTGCAGTCTGGGGCAGAGGTGAAGAAGCCAGGGGCCTCAGTCAAG
E V Q L [V] Q S G A E [V] K K P [P] G A S V K
GTGTCCTGCACAGCTTCTGGCTTCAACATTAAAGACTACTATATACACTGGGTGAGG
V S C T A S G F N I K D Y Y I H W V [R]
CAGGCCCCTGGACAGGGCCTGGAATGGATTGGATGGATTGATCCTGAGAATGGTGAT
Q [A] P [G] Q G L E W I G W I D P E N G D
ATTGAATATGCCCCGAAGTTCCAGGGCAGGGCCACTATCACTGCAGACACATCCACC
I E Y A P K F Q G [R] A T [I] T A D T S [T]
GATACAGCCTACATGGAGCTCAGCAGCCTGAGATCTGAGGACACTGCCGTCTATTAC
D T A Y M E L S S L [R] S E D T A V Y Y
TGTCTCTACCAAGAAGGTCCTGGGGGCCAAGGCACCACTCTCACAGTCTCCCTCA (SEQ ID NO: 67)
C L Y Q E G P G G Q G T T [V] T V S S (SEQ ID NO: 68)

FIG. 38E

CSR02-VK2 (kappa light chain)

ATGAGGGTCCCCGCTCAGCTCCTGGGGCTCCTGCTGCTCTGGCTCCCAGGCGCGGGA
 M  R  V  P  A  Q  L  L  G  L  L  L  L  W  L  P  G  A  R
TGTGATGTTGTGATGACCCAGTCT CCACTCTCC CTGCCTGTCACTCTTGGACAGCCA
 C  D  V  V  M  T  Q  [S] P  L  S  L  P  V  [T] L  G  Q  [P]
GCCTCCATCTCTTGCAGATCTAGTCAGAGCCTTGTCCACAGTAATGGAAACACCTAT
 A  S  I  S  C  R  S  S  Q  S  L  V  H  S  N  G  N  T  Y
TTACAGTGGTACCTGCAGAAGCCAGGCCAGTCTCCACAGCTCCTGATCTACACAGTT
 L  Q  W  Y  L  Q  K  P  G  Q  S  P  [Q] L  L  I  Y  T  V
TCCAACCGATTTTCTGGGGTCCCAGACAGGTTCAGTGGCAGTGGATCAGGGACCGAT
 S  N  R  F  S  G  V  P  D  R  F  S  G  S  G  S  G  [T] D
TTCACACTCAAGATCAGCAGAGTGGAGGCTGAGGATGTGGGAGTTTATTTCTGCTCT
 F  T  L  K  I  S  R  V  E  A  E  D  [V] G  V  Y  F  C  S
CAAAGTACACATGTTCCTTTCACGTTCGGCCAAGGGACAAAGTTGGAAATAAAACGT (SEQ ID NO: 69)
 Q  S  T  H  V  P  F  T  F  G  [Q] G  T  K  L  E  I  K  R (SEQ ID NO: 70)

FIG. 39A

CSR02-VK3 (kappa light chain)
ATGAGGGTCCCCGCTCAGCTCCTGGGGCTCCTGCTCCTCTGGCTCCCAGGCGCCCGA
 M  R  V  P  A  Q  L  L  G  L  L  L  L  W  L  P  G  A  R
TGTGATGTTGTGATGACCCAATCTCCACTCTCCCTGCCTGTCACTCTTGGACAGCCA
 C  D  V  V  M  T  Q  S  P  L  S  L  P  V  T  L  G  Q  P
GCCTCCATCTCTTGCAGATCTAGTCAGAGCCTTGTCCACAGTAATGGAAACACCTAT
 A  S  I  S  C  R  S  S  Q  S  L  V  H  S  N  G  N  T  Y
TTACAGTGGTACCTGCAGAAGCCAGGCCAGTCTCCACAGCTCCTGATCTACACAGTT
 L  Q  W  Y  L  Q  K  P  G  Q  S  P  Q  L  L  I  Y  T  V
TCCAACCGATTTTCTGGGGTCCCAGACAGGTTCAGTGGCAGTGGATCAGGGCCAGAT
 S  N  R  F  S  G  V  P  D  R  F  S  G  S  G  S  G  P  D
TTCACACTCAAGATCAGCAGAGTGGAGGCTGAGGATGTGGGAGTTTATTACTGCTCT
 F  T  L  K  I  S  R  V  E  A  E  D  V  G  V  Y  Y  C  S
CAAAGTACACACATGTTCCTTTCACGTTCGGCCAGGGGACAAAGTTGGAAATAAACGT (SEQ ID NO: 71)
 Q  S  T  H  V  P  F  F  G  Q  G  T  K  L  E  I  K  R    (SEQ ID NO: 72)

FIG. 39B

CSR02-VH4 (heavy chain)

ATGGGTTGGAGCCTTCATCTTCTGCTCTTCCTTGTCGCTGTTGCTACGGCGGTGTCCACTCC
 M  G  W  S  L  H  L  L  L  F  L  V  A  V  A  T  R  V  H  S

CAGGTCCAACTGGTGCAGTCTGGGGCTGAGCTGAAGAAGCCTGGGGCTTCAGTGAAG
 Q  V  Q  L  V  Q  S  G  S  E  L  K  K  P  G  A  S  V  K

GTGTCCTGCAAGGCTTCTGGCTACACCTTCACCAGCAACTACATAAACTGGGTGAGA
 V  S  C  K  A  S  G  Y  T  F  T  S  N  Y  I  N  W  V  R

CAGGCCCCTGGACAGGGCCTTGAGTGGATGGGAAATATCTATCCTTCTGATGGTTTT
 Q  A  P  G  Q  G  L  E  W  M  G  N  I  Y  P  S  D  G  F

ACTAACTACAATCAAAAGTTCAAGGACAGGGTGACAATCACTGTAGACAAATCCACC
 T  N  Y  N  Q  K  F  K  D  R  V  T  I  T  V  D  K  S  T

AGCACACAGCCTACATGGAGCTCAGCAGCCTGAGATCTGAGGACACCGCGGTCTATTAC
 S  T  Q  Y  M  E  L  S  S  L  R  S  E  D  T  A  V  Y  Y

TGTACAAGAAACTTCGATGTCTGGGGCCAAGGACCACGGTCACCGTCTCCTCA (SEQ ID NO: 73)
 C  T  R  N  F  D  V  W  G  Q  G  T  T  V  T  V  S  S  (SEQ ID NO: 74)

FIG. 39C

CSR02-Vh5 (heavy chain)
ATGGGTTGGAGCCTCATCTTGCTCTTCCTTGTGCTGTTGCTGCTACGCTGTCCACTCC
 M  G  W  S  L  I  L  F  L  V  A  V  A  T  R  V  H  S CAGGTCCAACTGGTGCAGTCTGGGGTCTGAGCTGAAGAAGCCTGGGGCTTCACTGAAG
 Q  V  Q  L  V  Q  S  G  [S]  E  L  [K]  K  P  G  A  S  V  K GTGTCCTGCAAGGCTTCTGGCTACACCTTCACCAGCAACTACATAAACTGGGTGAGA
 V  S  C  K  A  S  G  Y  T  F  T  S  N  Y  I  N  W  V  [R]

CAGGCCCCTGGACAGGGCCTTGAGTGGATGGGAAATATCTATCCTTCTGATGGTTTT
 Q  [A]  P  G  Q  G  L  E  W  [M]  G  N  I  Y  P  S  D  G  F

ACTAACTACAATCAAAAGTTCAAGGACAGGGTGACAATCACTGTAGACAAATCCACC
 T  N  Y  N  Q  K  F  K  D  R  [V]  T  [I]  T  V  D  K  S  [T]

AGCACAGCCTACATGGAGCTCAGCAGCCTGAGATCTGAGGACACCGCGGTCTATTAC
 S  T  A  Y  M  [E]  L  S  S  L  [R]  S  E  D  [T]  A  V  Y  Y

TGTACAAGAAACTTCGATGTCTGGGGCCAAGGACCACGGTCACCGTCTCCTCA (SEQ ID NO: 75)
 C  T  R  N  F  D  V  W  G  [Q]  G  T  T  V  T  V  S  S (SEQ ID NO: 76)

FIG. 39D

```
         10         20         30         40         50         60         70         80         90        100
CAGGTCCAACTGGTCCAGTCTGGGGCTGAACTGAAGAAGCCTGGGGCTTCAGTGAAGCTGTCCTGCAAGGCTTCTGGCTACACCTTCACCAGCAACTACA
 Q  V  Q  L  V  Q  S  G  A  E  L  K  K  P  G  A  S  V  K  L  S  C  K  A  S  G  Y  T  F  T  S  N  Y
                              1                             20                            30
                              0
        110        120        130        140        150        160        170        180        190        200
TAAACTGGGTAAAACAGGCCCCTGGACAGGGCCTTGAGTGGATTGGAAATATCTATCCTTCTGATGGTTTTACTAACTACAATCAAAAGTTCAAGGACAG
 I  N  W  V  K  Q  A  P  G  Q  G  L  E  W  I  G  N  I  Y  P  S  D  G  F  T  N  Y  N  Q  K  F  K  D  R
              40                             50 52 52a                       60
        210        220        230        240        250        260        270        280        290        300
GGCCACATTGACTGTAGACAAATCTACCAGCACAGCCTACATGGAGCTCAGCAGCCTGAGATCTGAGGACTCTGCGGTCTATTACTGTACAAGAACTTC
 A  T  L  T  V  D  K  S  T  S  T  A  Y  M  E  L  S  S  L  R  S  E  D  S  A  V  Y  Y  C  T  R  N  F
                 70                             80 82 82a b c                 90
        310        320        330        340
GATGTCTGGGGCCAAGGCACCACGGTCACCGTCTCCTCA
 D  V  W  G  Q  G  T  T  V  T  V  S  S             (SEQ ID NO: 77)
 98  103                    110      113            (SEQ ID NO: 78)

FIG. 41A
```

```
        10         20         30         40         50         60         70         80         90        100
CAGGTCCAACTGGTGCAGTCTGGTTCTGAGCTGAAGAAGCCTGGGGCTTCAGTGAAGGTGTCCTGCAAGGCTTCTGGCTACACCTTCACCAGCAACTACA
 Q  V  Q  L  V  Q  S  G  S  E  L  K  K  P  G  A  S  V  K  L  S  C  K  A  S  G  Y  T  F  T  S  N  Y
                    10                  20                                    30

110        120        130        140        150        160        170        180        190        200
TAAACTGGGTGAAACAGCAGCCTGGACAGGGCCTTGAGTGGATTGGAAATATTTATCCTTCTGATGGTTTTACTAACTACAATCAAAAGTTCAAGGACAG
 I  N  W  V  K  Q  A  P  G  Q  G  L  E  W  I  G  N  I  Y  P  S  D  G  F  T  N  Y  N  Q  K  F  K  D  R
              40                                 50 52 52a                     60

210        220        230        240        250        260        270        280        290        300
GGCCACATTGACTGTAGACAAATCCACCAGCACAGCCTACATGGAGCTCAGCAGCCTGAGATCTGAGGACACCGCGGTCTATTACTGTACAAGAAACTTC
 A  T  L  T  V  D  K  S  T  S  T  A  Y  M  E  L  S  S  L  R  S  E  D  T  A  V  Y  Y  C  T  R  N  F
              70                           80   82 82a b  c                     90

310        320        330        340
GATGTTTGGGGCCAAGGGACCACGGTCACCGTCTCCTCA
 D  V  W  G  Q  G  T  T  V  T  V  S  S
 98 103              110              113

(SEQ ID NO: 79)
(SEQ ID NO: 80)
```

FIG. 41B

```
         10          20         30         40         50         60         70         80         90        100
CAGGTCCAACTGGTGCAGTCTGGGTCTGAGCTGAAGAAGCCTGGGGCTTCAGTGAAGCTGTCCTGCAAGGCTTCTGGCTACACCTTCACTAGCAACTACA
 Q  V  Q  L  V  Q  S  G  S  E  L  K  K  P  G  A  S  V  K  L  S  C  K  A  S  G  Y  T  F  T  S  N  Y
                         10                        20                        30

110         120        130        140        150        160        170        180        190        200
TAAACTGGGTGAGACAAGCTCCAGGACAGGGCCTTGAGTGGATGGAATGGATTGGACTTTATCCTTCTGATGGTTTTACTAACTACAATCAAAAGTTCAAGGACAG
 I  N  W  V  R  Q  A  P  G  Q  G  L  E  W  I  G  L  I  Y  P  S  D  G  F  T  N  Y  N  Q  K  F  K  D  R
                         40                        50   52 52a                       60

210         220        230        240        250        260        270        280        290        300
GGTGACATTGACTGTAGACAAATCCACCAGCACAGCCTACATGGAGCTCAGCAGCCTGAGATCTGAGGACACCGCGGTCTATTACTGTGTACAAGAAACTTC
 V  T  L  T  V  D  K  S  T  S  T  A  Y  M  E  L  S  S  L  R  S  E  D  T  A  V  Y  Y  C  T  R  N  F
                         70                        80  82 82a b  c                   90

310         320        330        340
GATGTTTGGGGCCAAGGGACCACCGGTCACCGTCTCCTCA
 D  V  W  G  Q  G  T  T  V  T  V  S  S
 98 103                   110         113
```

(SEQ ID NO: 81)
(SEQ ID NO: 82)

FIG. 41C

```
         10         20         30         40         50         60         70         80         90        100
CAGGTCCAACTGGTGCAGTCTGGGGCTGAAGTGAAGAAGCCTGGGAGCTCTGAGCTGAAGGTGTCCTGCAAGGCTTCTGGCTACACCTTCACCAGCAACTACA
 Q  V  Q  L  V  Q  S  G  A  E  L  K  K  P  G  S  S  E  L  K  V  S  C  K  A  S  G  Y  T  F  T  S  N  Y
              1               10                  20                            30

110        120        130        140        150        160        170        180        190        200
TAAACTGGGTGAGACAGGCCCCTGGACAGGGCCTTGAGTGGATTGGAAATATCTATCCTTCTGATGGTTTTACTAACAATACAAAGTTCAAGGACAG
 I  N  W  V  R  Q  A  P  G  Q  G  L  E  W  I  G  N  I  Y  P  S  D  G  F  T  N  N  T  K  F  K  D  R
                  40                                50  52 52a                              60

210        220        230        240        250        260        270        280        290        300
GGTGACAATCACTGTAGACAAATCCACCAGCACAGCCTACATGGAGCTTAGCAGCCTGAGATCTGAGGACACCGCGGTCTATTACTGTACAAGAAACTTC
 V  T  I  T  V  D  K  S  T  S  T  A  Y  M  E  L  S  S  L  R  S  E  D  T  A  V  Y  Y  C  T  R  N  F
       70                               80 82 82a b c         b c                        90

310        320        330        340
GATGTCTGGGGCCAAGGGACCACGGTCACCGTCTCCTCA
 D  V  W  G  Q  G  T  T  V  T  V  S  S
98 103              110             113
```

(SEQ ID NO: 83)
(SEQ ID NO: 84)

FIG. 41D

```
         10         20         30         40         50         60         70         80         90        100
CAGGTCCAACTGGTGCAGTCTGGAGCTGAAGAAGCCTGGGGCCTCAGTGAAGGTGTCCTGCAAGGCTTCTGGCTACACCTTCACCAGCAACTACA
 Q  V  Q  L  V  Q  S  G  S  E  L  K  K  P  G  A  S  V  K  V  S  C  K  A  S  G  Y  T  F  T  S  N  Y
                        10                        20                        30

110        120        130        140        150        160        170        180        190        200
TAAACTGGGTGAGACAGGCCCCTGGACAGGGCCTTGAGTGGATGGGAAATCTATCCTTCTGATGGTTTTACTAACTACAATCAAAAGTTCAAGGACAG
 I  N  W  V  R  Q  A  P  G  Q  G  L  E  W  M  G  N  L  Y  P  S  D  G  F  T  N  Y  N  Q  K  F  K  D  R
                        40                        50 52 52a                    60

210        220        230        240        250        260        270        280        290        300
GGTGACAATCACTGTAGACAAATCCACTAGCACAGCCTACATGGAGCTCAGCAGCCTGAGATCTGAGGACACCGCGGTCTATTACTGTGTACAAGAATTC
 V  T  I  T  V  D  K  S  T  S  T  A  Y  M  E  L  S  S  L  R  S  E  D  T  A  V  Y  Y  C  T  R  N  F
                        70                        80  82 82a b c              90

310        320        330        340
GATGTCTGGGGCCAAGGGACCACGGTCACCGTCTCCTCA              (SEQ ID NO: 85)
 D  V  W  G  Q  G  T  T  V  T  V  S  S                 (SEQ ID NO: 86)
 99 103              110          113

FIG. 41E
```

```
         10         20         30         40         50         60         70         80         90        100
GATGTTGTGATGACCCAATCTCCACTCTCCCTGCCTGTCAGTCTTGGAGATCAAGCCTCCATCTCTTGCAGATCTAGTCAGAGCCTTGTCCACAGTAATG
 D  V  V  M  T  Q  S  P  L  S  L  P  V  T  L  G  Q  P  A  S  I  S  C  R  S  S  Q  S  L  V  H  S  N 110        120        130        140        150        160        170        180        190        200
GAAACACCTATTTACAGTGGTACCTGCAGAAGCCAGGCCAGTCTCCACAGCTCCTGATCTACAAAGTTTCAACCAGTTTCTGGGGTCCCAGACAGGTT
 G  N  T  Y  L  Q  W  Y  L  Q  K  P  G  Q  S  P  Q  L  L  I  Y  T  V  S  N  R  F  S  G  V  P  D  R  F 210        220        230        240        250        260        270        280        290        300
CAGTGGCAGTGGATCAGGGACAGATTTCACACTCAAGATCAGCAGAGTGGAGGCTGAGGATCTGGGAGTTTATTTCTGCTCTCAAAGTACAAGTTCCT
 S  G  S  G  S  G  T  D  F  T  L  K  I  S  R  V  E  A  E  D  L  G  V  Y  F  C  S  Q  S  T  H  V  P 310        320        330
TTCACGTTCGGCTCAGGGACAAAGTTGGAAATAAAA                    (SEQ ID NO: 87)
 F  T  F  G  Q  G  T  K  L  E  I  K                      (SEQ ID NO: 88)
                        105 106a
100
```

FIG. 42A

```
         10         20         30         40         50         60         70         80         90        100
GATGTTGTGATGACCCAATCTCCACTCTCCCTGCCTGTCACTCTTGGACAGCCAGCCTCCATCTCTTGCAGATCTAGTCAGAGCCTTGTCCACAGTAATG
 D  V  V  M  T  Q  S  P  L  S  L  P  V  T  L  G  Q  P  A  S  I  S  C  R  S  S  Q  S  L  V  H  S  N 110        120        130        140        150        160        170        180        190        200
GAAACACCTATTTACAGTGGTACCTGCAGAAGCCAGGCCAGTCTCCACAGCTCCTGATCTACAAAGTTTCCAACCGATTTTCTGGGGTCCCAGACAGGTT
 G  N  T  Y  L  Q  W  Y  L  Q  K  P  G  Q  S  P  Q  L  L  I  Y  T  V  S  N  R  F  S  G  V  P  D  R  F 210        220        230        240        250        260        270        280        290        300
CAGTGGCAGTGGATCAGGGACCGATTTCACACTCAAGATCAGCAGAGTGGAGGCTGAGGATGTGGGAGTTTATTTCTGCTCTCAAAGTACACATGTTCCT
 S  G  S  G  S  G  T  D  F  T  L  K  I  S  R  V  E  A  E  D  V  G  V  Y  F  C  S  Q  S  T  H  V  P 310        320        330
TTCACGTTCGGCCAGGGGACCAAAGTTGGAAATAAAA              (SEQ ID NO: 89)
 F  T  F  G  Q  G  T  K  V  G  N  K                (SEQ ID NO: 90)
                         106 106a
```

FIG. 42B

```
        10         20         30         40         50         60         70         80         90        100
GATGTTGTGATGACCCAATCTCCACTCTCCCTGCCTGTCACTCTTGGACAGCCAGCCTCCATCTCTTGCAGATCTAGTCAGAGCCTTGTCCACAGTAATG
 D  V  V  M  T  Q  S  P  L  S  L  P  V  T  L  G  Q  P  A  S  I  S  C  R  S  S  Q  S  L  V  H  S  N
       110        120        130        140        150        160        170        180        190        200
GAAACACCTATTTACAGTGGTACCTGCAGAAGCCAGGCCAGTCTCCACAGCTCCTGATCTACAAAGTTTCCAACCGATTTTCTGGGGTCCCAGACAGGTT
 G  N  T  Y  L  Q  W  Y  L  Q  K  P  G  Q  S  P  Q  L  L  I  Y  T  V  S  N  R  F  S  G  V  P  D  R  F
       210        220        230        240        250        260        270        280        290        300
CAGTGGCAGTGGATCAGGGACAGATTTCACACTCAAGATCAGCAGAGTGGAGGCTGAGGATGTGGGAGTTTATTACTGCTCTCAAAGTACACATGTTCCT
 S  G  S  G  S  G  T  D  F  T  L  K  I  S  R  V  E  A  E  D  V  G  V  Y  Y  C  S  Q  S  T  H  V  P
       310        320        330
TTCACGTTCGGCCCAGGGGACAAAGTTGGAAATAAAA                              (SEQ ID NO: 91)
 F  T  F  G  Q  G  T  K  L  E  I  K                                (SEQ ID NO: 92)
                100         105 106a
```

FIG. 42C

```
          10         20         30         40         50         60         70         80         90        100
GAGGTTCAGCTGGTGCAGTCTGGAGCAGAGTTTAAGAAGCCAGGGGCCTCAGTCAAGTTGTCCTGCACAGTTTCTGGCTTCAACATTAAAGACTACTATA
 E  V  Q  L  V  Q  S  G  A  E  F  K  K  P  G  A  S  V  K  L  S  C  T  A  S  G  F  N  I  K  D  Y  Y
                                  10                          20                          30

110        120        130        140        150        160        170        180        190        200
TACACTGGGTGAAGCAGGCCCCTGGACAGGGCCTGGAGTGGATTGGATGGATTGATCCTGAGAATGGTGATATTGAATATGCCCCGAAGTTCCAGGGCAG
 Y  T  G  W  V  K  Q  A  P  G  Q  G  L  E  W  I  G  W  I  D  P  E  N  G  D  I  E  Y  A  P  K  F  Q  G  R
                40                          50    52 52a                    60

210        220        230        240        250        260        270        280        290        300
GGCCACTATGACTGCAGACACATCCAGTAACACAGCCTACCTGGAGTTCAGTAGCCTGAGATCTGAGGACACTGCCGTCTATTACTGTCTACCAAGAA
 A  T  M  T  A  D  T  S  S  N  T  A  Y  L  E  F  S  S  L  R  S  E  D  T  A  V  Y  Y  C  L  Y  Q  E
                            70                          80  82 82a b c                      90

310        320        330        340
GGCTCCTGGGGCCAAGGGACCACTGTCACAGTCTCCTCA       (SEQ ID NO: 93)
 G  S  W  G  Q  G  T  T  V  T  V  S  S          (SEQ ID NO: 94)
 98 103                       110      113

FIG. 43A
```

```
        10         20         30         40         50         60         70         80         90        100
GAGGTTCAGCTGGTGCAGTCTGGGGCAGAGGTGAAGAAGCCAGGGGCCTCAGTCAAGGTGTCCTGCACAGCTTCTGGCTTCTCAACATTAAAGACTACTATA
 E  V  Q  L  V  Q  S  G  A  E  V  K  K  P  G  A  S  V  K  L  S  C  T  A  S  G  F  N  I  K  D  Y  Y
                                  A                                                            M
                            1                                      20                        30

110        120        130        140        150        160        170        180        190        200
TACACTGGGTGAGGCAGGCACCAGGCCAGGGCCTGGAGTGGATTGGATGGATTGATCCTGAGAATGGTGATATTGAATATGCCCCGAAGTTCCAGGGCAG
 I  H  W  V  R  Q  A  P  G  Q  G  L  E  W  I  G  W  I  D  P  E  N  G  D  I  E  Y  A  P  K  F  Q  G  R
                      A                                            50 52 52a                           R
                   40                                                                 60

210        220        230        240        250        260        270        280        290        300
GGCCACTATGACTGCAGACACATCCACCAATACAGCCTACCTGGAGTTCAGCAGCCTGAGATCTGAGGACACTGCCGTCTATTACTGTCTCTACCAAGAA
 A  T  M  T  A  D  T  S  T  N  T  A  Y  L  E  F  S  S  L  R  S  E  D  T  A  V  Y  Y  C  L  Y  Q  E
                                                           82 82a  b  c                    R
              70                               80                                    90

310        320        330        340
GGCTCCTGGGGCCAAGGCACCACTGTCACAGTCTCCTCA
 G  S  W  G  Q  G  T  T  V  T  V  S  S             (SEQ ID NO: 95)
                        110              113        (SEQ ID NO: 96)
98 103
```

FIG. 43B

```
       10         20         30         40         50         60         70         80         90        100
GAGGTTCAGCTGGTGCAGTCTGGGGCTGAGGTGAAGAAGCCAGGGGCCTCAGTCAAGGTGTCCTGCACGGCTTCTGGCTTCAACATTAAAGACTACTATA
 E  V  Q  L  V  Q  S  G  A  E  V  K  K  P  G  A  S  V  K  V  S  C  T  A  S  G  F  N  I  K  D  Y  Y
                                 10                      20                      30

110        120        130        140        150        160        170        180        190        200
TACACTGGGTGAGGCAGGCCCCTGGACAGGGCCTGGAGTGGATGGATTGGATTGATCCTGAGAATGGTGATATTGAATATGCCCCGAAGTTCCAGGGCAG
 I  H  W  V  R  Q  A  P  G  Q  G  L  E  W  M  D  W  I  D  P  E  N  G  D  I  E  Y  A  P  K  F  Q  G  R
            40                      50    52 52a                         60

210        220        230        240        250        260        270        280        290        300
GGCCACTATCACTGCAGACACATCCACCAATACAGCCTACATGGAGTTCAGCAGCCTGAGATCTGAGGACACTGCCGTCTATTACTGTCTCTACCAAGAA
 A  T  I  T  A  D  T  S  T  N  T  A  Y  M  E  F  S  S  L  R  S  E  D  T  A  V  Y  Y  C  L  Y  Q  E
         70                      80  82 82a b  c                         90

310        320        330        340
GGCTCCTGGGGCCAAGGGACCACCACTGTCACAGTCTCCTCA              (SEQ ID NO: 97)
 G  S  W  G  Q  G  T  T  V  T  V  S  S                  (SEQ ID NO: 98)
 93 103              110            113
```

FIG. 43C

```
        10         20         30         40         50         60         70         80         90        100
GAGGTTCAGCTGGTGCAGTCTGGGGCAGTCTGGAGAGGTGAAGAAGCCAGGGGCCTCAGTCAAGGTGTCCTGCACAGTTTCTGGCTTCAACATTAAAGACTACTATA
 E  V  Q  L  V  Q  S  G  A  E  V  K  K  P  G  A  S  V  K  V  S  C  T  A  S  G  F  N  I  K  D  Y  Y
                              10                         20                         30

110        120        130        140        150        160        170        180        190        200
TACACTGGGTGAGGCAGGCAGGCCCCTGGACAGGGCCCTTGGAGTGGATTGGATGGATTGATCCTGAGAATGGTGATATTGAATATGCCCCGAAGTTCCAGGGCAG
 I  H  W  V  R  Q  A  P  G  Q  G  L  E  W  I  G  W  I  D  P  E  N  G  D  I  E  Y  A  P  K  F  Q  G  R
                  40                                          50   52 52a                   60

210        220        230        240        250        260        270        280        290        300
GGCCACTATCACTGCAGACACATCCACCGATACAGCCTACATGGAGTTCAGCAGCCTGAGATCTGAGGACACTGCCGTCTATTACTGTCTCTACCAAGAA
 A  T  I  T  A  D  T  S  T  D  T  A  Y  M  E  F  S  S  L  R  S  E  D  T  A  V  Y  Y  C  L  Y  Q  E
          70                              80   82 82a b  c                        90

310        320        330        340
GGCTCCTGGGGCCAAGGCACCACTCTCACAGTCTCCTCA
 G  S  W  G  Q  G  T  T  L  T  V  S  S
            98 103         110        113
```

(SEQ ID NO: 99)
(SEQ ID NO: 100)

FIG. 43D

```
        10         20         30         40         50         60         70         80         90        100
GAGGTCAGCTGGTGCAGTCTGGGGCAGGTGAAGAAGCCAGGGCAGTCCCTGAGACTCTCCTGTGCAGCGTCTGGATTCAACATTAAAGACTACTATA
 E  V  Q  L  V  Q  S  G  A  E  V  K  K  P  G  A  S  V  K  V  S  C  T  A  S  G  F  N  I  K  D  Y  Y
                            10                          20                          30

110        120        130        140        150        160        170        180        190        200
TACACTGGGTGAGGCAGGCCCCTGGACAGGGCCTGGAGTGGATTGGATGGATTGATCCTGAGAATGGTGATATTGAATATGCCCCGAAGTTCCAGGGCAG
 I  H  W  V  R  Q  A  P  G  Q  G  L  E  W  I  G  W  I  D  P  E  N  G  D  I  E  Y  A  P  K  F  Q  G  R
                   40                          50  52 52a  b  c                    60

210        220        230        240        250        260        270        280        290        300
GGTGACTATTACTGCAGACACATCCACCGATACAGCCTACATGGAGCTGAGCAGCCTGAGATCTGAGGACACTGCCGTCTATTACTGTCTCTACCAAGAA
 V  T  I  T  A  D  T  S  T  D  T  A  Y  M  E  L  S  S  L  R  S  E  D  T  A  V  Y  Y  C  L  Y  Q  E
                   70                          80  82 82a  b  c                    90

310        320        330        340
CGCTCCTGGGGCCAAGGCACCACTGTCACAGTCTCCTCA
 G  S  W  G  Q  G  T  T  V  T  V  S  S
 99 103                        110        113
```

(SEQ ID NO: 101)
(SEQ ID NO: 102)

FIG. 43E

```
        10         20         30         40         50         60         70         80         90        100
GATGTTGTGATGACCCAGTCTCCACTCTCCCTGCCCGTCACCCTTGGACAGCCGGCCTCCATCTCTTGCAGGTCTAGTCAAAGCCTCTTACAATAGTGATG
 D  V  V  M  T  Q  S  P  L  S  L  P  V  T  L  G  Q  P  A  S  I  S  C  R  S  S  Q  S  L  L  N  S  D
                              10                          20                          27 27a b c d e 110        120        130        140        150        160        170        180        190        200
GAAAGACATATTTGAATTGGTTGCAGCAGAGGCCAGGCCAGTCTCCAAGGCGCCTAATCTATTGGGTCTCTAAATTGGACTCTGGAGTCCCTGACAGGTT
 G  K  T  Y  L  N  W  L  Q  Q  R  P  G  Q  S  P  R  R  L  I  Y  L  V  S  K  L  D  S  G  V  P  D  R  F
                 30                          40                          50                          60

210        220        230        240        250        260        270        280        290        300
CACTGGCAGTGGATCAGGGACAGATTTCACACTGAAAATCAGCAGAGTGGAGGCTGAGGATGTGGGAGTTTATTATTGCTGGCAAGGTACACATTTTCCG
 T  G  S  G  T  D  F  T  L  K  I  S  R  V  E  A  E  D  V  G  V  Y  Y  C  W  Q  G  T  H  F  P
                 70                          80                          90

310        320        330
TTCACGTTCGGAGGGGGGACCAAGGTGGAAATCAAAA           (SEQ ID NO: 103)
 F  T  F  G  G  G  T  K  V  E  I  K              (SEQ ID NO: 104)
                100 106 106a
```

FIG. 44A

```
         10        20        30        40        50        60        70        80        90       100
GATGTTGTGATGACCCAGTCTCCACTCAGTCTTGCCTGTTACCCTGGGACAGCCTCCATCTCCTTGCAAGTCAAGTCAGAGCCTCCTAAATAGTGATG
 D  V  V  M  T  Q  S  P  L  S  L  P  V  T  L  G  Q  P  A  S  I  S  C  K  S  S  Q  S  L  L  N  S  D
                         10                      20                          27 27a b  c  d  e 110       120       130       140       150       160       170       180       190       200
GAAAGACATATTTGAATTGGTTGCAGAGGCCAGGCCAGAGCCTCCAAGCGCCTAATTATTATCGGTGTCTAAATTGGACTCTGGAGTCCCTGACAGGTT
 G  K  T  Y  L  N  W  L  Q  Q  R  P  G  Q  S  P  R  R  L  I  Y  L  V  S  K  L  D  S  G  V  P  D  R
 30                      40                              50                          60

210       220       230       240       250       260       270       280       290       300
CACTGGCAGTGGATCAGGGACAGATTTCACACTGAAAATCAGCAGAGTGGAGGCTGAGGATGTGGGAGTTTATTATTGCTGGCAAGGTACACATTTTCCG
 T  G  S  G  S  G  T  D  F  T  L  K  I  S  R  V  E  A  E  D  V  G  V  Y  Y  C  W  Q  G  T  H  F  P
                 70                          80                              90

310       320       330
TTCACGTTCGGAGGGGGGACCAAGGTGGAAATAAAA
 F  T  F  G  G  G  T  K  V  E  I  K              (SEQ ID NO: 105)
                 100         106 106a            (SEQ ID NO: 106)
```

FIG. 44B

```
        10         20         30         40         50         60         70         80         90        100
GATGTTGTGATGACCCAGTCTCCACTCAGTCTTGCCTGTTACCCTGGGACAACCAGCCTCCATCTCTTGCAAGTCAAGTCAGAGCCTCTTAAATAGTGATGATG
 D  V  V  M  T  Q  S  P  L  S  L  P  V  T  L  G  Q  P  A  S  I  S  C  K  S  S  Q  S  L  L  N  S  D
                         10                        20                        27 27a b c d e 110        120        130        140        150        160        170        180        190        200
GAAAGACATATTTGAATTGGTTGCAGAGAGCCAGGCCAGTCTCCAAGGCCTAATCTATCTGGTGTCTAAATTGGACTCTGGAGTCCCTGACAGGTT
 G  K  T  Y  L  N  W  L  Q  R  E  G  Q  S  P  R  R  L  I  Y  L  V  S  K  L  D  S  G  V  P  D  R  F
    30                        40                                  50                        60

210        220        230        240        250        260        270        280        290        300
CTCTGGCAGTGGATCAGGGACAGATTTCACACTGAAAATCAGCAGAGTGGAGGCTGAGGATGTGGGAGTTTATTATTGCTGGCAAGGTACACATTTTCCG
 S  G  S  G  T  D  F  T  L  K  I  S  R  V  E  A  E  D  V  G  V  Y  Y  C  W  Q  G  T  H  F  P
                         70                        80                                  90

310         320        330
TTCACGTTCGGAGGGGGGACCAAGGTGGAAATAAAA     (SEQ ID NO: 107)
 F  T  F  G  G  G  T  K  V  E  I  K       (SEQ ID NO: 108)
             100              106 106a

METHODS AND AGENTS FOR THE DIAGNOSIS AND TREATMENT OF HEPATOCELLULAR CARCINOMA

RELATED APPLICATIONS

This application is a continuation of U.S. application Ser. No. 13/126,734, filed Jul. 13, 2011, now U.S. Pat. No. 8,821, 880, which is the U.S. National Stage of International Application No. PCT/US2009/056382, filed Sep. 9, 2009, which designates the U.S., is published in English, and claims the benefit of U.S. Provisional Application No. 61/197,650, filed Oct. 29, 2008.

The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

File name: 42611001022SubstSeqList.txt; created Sep. 25, 2014; 102 KB in size.

BACKGROUND OF THE INVENTION

Hepatocellular carcinoma (HCC) is the most frequent primary malignancy of the liver and is the fifth most common cancer in humans worldwide. HCC also is the fourth leading cause of cancer-related death (Parkin D M, Bray F, Ferlay J, Pisani P. Estimating the world cancer burden: Globocan 2000. Int J Cancer 2001; 94: 153-156). In 1990, the World Health Organization estimated that there were about 430,000 new cases of liver cancer worldwide, and that a similar number of patients died that year as a result of this disease.

The pathogenesis of HCC has been associated with chronic hepatitis B virus (HBV) and hepatitis C virus (HCV) infections, as well as cirrhosis-inducing conditions of liver (Bruix J, et al. J Hepatol 35:421-430, 2001; Bruix J, et al. Cancer Cell 5:215-219, 2004). Accordingly, the incidence of HCC is highest in East Asian countries, such as China, Hong Kong, Taiwan, Korea, and Japan, where HBV and HCV infections are most prevalent (Bruix J, et al. Cancer Cell 5:215-219, 2004; Haskell C M. Chapter 46 Liver: Natural History, Diagnosis and Staging in "Cancer Treatment" 5$^{th}$ edition, W. B, Saunders Company, Philadelphia, editors: Haskell C M & Berek J S). However, the incidence of HCC in western countries is steadily increasing (Parkin D M, et al. Int J Cancer 94; 153-156, 2001). Over the past decade, in the United States, HCC displayed the second highest increase in incidence, and the highest increase in death rate, of all cancers (Ann Int Med 139:817-823, 2003). Thus, in the United States and throughout the world, HCC is a major cause of mortality and morbidity, and a significant economic burden due to hospital costs and loss of work by people with HCC.

Successful control of HCC requires correct diagnosis of the disease at an early stage of disease progression. However, distinguishing small HCC tumors from other malignant or non-malignant liver diseases, including metastatic tumors, cholangiocarcinoma, focal nodular hyperplasia, dysplastic and regenerating liver nodules, using current techniques, such as imaging studies, needle core biopsy and/or fine needle aspiration, has proven to be challenging (Ferrell L D, et al. Am J Surg Pathol 17:1113-1123, 1993; Horigome H, et al. Hepato-Gatroenterology 47:1659-1662, 2000; Kalar S, et al. Arch Pathol Lab Med 131:1648-1654, 2007; Seki S, et al. Clin Cancer Res 6:3460-3473, 2000). Moreover, attempts to treat HCC therapeutically have been largely unsuccessful (Bruix J, et al. J Hepatol 35:421-430, 2001; Bruix J, et al. Cancer Cell 5:215-219, 2004; Haskell C M. Chapter 46 Liver: Natural History, Diagnosis and Staging in "Cancer Treatment" 5$^{th}$ edition, W. B, Saunders Company, Philadelphia, editors: Haskell C M & Berek J S; Szklaruk J, et al. AJR 180:441-453, 2003). As a result, despite active therapy, the 5-year survival rate of patients with HCC in the U.S. is only 10.5%, which is second in magnitude only to pancreatic cancer (ACS Cancer Facts & Figures (2007)). Thus, there is an urgent need to identify a more reliable marker to differentiate HCC from other liver pathologies and facilitate early detection of this disease. In addition, there is an urgent need to develop new and more-effective therapeutic agents for the treatment of HCC.

SUMMARY OF THE INVENTION

The present invention, in one embodiment, relates to a humanized antibody that specifically binds human Plasmalemma Vesicle-Associated Protein (PLVAP), wherein the antibody comprises at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, SEQ ID NO:102 and a combination thereof; and at least one kappa light chain amino acid sequence selected from the group consisting of SEQ ID NO:60, SEQ ID NO:62, SEQ ID NO:64, SEQ ID NO:104, SEQ ID NO:106, SEQ ID NO:108 and a combination thereof.

In another embodiment, the invention relates to a humanized antibody that specifically binds human PLVAP, wherein the antibody comprises at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, SEQ ID NO:86 and a combination thereof; and at least one kappa light chain amino acid sequence selected from the group consisting of SEQ ID NO:70, SEQ ID NO:72, SEQ ID NO:88, SEQ ID NO:90, SEQ ID NO:92 and a combination thereof.

In another embodiment, the invention provides a pharmaceutical composition comprising at least one humanized antibody that specifically binds a PLVAP protein (e.g., a human PLVAP protein). In another embodiment, the pharmaceutical composition further comprises a second therapeutic agent, such as a chemotherapeutic agent.

In a further embodiment, the invention relates to an isolated polypeptide that specifically binds human PLVAP, comprising at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, SEQ ID NO:102 and a combination thereof and at least one kappa light chain amino acid sequence selected from the group consisting of SEQ ID NO:60, SEQ ID NO:62, SEQ ID NO:64, SEQ ID NO:104, SEQ ID NO:106, SEQ ID NO:108 and a combination thereof. In another embodiment, the polypeptide is a chimeric antibody.

In an additional embodiment, the invention provides an isolated polypeptide that specifically binds human PLVAP, comprising at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, SEQ ID NO:86 and a combination thereof and at least one kappa light chain amino acid sequence selected from the group consisting of SEQ ID NO:70, SEQ ID NO:72, SEQ ID NO:88, SEQ ID NO:90, SEQ ID NO:92 and a combination thereof. In another embodiment, the polypeptide is a chimeric antibody.

In other embodiments, the invention relates to murine hybridoma KFCC-GY4 (ATCC Patent Deposit Designation PTA-9963), cells thereof, and antibodies produced by murine hybridoma KFCC-GY4.

In yet other embodiments, the invention relates to murine hybridoma KFCC-GY5 (ATCC Patent Deposit Designation PTA-9964), cells thereof, and antibodies produced by murine hybridoma KFCC-GY5.

In yet another embodiment, the invention relates to a method of treating hepatocellular carcinoma (HCC) in a subject in need thereof, comprising administering to the subject a therapeutically effective amount of a humanized antibody that specifically binds PLVAP. In a particular embodiment, the antibody is administered to the subject by intra-arterial infusion (e.g., hepatic arterial infusion, transarterial chemoembolization) and can inhibit tumor formation, tumor growth, tumor vascularization or tumor progression in the liver of the subject. In another embodiment, the PLVAP antagonist is administered in combination with a second therapeutic agent, such as a chemotherapeutic agent.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3B is a graph depicting PLVAP gene expression intensities in 18 paired HCC (PHCC) and adjacent non-tumorous liver tissue (PN) samples as determined by microarray analysis. PLVAP transcript levels were higher in HCC than in adjacent non-tumorous liver tissue from each individual for all individuals tested except one.

FIGS. 4A and 4B show the nucleotide sequence (SEQ ID NO:1) and the deduced amino acid sequence (SEQ ID NO:2) of the His-tagged human PLVAP$_{51-442}$ protein recombinant fusion protein used to generate mouse anti-PLVAP polyclonal antisera.

FIGS. 8C and 8D; and FIGS. 8E and 8F. PLVAP protein, which appears as a brown stain (arrows) in the HCC images, was detected only in capillary endothelial cells of hepatocellular carcinomas (FIGS. 8A, 8C, and 8E). No detectable PLVAP was present in non-tumorous liver tissue (FIGS. 8B, 8D, and 8F).

FIGS. 9A and 9B and FIGS. 9C and 9D show paired tissue samples of HCC and adjacent non-tumorous liver tissue. PLVAP protein, which appears as a brown stain (arrows) in the HCC images, was detected only in capillary endothelial cells of hepatocellular carcinomas (FIGS. 9A, 9C, 9E and 9F). No detectable PLVAP was present in non-tumorous liver tissue (FIGS. 9B and 9D).

FIGS. 10A-10F are images showing sections of formalin-fixed focal nodular hyperplasia tissues from six different patients that were stained immunohistochemically using anti-PLVAP polyclonal antisera to detect localization of PLVAP protein. PLVAP protein was not detected in endothelial cells lining the vascular sinusoids/capillary of non-tumorous liver tissues of focal nodular hyperplasia. Some positive staining (dark gray) was noted in epithelial cells of bile ducts (FIGS. 10A, 10D and 10F) and vessels of portal tracts (FIGS. 10D and 10F), but not in the endothelial cells of liver parenchyma. The positive staining of bile duct epithelial cells was due to binding of non-specific antibodies in the PLVAP antiserum.

FIGS. 12A and 12B are images showing sections of formalin-fixed tissue from two patients with chronic active hepatitis B that were stained immunohistochemically with anti-PLVAP polyclonal antiserum. PLVAP protein was not detected in endothelial cells lining the vascular sinusoids/capillary of non-tumorous liver tissues from chronic hepatitis B patients.

FIG. 15A shows the nucleotide gene (top) (SEQ ID NO:3) and deduced amino acid (middle) (SEQ ID NO:4) sequences of the $V_H$ domain of monoclonal antibody KFCC-GY4. The sequence of amino acid residues in CDRs 1 (SEQ ID NO:5), 2 (SEQ ID NO:6) and 3 (SEQ ID NO:7) also are indicated (bottom).

FIG. 15B shows the nucleotide gene (top) (SEQ ID NO:8) and deduced amino acid (middle) (SEQ ID NO:9) sequences of the $V_L$ domain of monoclonal antibody KFCC-GY4. The sequence of amino acid residues in CDRs 1 (SEQ ID NO:10), 2 (SEQ ID NO:11) and 3 (SEQ ID NO:12) also are indicated (bottom).

FIG. 16A shows the nucleotide gene (top) (SEQ ID NO:13) and deduced amino acid (middle) (SEQ ID NO:14) sequences of the $V_H$ domain of monoclonal antibody KFCC-GY5. The sequence of amino acid residues in CDRs 1 (SEQ ID NO:15), 2 (SEQ ID NO:16) and 3 (SEQ ID NO:17) also are indicated (bottom).

FIG. 16B shows the nucleotide gene (top) (SEQ ID NO:18) and deduced amino acid (middle) (SEQ ID NO:19) sequences of the $V_L$ domain of monoclonal antibody KFCC-GY5. The sequence of amino acid residues in CDRs 1 (SEQ ID NO:20), 2 (SEQ ID NO:21) and 3 (SEQ ID NO:22) also are indicated (bottom).

FIG. 20A is a fluorescence micrograph depicting immunofluorescence staining of human vascular endothelial cells (HUVEC) with control normal mouse IgG. Nuclei were stained with 4',6-diamidino-2-phenylindole (DAPI). Magnification=600×.

FIG. 20B is a fluorescence micrograph depicting immunofluorescence staining of human vascular endothelial cells (HUVEC) with monoclonal antibody to von Willebrand factor (VWF). VWF is a positive marker for human vascular endothelial cells. Nuclei were stained with 4',6-diamidino-2-phenylindole (DAPI). Magnification=600×.

FIG. 20C is a fluorescence micrograph depicting immunofluorescence staining of human vascular endothelial cells (HUVEC) with KFCC-GY4 monoclonal antibody to PLVAP. KFCC-GY4 monoclonal anti-PLVAP antibodies reacted positively with human vascular endothelial cells. Nuclei were stained with 4',6-diamidino-2-phenylindole (DAPI). Magnification=600×.

FIG. 20D is a fluorescence micrograph depicting immunofluorescence staining of human vascular endothelial cells (HUVEC) with KFCC-GY5 monoclonal antibody to PLVAP. KFCC-GY5 monoclonal anti-PLVAP antibodies reacted positively with human vascular endothelial cells. Nuclei were stained with 4',6-diamidino-2-phenylindole (DAPI). Magnification=600×.

FIGS. 22A-22H are light micrographs of sections of hepatoma tissues (FIGS. 22A, 22C, 22E, and 22G) and adjacent non-tumorous liver tissues (FIGS. 22B, 22D, 22F, and 22H) from four different randomly selected hepatoma patients. The sections were stained with KFCC-GY5 monoclonal anti-PLVAP antibodies. PLVAP signal (gray stain) was detected in vascular endothelial cells of hepatoma tissue, but not in vascular endothelial cells non-tumorous liver tissue. Magnification is 100×. FIGS. 22A and 22B, 22C and 22D, 22E and 22F, and 22G and 22H represent the four sets of paired hepatoma and non-tumorous liver tissues.

Figure 23A:
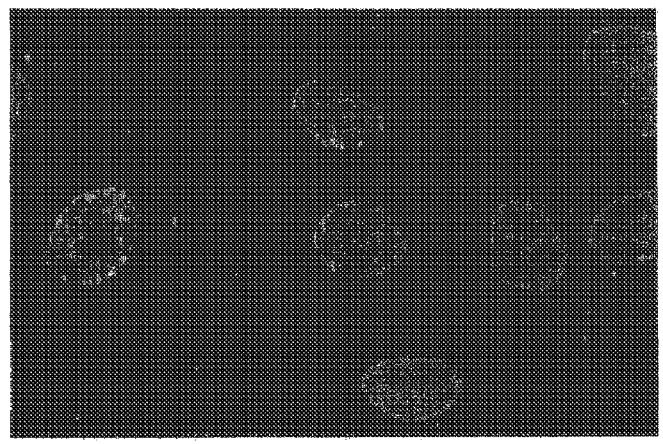

FIG. 23A is a fluorescence micrograph depicting human vascular endothelial cells (HUVECs) that were stained with control mouse IgG. Nuclei were stained with 4′,6-diamidino-2-phenylindole (DAPI).

Figure 23B:
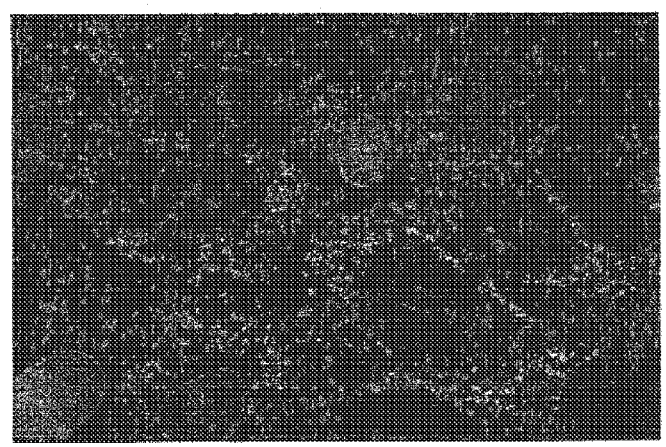

FIG. 23B is a fluorescence micrograph depicting human vascular endothelial cells (HUVECs) that were stained with KFCC-GY4 monoclonal antibody to PLVAP. KFCC-GY4 monoclonal anti-PLVAP antibodies reacted positively with the surfaces of the human vascular endothelial cells. Nuclei were stained with 4′,6-diamidino-2-phenylindole (DAPI).

Figure 23C:
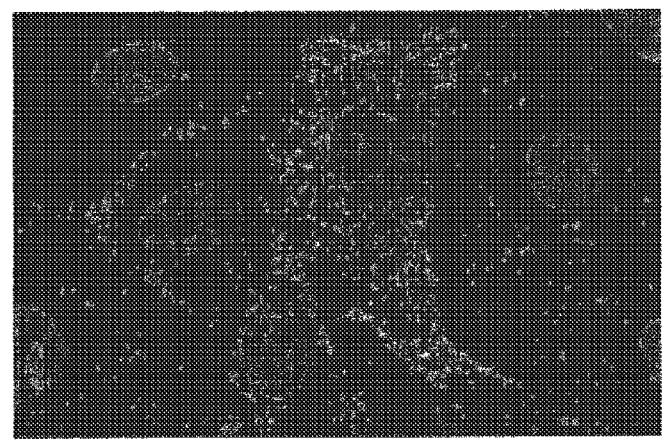

FIG. 23C is a fluorescence micrograph depicting human vascular endothelial cells (HUVECs) that were stained with KFCC-GY5 monoclonal antibody to PLVAP. KFCC-GY5 monoclonal anti-PLVAP antibodies reacted positively with the surfaces of the human vascular endothelial cells. Nuclei were stained with 4′,6-diamidino-2-phenylindole (DAPI).

FIG. 24 shows the amino acid sequence of human PLVAP protein (GENBANK® Accession No. NP_112600; SEQ ID NO:23).

FIGS. 25A and 25B show the nucleotide sequence of full-length human PLVAP cDNA (GENBANK® Accession No. NM_031310; SEQ ID NO:24).

FIG. 26 is a table indicating PLVAP expression in vascular endothelial cells in various normal tissues and organs in humans and two non-human primates, as determined by immunohistochemistry using KFCC-GY4 and Gy5 antibodies.

Figure 2:
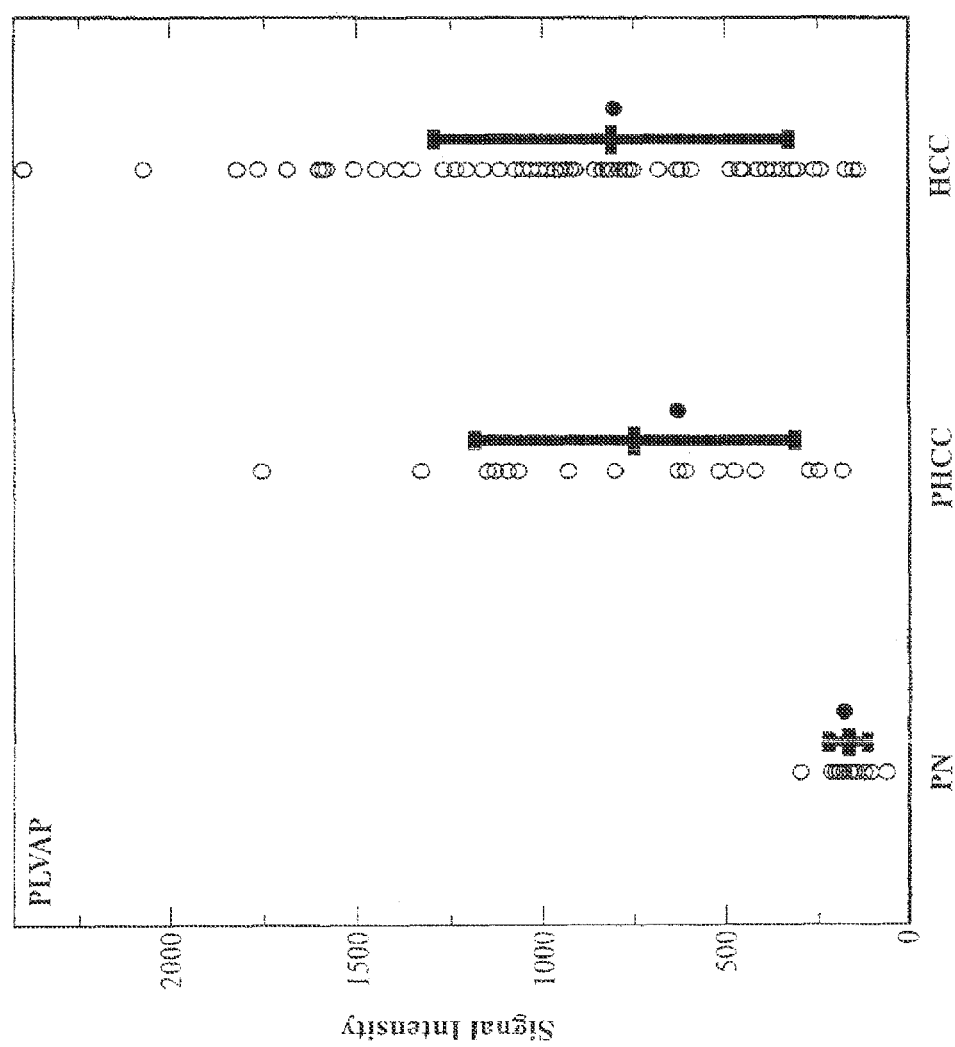
FIG. 2 is a graph depicting PLVAP gene expression intensities in paired HCC (PHCC) and adjacent non-tumorous liver tissue (PN) samples (n=18), as well as unpaired HCC samples (n=82) as determined by mRNA transcript profiling using Affymetrix gene chips.
Figure 27A:
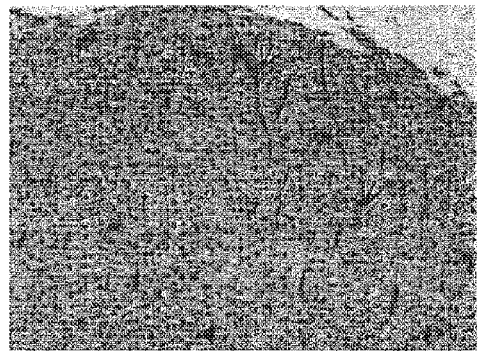
Figure 27B:
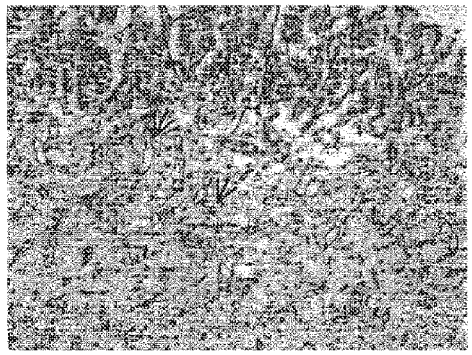
Figure 27C:
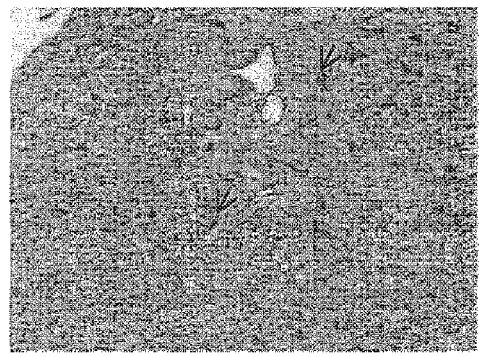
Figure 27D:
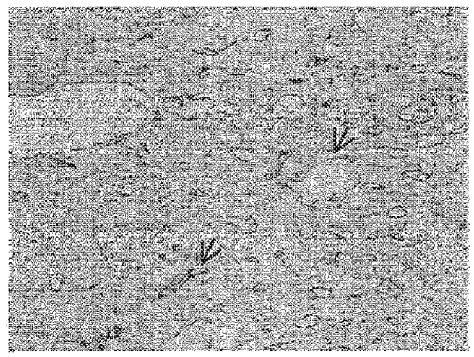
Figure 27E:
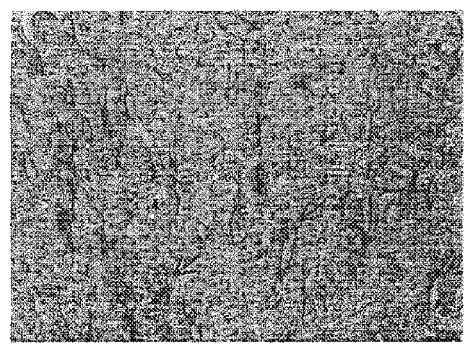
Figure 27F:
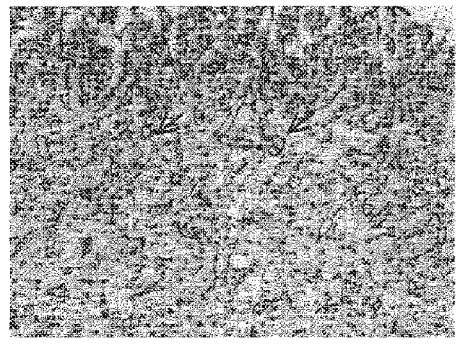

FIGS. 27A-27F2 show normal human and monkey tissues that were immunohistochemically stained with KFCC-GY4, KFCC-GY5 and anti-CD34 monoclonal antibodies (mAbs). Arrows point to capillary endothelial cells that express PLVAP in the respective tissues.

FIG. 27A shows a section of human adrenal gland tissue that has been stained with the KFCC-GY4 mAb. FIG. 27B shows a section of human adrenal gland tissue that has been stained with the anti-human CD34 mAb, which recognizes CD34, a marker for endothelial cells. FIG. 27C shows a section of adrenal gland tissue from cynomolgus monkey that has been stained with the KFCC-GY4 mAb. FIG. 27D shows a section of adrenal gland tissue from rhesus monkey that has been stained with the KFCC-GY4 mAb.

Figure 27G:
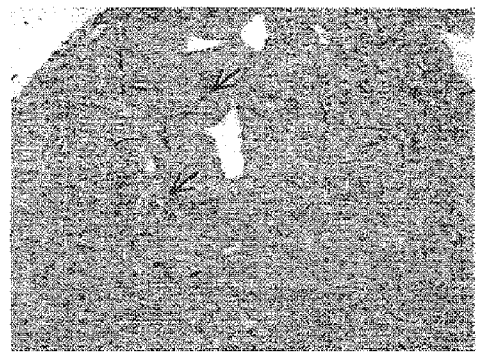
Figure 27H:
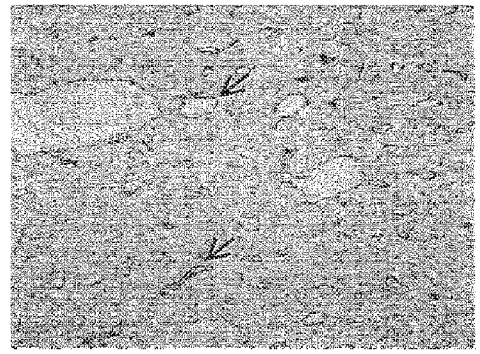

FIG. 27E shows a section of human adrenal gland tissue that has been stained with the KFCC-GY5 mAb. FIG. 27F shows a section of human adrenal gland tissue that has been stained with the anti-human CD34 mAb, which recognizes CD34, a marker for endothelial cells. FIG. 27G shows a section of adrenal gland tissue from cynomolgus monkey that has been stained with the KFCC-GY5 mAb. FIG. 27H shows a section of adrenal gland tissue from rhesus monkey that has been stained with the KFCC-GY5 mAb.

Figure 27I:
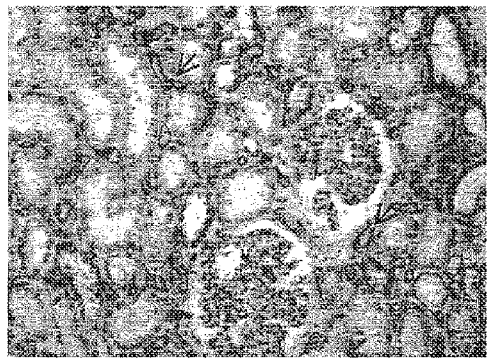
Figure 27J:
Figure 27K:
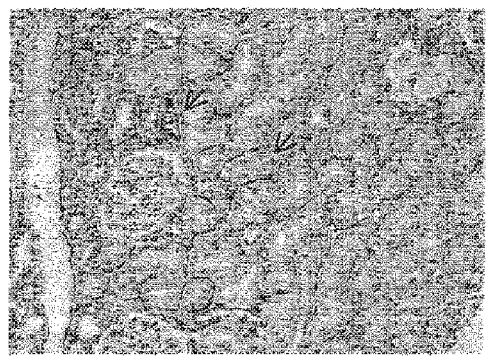
Figure 27L:
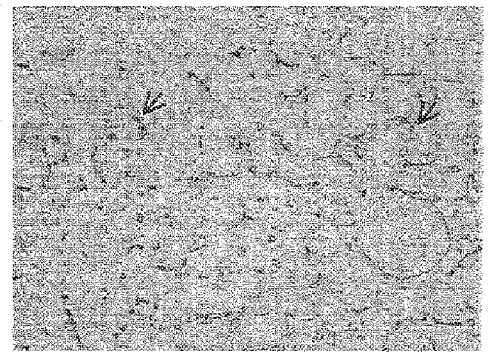

FIG. 27I shows a section of human kidney tissue that has been stained with the KFCC-GY4 mAb. FIG. 27J shows a section of human kidney tissue that has been stained with the anti-human CD34 mAb, which recognizes CD34, a marker for endothelial cells. FIG. 27K shows a section of kidney tissue from cynomolgus monkey that has been stained with the KFCC-GY4 mAb. FIG. 27L shows a section of kidney tissue from rhesus monkey that has been stained with the KFCC-GY4 mAb. KFCC-GY4 mAb stains capillary endothelial cells between renal tubules and does not stain endothelial cells in glomeruli. In contrast, Anti-CD34 antibody stains positively capillary endothelial cells between renal tubules and in glomeruli.

Figure 27M:
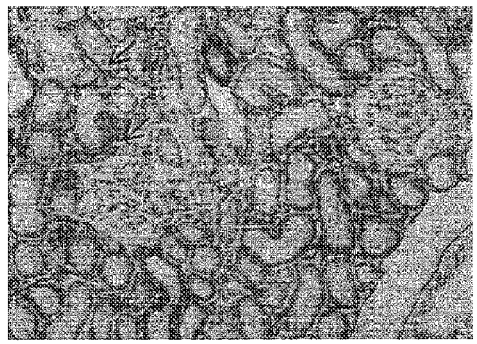
Figure 27N:
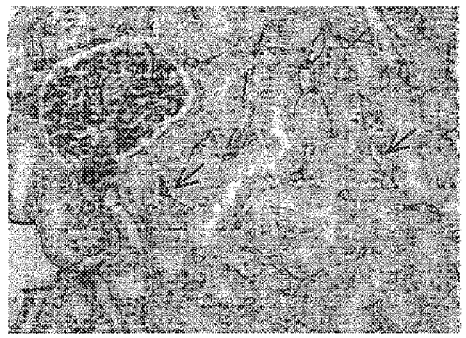
Figure 27O:
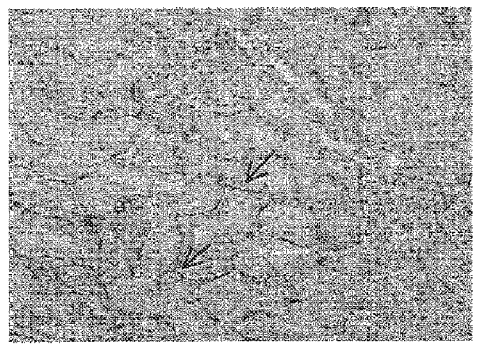
Figure 27P:
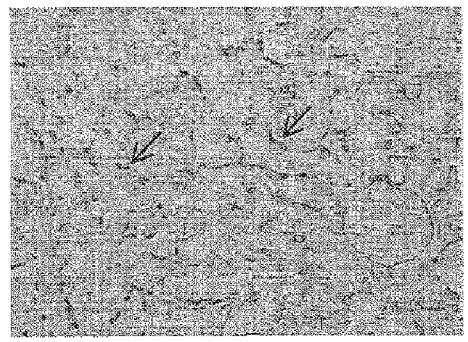

FIG. 27M shows a section of human kidney tissue that has been stained with the KFCC-GY5 mAb. FIG. 27N shows a section of human kidney tissue that has been stained with the anti-human CD34 mAb, which recognizes CD34, a marker for endothelial cells. FIG. 27O shows a section of kidney tissue from cynomolgus monkey that has been stained with the KFCC-GY5 mAb. FIG. 27P shows a section of kidney tissue from rhesus monkey that has been stained with the KFCC-GY5 mAb. Like KFCC-GY4 mAb, KFCC-GY5 mAb stains capillary endothelial cells between renal tubules and does not stain endothelial cells in glomeruli. In contrast, Anti-CD34 antibody stains positively capillary endothelial cells between renal tubules and in glomeruli.

Figure 27Q:
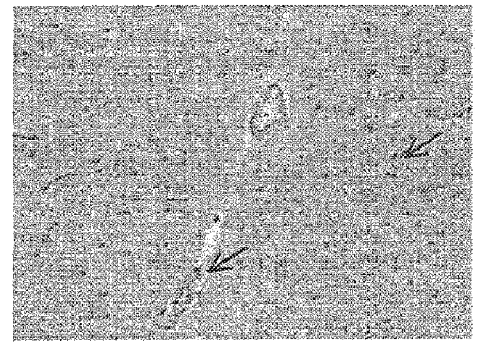
Figure 27R:
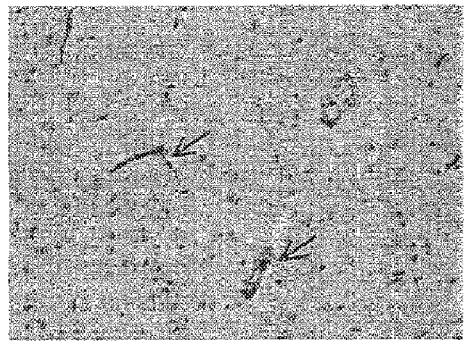
Figure 27S:
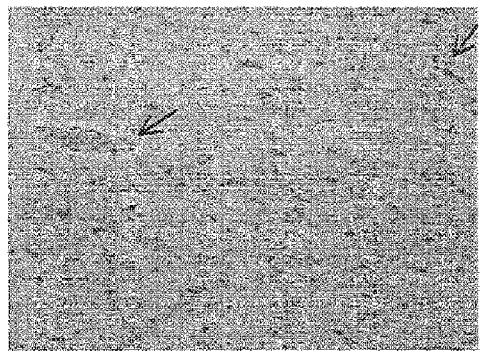
Figure 27T:
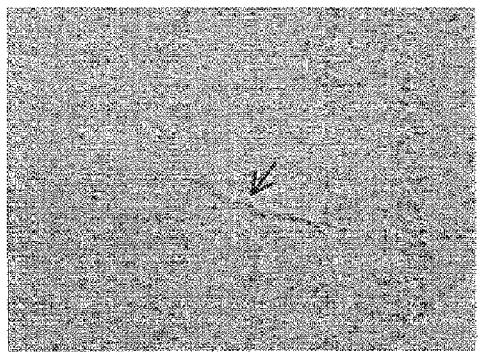

FIG. 27Q shows a section of human brain tissue that has been stained with the KFCC-GY4 mAb. FIG. 27R shows a section of human brain tissue that has been stained with the anti-human CD34 mAb, which recognizes CD34, a marker for endothelial cells. Vascular endothelial cells of brain stained positively for CD34 endothelial marker (arrows). FIG. 27S shows a section of brain tissue from cynomolgus monkey that has been stained with the KFCC-GY4 mAb. FIG. 27T shows a section of brain tissue from rhesus monkey that has been stained with the KFCC-GY4 mAb. Both human and monkey brain endothelial cells do not express PLVAP.

Figure 27U:
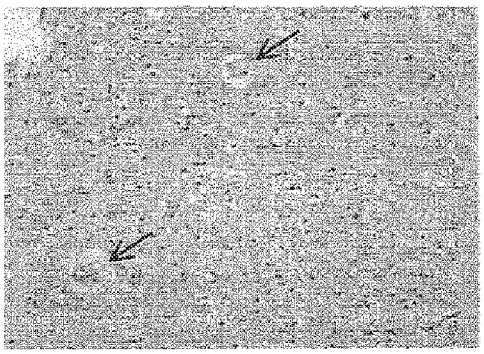
Figure 27V:
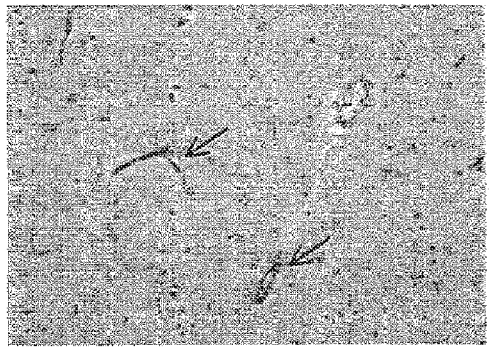
Figure 27W:
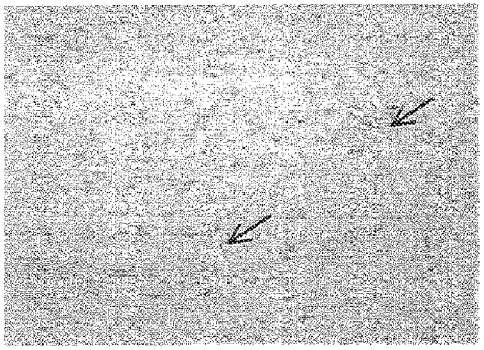
Figure 27X:
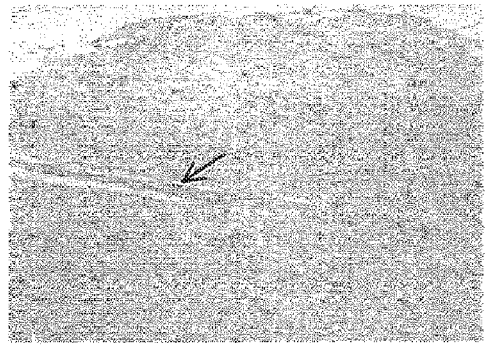

FIG. 27U shows a section of human brain tissue that has been stained with the KFCC-GY5 mAb. FIG. 27V shows a section of human brain tissue that has been stained with the anti-human CD34 mAb, which recognizes CD34, a marker for endothelial cells. Vascular endothelial cells of brain are stained positively for CD34 endothelial marker (arrows). FIG. 27W shows a section of brain tissue from cynomolgus monkey that has been stained with the KFCC-GY5 mAb. FIG. 27X shows a section of brain tissue from rhesus monkey that has been stained with the KFCC-GY5 mAb. Both human and monkey brain endothelial cells do not express PLVAP.

Figure 27Y:
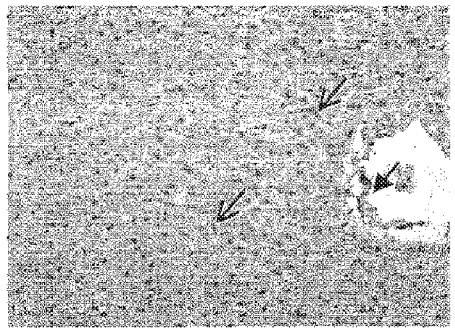
Figure 27Z:
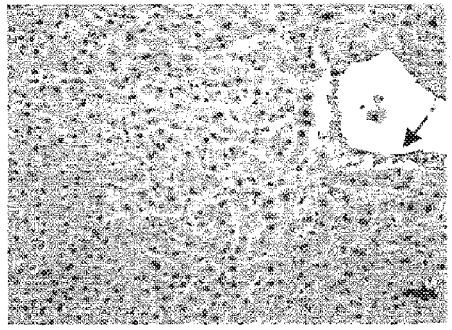

FIG. 27Y shows a section of human liver tissue that has been stained with the KFCC-GY4 mAb. FIG. 27Z shows a section of human liver tissue that has been stained with the anti-human CD34 mAb, which recognizes CD34, a marker for endothelial cells. Vascular endothelial cells of brain stained positively for CD34 endothelial marker (arrows). FIG. 27A2 shows a section of liver tissue from cynomolgus monkey that has been stained with the KFCC-GY4 mAb. FIG. 27B2 shows a section of liver tissue from rhesus monkey that has been stained with the KFCC-GY4 mAb. KFCC-GY4 mAb does not react with endothelial cells of liver sinusoid (thin arrows) and central vein (thick arrows) in human, cynomolgus monkey and rhesus monkey.

FIG. 27C2 shows a section of human liver tissue that has been stained with the KFCC-GY5 mAb. FIG. 27D2 shows a section of human liver tissue that has been stained with the anti-human CD34 mAb, which recognizes CD34, a marker for endothelial cells. Vascular endothelial cells of brain stained positively for CD34 endothelial marker (arrows). FIG. 27E2 shows a section of liver tissue from cynomolgus monkey that has been stained with the KFCC-GY4 mAb. FIG. 27F2 shows a section of liver tissue from rhesus monkey that has been stained with the KFCC-GY5 mAb. KFCC-GY5 mAb does not react with endothelial cells of liver sinusoid (thin arrows) and central vein (thick arrows) in human, cynomolgus monkey and rhesus monkey.

Figures 28A, 28B, 28C, 28D:
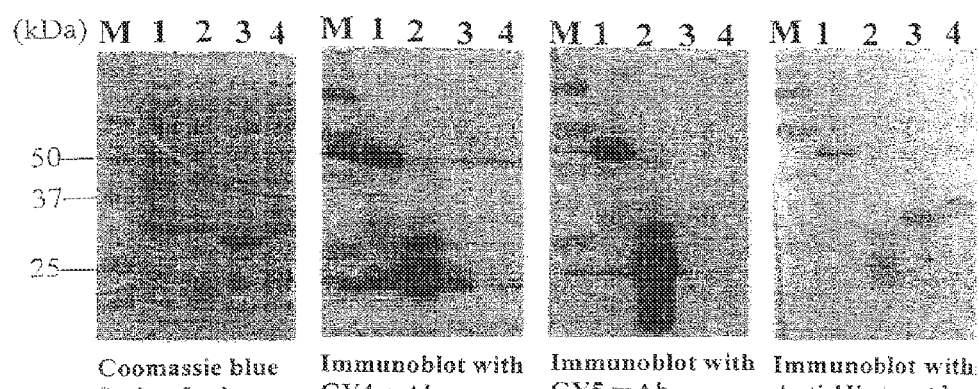

FIG. 28A shows a Coomassie blue-stained SDS-PAGE gel of total protein extract from $1\times10^8$ E. coli expressing His-tagged PLVAP51-442 (Lane 1); His-tagged PLVAP282-442 (Lane 2); His-tagged PLVAP51-292 (Lane 3); or His-tagged CEACAM6 (Lane 4). Molecular weight protein standards are resolved in Lane M.

FIG. 28B shows an immunoblot that was probed with mouse KFCC-GY4 mAb to detect PLVAP proteins in total protein extract from $1\times10^8$ E. coli expressing His-tagged PLVAP51-442 (Lane 1); His-tagged PLVAP282-442 (Lane 2); His-tagged PLVAP51-292 (Lane 3); or His-tagged CEACAM6 (Lane 4). Molecular weight protein standards are resolved in Lane M.

FIG. 28C shows an immunoblot that was probed with mouse KFCC-GY5 mAb to detect PLVAP proteins in total protein extract from $1\times10^8$ E. coli expressing His-tagged PLVAP51-442 (Lane 1); His-tagged PLVAP282-442 (Lane 2); His-tagged PLVAP51-292 (Lane 3); or His-tagged CEACAM6 (Lane 4). Molecular weight protein standards are resolved in Lane M.

FIG. 28D shows an immunoblot that was probed with anti-His tag antibody to detect His-tagged PLVAP proteins in total protein extract from $1\times10^8$ E. coli expressing His-tagged PLVAP51-442 (Lane 1); His-tagged PLVAP282-442 (Lane 2); His-tagged PLVAP51-292 (Lane 3); or His-tagged CEACAM6 (Lane 4). Molecular weight protein standards are resolved in Lane M.

Figure 29:
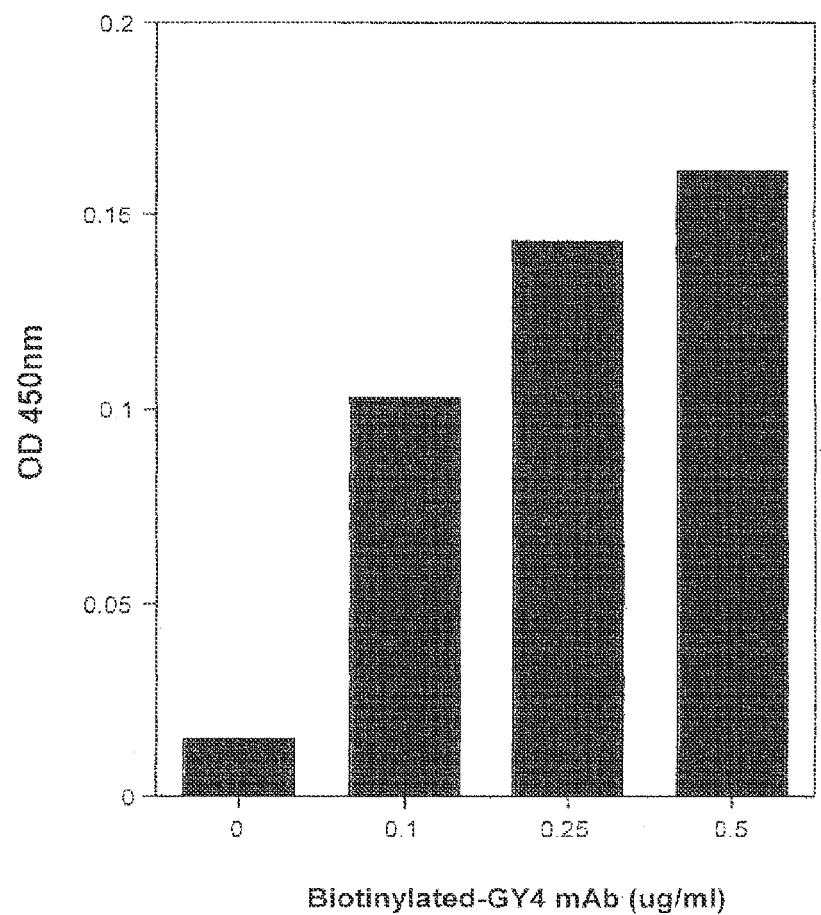

FIG. 29 is a bar graph showing binding of KFCC-GY4 monoclonal antibody (mAb) to PLVAP that was captured first by KFCC-GY5 mAb. ELISA was used for the study. Each value is a mean of duplicates.

Figure 30:
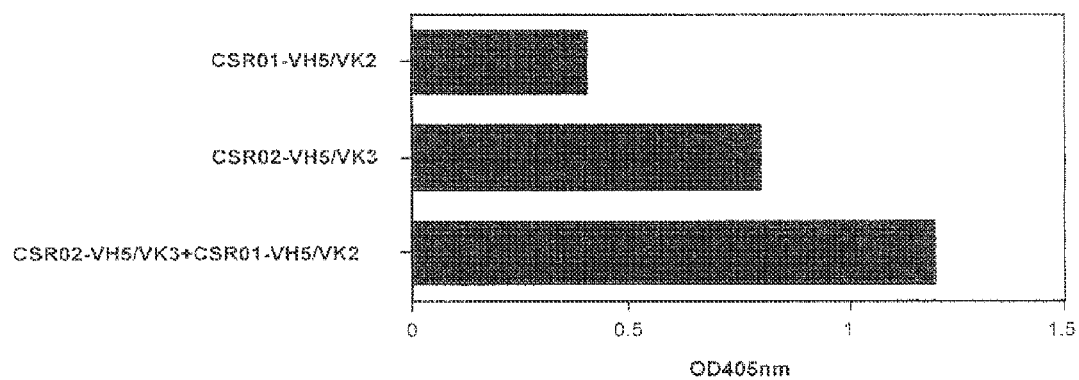

FIG. 30 is a bar graph depicting additive binding of fully humanized composite monoclonal antibodies derived from KFCC-GY4 (CSR01-VH5NK2) and KFCC-GY5 (CAS02-VH5NK3) to PLVAP protein. The values are an average of duplicates.

Figure 31:
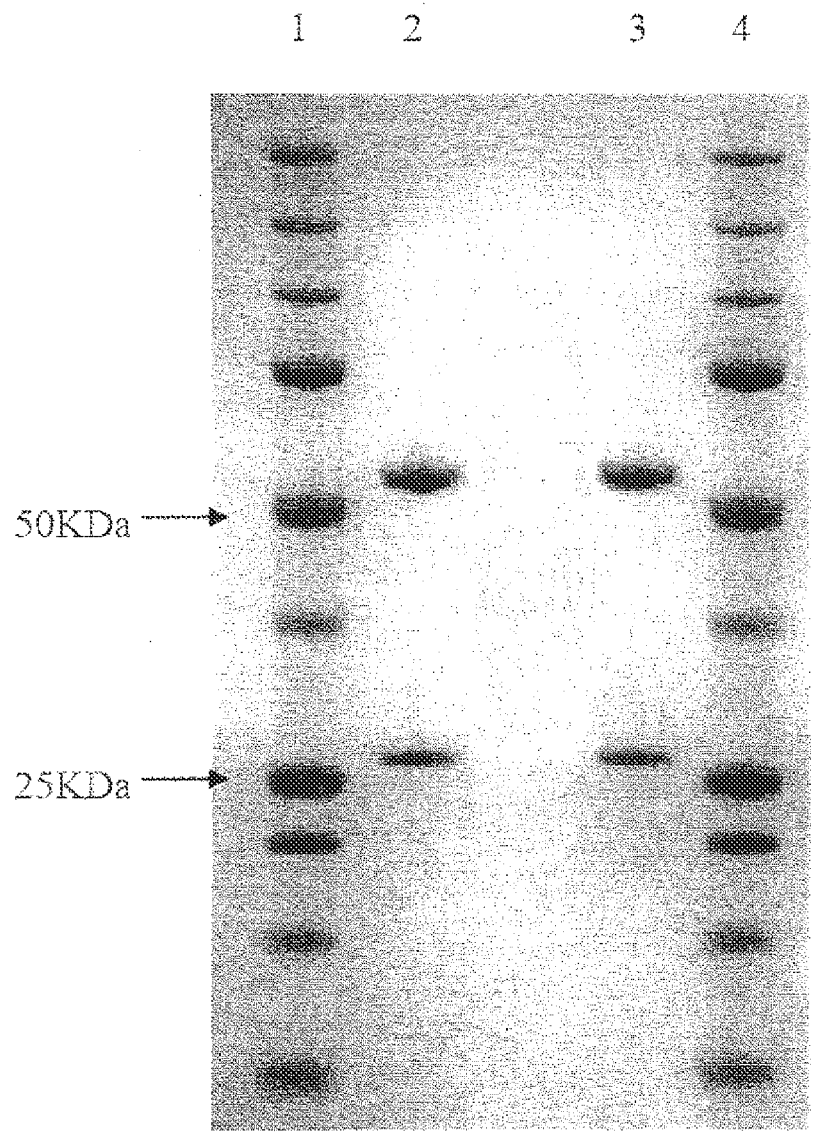
Figures 2, 32A:
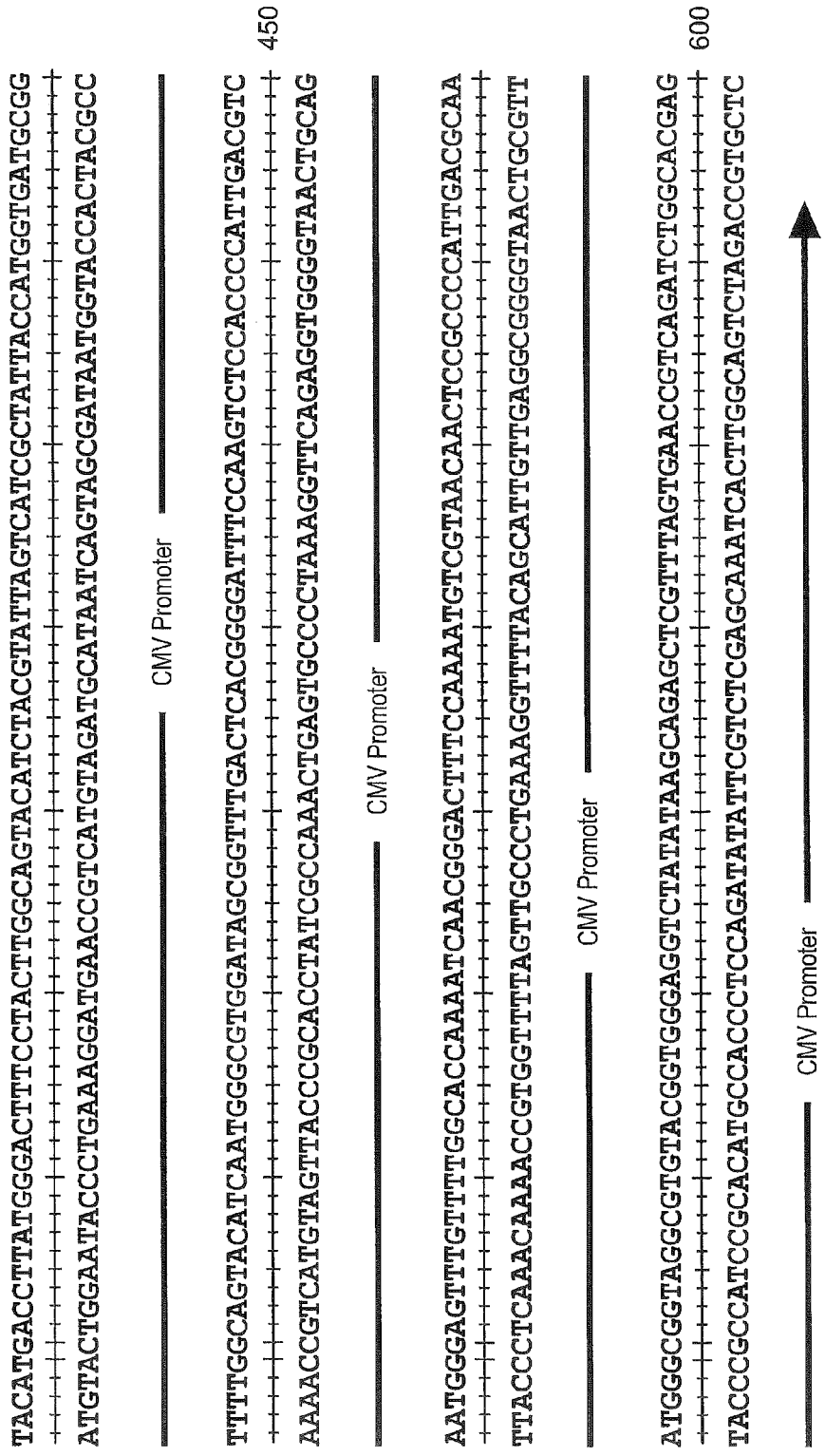
Figures 1, 32F:
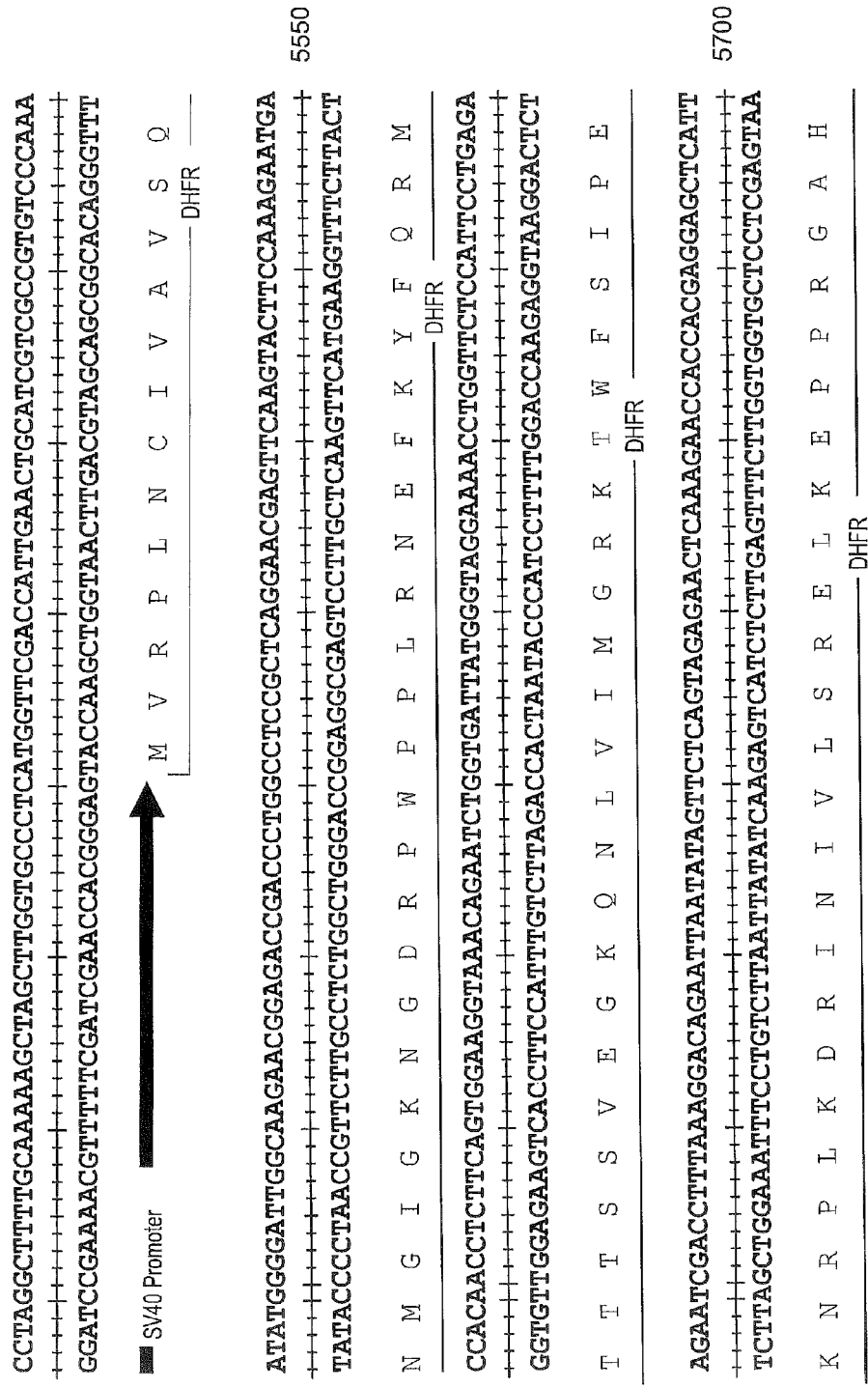
Figures 2, 33A:
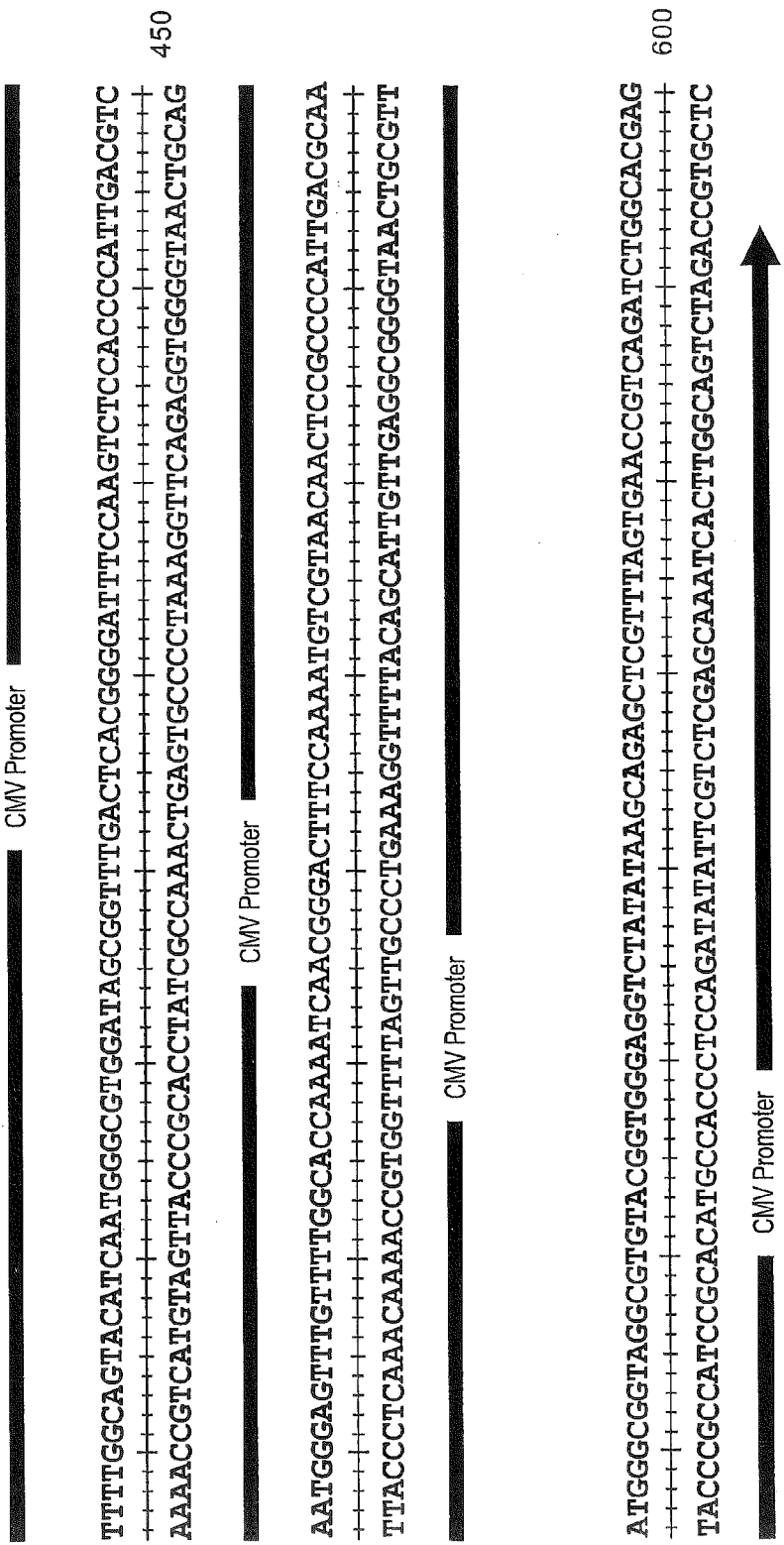
Figures 2, 34A:
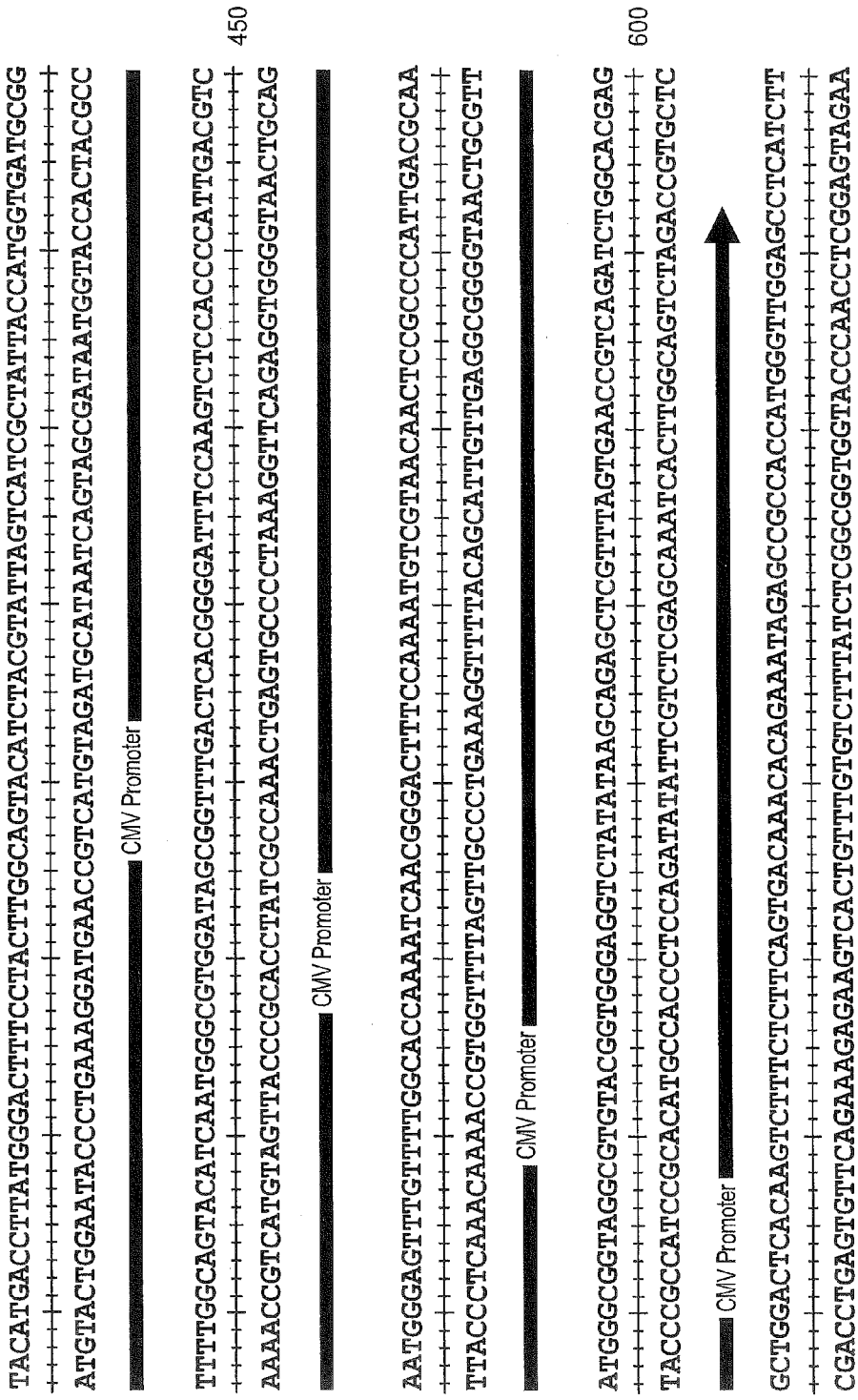
Figures 5, 34D:
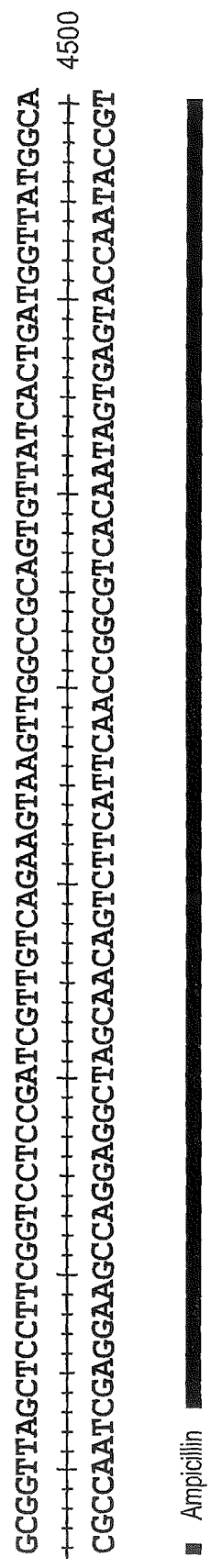
Figures 2, 34E:
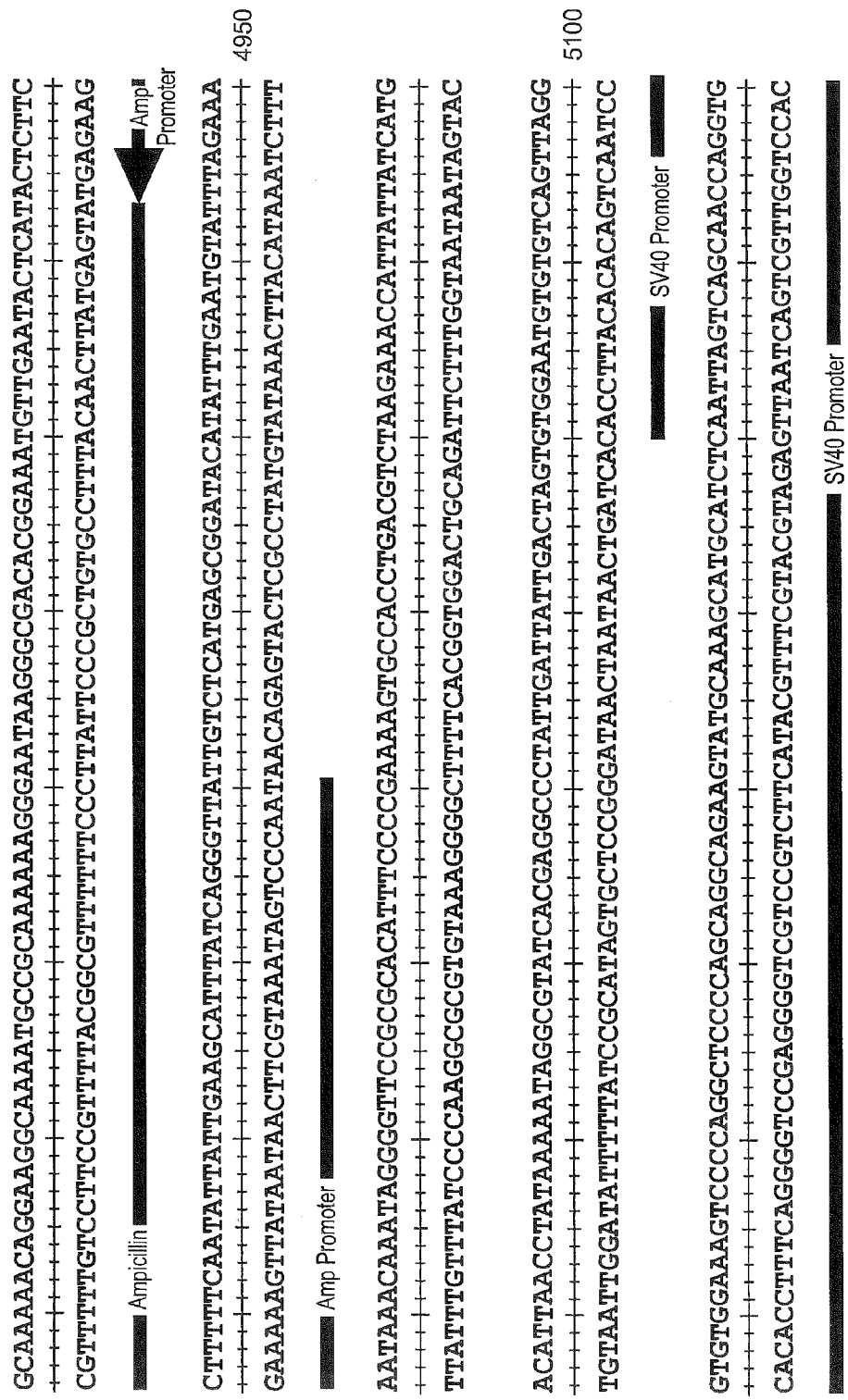

FIG. 31 shows a Coomassie blue-stained SDS-PAGE gel of protein-A purified chimeric KFCC-GY4 and KFCC-GY5 antibodies after reduction of disulfide bonds. Lane 1: Precision plus protein standards (Bio-Rad); Lane 2: 1.0 µg chimeric KFCC-GY4 antibody; Lane 3: 1.0 µg chimeric KFCC-GY5 antibody; Lane 4: Precision plus protein standards (Bio-Rad).

FIGS. 32A-1 to 32A-4, 32B-1 to 32B-3, 32C-1 to 32C-3, 32D-1 to 32D-5, 32E-1 to 32E-3, 32F-1 to 32F-2 and 32G show the nucleotide sequence of the pANT12-based plasmid vector encoding the KFCC-GY4 VH Chimera and the deduced amino acid sequence of the chimera.

FIGS. 33A-1 to 33A-4, 33B-1 to 33B-3, 33C-1 to 33C-5 and 33D-1 to 33D-4 show the nucleotide sequence of the pANT13-based plasmid vector encoding the KFCC-GY4 VK Chimera and the deduced amino acid sequence of the chimera.

FIGS. 34A-1 to 34A-4, 34B-1 to 34B-3, 34C-1 to 34C-4, 34D-1 to 34D-5, 34E-1 to 34E-4 and 34F-1 to 34F-3 show the nucleotide sequence of the pANT12-based plasmid vector encoding the KFCC-GY5 VH Chimera and the deduced amino acid sequence of the chimera.

FIGS. 35A-1 to 35A-4, 35B-1 to 35B-4, 35C-1 to 35C-3 and 35D-1 to 35D-4 show the nucleotide sequence of the pANT13-based plasmid vector encoding the KFCC-GY5 VK Chimera and the deduced amino acid sequence of the chimera.

Figure 36:
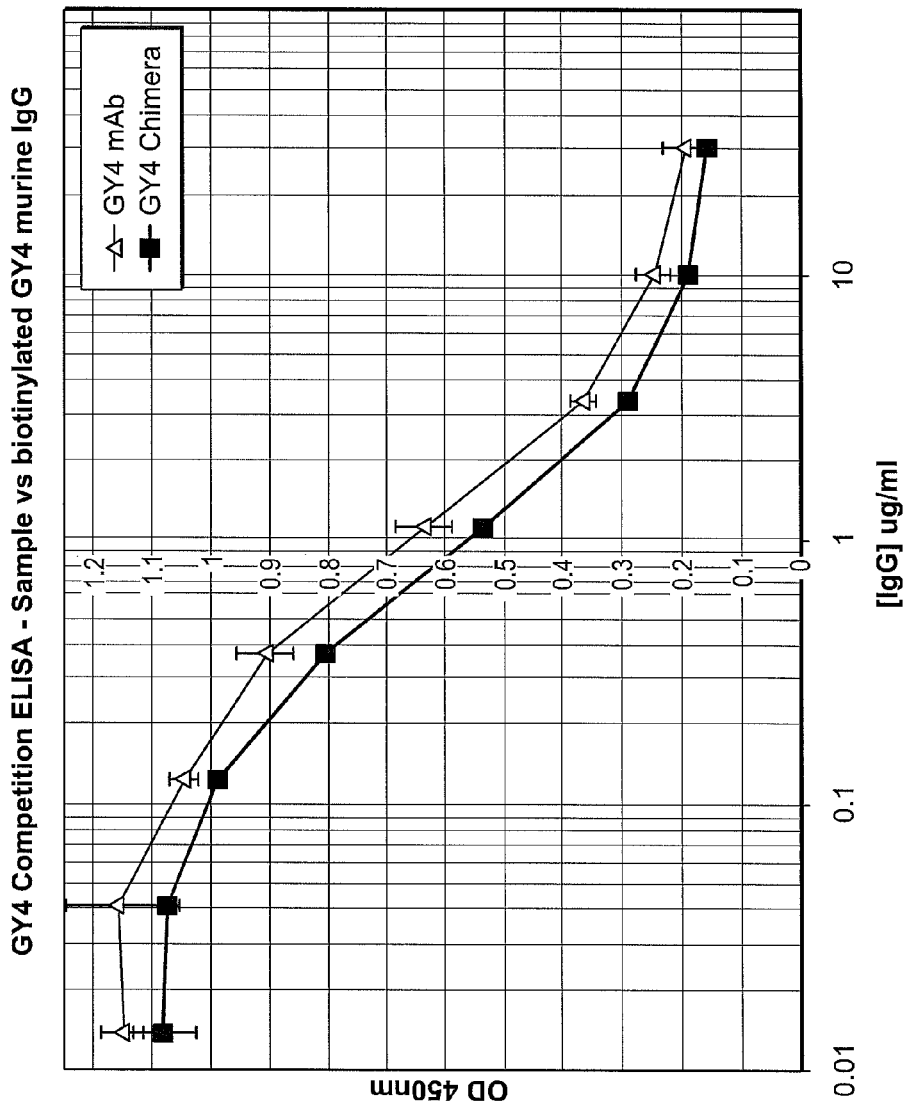

FIG. 36 is a graph depicting the results of a KFCC-GY4 antibody competition ELISA in which a dilution series of chimeric and murine KFCC-GY4 antibodies were tested against a fixed concentration of biotinylated-GY4 for binding to PLVAP. Binding of biotinylated antibody decreases with increasing amounts of chimeric and control murine antibodies.

Figure 37:
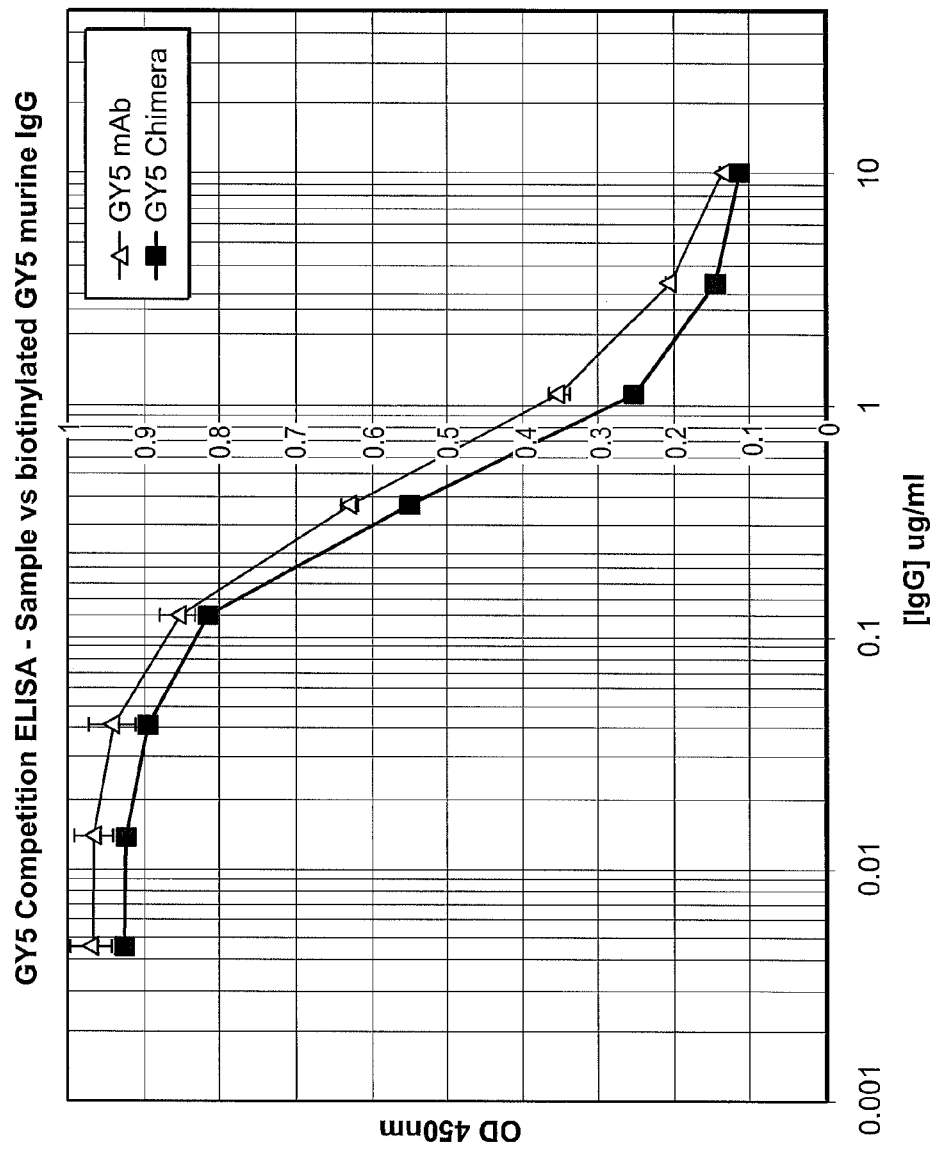

FIG. 37 is a graph depicting the results of a KFCC-GY5 antibody competition ELISA in which a dilution series of chimeric and murine KFCC-GY5 antibodies were tested against a fixed concentration of biotinylated-GY5 for binding to PLVAP. Binding of biotinylated antibody decreases with increasing amounts of chimeric and control murine antibodies.

FIGS. 38A-38E show the nucleotide and amino acid sequences of the variable domains of heavy and light chains from the humanized antibodies derived from chimeric KFCC-GY4 antibody CSR01. FIG. 38A shows the nucleotide and amino acid sequences of the kappa light chain CSR01-VK1 (SEQ ID NOS:59 and 60). FIG. 38B shows the nucleotide and amino acid sequences of the kappa light chain CSR01-VK2 (SEQ ID NOS:61 and 62). FIG. 38C shows the nucleotide and amino acid sequences of the kappa light chain CSR01-VK3 (SEQ ID NOS:63 and 64). FIG. 38D shows the nucleotide and amino acid sequences of the heavy chain CSR01-VH4 (SEQ ID NOS:65 and 66). FIG. 38E shows the nucleotide and amino acid sequences of the heavy chain CSR01-VH5 (SEQ ID NOS:67 and 68). The amino acid sequences of the CDRs are underlined. The amino acids that are altered to reduce potential antigenicity are shown in a square box.

FIGS. 39A-39D show the nucleotide and amino acid sequences of the variable domains of heavy and light chains from the humanized antibodies derived from chimeric KFCC-GY5 antibody CSR02. FIG. 39A shows the nucleotide and amino acid sequences of the kappa light chain CSR02-VK2 (SEQ ID NOS:69 and 70). FIG. 39B shows the nucleotide and amino acid sequences of the kappa light chain CSR02-VK3 (SEQ ID NOS:71 and 72). FIG. 39C shows the nucleotide and amino acid sequences of the heavy chain CSR02-VH4 (SEQ ID NOS:73 and 74). FIG. 39E shows the nucleotide and amino acid sequences of the heavy chain CSR02-VH5 (SEQ ID NOS:75 and 76). The amino acid sequences of the CDRs are underlined. The amino acids that are altered to reduce potential antigenicity are shown in a square box.

Figure 40:
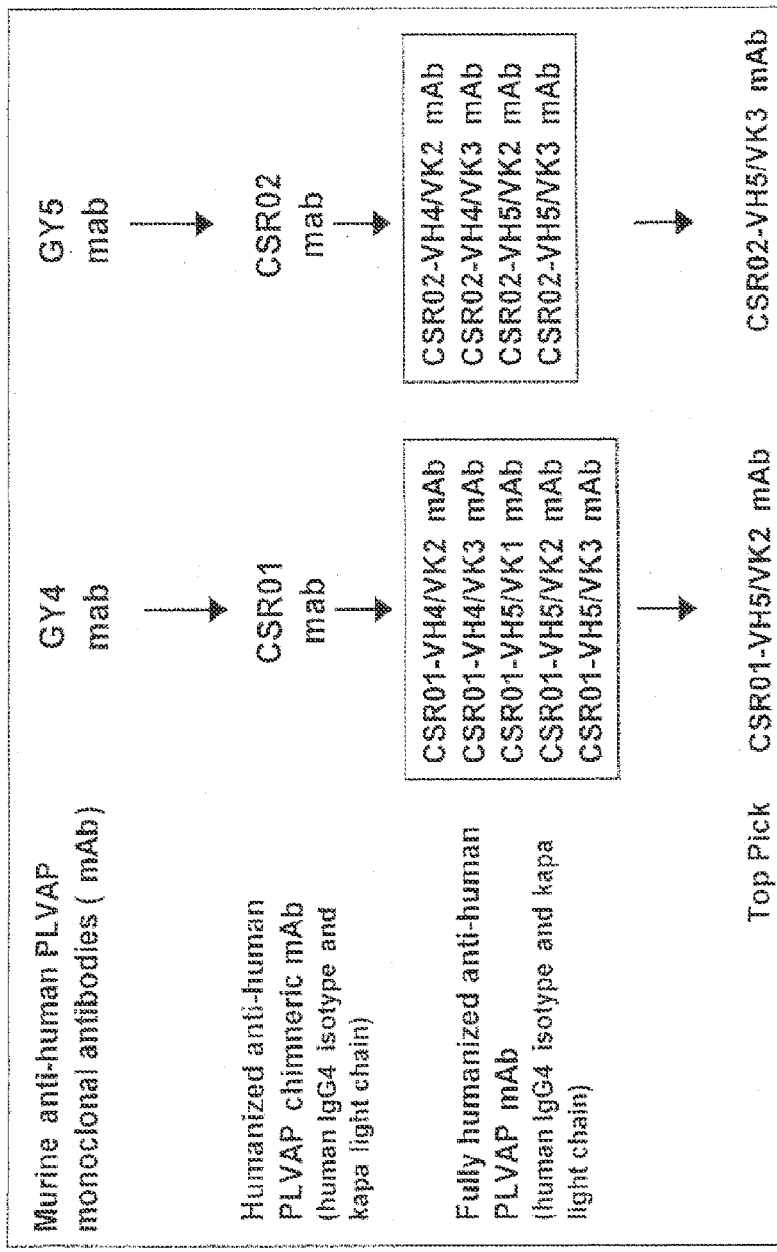

FIG. 40 is a flowchart diagram depicting the derivation of fully humanized anti-human PLVAP composite monoclonal antibodies (mAb) from murine KFCC-GY4 and KFCC-GY5 mAbs.

FIG. 41A depicts the nucleotide and deduced amino acid sequences of the KFCC-GY5 variable heavy chain VH variant 1 (SEQ ID NOS:77 and 78). CDR nucleotide and protein sequences are lightly shaded. Variant amino acids changed from the original hybridoma sequence are underlined.

FIG. 41B depicts the nucleotide and deduced amino acid sequences of the KFCC-GY5 variable heavy chain VH variant 2 (SEQ ID NOS:79 and 80). CDR nucleotide and protein sequences are lightly shaded. Variant amino acids changed from the original hybridoma sequence are underlined.

FIG. 41C depicts the nucleotide and deduced amino acid sequences of the KFCC-GY5 variable heavy chain VH variant 3 (SEQ ID NOS:81 and 82). CDR nucleotide and protein sequences are lightly shaded. Variant amino acids changed from the original hybridoma sequence are underlined.

FIG. 41D depicts the nucleotide and deduced amino acid sequences of the KFCC-GY5 variable heavy chain VH variant 4 (SEQ ID NOS:83 and 84). CDR nucleotide and protein sequences are lightly shaded. Variant amino acids changed from the original hybridoma sequence are underlined.

FIG. 41E depicts the nucleotide and deduced amino acid sequences of the KFCC-GY5 variable heavy chain VH variant 5 (SEQ ID NOS:85 and 86). CDR nucleotide and protein sequences are lightly shaded. Variant amino acids changed from the original hybridoma sequence are underlined.

FIG. 42A depicts the nucleotide and deduced amino acid sequences of the KFCC-GY5 variable light chain VK variant 1 (SEQ ID NOS:87 and 88). CDR nucleotide and protein sequences are lightly shaded. Variant amino acids changed from the original hybridoma sequence are underlined.

FIG. 42B depicts the nucleotide and deduced amino acid sequences of the KFCC-GY5 variable light chain VK variant 2 (SEQ ID NOS:89 and 90). CDR nucleotide and protein sequences are lightly shaded. Variant amino acids changed from the original hybridoma sequence are underlined.

FIG. 42C depicts the nucleotide and deduced amino acid sequences of the KFCC-GY5 variable light chain VK variant 3 (SEQ ID NOS:91 and 92). CDR nucleotide and protein sequences are lightly shaded. Variant amino acids changed from the original hybridoma sequence are underlined.

FIG. 43A depicts the nucleotide and deduced amino acid sequences of the KFCC-GY4 variable heavy chain VH variant 1 (SEQ ID NOS:93 and 94). CDR nucleotide and protein sequences are lightly shaded. Variant amino acids changed from the original hybridoma sequence are underlined.

FIG. 43B depicts the nucleotide and deduced amino acid sequences of the KFCC-GY4 variable heavy chain VH variant 2 (SEQ ID NOS:95 and 96). CDR nucleotide and protein sequences are lightly shaded. Variant amino acids changed from the original hybridoma sequence are underlined.

FIG. 43C depicts the nucleotide and deduced amino acid sequences of the KFCC-GY4 variable heavy chain VH variant 3 (SEQ ID NOS:97 and 98). CDR nucleotide and protein sequences are lightly shaded. Variant amino acids changed from the original hybridoma sequence are underlined.

FIG. 43D depicts the nucleotide and deduced amino acid sequences of the KFCC-GY4 variable heavy chain VH variant 4 (SEQ ID NOS:99 and 100). CDR nucleotide and protein sequences are lightly shaded. Variant amino acids changed from the original hybridoma sequence are underlined.

FIG. 43E depicts the nucleotide and deduced amino acid sequences of the KFCC-GY4 variable heavy chain VH variant 5 (SEQ ID NOS:101 and 102). CDR nucleotide and protein sequences are lightly shaded. Variant amino acids changed from the original hybridoma sequence are underlined.

FIG. 44A depicts the nucleotide and deduced amino acid sequences of the KFCC-GY4 variable light chain VK variant 1 (SEQ ID NOS:103 and 104). CDR nucleotide and protein sequences are lightly shaded. Variant amino acids changed from the original hybridoma sequence are underlined.

FIG. 44B depicts the nucleotide and deduced amino acid sequences of the KFCC-GY4 variable light chain VK variant 2 (SEQ ID NOS:105 and 106). CDR nucleotide and protein sequences are lightly shaded. Variant amino acids changed from the original hybridoma sequence are underlined.

FIG. 44C depicts the nucleotide and deduced amino acid sequences of the KFCC-GY4 variable light chain VK variant 3 (SEQ ID NOS:107 and 108). CDR nucleotide and protein sequences are lightly shaded. Variant amino acids changed from the original hybridoma sequence are underlined.

Figure 45:
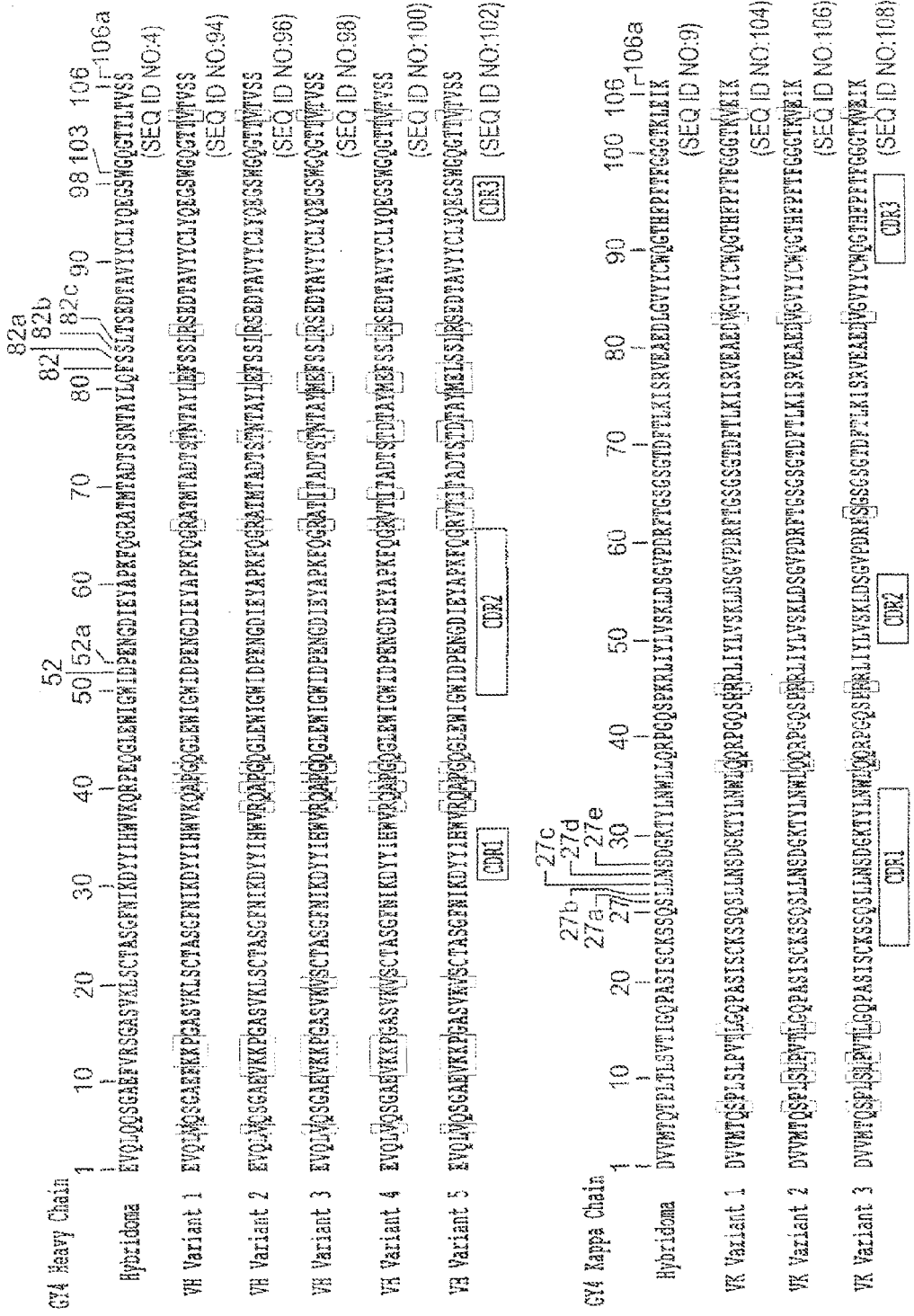

FIG. 45 shows alignments of variable domain sequences of humanized KFCC-GY4 antibody variant heavy chains (top alignment) and Kappa light chains (bottom alignment).

FIG. 46 shows alignments of variable domain sequences of humanized KFCC-GY5 antibody variant heavy chains (top alignment) and Kappa light chains (bottom alignment).

Figure 47A:
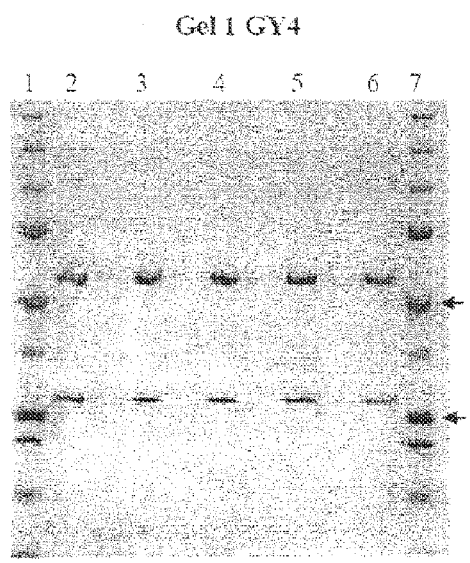

FIG. 47A shows a Coomassie Blue-stained SDS-PAGE gel of purified humanized KFCC-GY4 antibodies after reduction of disulfide bonds. Lane 1: Precision Plus marker (Biorad); Lane 2: 1.0 µg VH4/VK2 IgG4; Lane 3: 1.0 µg VH4/VK3 IgG4; Lane 4: 1.0 µg VH5/VK1 IgG4; Lane 5: 1.0 µg VH5/VK2 IgG4; Lane 6: 1.0 µg VH5/VK3 IgG4; Lane 7: Precision Plus marker.

Figure 47B:
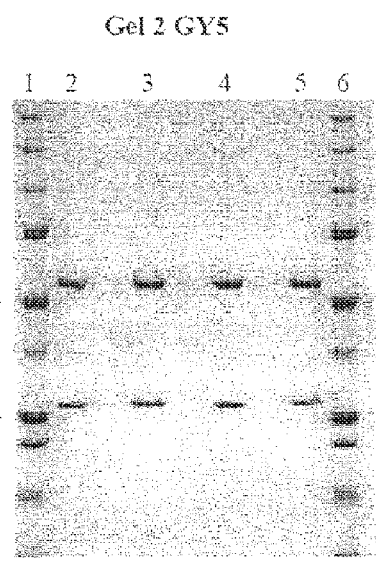

FIG. 47B shows a Coomassie Blue-stained SDS-PAGE gel of purified humanized KFCC-GY5 antibodies after reduction of disulfide bonds. Lane 1: Precision Plus marker; Lane 2: 1.0 µg VH4/VK2 IgG4; Lane 3: 1.0 µg VH4/VK3 IgG4; Lane 4: 1.0 µg VH5/VK2 IgG4; Lane 5: 1.0 µg VH5/VK3 IgG4; Lane 6: Precision Plus marker.

Figure 48:
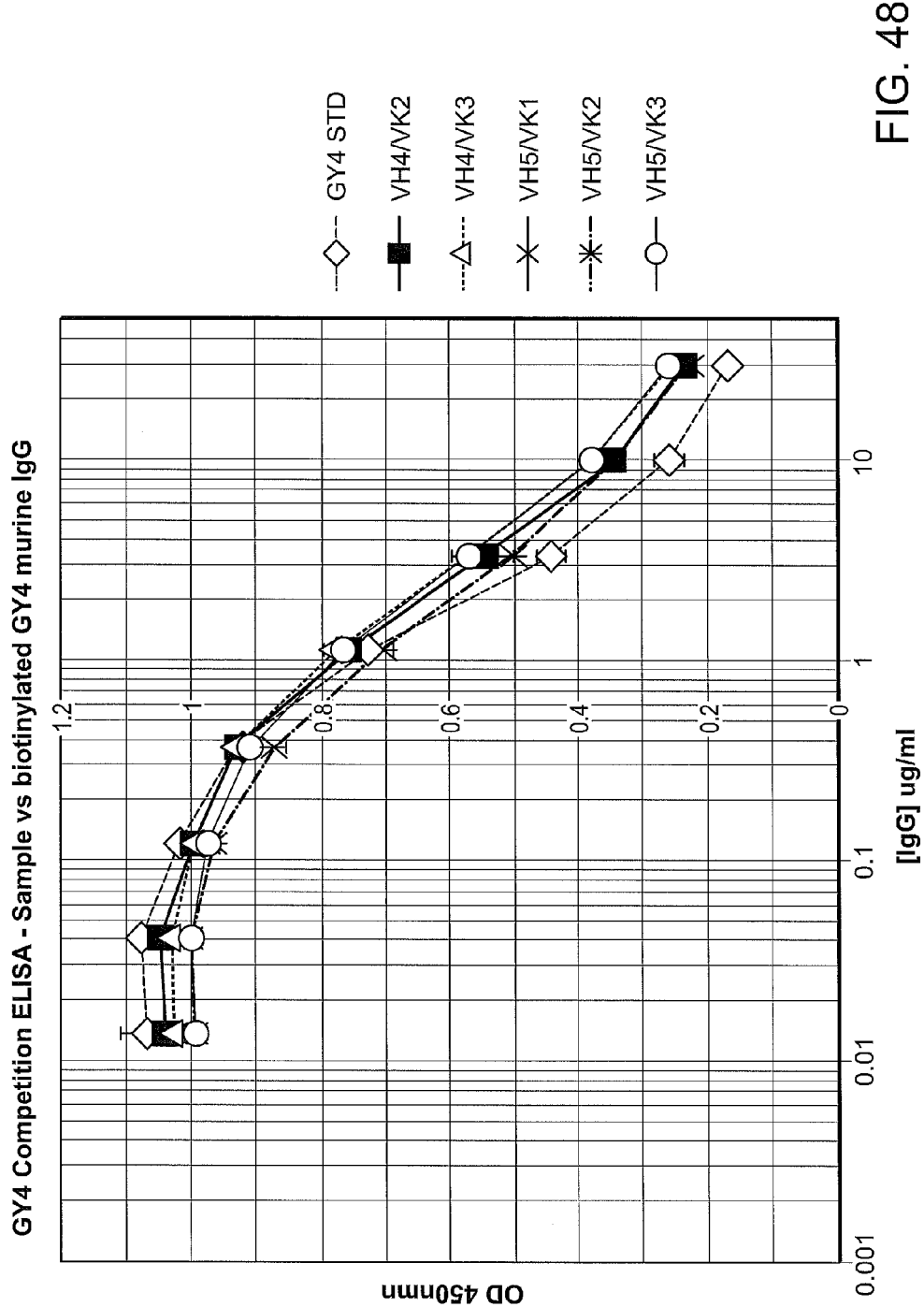

FIG. 48 is a graph depicting the results of a PLVAP competition ELISA illustrating the binding of purified variant KFCC-GY4 humanized antibodies that were mixed with a fixed concentration of competitor biotinylated-murine KFCC-GY4 antibody to PLVAP protein at varying concentrations.

Figure 49:
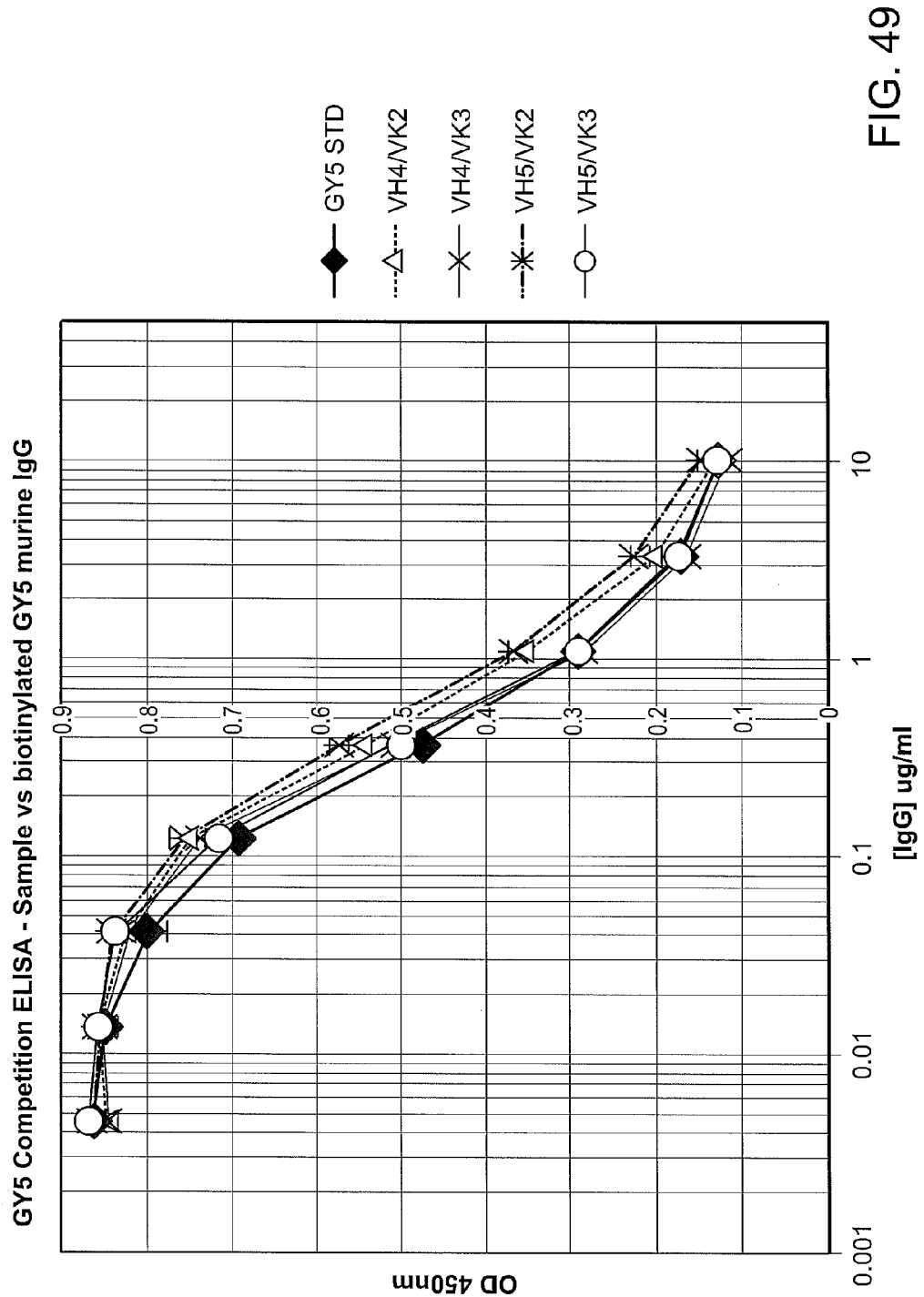

FIG. 49 is a graph depicting the results of a PLVAP competition ELISA illustrating the binding of purified variant KFCC-GY5 humanized antibodies that were mixed with a fixed concentration of competitor KFCC-GY5 antibody to PLVAP protein at varying concentrations.

Figure 50:
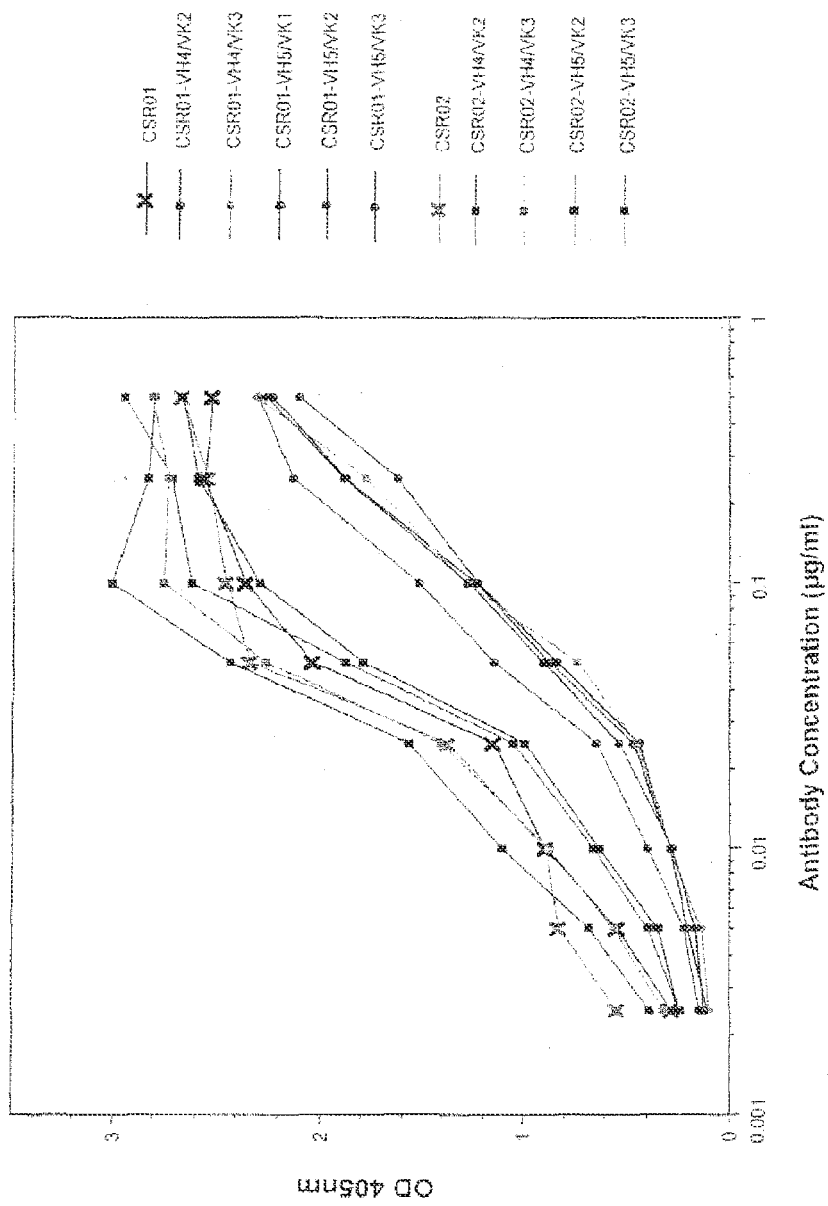

FIG. 50 depicts a titration curve illustrating binding of both chimeric and fully humanized composite anti-PLVAP monoclonal antibodies to PLVAP, as determined by ELISA.

Figure 51A:
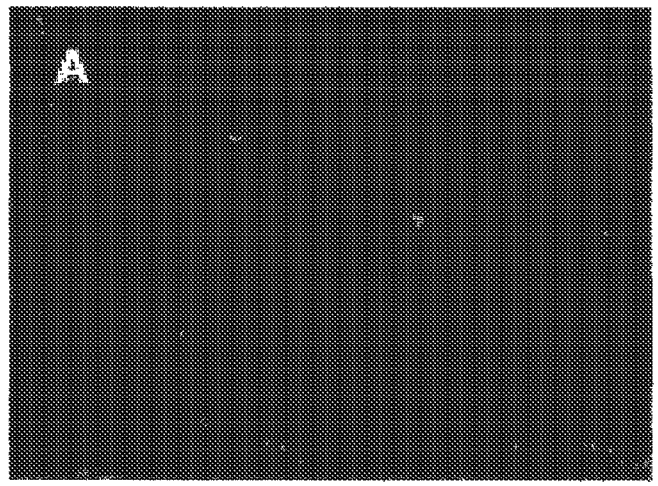
Figure 51B:
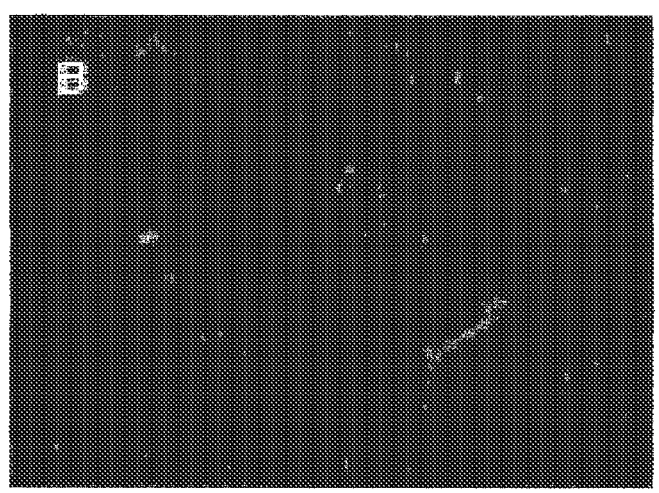
Figure 51C:
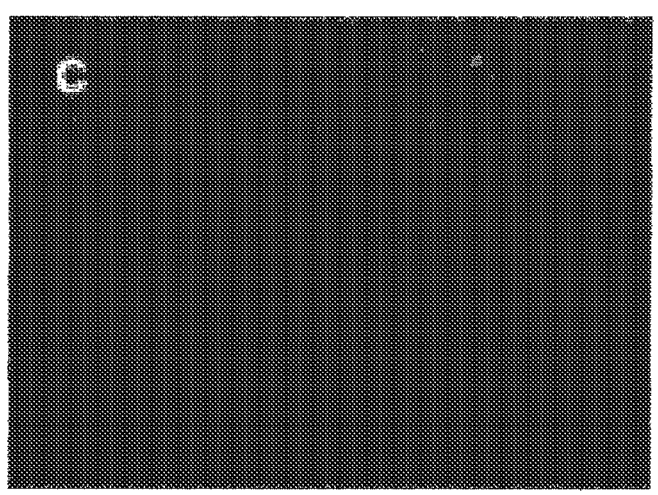

FIGS. 51A-51C are images of human umbilical cord vascular endothelial cells that have been stained with murine KFCC-GY4 and KFCC-GY5 monoclonal antibodies in immunofluorescence studies. FIG. 51A shows immunofluorescence staining of human umbilical cord vascular endothelial cells with murine KFCC-GY4 mAbs. FIG. 51B shows immunofluorescence staining of human umbilical cord vascular endothelial cells with murine KFCC-GY5 mAbs. FIG. 51C shows immunofluorescence staining of human umbilical cord vascular endothelial cells with mouse IgG as a negative control.

Figure 52A:
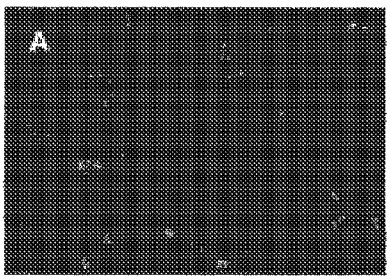
Figure 52B:
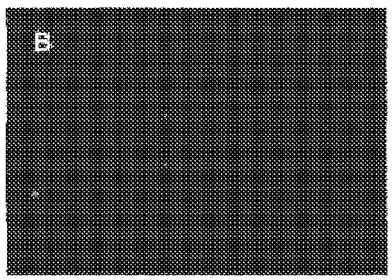
Figure 52C:
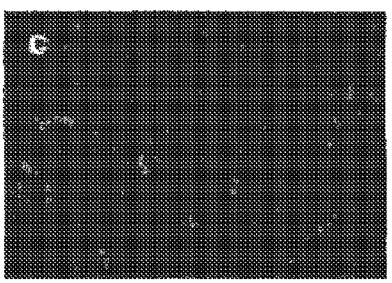
Figure 52D:
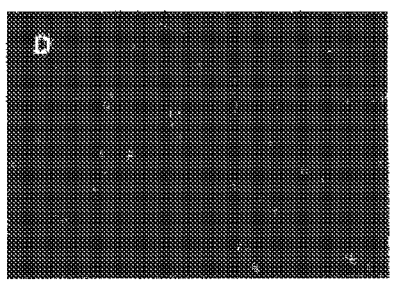
Figure 52E:
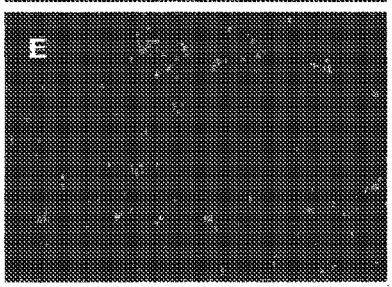
Figure 52F:
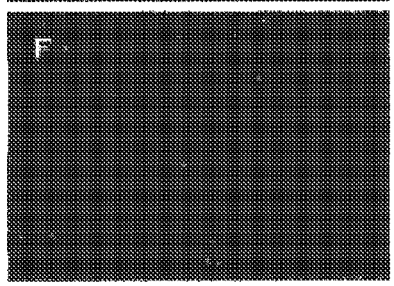
Figure 52G:
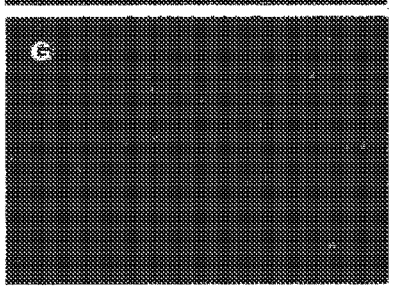

FIGS. 52A-52G are images of human umbilical cord vascular endothelial cells that have been stained with chimeric or humanized KFCC-GY4 (CSR01) antibodies in immunofluorescence studies. FIG. 52A: chimeric KFCC-GY4 mAb; FIG. 52B: CSR01-VH4NK2; FIG. 52C: CSR01-VH4NK3; FIG. 52D: CSR01-VH5NK1; FIG. 52E: CSR01-VH5/VK2; FIG. 52F: CSR01-VH5/VK3; FIG. 52G: human IgG.

Figure 53A:
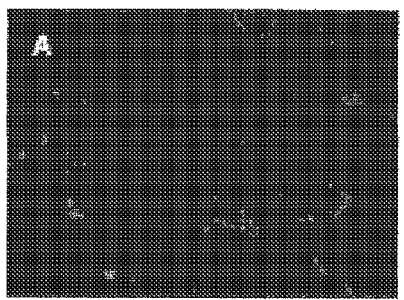
Figure 53B:
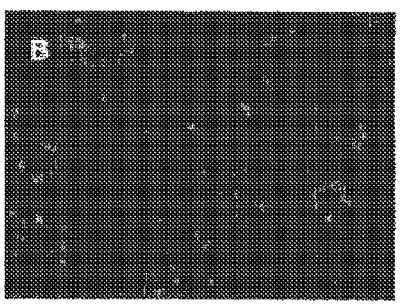
Figure 53C:
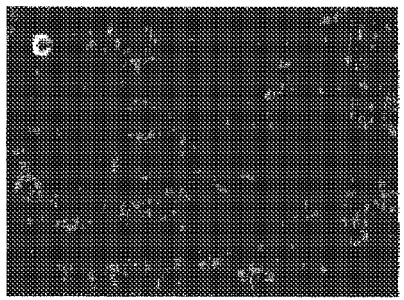
Figure 53D:
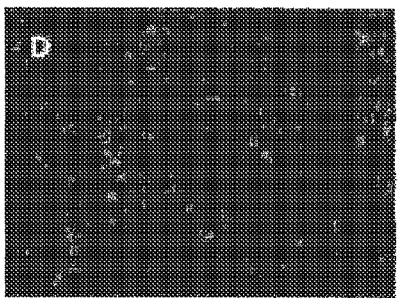
Figure 53E:
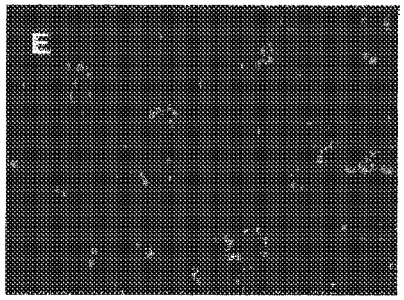
Figure 53F:
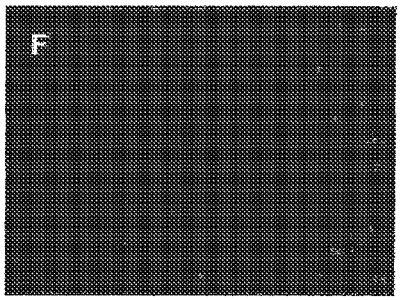

FIGS. 53A-53F are images of human umbilical cord vascular endothelial cells that have been stained with chimeric or humanized KFCC-GY5 antibodies in immunofluorescence studies. FIG. 53A: chimeric KFCC-GY5 (CSR02) mAb; FIG. 53B: CSR02-VH4NK2; FIG. 53C: CSR02-VH4/VK3; FIG. 53D: CSR02-VH5NK2; FIG. 53E: CSR02-VH5NK3; FIG. 53F: human IgG.

Figure 54:
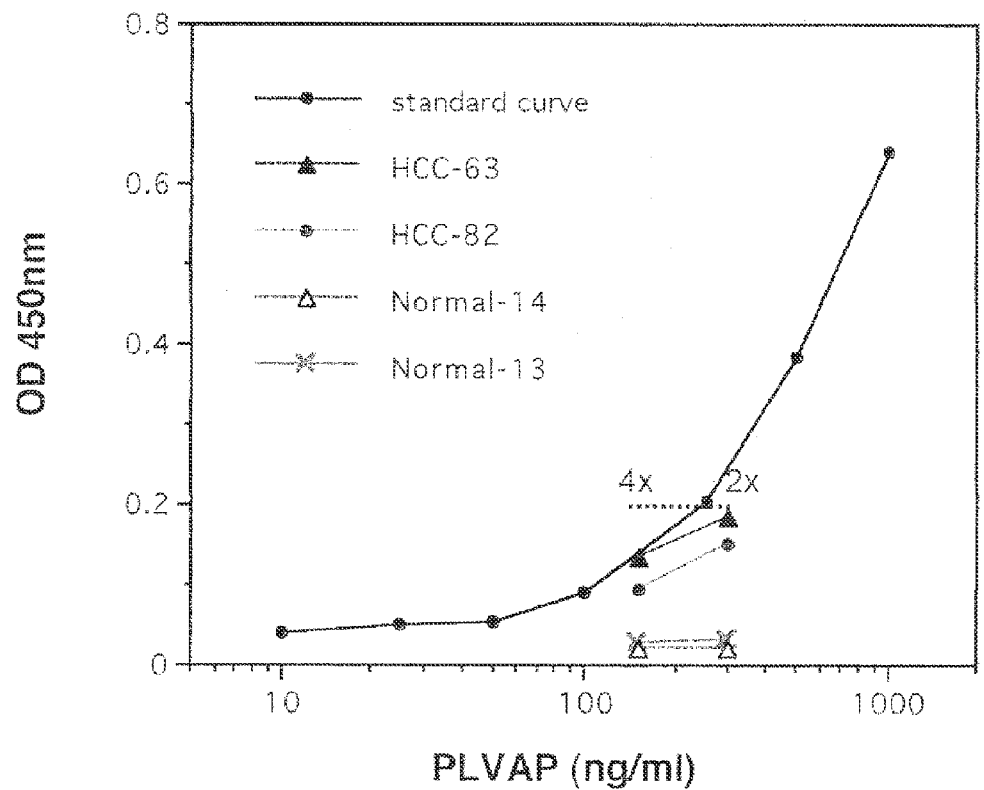

FIG. 54 is a graph depicting the detection of PLVAP protein in two HCC patient serum samples and in serially diluted PLVAP standards (1000 ng/ml to 10 ng/ml). No PLVAP was detected in two normal serum samples. Serum samples were obtained from two patients with hepatocellular carcinoma (HCC-63 and HCC-82) and two normal adults (Normal-13 and Normal-14). Serum samples were assayed at 2-fold and 4-fold dilutions.

DETAILED DESCRIPTION OF THE INVENTION

A description of example embodiments of the invention follows.

DEFINITIONS

As used herein, the terms "Plasmalemma Vesicle-Associated Protein," "PLVAP," and "PV-1" refer to a naturally occurring or endogenous PLVAP (e.g., mammalian, human) protein, and to proteins having an amino acid sequence that is the same or substantially the same as that of naturally occurring or endogenous PLVAP protein (e.g., recombinant proteins, synthetic proteins). Accordingly, the terms "Plasmalemma Vesicle-Associated Protein," "PLVAP," and "PV-1," which are used interchangeably herein, include polymorphic or allelic variants and other isoforms of a PLVAP protein produced by, e.g., alternative splicing or other cellular processes, that occur naturally in mammals (e.g., humans). Preferably, the PLVAP protein is a human protein that has the amino acid sequence of SEQ ID NO:23 (see GENBANK® Accession No. NP_112600 and FIG. 24).

As defined herein, a "PLVAP antagonist" is an agent (e.g., antibody, small molecule, peptide, peptidomimetic, nucleic acid) that, in one embodiment, inhibits (e.g., reduces, prevents) an activity of a PLVAP protein; or, in another embodiment, inhibits (e.g., reduces, prevents) the expression of a PLVAP gene and/or gene product. Activities of a PLVAP protein that can be inhibited by an antagonist of the invention include, but are not limited to, formation, growth, vascularization and/or progression of a hepatocellular carcinoma tumor. In a particular embodiment, the PLVAP antagonist specifically binds a mammalian (e.g., human) PLVAP protein and inhibits an activity of the PLVAP protein.

As used herein, "specifically binds" refers to binding of an agent (e.g., an antibody) to a PLVAP gene product (e.g., RNA, protein) with an affinity (e.g., a binding affinity) that is at least about 5 fold, preferably at least about 10 fold, greater than the affinity with which the PLVAP antagonist binds a non-PLVAP protein.

As used herein, the term "polypeptide" refers to a polymer of amino acids, and not to a specific length. Thus, "polypeptide" encompasses proteins, peptides, and oligopeptides.

As used herein, the term "antibody" refers to a polypeptide having affinity for a target, antigen, or epitope, and includes both naturally-occurring and engineered antibodies. The term "antibody" encompasses polyclonal, monoclonal, human, chimeric, humanized, primatized, veneered, and single chain antibodies, as well as fragments of antibodies (e.g., Fv, Fc, Fd, Fab, Fab', F(ab'), scFv, scFab, dAb). (See, e.g., Harlow et al., *Antibodies A Laboratory Manual*, Cold Spring Harbor Laboratory, 1988).

The term "antibody variable region" refers to the region of an antibody that specifically binds an epitope (e.g., $V_H$, $V_{HH}$, $V_L$), either independently or when combined with other antibody variable regions (e.g., a $V_H/V_L$ pair).

The term "epitope" refers to a unit of structure conventionally bound by an antibody $V_H/V_L$ pair. An epitope defines the minimum binding site for an antibody and, thus, represents the target of specificity of an antibody.

The term "complementarity determining region," or "CDR," refers to a hypervariable region of an antibody variable region from a heavy chain or light chain that contains amino acid sequences capable of specifically binding to an antigenic target (e.g., epitope). A typical heavy or light chain will have three CDRs (CDR1, CDR2, CDR3), which account for the specificity of the antibody for a particular epitope.

As defined herein, the term "antigen binding fragment" refers to a portion of an antibody that contains one or more CDRs and has affinity for an antigenic determinant by itself. Non-limiting examples include Fab fragments, F(ab)'$_2$ fragments, heavy-light chain dimers, and single chain structures, such as a complete light chain or a complete heavy chain.

As used herein, the term "specificity" refers to the ability of an antibody to bind preferentially to an epitope, and does not necessarily imply high affinity.

The term "affinity" refers to a measure of the binding strength between an antibody and an antigenic determinant. Affinity depends on a number of factors, including the closeness of stereochemical fit between the antibody and antigenic determinant, the size of the area of contact between them, and the distribution of charged and hydrophobic groups.

As used herein, the term "affinity constant," or "$K_d$," refers to a dissociation constant used to measure the affinity of an antibody for an antigen. The lower the affinity constant, the higher the affinity of the immunoglobulin for the antigen or antigenic determinant, and vice versa. Such a constant is readily calculated from the rate constants for the association-dissociation reactions as measured by standard kinetic methodology for antibody reactions.

As referred to herein, the term "competes" means that the binding of a first polypeptide (e.g., antibody) to a target antigen is inhibited by the binding of a second polypeptide (e.g., antibody). For example, binding may be inhibited sterically, for example, by physical blocking of a binding domain or by alteration of the structure or environment of a binding domain such that its affinity or avidity for a target is reduced.

As used herein, the term "peptide" refers to a compound consisting of from about 2 to about 100 amino acid residues wherein the amino group of one amino acid is linked to the carboxyl group of another amino acid by a peptide bond. Such peptides are typically less than about 100 amino acid residues in length and preferably are about 10, about 20, about 30, about 40 or about 50 residues.

As used herein, the term "peptidomimetic" refers to molecules which are not peptides or proteins, but which mimic aspects of their structures. Peptidomimetic antagonists can be prepared by conventional chemical methods (see, e.g., Damewood J. R. "Peptide Mimetic Design with the Aid of Computational Chemistry" in *Reviews in Computational Biology*, 2007, Vol. 9, pp. 1-80, John Wiley and Sons, Inc., New York, 1996; Kazmierski W. K., "*Methods of Molecular Medicine: Peptidomimetic Protocols*," Humana Press, New Jersey, 1999).

The terms "hepatocellular carcinoma," "HCC," and "hepatoma" are used interchangeably herein to refer to cancer that arises from hepatocytes, the major cell type of the liver.

As defined herein, "therapy" is the administration of a particular therapeutic or prophylactic agent to a subject (e.g., a mammal, a human) that results in a desired therapeutic or prophylactic benefit to the subject.

As defined herein, a "therapeutically effective amount" is an amount sufficient to achieve the desired therapeutic or prophylactic effect under the conditions of administration, such as an amount sufficient to inhibit (i.e., reduce, prevent) tumor formation, tumor growth (proliferation, size), tumor vascularization and/or tumor progression (invasion, metastasis) in the liver of a patient with HCC. The effectiveness of a therapy (e.g., the reduction/elimination of a tumor and/or prevention of tumor growth) can be determined by any suitable method (e.g., in situ immunohistochemistry, imaging (ultrasound, CT scan, MRI, NMR), $^3$H-thymidine incorporation).

As defined herein, a "treatment regimen" is a regimen in which one or more therapeutic or prophylactic agents are administered to a mammalian subject at a particular dose (e.g., level, amount, quantity) and on a particular schedule or at particular intervals (e.g., minutes, days, weeks, months).

As used herein, a "subject" refers to a mammalian subject. The term "mammalian subject" is defined herein to include mammals, such as primates (e.g., humans), cows, sheep, goats, horses, dogs cats, rabbits, guinea pigs, rats, mice or other bovine, ovine, equine, canine feline, rodent or murine species. Examples of suitable subjects include, but are not limited to, human patients who have, or are at risk for developing, HCC. Examples of high-risk groups for the development of HCC include individuals with chronic hepatitis infection (hepatitis B, hepatitis C) and individuals who have cirrhosis of the liver or related hepatic conditions.

The terms "prevent," "preventing," or "prevention," as used herein, mean reducing the probability/likelihood or risk of HCC tumor formation or progression by a subject, delaying the onset of a condition related to HCC in the subject, lessening the severity of one or more symptoms of an HCC-related condition in the subject, or any combination thereof. In general, the subject of a preventative regimen most likely will be categorized as being "at-risk," e.g., the risk for the subject developing HCC is higher than the risk for an individual represented by the relevant baseline population.

As used herein, the terms "treat," "treating," or "treatment" mean to counteract a medical condition (e.g., a condition related to HCC) to the extent that the medical condition is improved according to a clinically-acceptable standard (e.g., reduced number and/or size of HCC tumors in a subject's liver).

As used herein, the terms "low stringency," "medium stringency," "high stringency," and "very high stringency conditions" describe conditions for nucleic acid hybridization and washing. Guidance for performing hybridization reactions can be found in Current Protocols in Molecular Biology, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60 C; (3) high stringency hybridization conditions in 6×SSC at about 45° C., followed by one or more washes in 0.2×SSC, 0.1% SDS at 65° C.; and preferably (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4_{th}$ Ed, John Wiley & Sons, Inc., which are incorporated herein by reference) and chemical methods.

PLVAP

Plasmalemma vesicle-associated protein (PLVAP), also known as PV1, is a type II integral membrane glycoprotein whose expression is restricted to certain vascular endothelial cells (*Mol Biol Cell* 15:3615-3630 (2004)). PLVAP has been shown to be a key structural component of fenestral and stomatal diaphragms of fenestrated endothelia. See id. In addition, PLVAP expression is necessary for the formation of endothelial fenestral diaphragms and may be involved in modulating endothelial permeability and transport (Am J Physiol Heart Circ Physiol 286:H1347-1353, 2004). The genomic organization of human PLVAP gene has been reported (Stan R V, Arden K C, Palade G E. cDNA and protein sequence, genomic organization, and analysis of cis regulatory elements of mouse and human PLVAP genes. Genomics 72; 304-313, 2001).

As described herein, the inventors have demonstrated that PLVAP gene expression is significantly elevated in hepatocellular carcinoma tissues relative to adjacent non-tumorous tissues in the liver of human HCC patients. In addition, the present inventors have determined that PLVAP protein is mainly expressed in, and localizes to, vascular endothelial cells surrounding or within HCC tumors, but is not expressed in, or localized to, cells associated with other liver pathologies. Accordingly, PLVAP represents a novel target for the diagnosis and treatment of HCC.

Methods of Therapy

In one aspect, the invention relates to a method of treating hepatocellular carcinoma (HCC) in a subject in need thereof, comprising administering to the subject a therapeutically effective amount of at least one PLVAP antagonist, wherein the PLVAP antagonist inhibits formation, growth, vascularization and/or progression of one or more HCC tumors in the liver of the subject. In a particular aspect, a PLVAP antagonist of the invention inhibits the expression or activity of PLVAP protein in vascular endothelial cells surrounding hepatocytes in the liver of HCC patients.

In one aspect, a therapeutically-effective amount of a PLVAP antagonist is administered to a subject in need thereof to inhibit tumor growth or kill tumor cells. For example, agents which directly inhibit tumor growth (e.g., chemotherapeutic agents) are conventionally administered at a particular dosing schedule and level to achieve the most effective therapy (e.g., to best kill tumor cells). Generally, about the maximum tolerated dose is administered during a relatively short treatment period (e.g., one to several days), which is followed by an off-therapy period. In a particular example, the chemotherapeutic cyclophosphamide is administered at a maximum tolerated dose of 150 mg/kg every other day for three doses, with a second cycle given 21 days after the first cycle. (Browder et al. *Can Res* 60:1878-1886, 2000).

A therapeutically-effective amount of PLVAP antagonist (e.g., inhibitory small molecules, neutralizing antibodies, inhibitory nucleic acids (e.g., siRNA, antisense nucleotides)) can be administered, for example, in a first cycle in which about the maximum tolerated dose of the antagonist is administered in one interval/dose, or in several closely spaced intervals (minutes, hours, days) with another/second cycle administered after a suitable off-therapy period (e.g., one or more weeks). Suitable dosing schedules and amounts for a PLVAP antagonist can be readily determined by a clinician of ordinary skill. Decreased toxicity of a particular PLVAP antagonist as compared to chemotherapeutic agents can allow for the time between administration cycles to be shorter. When used as an adjuvant therapy (to, e.g., surgery, radiation therapy, other primary therapies), a therapeutically-effective amount of a PLVAP antagonist is preferably administered on a dosing schedule that is similar to that of the other cancer therapy (e.g., chemotherapeutics), or on a dosing schedule determined by the skilled clinician to be more/most effective at inhibiting (reducing, preventing) tumor growth. A treatment regimen for a therapeutically-effective amount of an antibody PLVAP antagonist can be, for example, from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg every 1 to 7 days over a period of about 4 to about 6 months. A treatment regimen for an anti-tumor effective amount of a small molecule PLVAP antagonist can be, for example, from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg, every 1 to 7 days over a period of about 4 to about 6 months.

In another aspect, a PLVAP antagonist can be administered in a metronomic dosing regime, whereby a lower dose is administered more frequently relative to maximum tolerated dosing. A number of preclinical studies have demonstrated superior anti-tumor efficacy, potent antiangiogenic effects, and reduced toxicity and side effects (e.g., myelosuppression) of metronomic regimes compared to maximum tolerated dose (MTD) counterparts (Bocci, et al., *Cancer Res*, 62:6938-6943, (2002); Bocci, et al., *Proc. Natl. Acad. Sci*., 100(22): 12917-12922, (2003); and Bertolini, et al., *Cancer Res*, 63(15):4342-4346, (2003)). Metronomic chemotherapy appears to be effective in overcoming some of the shortcomings associated with chemotherapy.

A PLVAP antagonist can be administered in a metronomic dosing regime to inhibit (reduce, prevent) angiogenesis in a patient in need thereof as part of an anti-angiogenic therapy. Such anti-angiogenic therapy may indirectly affect (inhibit, reduce) tumor growth by blocking the formation of new blood vessels that supply tumors with nutrients needed to sustain tumor growth and enable tumors to metastasize. Starving the tumor of nutrients and blood supply in this manner can eventually cause the cells of the tumor to die by necrosis and/or apoptosis. Previous work has indicated that the clinical outcomes (inhibition of endothelial cell-mediated tumor angiogenesis and tumor growth) of cancer therapies that involve the blocking of angiogenic factors (e.g., VEGF, bFGF, TGF-α, IL-8, PDGF) or their signaling have been more efficacious when lower dosage levels are administered more frequently, providing a continuous blood level of the antiangiogenic agent. (See Browder et al. *Can. Res*. 60:1878-1886, 2000; Folkman J., *Sem. Can. Biol*. 13:159-167, 2003). An anti-angiogenic treatment regimen has been used with a targeted inhibitor of angiogenesis (thrombospondin 1 and platelet growth factor-4 (TNP-470)) and the chemotherapeutic agent cyclophosphamide. Every 6 days, TNP-470 was administered at a dose lower than the maximum tolerated dose and cyclophosphamide was administered at a dose of 170 mg/kg. See id. This treatment regimen resulted in complete regression of the tumors. See id. In fact, anti-angiogenic treatments are most effective when administered in concert with other anti-cancer therapeutic agents, for example, those agents that directly inhibit tumor growth (e.g., chemotherapeutic agents). See id.

The therapeutic methods described herein comprise administering a PLVAP antagonist to a subject. The PLVAP antagonist may be administered to the individual in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy (e.g., chemotherapy (e.g., tamoxifen, cisplatin, mitomycin, 5-fluorouracil, doxorubicin, sorafenib, octreotide, dacarbazine (DTIC), Cis-platinum, cimetidine, cyclophophamide), radiation therapy (e.g., proton beam therapy), hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene)), or biological therapy). Numerous other therapies can also be administered during a cancer treatment regime to mitigate the effects of the disease and/or side effects of the cancer treatment, including therapies to manage pain (narcotics, acupuncture), gastric discomfort (antacids), dizziness (anti-vertigo medications), nausea (anti-nausea medications), infection (e.g., medications to increase red/white blood cell counts) and the like, all of which are readily appreciated by the person skilled in the art.

Thus, a PLVAP antagonist can be administered as an adjuvant therapy (e.g., with another primary cancer therapy or treatment). As an adjuvant therapy, the PLVAP antagonist can be administered before, after or concurrently with a primary therapy like radiation and/or the surgical removal of a tumor(s). In some embodiments, the method comprises administering a therapeutically effective amount of a PLVAP antagonist and one or more other therapies (e.g., adjuvant therapies, other targeted therapies). An adjuvant therapy (e.g., a chemotherapeutic agent) and/or the one or more other targeted HCC therapies and the PLVAP antagonist can be co-administered simultaneously (e.g., concurrently) either as separate formulations or as a joint formulation. Alternatively, the therapies can be administered sequentially, as separate compositions, within an appropriate time frame (e.g., a cancer treatment session/interval such as 1.5 to 5 hours) as determined by the skilled clinician (e.g., a time sufficient to allow an overlap of the pharmaceutical effects of the therapies). The adjuvant therapy and/or one or more other targeted HCC therapies and the PLVAP antagonist can be administered in a single dose or multiple doses in an order and on a schedule suitable to achieve a desired therapeutic effect (e.g., inhibition of tumor growth, inhibition of angiogenesis, and/or inhibition of cancer metastasis).

One or more agents that are PLVAP antagonists can be administered in single or multiple doses. Suitable dosing and regimens of administration can be determined by a clinician and are dependent on the agent(s) chosen, pharmaceutical formulation and route of administration, various patient factors and other considerations. With respect to the administration of a PLVAP antagonist with one or more other therapies or treatments (adjuvant, targeted, cancer treatment-associated, and the like) the PLVAP antagonist is typically administered as a single dose (e.g., by injection, by infusion, orally), followed by repeated doses at particular intervals (e.g., one or more hours) if desired or indicated.

The amount of the PLVAP antagonist to be administered (e.g., a therapeutically effective amount) can be determined by a clinician using the guidance provided herein and other methods known in the art and is dependent on several factors, including, for example, the particular agent chosen, the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Where the PLVAP antagonist is a polypeptide (linear, cyclic, mimetic), the preferred dosage will result in a plasma concentration of the peptide from about 0.1 µg/mL to about 200 µg/mL. Determining the dosage for a particular agent, patient and cancer is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

Methods for Administration

According to the methods of the invention, a therapeutically effective amount of a PLVAP antagonist (e.g., antibody, such as an antibody labeled with a radioactive isotope) is administered to a mammalian subject to treat HCC.

A variety of routes of administration can be used, including, for example, oral, dietary, topical, transdermal, rectal, parenteral (e.g., intraarterial, intravenous, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen; however, intraarterial administration (e.g., hepatic arterial infusion, trans-arterial chemoembolization (TACE)) is generally preferred to administer therapeutic agents (e.g., antibodies, such as antibodies labeled with a radioactive isotope) of the invention to treat hepatocellular carcinoma.

For example, using hepatic arterial infusion, chemotherapeutic agents (e.g., PLVAP antibodies, such as PLVAP antibodies labeled with a radioactive isotope) can be delivered directly to an HCC tumor through the hepatic artery, for example, during routine TACE treatment of HCC (Camma, et al. *Radiology* 224:47-54, 2002; Befeler, et al. *Clinics in Liver Disease* 9:287-300, 2005; Abou-Alfa *JAMA* 299:1716-1718, 2008). This procedure is done with the help of fluoroscopy (type of x-ray) imaging. Briefly, a catheter is inserted into the femoral artery in the groin and is threaded into the aorta. From the aorta, the catheter is advanced into the hepatic artery or its branches. Once the branches of the hepatic artery that feed the liver cancer are identified, the chemotherapy is infused. An interventional radiologist, who usually carries out this procedure, can determine the amount of chemotherapy that a patient receives at each session. Some patients may undergo repeat sessions at 6 to 12 week intervals. Imaging studies of the liver are repeated in six to 12 weeks to assess the size of the tumor in response to the treatment.

Alternatively, trans-arterial chemoembolization (TACE), a procedure that is similar to intraarterial infusion, can be used to administer PLVAP antagonists (e.g., antibodies) to a subject in need thereof. In TACE, intraarterial infusion of a therapeutic agent is combined with the additional step of blocking (i.e., embolizing) the small blood vessels with particular blocking compounds, such as gelfoam, oil emulsion, or even small metal coils. Thus, TACE has the potential advantages of exposing the tumor to high concentrations of chemotherapy and confining the agents locally in order to prevent or reduce their being carried away by the blood stream. At the same time, TACE deprives the tumor of its needed blood supply, which can result in the damage or death of the tumor cells.

For intraarterial administration of PLVAP antibodies, it is preferred to use antibodies having high affinities to PLVAP (e.g., a $K_d$ less than $10^{-7}$ M) so that the infused antibodies will be concentrated in blood vessels of HCC. Chimeric and humanized antibodies are expected to have circulatory half-lives of up to four and up to 14-21 days, respectively. In a particular embodiment, high affinity PLVAP antibodies (e.g., antigen binding fragments, single chain antibodies) with short circulatory half-lives (e.g., about 1 day to about 5 days, for example, about 1, 2, 3, 4 or 5 days) are administered to a patient in order to reduce any toxicity and other adverse side-effects resulting from their administration. In another embodiment, high affinity PLVAP antibodies with long circulatory half-lives (e.g., about 5 days to about 24 days) are administered to a patient to treat HCC.

In many cases, it will be preferable to administer a large loading dose followed by periodic (e.g., weekly) maintenance doses over the treatment period. Antibodies can also be delivered by slow-release delivery systems, pumps, and other known delivery systems for continuous infusion into HCC. Dosing regimens may be varied to provide the desired circulating levels of a particular antibody based on its pharmacokinetics. Thus, doses will be calculated so that the desired therapeutic level is maintained.

The actual dose and treatment regimen will be determined by the physician, taking into account the nature of the cancer (primary or metastatic), number and size of tumors, other therapies, and patient characteristics. In view of the life-threatening nature of hepatocellular carcinoma, large doses with significant side effects may be employed.

Nucleic acid-based PLVAP antagonists (e.g., siRNAs, antisense oligonucleotides, natural or synthetic nucleic acids, nucleic acid analogs) can be introduced into a mammalian subject of interest in a number of ways. For instance, nucleic acids may be expressed endogenously from expression vectors or PCR products in host cells or packaged into synthetic or engineered compositions (e.g., liposomes, polymers, nanoparticles) that can then be introduced directly into the bloodstream of a mammalian subject (by, e.g., injection, infusion). Anti-PLVAP nucleic acids or nucleic acid expression vectors (e.g., retroviral, adenoviral, adeno-associated and herpes simplex viral vectors, engineered vectors, non-viral-mediated vectors) can also be introduced into a mammalian subject directly using established gene therapy strategies and protocols (see, e.g., Tochilin V. P. *Annu Rev Biomed Eng* 8:343-375, 2006; Recombinant DNA and Gene Transfer, Office of Biotechnology Activities, National Institutes of Health Guidelines).

Similarly, where the agent is a protein or polypeptide, the agent can be administered via in vivo expression of recombinant protein. In vivo expression can be accomplished by somatic cell expression according to suitable methods (see, e.g., U.S. Pat. No. 5,399,346). Further, a nucleic acid encoding the polypeptide can also be incorporated into retroviral, adenoviral or other suitable vectors (preferably, a replication deficient infectious vector) for delivery, or can be introduced into a transfected or transformed host cell capable of expressing the polypeptide for delivery. In the latter embodiment, the cells can be implanted (alone or in a barrier device), injected or otherwise introduced in an amount effective to express the polypeptide in a therapeutically effective amount.

Diagnostic and Prognostic Methods

The present invention encompasses diagnostic and prognostic methods that comprise assessing expression of PLVAP in a sample (e.g., liver biopsy, fine needle aspiration sample)

from a mammalian subject (e.g., a mammalian subject who has a liver tumor). For diagnostic methods of the invention, expression of PLVAP in the sample, or increased expression of PLVAP in the sample relative to a suitable control, indicates that the subject has HCC, and/or that the subject is a candidate for an anti-cancer therapy using a PLVAP antagonist.

For prognostic methods of the invention, expression of PLVAP in a sample from a subject, or increased expression of PLVAP in the sample relative to a suitable control, indicates a poor prognosis. The prognosis can be a prognosis for patient survival, a prognosis for risk of metastases and/or a prognosis for risk of relapse.

Suitable samples for these methods include a tissue sample, a biological fluid sample, a cell(s) (e.g., a tumor cell) sample, and the like. Any means of sampling from a subject, for example, by blood draw, spinal tap, tissue smear or scrape, or tissue biopsy, can be used to obtain a sample. Thus, the sample can be a biopsy specimen (e.g., tumor, polyp, mass (solid, cell)), aspirate, smear or blood sample. The sample can be a tissue from a liver that has a tumor (e.g., cancerous growth) and/or tumor cells, or is suspected of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy). The biopsy samples can be examined cytologically (e.g., smear), histologically (e.g., frozen or paraffin section) or using any other suitable method (e.g., molecular diagnostic methods). A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime. If desired, freezing can be performed in the presence of a cryoprotectant, for example, dimethyl sulfoxide (DMSO), glycerol, or propanediol-sucrose. Tumor samples can be pooled, as appropriate, before or after storage for purposes of analysis. The tumor sample can be from a patient who has a liver cancer, for example, hepatocellular carcinoma.

Suitable assays that can be used to assess the presence or amount of a PLVAP in a sample (e.g., biological sample) are known to those of skill in the art. Methods to detect a PLVAP protein or peptide include immunological and immunochemical methods like flow cytometry (e.g., FACS analysis), enzyme-linked immunosorbent assays (ELISA), including chemiluminescence assays, radioimmunoassay, immunoblot (e.g., Western blot), immunohistochemistry (IHC), and other antibody-based quantitative methods (e.g., Luminex® beads-based assays). Other suitable methods include, for example, mass spectroscopy. For example, antibodies to PLVAP can be used to determine the presence and/or expression level of PLVAP in a sample directly or indirectly using, e.g., immunohistochemistry (IHC). For instance, paraffin sections can be taken from a biopsy, fixed to a slide and combined with one or more antibodies by suitable methods. In a particular embodiment, detection of PLVAP protein in vascular endothelial cells surrounding hepatocytes in a sample is indicative of HCC.

An exemplary ELISA assay for use in diagnostic and prognostic applications of the invention is described in Example 9 herein.

Methods to detect PLVAP gene expression include PLVAP nucleic acid amplification and/or visualization. To detect PLVAP gene expression, a nucleic acid can be isolated from an individual by suitable methods which are routine in the art (see, e.g., Sambrook et al., 1989). Isolated nucleic acid can then be amplified (by, e.g., polymerase chain reaction (PCR) (e.g., direct PCR, quantitative real time PCR, reverse transcriptase PCR), ligase chain reaction, self sustained sequence replication, transcriptional amplification system, Q-Beta Replicase, or the like) and visualized (by, e.g., labeling of the nucleic acid during amplification, exposure to intercalating compounds/dyes, probes). PLVAP RNA (e.g., mRNA) or expression thereof can also be detected using a nucleic acid probe, for example, a labeled nucleic acid probe (e.g., fluorescence in situ hybridization (FISH)) directly in a paraffin section of a tissue sample taken from, e.g., a tumor biopsy, or using other suitable methods. PLVAP gene expression thereof can also be assessed by Southern blot or in solution (e.g., dyes, probes). Further, a gene chip, microarray, probe (e.g., quantum dots) or other such device (e.g., sensor, nanonsensor/detector) can be used to detect expression and/or differential expression of a PLVAP gene.

In one embodiment, a hepatocellular carcinoma can be diagnosed by detecting expression of a PLVAP gene product (e.g., PLVAP mRNA, PLVAP protein) in a sample from a patient. Thus, the method does not require that PLVAP expression in the sample from the patient be compared to the expression of PLVAP in a control. The presence or absence of PLVAP can be ascertained by the methods described herein or other suitable assays. In another embodiment, an increase in expression of PLVAP can be determined by comparison of PLVAP expression in the sample to that of a suitable control. Suitable controls include, for instance, a non-neoplastic tissue sample from the individual, non-cancerous cells, non-metastatic cancer cells, non-malignant (benign) cells or the like, or a suitable known or determined reference standard. The reference standard can be a typical, normal or normalized range or level of expression of a PLVAP protein or RNA (e.g., an expression standard). Thus, the method does not require that expression of the gene/protein be assessed in a suitable control.

In another embodiment, a hepatocellular carcinoma can be diagnosed by detecting the PLVAP gene copy number in a sample from a patient. For example, in some embodiments, a PLVAP gene copy number that is greater than two (e.g., a gene copy number of 3 or 4) can be diagnostic of HCC. Typically, a normal human cell will have a PLVAP gene copy number of two. Therefore, a method of diagnosis based on PLVAP gene copy number does not require detecting the PLVAP gene copy number in a control sample from the patient, although a control may be used. Suitable controls include, for instance, a non-neoplastic tissue sample from the individual, non-cancerous cells, non-metastatic cancer cells, non-malignant (benign) cells or the like, or a suitable known or determined reference standard (e.g., a PLVAP gene copy number of two). The copy number of the PLVAP gene in a sample from a patient can be ascertained by suitable techniques, such as, for example, fluorescence in situ hybridization (FISH).

PLVAP Antibodies

As described herein, antibodies that bind PLVAP have utility in the diagnosis and treatment of HCC in human subjects. For example, antibodies that specifically bind PLVAP can be used to detect the presence of PLVAP on capillary endothelial cells of hepatocellular carcinoma in specimens of liver core biopsies or needle aspirates by immunohistochemical staining (IHC). In addition, antibodies (e.g., humanized antibodies, chimeric antibodies) to PLVAP can be labeled with a proper tracer (e.g., radioisotope) for immuno-positron emission tomography (immuno-PET) (Clin Cancer Res 12:1958-1960, 2006; Clin Cancer Res 12:2133-2140, 2006) to determine whether a space occupying lesion(s) in the liver of a subject is hepatocellular carcinoma. Anti-PLVAP antibodies (e.g., humanized antibodies) can also be labeled with a cytotoxic agent (radioactive or non-radioactive) for therapeutic purposes (Weiner L M, Adams G P, Von Mehren M. Therapeutic monoclonal antibodies: General principles. In: Cancer: Principles & Practice of Oncology. 6$^{th}$ ed. DeVita V T, Hellman S, Rosenberg S A, eds. Philadelphia: Lippincott Williams & Wilkins; 2001:495-508.; Levinson W, Jawetz E. Medical Microbiology & Immunology. 4$^{th}$ ed. Stamford: Appleton & Lange; 1996:307-47; Scheinberg D A, Sgouros G, Junghans R P. Antibody-based immunotherapies for cancer. In: Cancer Chemotherapy & Biotherapy: Principles and Practice. 3$^{rd}$ ed. Chabner B A, Longo D L, eds. Philadelphia: Lippincott Williams & Wilkins; 2001:850-82).

Accordingly, in one embodiment, the invention provides an antibody that binds (e.g., specifically binds) a PLVAP protein (e.g., a human PLVAP protein (SEQ ID NO:23)). Antibodies that specifically bind to a PLVAP protein can be polyclonal, monoclonal, human, chimeric, humanized, primatized, veneered, and single chain antibodies, as well as fragments of antibodies (e.g., Fv, Fc, Fd, Fab, Fab', F(ab'), scFv, scFab, dAb), among others. (See, e.g., Harlow et al., Antibodies A Laboratory Manual, Cold Spring Harbor Laboratory, 1988). Antibodies that specifically bind to a PLVAP protein can be produced, constructed, engineered and/or isolated by conventional methods or other suitable techniques. For example, antibodies which are specific for a PLVAP protein can be raised against an appropriate immunogen, such as a recombinant mammalian (e.g., human) PLVAP protein (e.g., SEQ ID NO:23) or a portion thereof (e.g., SEQ ID NO:2, SEQ ID NO:38, SEQ ID NO:40) (including synthetic molecules, e.g., synthetic peptides). A variety of such immunization methods have been described (see, e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Antibodies can also be raised by immunizing a suitable host (e.g., mouse) with cells that express PLVAP (e.g., cancer cells/cell lines) or cells engineered to express PLVAP (e.g., transfected cells). (See, e.g., Chuntharapai et al., J. Immunol., 152:1783-1789 (1994); Chuntharapai et al. U.S. Pat. No. 5,440,021).

At an appropriate time after immunization, e.g., when the antibody titers are highest, antibody-producing cells can be obtained from the immunized animal and used to prepare monoclonal antibodies by standard techniques, such as the hybridoma technique originally described by Kohler and Milstein (Nature 256:495-497, 1975), the human B cell hybridoma technique (Kozbor et al., Immunol. Today 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, Coligan et al., (eds.) John Wiley & Sons, Inc., New York, N.Y., 1994). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide described herein.

Any of the many well known protocols used for fusing lymphocytes and immortalized cell lines can be applied for the purpose of generating a monoclonal antibody to a polypeptide of the invention (see, e.g., Current Protocols in Immunology, supra; Galfre et al., Nature, 266:55052, 1977; R. H. Kenneth, in Monoclonal Antibodies: A New Dimension In Biological Analyses, Plenum Publishing Corp., New York, N.Y., 1980; and Lerner, Yale J. Biol. Med. 54:387-402, 1981). Moreover, the ordinarily skilled worker will appreciate that there are many variations of such methods that also would be useful.

In one embodiment, the invention relates to a monoclonal anti-PLVAP antibody produced by murine hybridoma KFCC-GY4 (ATCC Patent Deposit Designation PTA-9963), having been deposited on Apr. 8, 2009, at the American Type Culture Collection (ATCC), P.O. Box 1549, Manassas, Va. 20108, United States of America. In another embodiment, the invention relates to a monoclonal anti-PLVAP antibody produced by murine hybridoma KFCC-GY5 (ATCC Patent Deposit Designation PTA-9964), having been deposited on Apr. 8, 2009, at the American Type Culture Collection (ATCC), P.O. Box 1549, Manassas, Va. 20108, United States of America. The invention further relates to the murine hybridoma cell lines KFCC-GY4 (ATCC Patent Deposit Designation PTA-9963) and KFCC-GY5 (ATCC Patent Deposit Designation PTA-9964) themselves, as well as cells obtained from these hybridomas.

In one alternative to preparing monoclonal antibody-secreting hybridomas, a monoclonal antibody to a PLVAP protein can be identified and isolated by screening a recombinant combinatorial immunoglobulin library (e.g., an antibody phage display library) with the target polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display libraries can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9:1370-1372, 1991; Hay et al., Hum. Antibodies Hybridomas 3:81-85, 1992; Huse et al., Science 246: 1275-1281, 1989; and Griffiths et al., EMBO J. 12:725-734, 1993.

Antibody fragments (e.g., antigen-binding fragments) can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments.

Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Single chain, human, chimeric, humanized, primatized (CDR-grafted), or veneered antibodies comprising portions derived from different species are also encompassed by the present invention and the term "antibody." The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also Newman, R. et al., *BioTechnology*, 10: 1455-1460 (1992) regarding primatized antibody, and Ladner et al., U.S. Pat. No. 4,946,778 and Bird, R. E. et al., *Science*, 242: 423-426 (1988)) regarding single chain antibodies.

In a particular embodiment, the invention relates to chimeric antibodies that specifically bind to PLVAP (e.g., a human PLVAP protein comprising SEQ ID NO:23). In one embodiment, chimeric antibody of the invention comprises at least one heavy chain and at least one light chain (e.g., kappa light chain) of human IgG4. The production and characterization of exemplary chimeric antibodies of the invention are described in Example 7 herein.

In another embodiment, the invention relates to humanized antibodies that specifically bind to PLVAP (e.g., a human PLVAP protein comprising SEQ ID NO:23). Humanized antibodies of the invention can comprise, for example, at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, SEQ ID NO:86, SEQ ID NO:66, SEQ ID NO:68, SEQ ID NO:94, SEQ ID NO:96, SEQ ID NO:98, SEQ ID NO:100, SEQ ID NO:102 and a combination thereof and/or at least one kappa light chain amino acid sequence selected from the group consisting of SEQ ID NO:70, SEQ ID NO:72, SEQ ID NO:88, SEQ ID NO:90, SEQ ID NO:92, SEQ ID NO:60, SEQ ID NO:62, SEQ ID NO:64, SEQ ID NO:104, SEQ ID NO:106, SEQ ID NO:108 and a combination thereof.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see, e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, *Gene*, 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see, e.g., Krebber et al., U.S. Pat. No. 5,514,548; Hoogenboom et al., WO 93/06213, published Apr. 1, 1993).

Humanized antibodies can also be produced by and/or obtained from commercial sources, including, for example, Antitope Limited (Cambridge, UK). An exemplary method of producing humanized antibodies that is based on the Composite Human Antibody™ technology of Antitope Limited is described in Example 8 herein.

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see, e.g., Jakobovits et al., *Proc. Natl. Acad. Sci. USA*, 90: 2551-2555 (1993); Jakobovits et al., *Nature*, 362: 255-258 (1993); Lonberg et al., U.S. Pat. No. 5,545,806; Surani et al., U.S. Pat. No. 5,545,807; Lonberg et al., WO 97/13852).

Once produced, an antibody specific for PLVAP can be readily identified using methods for screening and isolating specific antibodies that are well known in the art. See, for example, Paul (ed.), Fundamental Immunology, Raven Press, 1993; Getzoff et al., Adv. in Immunol. 43:1-98, 1988; Goding (ed.), Monoclonal Antibodies: Principles and Practice, Academic Press Ltd., 1996; Benjamin et al., Ann. Rev. Immunol. 2:67-101, 1984. A variety of assays can be utilized to detect antibodies that specifically bind to PLVAP proteins. Exemplary assays are described in detail in Antibodies: A Laboratory Manual, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assays, inhibition or competition assays, and sandwich assays.

In certain embodiments, the antibodies of the invention have a high binding affinity for PLVAP. Such antibodies will preferably have an affinity (e.g., binding affinity) for PLVAP, expressed as $K_d$, of at least about $10^{-7}$ M (e.g., about $0.4 \times 10^{-7}$ M, about $0.6 \times 10^{-7}$ M, about $4.06 \times 10^{-7}$ M, about $4.64 \times 10^{-7}$ M), or higher, for example, at least about $10^{-8}$ M (e.g., about $5.98 \times 10^{-8}$ M), at least about $10^{-9}$ M, or at least about $10^{-10}$ M (e.g., about $9.78 \times 10^{-10}$ M), such as about $9.78 \times 10^{-10}$ M. The binding affinity of an antibody can be readily determined by one of ordinary skill in the art, for example, by Scatchard analysis (Scatchard, G., Ann. NY Acad. Sci. 51: 660-672, 1949). Binding affinity can also be determined using a commercially available biosensor instrument (BIACORE, Pharmacia Biosensor, Piscataway, N.J.), wherein protein is immobilized onto the surface of a receptor chip. See Karlsson, J. Immunol. Methods 145:229-240, 1991 and Cunningham and Wells, J. Mol. Biol. 234:554-563, 1993. This system allows the determination of on- and off-rates, from which binding affinity can be calculated, and assessment of stoichiometry of binding.

The antibodies of the present invention can include a label, such as, for example, a detectable label that permits detection of the antibody, and proteins bound by the antibody (e.g., PLVAP), in a biological sample. A detectable label is particularly suitable for diagnostic applications. For example, a PLVAP antibody can be labeled with a radioactive isotope (radioisotope), which can be detected by one of skill in the art using a gamma counter or a scintillation counter or by autoradiography or other suitable means. Isotopes which are useful for the purpose of the present invention include, but are not limited to: $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe and $^{75}$Se.

Antibodies of the invention can also be labeled with a fluorescent compound (e.g., dyes). When the fluorescently labeled antibody is exposed to light of the proper wavelength, its presence can then be detected due to the fluorescence of the compound. Among the most commonly used fluorescent labels are fluorescein isothiocyanate, rhodamine, phycoerytherin, phycocyanin, allophycocyanin, o-phthaldehyde and fluorescamine. The antibodies of the invention can also be labeled using fluorescence emitting metals, such as $^{152}$Eu or others of the lanthanide series. These metals can be attached to the antibody molecule using such metal chelating groups as diethylenetriaminepentaacetic acid (DTPA), tetraaza-cyclododecane-tetraacetic acid (DOTA) or ethylenediaminetetraacetic acid (EDTA).

The antibodies of the present invention also can be coupled to a chemiluminescent compound. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Useful bioluminescent compounds for purposes of labeling antibodies are luciferin, luciferase and aequorin.

Detection of the labeled antibodies can be accomplished by a scintillation counter, for example, if the detectable label is a radioactive gamma emitter, or by a fluorometer, for example, if the label is a fluorescent material. In the case of an enzyme label, the detection can be accomplished by colorimetric methods that employ a substrate for the enzyme. Detection may also be accomplished by visual comparison of the extent of the enzymatic reaction of a substrate to similarly prepared standards.

Accordingly, the antibodies of the present invention can also be used as a stain for tissue sections. For example, a labeled antibody that binds to PLVAP can be contacted with a tissue sample, e.g., a liver tissue biopsy or fine needle aspirate from a patient. This section may then be washed and the label detected using an appropriate means.

For the purpose of treating HCC, PLVAP antibodies of the invention may include a radiolabel or other therapeutic agent that enhances destruction of cells expressing PLVAP (e.g., vascular endothelial cells surrounding HCC cells). Examples of suitable radioisotope labels for use in HCC therapy include, but are not limited to, $^{125}$I, $^{131}$I, $^{90}$Y, $^{67}$Cu, $^{217}$Bi, $^{211}$At, $^{212}$Pb, $^{47}$Sc, $^{109}$Pd, $^{111}$In and $^{118}$Re. Optionally, a label that emits α and β particles upon bombardment with neutron radiation, such as boron, can be used as a label for therapeutic PLVAP antibodies.

Therapeutic antibodies also may include a cytotoxic agent that is capable of selectively killing cells that express PLVAP. For example, bacterial toxins, such as diphtheria toxin or ricin, can be used. Methods for producing antibodies comprising fragment A of diphtheria toxin are taught in U.S. Pat. No. 4,675,382 (1987). Diphtheria toxin contains two polypeptide chains. The B chain binds the toxin to a receptor on a cell surface. The A chain actually enters the cytoplasm and inhibits protein synthesis by inactivating elongation factor 2, the factor that translocates ribosomes along mRNA concomitant with hydrolysis of ETP. See Darnell, J. et al., in Molecular Cell Biology, Scientific American Books, Inc., page 662 (1986). Alternatively, an antibody comprising ricin, a toxic lectin, may be prepared. Other suitable cytotoxic agents are known by those of skill in the art.

For in vivo detection, PLVAP antibodies of the invention may be conjugated to radionuclides either directly or by using an intermediary functional group. An intermediary group which is often used to bind radioisotopes, which exist as metallic cations, to antibodies is diethylenetriaminepentaacetic acid (DTPA) or tetraaza-cyclododecane-tetraacetic acid (DOTA). Typical examples of metallic cations which are bound in this manner are $^{99}$Tc, $^{123}$I, $^{111}$In, $^{131}$I, $^{97}$Ru, $^{67}$Cu, $^{67}$Ga, and $^{68}$Ga.

Moreover, the antibodies of the invention may be tagged with an NMR imaging agent that includes paramagnetic atoms. The use of an NMR imaging agent allows the in vivo diagnosis of the presence of and the extent of HCC in a patient using NMR techniques. Elements which are particularly useful in this manner are $^{157}$Gd, $^{55}$Mn, $^{162}$Dy, $^{52}$Cr, and $^{56}$Fe.

PLVAP Antagonists

A PLVAP antagonist of the invention can be any agent that inhibits (e.g., reduces, prevents) an activity of a PLVAP gene product. PLVAP activities include, but are not limited to, formation, growth, vascularization or progression of an HCC tumor. In a particular embodiment, a PLVAP antagonist inhibits an activity of a PLVAP gene product (e.g., PLVAP RNA, PLVAP protein) by specifically binding to the PLVAP gene product. PLVAP antagonists also encompass agents that inhibit (reduce, decrease, prevent) the expression (e.g., transcription, mRNA processing, translation) of a PLVAP gene or gene product (e.g., PLVAP RNA, PLVAP protein). A PLVAP antagonist can be an antibody, a small molecule, a peptide, a peptidomimetic, or a nucleic acid, among others.

Antibody Antagonists

A PLVAP antagonist of the invention can be an antibody that specifically binds a PLVAP protein. Such antibodies include, but are not limited to, any of the PLVAP-specific antibodies described herein.

Small Molecule Antagonists

PLVAP antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g., a carbon-carbon chain or a carbon-heteroatom chain), or may represent a ring containing carbon atoms, e.g., benzene or a policyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic PLVAP antagonists can be found in nature (e.g., identified, isolated, purified) and/or produced synthetically (e.g., by traditional organic synthesis, bio-mediated synthesis, or a combination thereof). See, e.g., Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

Peptide Antagonists

The PLVAP antagonist of the invention can also be a peptide that binds to a PLVAP protein. The peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups and methods for adding or removing protecting groups are known in the art and are disclosed in, for example, Green and Wuts, "*Protecting Groups in Organic Synthesis*," John Wiley and Sons, 1991. The functional groups of a peptide can also be derivatized (e.g., alkylated) using art-known methods.

The peptide PLVAP antagonist can comprise one or more modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its PLVAP antagonist activity.

PLVAP antagonists that are peptides can be linear, branched or cyclic, e.g., a peptide having a heteroatom ring structure that includes several amide bonds. In a particular embodiment, the peptide is a cyclic peptide. Such peptides can be produced by one of skill in the art using standard techniques. For example, a peptide can be derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis*," John Wiley & Sons, Second Edition, 1976). Peptides that are PLVAP antagonists can also be produced, for example, using recombinant DNA methodologies or other suitable methods (see, e.g., Sambrook J. and Russell D. W., *Molecular Cloning: A Laboratory Manual*, 3$^{rd}$ Edition, Cold Spring Harbor Laboratory Press, Cold Spring Harbor, N.Y., 2001).

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods known by those of skill in the art.

Peptidomimetic Antagonists

PLVAP antagonists can also be peptidomimetics. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for instance, human PLVAP. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of peptides that bind PLVAP proteins. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more -CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

Nucleic Acid Antagonists

PLVAP antagonists also include various nucleic acids, including nucleic acid molecules that inhibit PLVAP gene expression (e.g., siRNA, antisense oligonucleotides, ribozymes). For example, small interfering ribonucleic acids (siRNAs) and, similarly, short hairpin ribonucleic acids (shRNAs), which are processed into short siRNA-like molecules in a cell, can prevent the expression (translation) of the PLVAP protein. siRNA molecules can be polynucleotides that are generally about 20 to about 25 nucleotides long and are designed to bind a specific RNA sequence (e.g., a PLVAP mRNA sequence). siRNAs silence gene expression in a sequence-specific manner, binding to a target RNA (e.g., an RNA having the complementary sequence) and causing the RNA to be degraded by endoribonucleases. siRNA molecules able to inhibit the expression of the PLVAP gene product can be produced by suitable methods. There are several algorithms that can be used to design siRNA molecules that bind the sequence of a gene of interest (see, e.g., Mateeva O. et al. *Nucleic Acids Res.* 35(8):Epub, 2007; Huesken D. et al., *Nat. Biotechnol.* 23:995-1001; Jagla B. et al., RNA 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See, e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001.). Stable expression of siRNA/shRNA molecules is advantageous in the treatment of cancer as it enables long-term expression of the molecules, potentially reducing and/or eliminating the need for repeated treatments.

Antisense oligonucleotides (e.g., DNA, riboprobes) can also be used as PLVAP antagonists to inhibit PLVAP expression. Antisense oligonucleotides are generally short (~13 to ~25 nucleotides) single-stranded nucleic acids which specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See, e.g., Dias N. and Stein C. A., *Mol. Can. Ther.* 1:347-355, 2002). There are a number of different types of antisense oligonucleotides that can be used as PLVAP antagonists including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be designed to be specific for a protein using predictive algorithms. (See, e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells (e.g., tumor cells) via the process of adsorptive endocytosis. Thus, in the treatment of a subject (e.g., mammalian), antisense PLVAP oligonucleotides can be delivered to target cells (e.g., tumor cells) by, for example, injection or infusion. For instance, purified oligonucleotides or siRNA/shRNA can be administered alone or in a formulation with a suitable drug delivery vehicle (e.g., liposomes, cationic polymers, (e.g., poly-L-lysine, PAMAM dendrimers, polyalkylcyanoacrylate nanoparticles and polyethyleneimine)) or coupled to a suitable carrier peptide (e.g., homeotic transcription factor, the Antennapedia peptide, Tat protein of HIV-1, E5CA peptide).

Ribozymes can also be used as PLVAP antagonists to inhibit PLVAP expression. Ribozymes are RNA molecules possessing enzymatic activity. One class of ribozymes is capable of repeatedly cleaving other separate RNA molecules into two or more pieces in a nucleotide base sequence specific manner. See Kim et al., *Proc Natl Acad Sci USA*, 84:8788 (1987); Haseloff & Gerlach, *Nature*, 334:585 (1988); and Jefferies et al., *Nucleic Acid Res*, 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, typically reducing its stability and destroying its ability to directly translate an encoded protein. After a ribozyme has cleaved its RNA target, it is released from that target RNA and thereafter can bind and cleave another target. That is, a single ribozyme molecule can repeatedly bind and cleave new targets.

In accordance with the present invention, a ribozyme may target any portion of the mRNA encoding PLVAP. Methods for selecting a ribozyme target sequence and designing and making ribozymes are generally known in the art. See, e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See, e.g., U.S. Pat. Nos. 4,987,071; 5,496,698; 5,525,468; 5,631,359; 5,646,020; 5,672,511; and U.S. Pat. No. 6,140,491; Rossi et al., *AIDS Res Human Retroviruses* 8:183 (1992); Hampel & Tritz, *Biochemistry* 28:4929 (1989); Hampel et al., *Nucleic Acids Res*, 18:299 (1990); Perrotta & Been, *Biochemistry* 31:16 (1992); and Guerrier-Takada et al., *Cell*, 35:849 (1983).

Ribozymes can be synthesized by the same methods used for normal RNA synthesis. For example, suitable methods are disclosed in Usman et al., *J Am Chem Soc*, 109:7845-7854 (1987) and Scaringe et al., *Nucleic Acids Res*, 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman & Cedergren, *Trends Biochem Sci*, 17:334 (1992).

PLVAP antagonists of the invention can also be nucleic acid molecules (e.g., oligonucleotides) that bind to, and inhibit the activity of, a PLVAP protein. Suitable nucleic acid PLVAP antagonists include aptamers, which are capable of binding to a particular molecule of interest (e.g., human PLVAP) with high affinity and specificity through interactions other than classic Watson-Crick base pairing (Tuerk and Gold, Science 249:505 (1990); Ellington and Szostak, Nature 346:818 (1990)).

Aptamers, like peptides generated by phage display or monoclonal antibodies (MAbs), are capable of specifically binding to selected targets and, through binding, block their targets' ability to function. Created by an in vitro selection process from pools of random sequence oligonucleotides, aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

An aptamer that binds to a target of interest (e.g., a human PLVAP protein) can be generated and identified using a standard process known as "Systematic Evolution of Ligands by Exponential Enrichment" (SELEX), described in, e.g., U.S. Pat. Nos. 5,475,096 and 5,270,163.

Identification of PLVAP Antagonists

Agents having binding specificity for PLVAP gene products can be identified in a screen, for example, a high-throughput screen of chemical compounds and/or libraries (e.g., chemical, peptide, nucleic acid libraries).

Antibodies that specifically bind human PLVAP can be identified, for example, by screening commercially available combinatorial antibody libraries (Dyax Corp., MorphoSys AG). Suitable combinatorial antibody libraries and standard methods of screening these libraries are described in Hoet et al., *Nature Biotechnology* 23(3):344-348 (2005) and Rauchenberger et al., *J. Biol. Chem.* 278(40):38194-38205 (2003), the contents of which are incorporated herein by reference. Such libraries or collections of molecules can also be prepared using well-known chemical methods.

Alternatively murine antibodies that specifically bind human PLVAP can be identified, for example, by immunizing mice with PLVAP proteins, protein fragments or peptides, along with an adjuvant to break tolerance to the antigen. These antibodies can be screened for the desired specificity and activity and then humanized using known techniques to create suitable agents for the treatment of human disease.

Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screened to identify compounds that bind and inhibit PLVAP.

Identified compounds can serve as lead compounds for further diversification using well-known methods of medicinal chemistry. For example, a collection of compounds that are structural variants of the lead can be prepared and screened for PLVAP binding and/or inhibitory activity. This can result in the development of a structure activity relationship that links the structure of the compounds to biological activity. Compounds that have suitable binding and inhibitory activity can be developed further for in vivo use.

Agents that bind PLVAP can be evaluated further for PLVAP antagonist activity. For example, a composition comprising a PLVAP protein can be used in a screen or binding assay to detect and/or identify agents that bind and antagonize the PLVAP protein. Compositions suitable for use include, for example, cells that naturally express a PLVAP protein (e.g., liver vascular endothelial cells), extracts of such cells, and recombinant PLVAP protein.

An agent that binds a PLVAP protein can be identified in a competitive binding assay, for example, in which the ability of a test agent to inhibit the binding of PLVAP to a reference agent is assessed. The reference agent can be a full-length PLVAP protein or a portion thereof. The reference agent can be labeled with a suitable label (e.g., radioisotope, epitope label, affinity label (e.g., biotin and avidin or streptavadin), spin label, enzyme, fluorescent group, chemiluminescent group, dye, metal (e.g., gold, silver), magnetic bead) and the amount of labeled reference agent required to saturate the PLVAP protein in the assay can be determined. The specificity of the formation of the complex between the PLVAP protein and the test agent can be determined using a suitable control (e.g., unlabeled agent, label alone).

The capacity of a test agent to inhibit formation of a complex between the reference agent and a PLVAP protein can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents suitable for use in the method include molecules and compounds which specifically bind to PLVAP, e.g., an antibody that binds PLVAP.

An agent that antagonizes a PLVAP protein can be identified by screening for agents that have an ability to antagonize (reduce, prevent, inhibit) one or more activities of PLVAP, such as, for example, tumor vascularization. Such activities can be assessed by one of skill in the art using any appropriate in vitro or in vivo assay.

Pharmaceutical Compositions

A PLVAP antagonist of the invention can be administered to a mammalian subject as part of a pharmaceutical or physiological composition, for example, as part of a pharmaceutical composition comprising a PLVAP antagonist and a pharmaceutically acceptable carrier. Formulations or compositions comprising a PLVAP antagonist (e.g., an antibody that specifically binds PLVAP) or compositions comprising a PLVAP antagonist and one or more other therapeutic agents (e.g., a chemotherapeutic agent, for example, doxorubicin, 5-fluorouracil, tamoxifen, octreotide) will vary according to the route of administration selected (e.g., solution, emulsion or capsule). Suitable pharmaceutical carriers can contain inert ingredients which do not interact with the PLVAP antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Diagnostic Kits

The invention also provides diagnostic kits for detecting the presence of a hepatocellular carcinoma in a subject. Such kits comprise at least one agent (e.g., a nucleic acid probe, an antibody) for detecting PLVAP gene expression in a sample (e.g., a biological sample from a mammalian subject). PLVAP gene expression can be detected, for example, by detecting a PLVAP gene product, such as a PLVAP mRNA or a PLVAP protein, in the sample.

Accordingly, in one embodiment, the kit comprises at least one nucleic acid probe (e.g., an oligonucleotide probe) that specifically hybridizes to a PLVAP RNA (e.g., mRNA, hnRNA) transcript. Such probes are capable of hybridizing to PLVAP RNA under conditions of high stringency.

In another embodiment, the kit includes a pair of oligonucleotide primers that are capable of specifically hybridizing to a PLVAP gene product (e.g., mRNA, cDNA) in a sample. Such primers can be used in any standard nucleic acid amplification procedure (e.g., polymerase chain reaction (PCR), for example, RT-PCR, quantitative real time PCR) to determine the level of the PLVAP gene product in the sample.

In another embodiment, the kits of the invention include an antibody that specifically binds a PLVAP protein (e.g., a human PLVAP protein). Such antibodies include any of the PLVAP antibodies of the invention described herein. In one embodiment, the antibody comprises a $V_H$ domain having the amino acid sequence of SEQ ID NO:4 and a $V_L$ domain having the amino acid sequence of SEQ ID NO:9. In another embodiment, the antibody comprises a $V_H$ domain having the amino acid sequence of SEQ ID NO:14 and a $V_L$ domain having the amino acid sequence of SEQ ID NO:19.

The diagnostic agents in the kits of the invention can include one or more labels (e.g., detectable labels). Numerous suitable labels for diagnostic agents are known in the art and include, but are not limited to, any of the labels described herein. In a particular embodiment, the diagnostic agent (e.g., antibody) includes a radioisotope, such that agent can be used for immuno-positron emission tomography (immuno-PET).

The present invention will now be illustrated by the following Examples, which are not intended to be limiting in any way.

EXEMPLIFICATION

Example 1

PLVAP Expression is Elevated in HCC Liver Tissues Relative to Non-HCC Liver Tissues Materials and Methods:
Tissue Samples Tissues of HCC and adjacent non-tumorous liver were collected from fresh specimens surgically removed from human patients for therapeutic purpose. These specimens were collected under direct supervision of attending pathologists. The collected tissues were immediately stored in liquid nitrogen at the Tumor Bank of the Koo Foundation Sun Yat-Sen Cancer Center (KF-SYSCC). Paired tissue samples from eighteen HCC patients were available for the study. The study was approved by the Institutional Review Board and written informed consent was obtained from all patients. The clinical characteristics of the eighteen HCC patients from this study are summarized in Table 1.

mRNA Transcript Profiling

Total RNA was isolated from tissues frozen in liquid nitrogen using Trizol® reagents (Invitrogen, Carlsbad, Calif.). The isolated RNA was further purified using RNAEasy® Mini kit (Qiagen, Valencia, Calif.) and its quality assessed using the RNA 6000 Nano assay in an Agilent 2100 Bioanalyzer (Agilent Technologies, Waldbronn, Germany). All RNA samples used for the study had an RNA Integrity Number (RIN) greater than 5.7 (8.2±1.0, mean±SD). Hybridization targets were prepared from 8 µg total RNA according to Affymetrix® protocols and hybridized to an Affymetrix® U133A GeneChip®, which contains 22,238 probe-sets for approximately 13,000 human genes. Immediately following hybridization, the hybridized array underwent automated washing and staining using an Affymetrix® GeneChip® fluidics station 400 and the EukGE WS2v4 protocol. Thereafter, U133A GeneChip® microarray chips were scanned in an Affymetrix® GeneArray scanner 2500.

Determination of Present and Absent Call of Microarray Data

Affymetrix® Microarray Analysis Suite (MAS) 5.0 software was used to generate present calls for the microarray data for all 18 pairs of HCC and adjacent non-tumor liver tissues. All parameters for present call determination were default values. Each probe-set was determined as "present," "absent" or "marginal" by MAS 5.0. Similarly, the same microarray data were processed using dChip version-2004 software to determine "present," "absent" or "marginal" status for each probe-set on the microarrays.

Identification of Probe-Sets with Extreme Differential Expression

Figure 1:
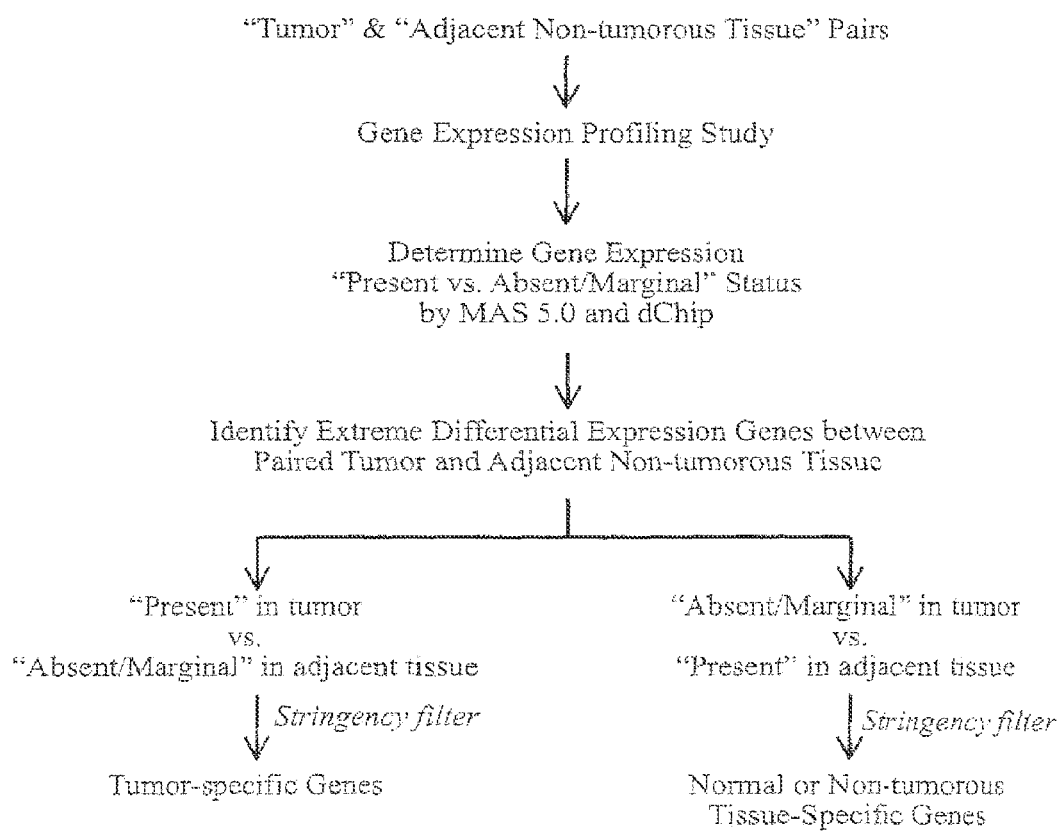
FIG. 1 is a flow chart diagram depicting an algorithm for the identification of genes that show extreme differential expression between tumor and adjacent non-tumorous tissues.

For identification of genes with extreme differential expression between HCC and adjacent non-tumor liver tissue, software written using Practical Extraction and Report Language (PERL) was used according to the following rules: "Tumor-specific genes" were defined as probe-sets that were called "present" in HCC and "absent" or "marginal" in the adjacent non-tumor liver tissue by both MAS 5.0 and dChip. "Non-tumor liver tissue-specific genes" were defined as probe-sets called 'absent' or 'marginal' in HCC and 'present' in the paired adjacent non-tumor liver tissue by both MAS 5.0 and dChip. A flowchart diagram depicting the identification algorithm is shown in FIG. 1.

TABLE 1

Clinical data for eighteen HCC patients from which paired HCC and adjacent non-tumorous liver tissue samples were obtained

| Case No | Sex | Age | HBsAg | HBsAb | HCV IgG | TNM Stage | AFP (ng/ml) | Differentiation |
|---|---|---|---|---|---|---|---|---|
| 1 | M | 70 | + | | − | 2 | 2 | Moderate |
| 2 | M | 75 | − | + | + | 4A | 5 | Well |
| 3 | M | 59 | + | | − | 4A | 1232 | Moderate |
| 4 | F | 53 | + | | + | 1 | 261 | Moderate |
| 5 | M | 45 | + | | − | 2 | 103 | Moderate |
| 6 | M | 57 | + | + | − | 2 | 5 | Moderate |
| 7 | M | 53 | + | + | − | 3A | 19647 | Moderate |
| 8 | M | 54 | − | − | + | 3A | 7 | Moderate |
| 9 | M | 44 | + | | − | 4A | 306 | Moderate |
| 10 | M | 76 | − | − | + | 3A | 371 | Moderate |
| 11 | F | 62 | + | − | − | 3A | 302 | Moderate |
| 12 | F | 73 | − | − | + | 2 | 42 | Moderate |
| 13 | M | 46 | + | | − | 4A | 563 | Moderate |
| 14 | M | 45 | − | | − | 3A | 64435 | Moderate |
| 15 | M | 41 | + | | − | 2 | 33.9 | Well |
| 16 | M | 44 | + | + | − | 2 | 350 | Moderate |
| 17 | M | 67 | + | | − | 3A | 51073 | Moderate |
| 18 | M | 34 | + | | − | 4A | 2331 | Moderate |

Real-Time Quantitative Reverse-Transcriptase Polymerase Chain Reaction (RT-PCR)

TaqMan™ real-time quantitative reverse transcriptase-PCR (qRT-PCR) was used to quantify mRNA. cDNA was synthesized from 8 μg of total RNA for each sample using 1500 ng oligo(dT) primer and 600 units SuperScript™ II Reverse Transcriptase from Invitrogen (Carlsbad, Calif.) in a final volume of 60 μl according to the manufacturer's instructions. For each RT-PCR reaction, 0.5 μl cDNA was used as template in a final volume of 25 μl following the manufacturers' instructions (ABI and Roche). The PCR reactions were carried out using an Applied Biosystems 7900HT Real-Time PCR system. Probes and reagents required for the experiments were obtained from Applied Biosystems (ABI) (Foster City, Calif.). The sequences of primers and the probes used for real-time quantitative RT-PCR of PLVAP are 5'-CCTG-CAGGCATCCCTGTA-3' (forward primer) (SEQ ID NO:25); 5'-CGGGCCATCCCTTGGT-3' (reverse primer) (SEQ ID NO:26); and 5'-CCCCATCCAGTGGCTG-3' (probe) (SEQ ID NO:27). Hypoxanthine-guanine phosphoribosyltransferase (HPRT) housekeeping gene was used as an endogenous reference for normalization. All samples were run in duplicate on the same PCR plate for the same target mRNA and the endogenous reference HPRT mRNA. The relative quantities of target mRNAs were calculated by comparative Ct method according to manufacturer's instructions (User Bulletin #2, ABI Prism® 7700 Sequence Detection System). A non-tumorous liver sample was chosen as the relative calibrator for calculation.

Results:

The PLVAP gene expression intensities in 18 pairs of HCC and adjacent non-tumorous liver tissues are shown in FIG. 2. The average gene expression intensities were 759.8±436.5 and 170.6±53.4 (mean±SD) for paired HCC and adjacent non-tumorous liver tissue, respectively. The p value of paired t-test between the two groups was $2.8 \times 10^{-5}$. These results indicate that PLVAP is expressed in HCC and not in non-tumorous liver tissue. This elevated expression of PLVAP in HCC was further confirmed when 82 unpaired HCC samples showed an average expression intensity of 810.4±482.0 (mean±SD), which is essentially the same as the finding from the 18 paired HCC samples (p=0.62 by t-test) (FIG. 2).

Figure 3A:
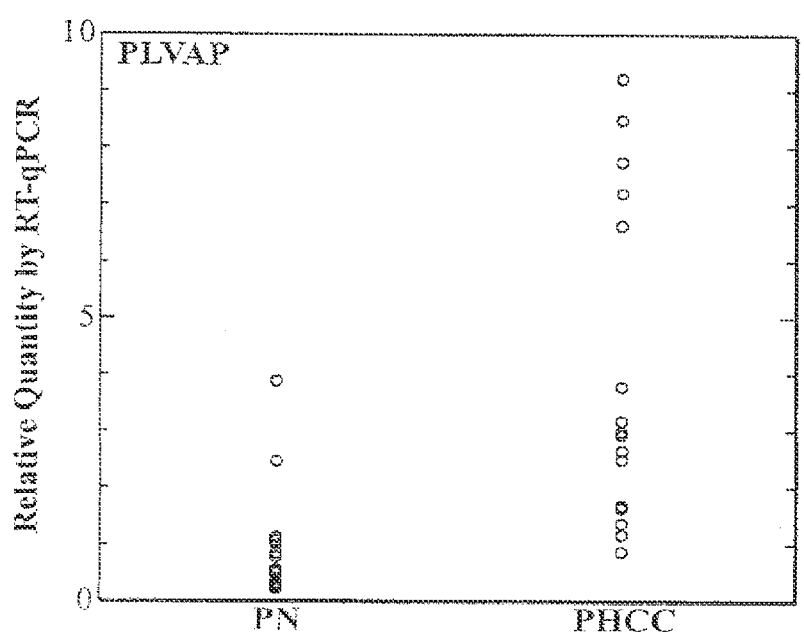
FIG. 3A is a graph depicting relative PLVAP expression quantities in paired HCC (PHCC) and adjacent non-tumorous liver tissue (PN) samples as determined by Taqman quantitative RT-PCR. PLVAP mRNA levels are significantly higher in HCC relative to non-tumorous liver tissues.
Figure 5:
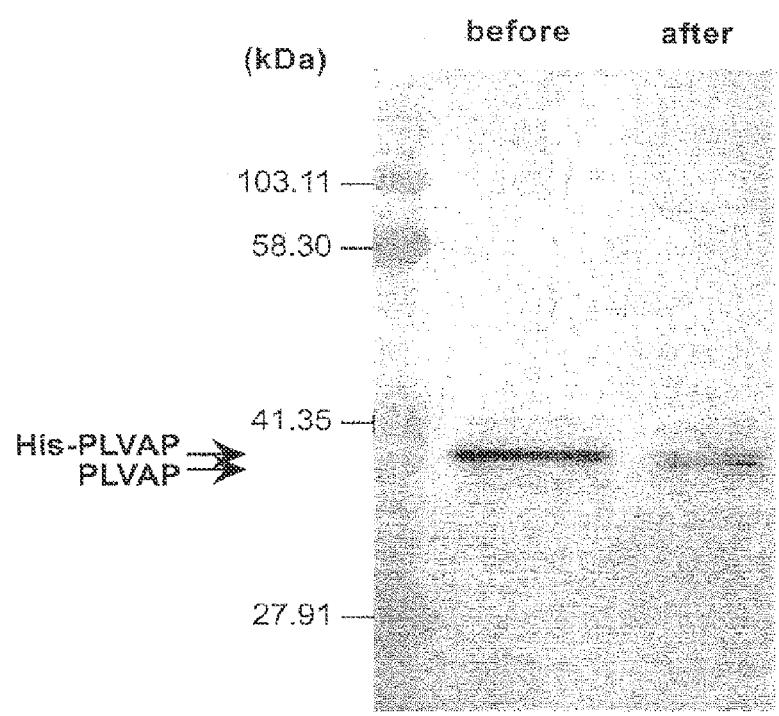
FIG. 5 is an image of a Western blot depicting the detection of recombinant PLVAP protein before and after thrombin digestion to remove the His tag. Arrows to the left of the blot indicate the locations of His-PLVAP and PLVAP on the blot. The numbers to the left of the blot indicate the positions of molecular weight standards.

In order to confirm that PLVAP is significantly expressed in HCC liver tissue and not in non-tumorous liver tissue, real-time quantitative RT-PCR was performed on RNA samples from 18 pairs of HCC and adjacent non-tumorous liver tissue. Quantities of PLVAP mRNA were significantly higher in HCC relative to non-tumorous liver tissues (see FIG. 3A and Table 2). Although the results showed some overlap between two groups, PLVAP transcripts were higher in HCC than in adjacent non-tumorous liver tissue within the same individual for all individuals tested except one (FIG. 3B). This exception was likely associated with uneven degrees of RNA degradation during storage process of tissues.

TABLE 2

PLVAP gene expression intensities for 18 pairs of HCC and adjacent non-tumorous liver tissue

| Sample Number | Expression Intensity* | |
|---|---|---|
| | HCC | Adjacent non-tumorous liver tissue |
| 1 | 1757 | 195 |
| 2 | 1329 | 210 |
| 3 | 1148 | 168 |

TABLE 2-continued

PLVAP gene expression intensities for 18 pairs of HCC and adjacent non-tumorous liver tissue

| Sample Number | Expression Intensity* | |
|---|---|---|
| | HCC | Adjacent non-tumorous liver tissue |
| 4 | 1130 | 211 |
| 5 | 1096 | 213 |
| 6 | 1068 | 181 |
| 7 | 932 | 101 |
| 8 | 804 | 60 |
| 9 | 630 | 155 |
| 10 | 612 | 175 |
| 11 | 607 | 125 |
| 12 | 519 | 146 |
| 13 | 478 | 300 |
| 14 | 422 | 180 |
| 15 | 275 | 105 |
| 16 | 251 | 204 |
| 17 | 251 | 155 |
| 18 | 186 | 184 |

Example 2

PLVAP is Specifically Expressed by HCC Vascular Endothelial Cells

Materials and Methods:

Laser Capture Microdissection (LCM) of Formalin-Fixed Paraffin Embedded Tissues

LCM of formalin fixed tissue from paraffin blocks was carried out using Arcturus PixCell® IIe system, CapSure™ HS LCM caps, and Paradise™ reagent system from Arcturus Bioscience, Inc. (Mountain View, Calif.). Seven micrometer thick tissue sections were cut, deparaffinized, rehydrated, stained and dehydrated for LCM according to manufacturer's instructions. Target cells were captured onto CapSure™ HS LCM caps using 7.5 μm laser spot size at 50 mW power and 1.3 ms duration. Approximately 5000 to 6000 cells were captured on each cap. However, only 1000 to 2000 hepatocellular carcinoma vascular endothelial cells were captured onto each cap due to paucity of cells.

RNA Extraction from LCM Tissue Sections for Quantitative RT-PCR

Cells captured onto the CapSure™ HS LCM caps as described above were processed for RNA extraction, cDNA synthesis, in vitro transcription and antisense RNA amplification using the Paradise™ reagent system according to manufacturer's instructions. The synthesized anti-sense RNA was then used as a template for two-step TaqMan® real time quantitative RT-PCR for quantitation of PLVAP and beta-actin mRNA in the cells captured by LCM. The first step (i.e., reverse transcription) was carried out using 4.5 μl anti-sense RNA and TaqMan® Reverse Transcription Reagents (ABI) in a final volume of 10 μl following the manufacturer's protocol. The second step (i.e., real-time PCR) was performed using 2.4 μl of cDNA template, the primers/probe mix and the TaqMan® universal PCR Master Mix from Applied Biosystems in a final volume of 25 μl. Real-time PCR was carried out in a Smart Cycler® II machine (Cephid, Inc., Sunnyvale, Calif.). The reactions were initially incubated at 50° C. for 2 minutes and then at 95° C. for 10 minutes. Thereafter, 45 cycles of denaturation at 95° C. for 15 seconds and annealing/extension at 60° C. for 40 seconds were performed. The sequences of the primers and the probes are listed in Table 3.

TABLE 3

Primer and probe sequences for real-time quantitative RT-PCR for PLVAP and beta-actin levels in samples prepared by laser-captured microdissection

| | PLVAP gene | beta-Actin gene |
|---|---|---|
| forward primer | 5'-CCTTGAGCGTGAGTGTTTCCA-3' (SEQ ID NO: 28) | 5'-GTCCCCCAACTTGAGATGTATGAAG-3' (SEQ ID NO: 29) |
| reverse primer | 5'-GGCAGGGCTGGGAGTTG-3' (SEQ ID NO: 30) | 5'-GTCTCAAGTCAGTGTACAGGTAAGC-3' (SEQ ID NO: 31) |
| Taqman probe | 5'-CTCCCAGGGAGACCAA-3' (SEQ ID NO: 32) | 5'-AAGGAGTGGCTCCCCTCC-3' (SEQ ID NO: 33) |

Preparation of Expression Vector for Recombinant Fusion PLVAP$_{51-442}$ Protein Plasmid pGEM®-T Easy-PLVAP$_{51-442}$ was generated by inserting a PCR fragment encoding amino acid residues 51 to 442 of PLVAP into the pGEM®-T Easy Vector (Promega, Inc., Madison, Wis.). The PCR fragment was amplified from a cDNA clone of PLVAP from OriGene (Rockville, Md.) by using the primer set of 5'-CATATG AACGTGCACGTGAGCACAGAGTCC-3' (SEQ ID NO:34) and 5'-GGATCC TGAGCATATCCCTGCATCCTCC-3' (SEQ ID NO:35). For construction of plasmid pET-15b-PLVAP$_{51-442}$, a cDNA fragment encoding amino acid residues 51 to 442 of PLVAP with NdeI and BamHI recognition sequences at each respective end was excised from pGEM®-T Easy-PLVAP$_{51-442}$ and inserted into pET-15b (Novagen, Inc., San Diego, Calif.). The expression construct described above was verified by DNA sequencing.

Expression and Purification of Recombinant Fusion PLVAP$_{51-442}$ Protein

For production of recombinant His-tagged PLVAP$_{51-442}$ protein (SEQ ID NO:2) (FIG. 4), Escherichia coli (Rosetta-Gami™2(DE3)pLysS cells) (Novagen) was transformed by incubating competent cells with pET-15b-PLVAP$_{51-442}$ plasmid DNA on ice for 5 min, followed by incubation in a 42° C. water bath for 30 s and then again on ice for 2 min. Prior to plating on selective medium, the transformants were incubated at 37° C. while shaking at 250 rpm with SOC medium (0.5% Yeast Extract; 2% Tryptone; 10 mM NaCl; 2.5 mM KCl; 10 mM MgCl$_2$; 10 mM MgSO$_4$; 20 mM Glucose) for 60 min. Expression of His-tagged fusion protein in Rosetta-Gami™2(DE3)pLysS Escherichia coli was induced with 1 mM isopropyl-B-D-thiogalactopyranoside for 16 hours at 30° C. Following the induction, the bacterial cells were subjected to lysis by sonication in equilibration buffer (50 mM sodium phosphate, 300 mM NaCl, pH 7) supplemented with 8 M urea and separated into soluble and insoluble fractions by centrifugation at 5,600×g for 30 minutes. For further purification of the His-PLVAP$_{51-442}$ protein, soluble fraction was loaded on a TALON® Metal Affinity Resin (Clontech, Inc., Palo Alto, Calif.), washed with equilibration buffer and eluted with elution buffer (50 mM sodium phosphate, 300 mM NaCl, pH 7, 250 mM imidazole). The His-tag of the purified fusion protein was removed by thrombin cleavage (Novagen) according to manufacturer's instructions (see FIG. 5). The resulting PLVAP$_{51-442}$ protein was recovered by extensive dialysis against PBS. To verify the identity of the recombinant PLVAP protein, a small quantity of mouse antiserum against GST-PLVAP$_{331-430}$ fusion protein was purchased from the Biodesign Insitute (Tempe, Ariz.). The recombinant PLVAP$_{51-442}$ protein without the His-tag was detected by Western blot analysis using this antibody, but did not react with antibodies to the His-tag. These results confirm the identity of the recombinant PLVAP protein.

Generation of Mouse Anti-Human PLVAP Serum

Purified PLVAP$_{51-442}$ recombinant protein in PBS was used to immunize 6 weeks old Balb/cByj mice. Each mouse was initially immunized with subcutaneous injection at multiple sites with a total of 14 µg PLVAP$_{51-442}$ protein in complete Freund's adjuvant (Sigma, Inc., St Louis, Mo.). Thereafter, immunization was boosted with 7 µg PLVAP$_{51-442}$ recombinant protein in incomplete Freund's adjuvant once every two weeks for three times. A week after the last boosting immunization, mice were bled for preparation of antiserum.

Enzyme-Linked Immunosorbent Assay (ELISA)

Reagents and Solutions:
1. Recombinant PLVAP protein
2. Anti-mouse IgG-alkaline phosphatase conjugate (Cat. #: AP124A, CHEMICON)
3. Coating buffer (0.137 M Sodium Chloride, 0.01 M Sodium Phosphate Dibasic Heptahydrate, 2 mM Potassium Phosphate Monobasic, 0.002% (0.3 mM) Sodium azide, pH 7.2-7.4)
4. Washing buffer (0.137 M Sodium Chloride, 0.01 M Sodium Phosphate Dibasic Heptahydrate, 2 mM Potassium Phosphate Monobasic, 0.2% Tween20 (Cat. #: P1379, SIGMA, pH 7.2-7.4)
5. Blocking buffer (0.137 M Sodium Chloride, 0.01 M Sodium Phosphate Dibasic Heptahydrate, 2 mM Potassium Phosphate Monobasic, 2% Bovine Serum Albumin (Cat. #: 82-045, PENTEX), 0.05% Tween20 (Cat. #: P1379, SIGMA), pH 7.2-7.4)
6. Carbonate buffer (0.016 M Sodium Bicarbonate, 0.014 M Sodium Carbonate, 2 mM Magnesium Chloride, 0.002% (0.3 mM) Sodium Azide, pH 9.6)
7. Akaline Phosphatase substrate: One 40 mg phosphatase substrate tablet (Cat. #: P5994, SIGMA) dissolved in 40 ml carbonate buffer Procedure:

The titers of antibodies in the anti-PLVAP sera were determined using ELISA. First, the 96 well ELISA plate was coated with 50 µl of PLVAP protein dissolved in Phosphate buffered saline (PBS) containing 0.002% sodium azide (i.e., coating buffer) at a concentration in the range of 2.5 µg/m overnight at 4° C. After three washes with 200 µl of washing buffer (PBS containing 0.05% Tween-20), each well of the coated plate was blocked with 150 µl blocking buffer (i.e., washing buffer containing 2% bovine serum albumin) at room temperature for 30 minutes. After three further washes, each well was incubated with 50 µl of diluted antiserum (serial two fold dilution from 1,000× to 128,000×) prepared in the dilution buffer for 45 minutes at room temperature. Thereafter, each well was incubated with anti-mouse IgG alkaline phosphatase conjugate at 5,000× dilution (Chemico, Inc., Temecula, Calif.) for 30 minutes at room temperature. After three washes, the bound antibodies were quantified with 100 µl alkaline phosphatase substrate (Sigma, Inc., St Louis, Mo.) and measurement of absorbance was performed at 405 nm after an incubation period of 25 to 40 min. using an ELISA plate reader.

Immunohistochemical (IHC) Detection of PLVAP in Formalin-Fixed Tissues

Six micrometer sections were cut from paraffin blocks of formalin-fixed tissues. The sections were mounted on SuperFrost™ plus adhesion glass slides (Menzel Glaser GmbH, Braunschweig, Germany). The sections then were processed for immunostaining of PLVAP in a Benchmark XT automated staining instrument (Ventana Medical Systems, Inc., Tucson, Ariz.) using XT-iView-DAB-V.1 protocol with mild CCI conditioning for 30 minutes and sections were incubated with 400× diluted anti-human PLVAP serum at 37° C. for 36 minutes. The second antibody and the reagents used to detect binding of mouse anti-human PLVAP antibodies were from the iView™DAB Detection Kit from Ventana Medical Systems, Inc. (Tucson, Ariz.). All reagents and buffers were purchased from Ventana Medical Systems.

Figure 6A:
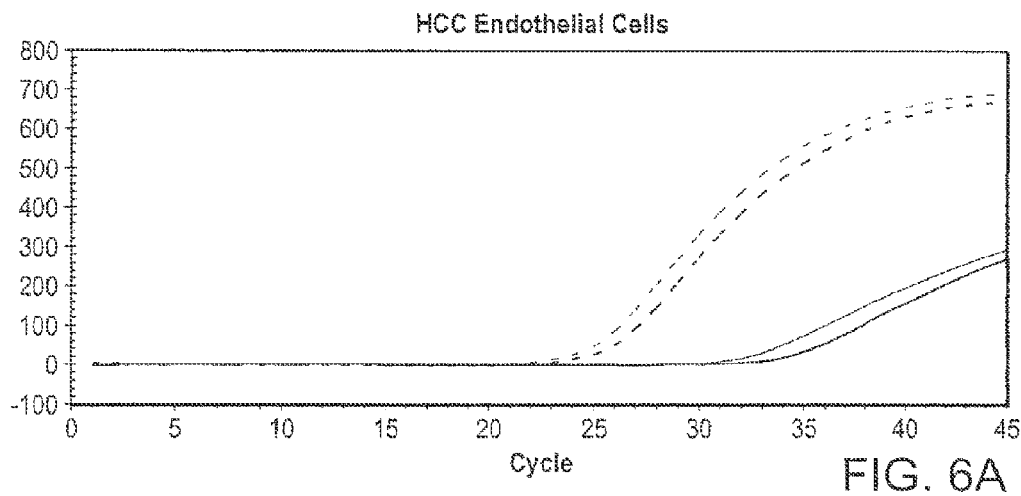
FIG. 6A is a graph depicting the presence of significant relative quantities of PLVAP mRNA in HCC endothelial cells obtained by laser-capturing microdissection from two HCC tissue samples (Sample A (black) and Sample B (gray)) as determined by two-step real-time quantitative RT-PCR. Dashed lines represent Taqman quantitative RT-PCR signals from beta-actin mRNA in the same samples used for quantitative RT-PCR of PLVAP mRNA. The results indicate presence of readily measurable PLVAP mRNA in the dissected endothelial cells (solid lines).
Figure 6B:
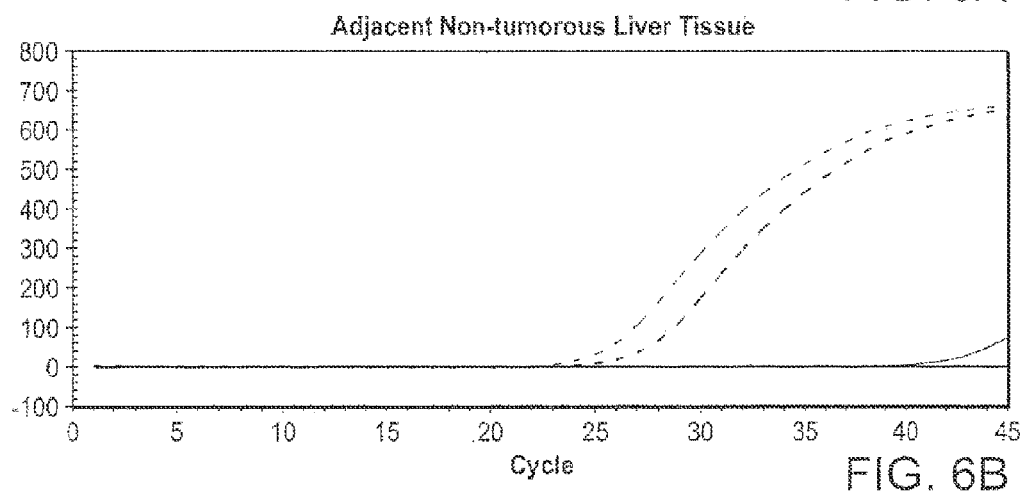
FIG. 6B is a graph depicting the absence of significant relative quantities of PLVAP mRNA in cells obtained by laser-capturing microdissection from non-tumorous liver tissue adjacent to HCC tissue in two HCC samples (Sample A (black) and Sample B (gray)) as determined by two-step Taqman real-time quantitative RT-PCR. The results indicate no detectable (solid black line) and barely detectable (solid gray line) PLVAP mRNA in the dissected cells.
Figure 6C:
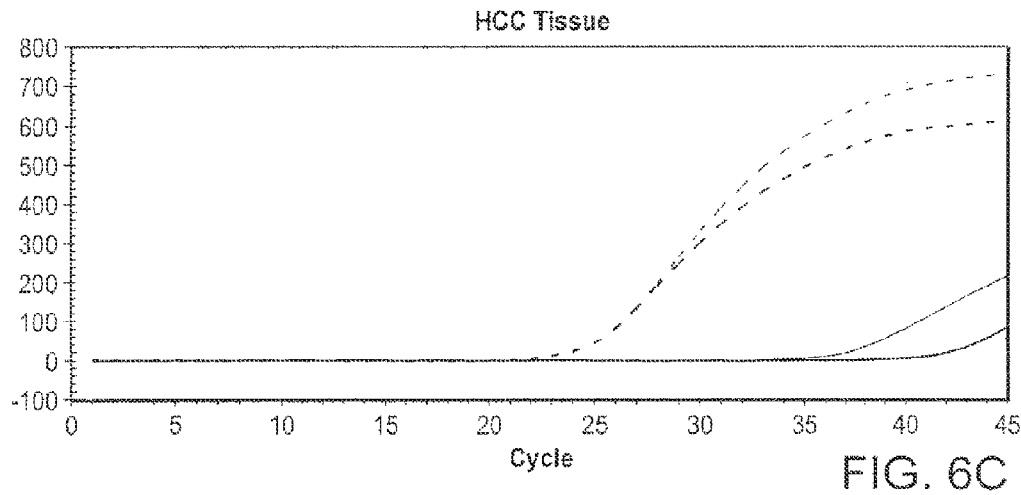
FIG. 6C is a graph depicting the relative quantities of PLVAP mRNA in HCC tumor cells obtained by laser-capturing microdissection from two HCC tissue samples (Sample A (black) and Sample B (gray)) as determined by two-step Taqman real-time quantitative RT-PCR. The results indicate presence of very small amounts of PLVAP mRNA (solid lines) in the dissected HCC cells due to unavoidable minor contamination from portion of vascular endothelial cells attached to the dissected HCC cells.

Results:

To determine the cellular source of PLVAP in HCC samples, HCC vascular endothelial cells, tumor cells of hepatocellular carcinoma and non-tumorous hepatocytes, including lining sinusoidal endothelial cells, were dissected out of the samples using laser capture microdissection (LCM). Due to close apposition between hepatoma cells and capillary-lining endothelial cells, effort was made to avoid inclusion of capillary-lining endothelial cells during dissection. The RNAs extracted from the dissected cells were used for two-step real time quantitative RT-PCR to determine the relative quantities of PLVAP mRNA. Specimens from two different patients were studied. The results shown in Table 4 and FIGS. 6A-6C indicate that PLVAP is expressed by HCC vascular endothelial cells (FIG. 6A), while no detectable PLVAP transcript was detected in adjacent non-tumorous liver tissues (FIG. 6B).

TABLE 4

Determination of PLVAP mRNA relative quantities in two HCC samples by Taqman real time quantitative RT-PCR in cells dissected by laser-capturing microdissection

| HCC Sample | Relative Quantity of PLVAP mRNA | | |
| --- | --- | --- | --- |
| | HCC Endothelial Cells | Adjacent Non-tumorous Liver Tissue | HCC Tumor Cells |
| A | 1 | 0 | 0.002 |
| B | 1 | 0.001 | 0.057 |

Figure 7:
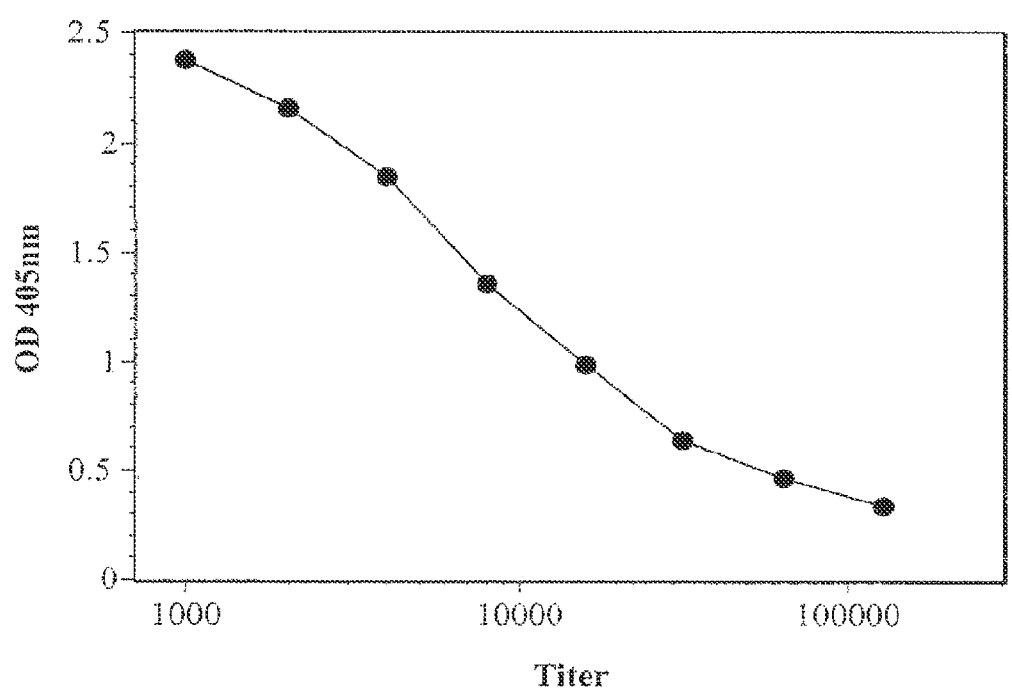
FIG. 7 is a graph depicting anti-PLVAP antibody titer in mouse antiserum raised against recombinant PLVAP$_{51-442}$ protein as determined by ELISA.
Figure 8B:
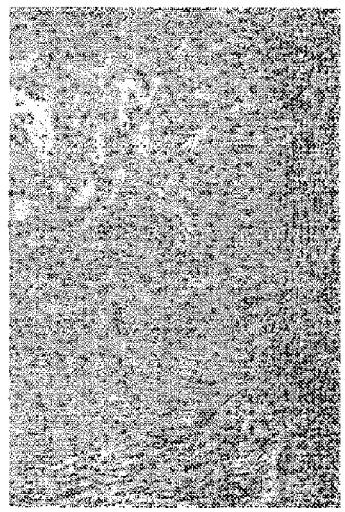
FIGS. 8A-8F are images showing sections of formalin-fixed paired HCC (FIGS. 8A, 8C, and 8E) and adjacent non-tumorous liver tissues (FIGS. 8B, 8D, and 8F) from three patients with hepatocellular carcinoma that were stained immunohistochemically using anti-PLVAP polyclonal antisera to detect localization of PLVAP protein. Paired tissues are shown in FIGS. 8A and 8B.
Figure 8A:
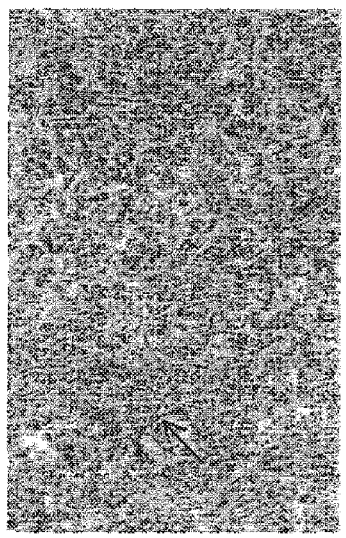
Figure 8D:
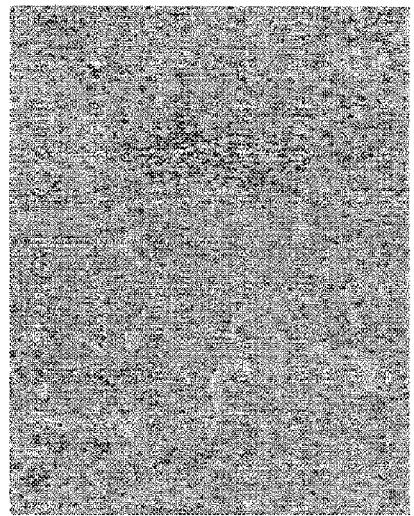
Figure 8C:
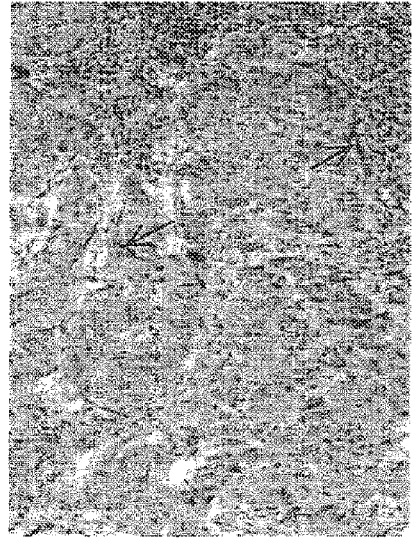
Figure 8F:
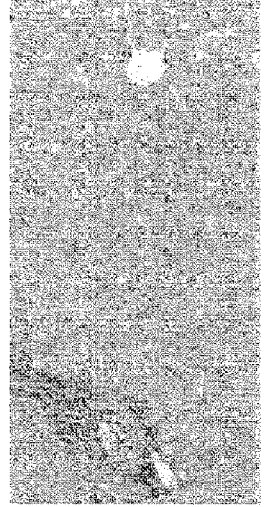
Figure 8E:
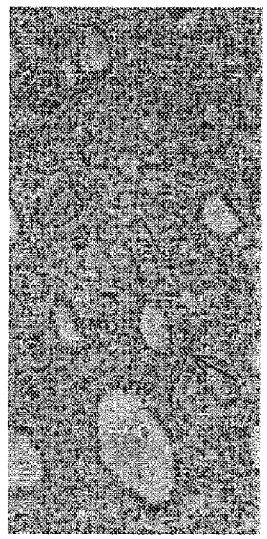
Figure 9A:
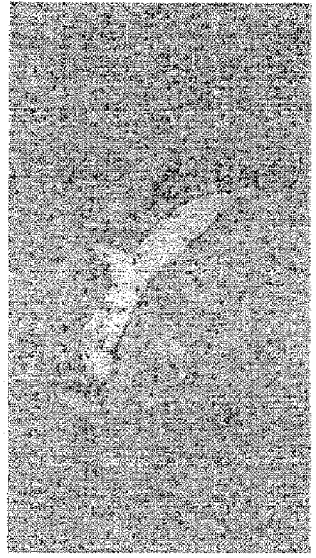
FIGS. 9A-9F are images showing sections of formalin-fixed HCC (FIGS. 9A, 9C, 9E and 9F) and non-tumorous liver tissues (FIGS. 9B and 9D) from three additional patients with hepatocellular carcinoma that were stained immunohistochemically using anti-PLVAP polyclonal antisera to detect localization of PLVAP protein.
Figure 9C:
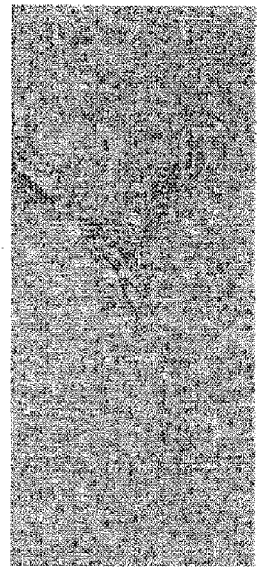
Figure 9E:
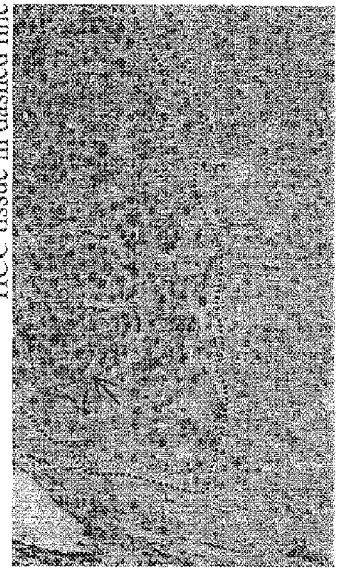
Figure 9B:
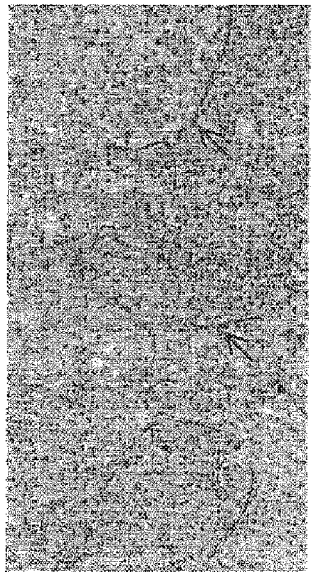
Figure 9D:
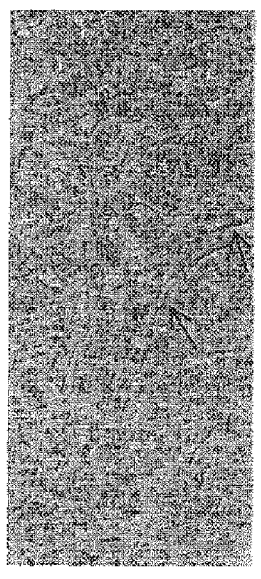
Figure 9F:
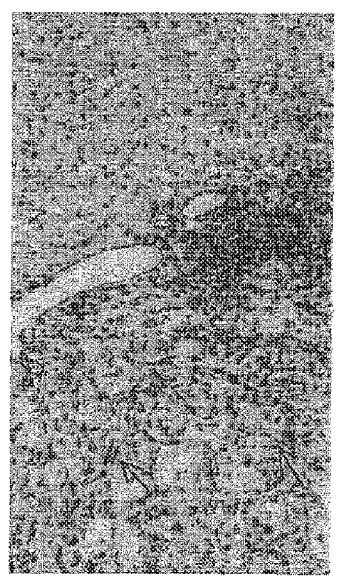

In order to further investigate the tissue and disease specificity of PLVAP expression, polyclonal antibodies for use in immunohistochemistry (IHC) studies were generated against the extracellular domain of human PLVAP (amino acids 51 to 442). As shown in FIG. 7, antiserum obtained from Balb/c mice that were immunized with recombinant PLVAP$_{51-442}$ protein contained a high titer of anti-PLVAP antibodies.

Figures 11A, 11B:
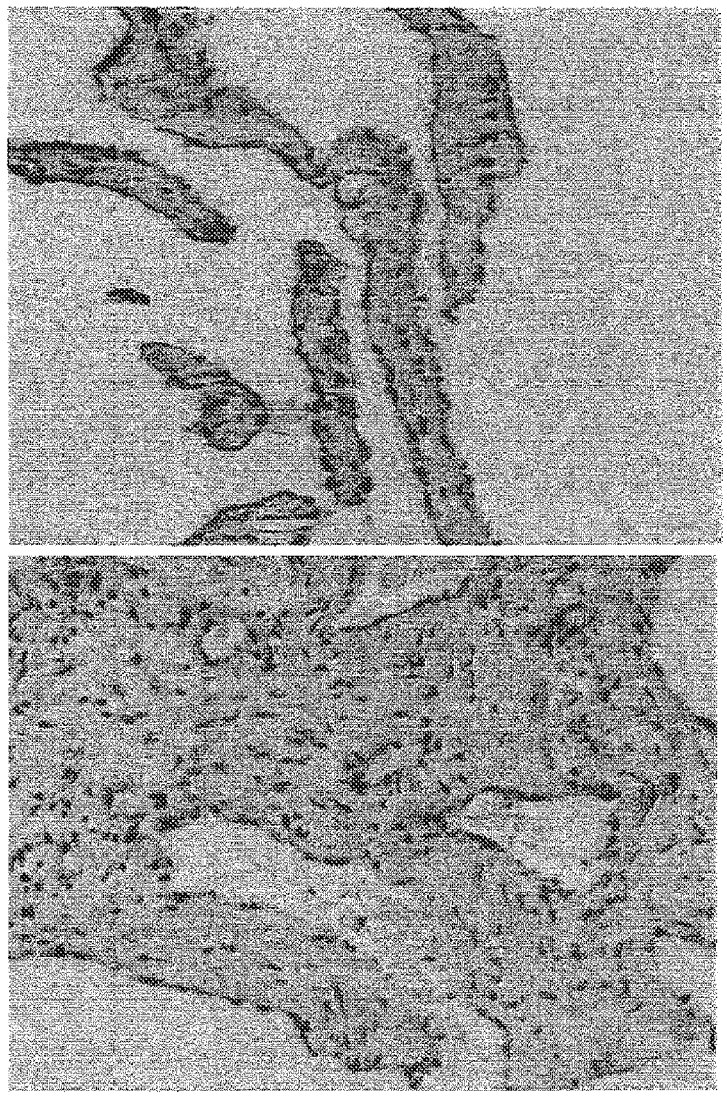
FIGS. 11A and 11B are images showing sections of formalin-fixed tissue from two patients with hepatic hemangioma that were stained immunohistochemically with anti- PLVAP polyclonal antiserum. Endothelial lining cells of hepatic hemangioma did not show significant expression of PLVAP protein.
Figure 13A:
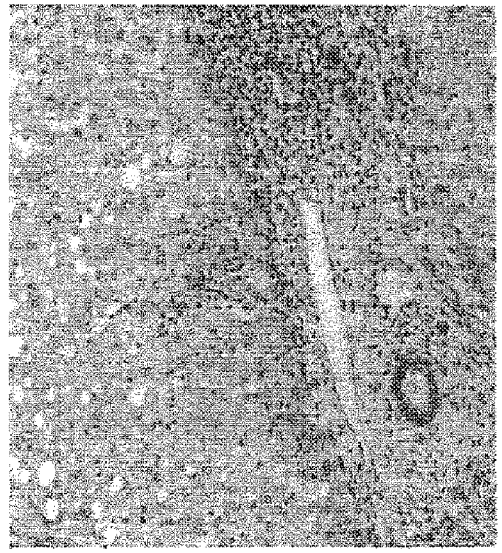
FIGS. 13A-13D are images showing sections of formalin-fixed tissue from three different patients with chronic active hepatitis C that were stained immunohistochemically with anti-PLVAP polyclonal antiserum. The tissue sections shown in FIGS. 13B and 13D are from the same patient. PLVAP protein was not detected in endothelial cells lining the vascular sinusoids/capillary of non-tumorous liver tissues from chronic hepatitis C patients.
Figure 13B:
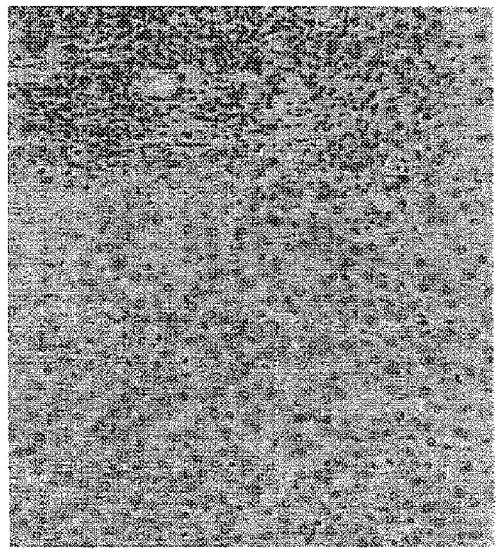
Figure 13C:
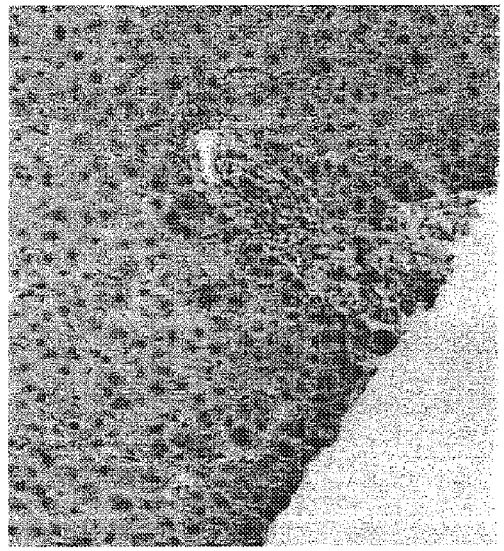
Figure 13D:
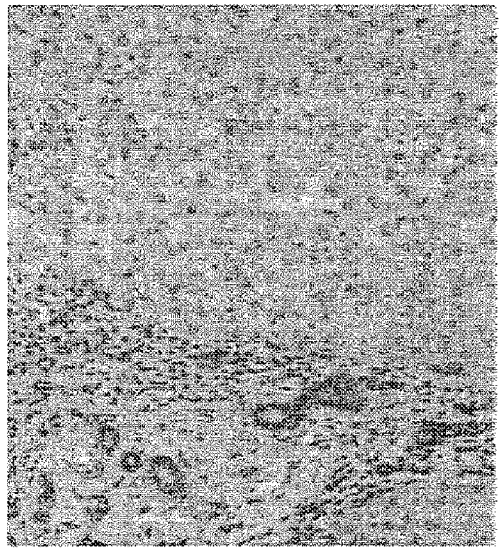
Figure 14A:
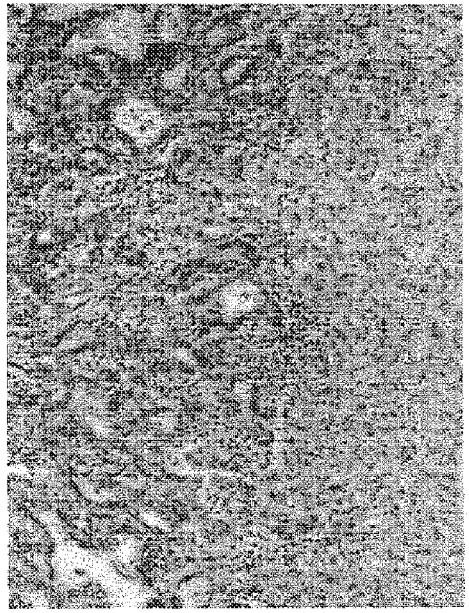
FIGS. 14A-14D are images showing sections of formalin-fixed tissue from three different patients with metastatic liver cancers that were stained immunohistochemically with anti-PLVAP polyclonal antiserum. The tissue sections are from patients with metastatic colorectal adenocarcinoma (FIG. 14A), intrahepatic cholangiocarcinoma (FIGS. 14B and 14C) or metastatic ovarian carcinoma (FIG. 14D). The tissue sections shown in FIGS. 14B and 14C are from the same patient. PLVAP protein was not detected in endothelial cells lining the vascular sinusoids/capillary of metastatic cancer tissues.
Figure 14B:
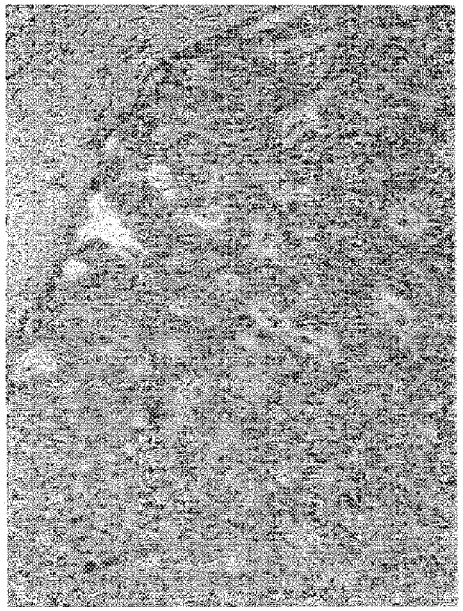
Figure 14C:
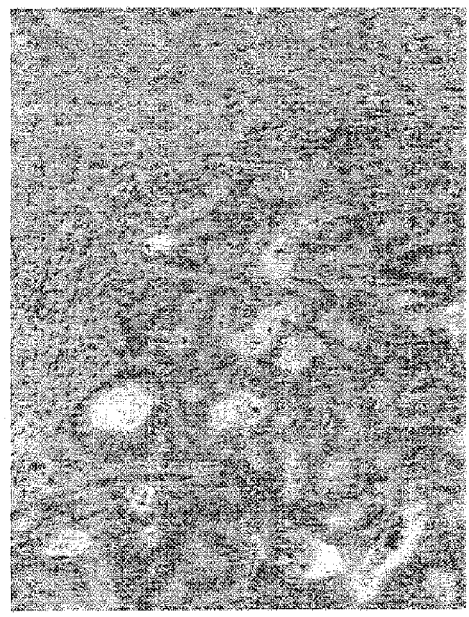
Figure 14D:

The anti-PLVAP antiserum was then used to determine the localization of PLVAP expression in tissue sections from patients with hepatocellular carcinoma (n=7) (FIGS. 8A-8F and 9A-9F), focal nodular hyperplasia (n=4) (FIGS. 10A-10F), hepatic hemangioma (n=2) (FIGS. 11A and 11B), chronic active hepatitis B (n=2) (FIGS. 12A and 12B) or C (n=4) (FIGS. 13A-13D), and metastatic cancer (n=4) (i.e., intrahepatic cholangiocarcinoma, metastatic colorectal adenocarcinoma, or metastatic ovarian carcinoma) (FIGS. 14A-14D). The results showed that only capillary endothelial cells of hepatocellular carcinomas expressed PLVAP protein (FIGS. 8A, 8C, 8E, 9A, 9C, 9E and 9F). PLVAP protein was not expressed by endothelial cells lining the vascular sinusoids/capillary of non-tumorous liver tissues, including cirrhotic liver, liver of focal nodular hyperplasia (FIGS. 10A-10F), and chronic hepatitis (FIGS. 12A and 12B; FIGS. 13A-13D). Endothelial lining cells of hepatic hemagioma did not show significant expression of PLVAP, either (FIGS. 11A and 11B). These results demonstrate that PLVAP is a vascular endothelial biomarker that is specific for hepatocellular carcinoma, but not for other diseases of liver. Therefore, PLVAP can be used as a diagnostic marker and therapeutic target for HCC.

Example 3

Production and Characterization of Mouse Monoclonal Antibodies that Specifically Bind PLVAP Materials and Methods:

Immunization Procedures

Five six-week-old female Balb/cByJ mice were immunized initially with 20 µg of purified recombinant PLVAP protein dissolved in 0.125 mL phosphate buffered saline (PBS) and emulsified in an equal volume of complete Freund's adjuvant. The PLVAP-adjuvant mixture was injected in 0.05 mL volumes into each of four separate subcutaneous sites on the ventral side of the mice near the axillary and inguinal lymphatics, as well as a fifth subcutaneous site, which was located between the scapulae. All mice received a booster immunization of 20 µg of recombinant PLVAP protein injected intraperitoneally three times every two weeks. One week after the last booster immunization, test bleedings were taken to measure whether mice were producing sufficiently high titers of anti-PLVAP antibodies (>10,000×). A solid-phase enzyme-linked immunosorbent assay (ELISA) was used for this purpose. The mouse that produced the highest titer of PLVAP antibody was selected for the production of hybridomas.

Development of Murine Monoclonal Anti-PLVAP Antibodies

Three days before the scheduled fusion experiment to produce hybridomas, the mouse that produced the highest titer of PLVAP antibody was injected intravenously with 20 µg of recombinant PLVAP. Hybridomas producing monoclonal antibodies (MAbs) against PLVAP were produced according to a previously described protocol (see Unit 2.5 Production of Monoclonal Antibodies, in Current Protocols in Immunology, editors: Coligan J E, Kruisbeek A M, Margulies D H, Shevach E M, and Strober W. Published by John Wiley & Sons, Inc., New York, 2001) with minor modification. Specifically, spleen cells harvested from the immunized mouse were fused with SP2/0 myeloma cells at a ratio of 7.5:1 (spleen cell:myeloma cells) using 50% polyethylene glycol 1540. The fusion products were seeded into 96-well flat-bottom tissue culture plates, and hypoxanthine-aminopterin-thymidine (HAT) selective medium was added the next day. Seven to ten days later, the supernatants of growth-positive wells were screened for production of anti-PLVAP antibodies by ELISA. Hybridomas initially producing anti-PLVAP MAbs were expanded and re-screened. Hybridomas that showed continued production of antibodies were cloned by the limiting dilution method. MAb isotypes were determined using an ELISA. Monoclonal antibodies were purified from ascites or culture media by Protein G affinity column chromatography (Unit 2.7 Purification and Fragmentation of Antibodies, in Current Protocols in Immunology, editors: Coligan J E, Kruisbeek A M, Margulies D H, Shevach E M, and Strober W. Published by John Wiley & Sons, Inc., New York, 2001).

ELISA Assay

ELISA assays were performed as described herein (see Example 2).

Determination of Binding Affinities

Binding affinities of KFCC-GY4 and KFCC-GY5 anti-PLVAP monoclonal antibodies were measured at the ANT Technology Co., Ltd. (Taipei, Taiwan) using ANTQ300 quartz crystal microbalance technology (Lin S., et al. *J Immunol Methods* 239:121-124 (2000)).

Isolation and Culture of Human Umbilical Vascular Endothelial Cells (HUVEC)

Isolation and culture of HUVEC were carried out according to the established protocol described in Baudin B, Brunee A, Bosselut N and Vaubourdolle M. *Nature Protocols* 2:481-485 (2007). During the maintenance of endothelial cell culture, 1% gelatin (DIFCO, Corp.) dissolved in phosphate buffered saline was used to replace collagen solution for coating culture plates or coverslips.

Extraction of Hydrophobic Membrane Proteins of HUVEC by Triton X-114 (TX-114) Containing Buffer Five hundred thousand HUVEC were seeded in a 10 cm culture dish for 24 hours. The cells were then stimulated with human VEGF at 40 ng/ml for an additional 72 hours. The cultured cells were washed with 5 ml phosphate buffered saline (PBS) twice. The cells then were detached and lifted from the dish by incubation with 1 ml PBS containing 2 mM EDTA, were placed into a centrifuge tube, and were collected by centrifugation at 300×g for 5 minutes. There were approximately 2 million cells in the pellet produced by centrifugation. The cell pellets were re-suspended in 200 µl ice cold 0.05 M Tris buffer containing 5 mM EDTA and 0.5% (v/v) Triton™ X-114 (TX-114) detergent, pH 7.4. The solubilized cell suspension was incubated on ice with occasional gentle vortexing. Thereafter, the cells suspension was centrifuged at 10,000×g for 10 minutes at 4° C. to remove insoluble cellular debris. The supernatant was transferred to a clean microfuge tube and incubated at 37° C. for 5 minutes. During the incubation, TX-114 became separated from the aqueous phase. The microfuge tube was then centrifuged at 1000×g for 10 minutes at room temperature, such that the TX-114 was centrifuged to the bottom of the tube. The aqueous phase at the top of the tube was removed and the TX-114 pellet containing hydrophobic cellular proteins was dissolved in 2×SDS acrylamide gel sample buffer in a final volume of 50 µl. Fifteen µl of sample was used for SDS acrylamide gel electrophoresis.

SDS Acrylamide Gel Electrophoresis, Preparation of Western Blot and Immunoblotting The procedures are the same as previously described by Kao K J, Scornik J C and McQueen C F. Human Immunol 27:285-297 (1990), with slight modification. Detection of antibody binding on Western blots was carried out using alkaline phosphatase chemiluminescent substrate and an LAS-4000 Luminescent Image Analyzer (Fujifilm Corp.).

Immunofluorescent Microscopy

Materials:

1) Primary Antibodies:
   a) Normal mouse IgG (Sigma Corp., catalog #: I-5381) dissolved in phosphate buffered saline (PBS) to 1 mg/mL as a stock solution, diluted with PBS-0.5% BSA to a concentration of 5 µg/mL before use;
   b) Monoclonal mouse anti-human von Willebrand factor (vWF) (DakoCytomation Corp., catalog #: M0616) diluted 50× with PBS containing 0.5% BSA before use;
   c) Purified KFCC-GY4 and KFCC-GY5 anti-PLVAP monoclonal antibodies were diluted to 5 µg/m with PBS containing 0.5% BSA before use;
2) Secondary antibody: FITC-conjugated Goat F(ab')$_2$ anti-mouse IgG (H&L) (Serotec Corp., catalog #: Star105F);
3) VectaShield® Mounting Medium with DAPI (Vector Labs Corp., catalog #: H-1200);
4) 100% Methanol (Merck Corp., catalog #: 1.06009); and
5) Hank's Balanced Salt Solution (HBSS) (Gibco Corp., catalog #: 12065-056) diluted to 1× before use.

Procedure:

To prepare human umbilical cord vascular endothelial cells for immunofluorescent study, fifty thousand cells were placed in each well of a 24-well culture plate with a 1.5 cm sterile round coverslip placed at the bottom of each well. Each well contained 0.5 ml M199 culture media that was supplemented with 20% fetal calf serum, 1% L-glutamine, 1% antibiotic/antimycotic solution, 50 µg/ml heparin and 75 µg/m endothelial cell growth supplement (Sigma Corp. E0760). Each coverslip was pre-coated with 200 µl of 0.4 mg/ml calf skin collagen (Sigma Corp. C9791) in 0.04% acetic acid (v/v) overnight. The coverslips were then washed with sterile 1× phosphate buffered saline (PBS) and subsequently air-dried for use. Cells were cultured overnight and then stimulated with 40 ng/ml vascular endothelial growth factor (VEGF) for an additional 72 hours. The cells on the coverslips were used for the immunofluorescent procedure.

To stain the cells for immunofluorescent microscopy, the cells grown on the coverslip in each well were washed with 0.5 ml 1×HBSS. The cells were then fixed and permeabilized in 0.5 ml ice cold methanol for 5 minutes. The fixed cells were washed 3 times with 0.5 ml 1×PBS for 5 minutes per wash. The fixed cells were then blocked with 0.5 ml 1×PBS containing 0.5% BSA for 1 hour at room temperature. The coverslip containing the fixed cells was removed and placed on top of 0.2 ml diluted primary antibody solution, which contained 5 µg/m normal IgG, KFCC-GY4 or KFCC-GY5 anti-PLVAP monoclonal antibody, or a 50× dilution of anti-human vWF monoclonal antibody, with the fixed cells facing down and in contact with antibody solution. The antibody solution was placed on a piece of parafilm in a small covered plastic container. The humidity inside was maintained by placing a small piece of filter paper wetted with water.

After incubation at 37° C. for one hour in a humidified container, the coverslip was removed and the cells on the coverslip were washed 3 times with 0.5 ml PBS for 5 minutes each time. The fixed cells were then incubated with 0.2 ml 200×-diluted FITC-conjugated Goat F(ab')$_2$ anti-mouse IgG secondary antibody for 50 minutes at 37° C. as described for incubation with primary antibody solution. Thereafter, the cells were washed 3 times with PBS as described above. The stained cells were mounted on a glass slide using VectaShield® anti-fade solution. Excess mounting media was removed from the edge of the coverslip and the edge was sealed with nail polish. The stained cells were examined using a fluorescent microscope.

Results:
Immunization of Balb/cByJ mice with recombinant human PLVAP protein led to the development of hybridomas producing monoclonal antibodies (mAbs) that recognized human PLVAP protein. Two hybridomas were selected for further study. The antibodies produced by these hybridomas were named KFCC-GY4 and KFCC-GY5. The sequences of the $V_H$ and $V_L$ domains of monoclonal antibodies KFCC-GY4 and KFCC-GY5, and the CDRs of these domains, are shown in FIGS. 15A and 15B and FIGS. 16A and 16B, respectively.

The hybridoma cell line referred to as KFCC-GY4 has the A.T.C.C. Patent Deposit Designation PTA-9963, having been deposited on Apr. 8, 2009. The hybridoma cell line referred to as KFCC-GY5 has the A.T.C.C. Patent Deposit Designation PTA-9964, having been deposited on Apr. 8, 2009.

Figure 17:
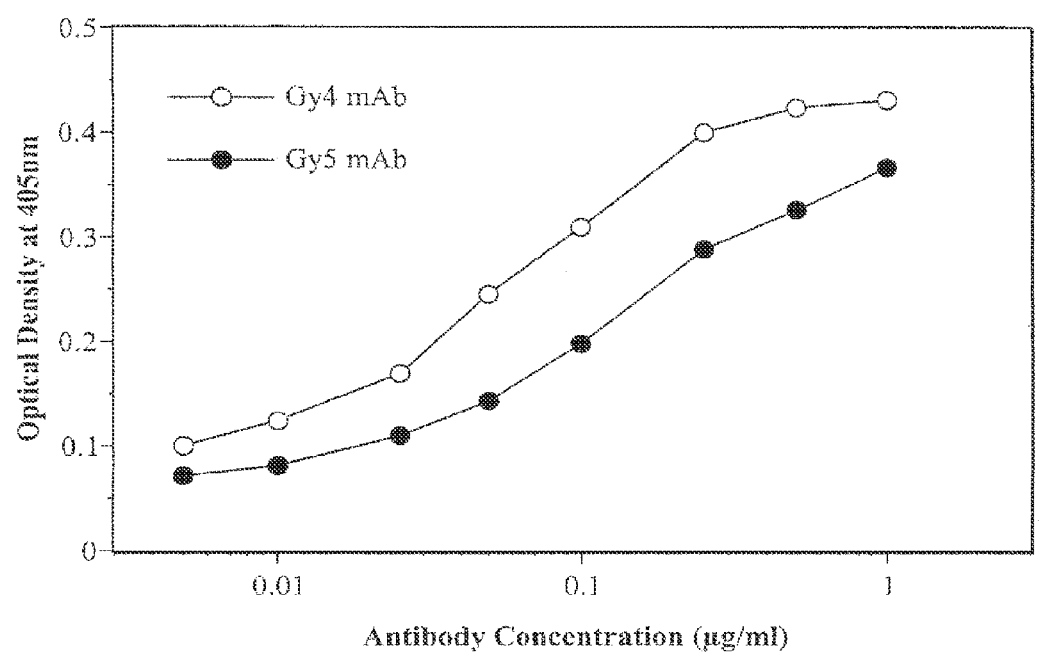
FIG. 17 is a graph depicting the binding of KFCC-GY4 (open circles) and KFCC-GY5 (filled circles) monoclonal antibodies to recombinant PLVAP protein at various antibody concentrations, as determined by ELISA.
Figure 18:
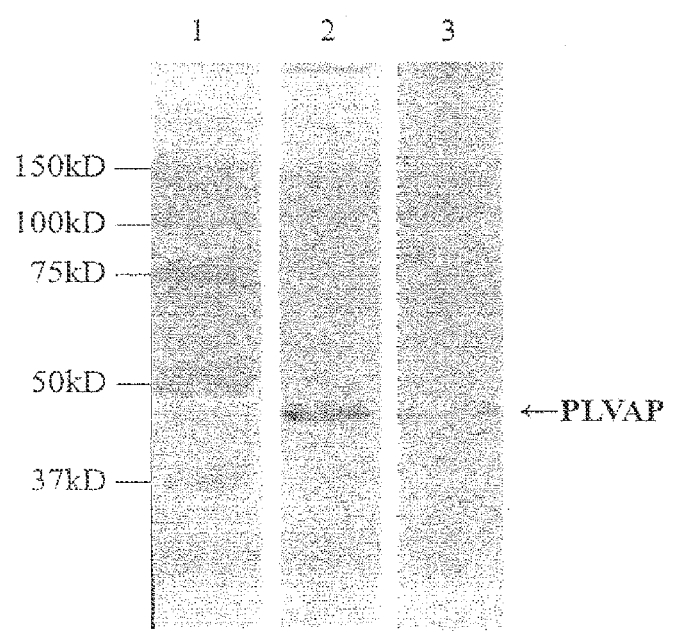
FIG. 18 is an immunoblot showing that KFCC-GY4 and KFCC-GY5 monoclonal antibodies can detect 5 ng of recombinant PLVAP protein. Lane 1: molecular weight standard; Lane 2: immunoblot with KFCC-GY4 monoclonal antibody; Lane 3: immunoblot with KFCC-GY5 monoclonal antibody. The molecular weight of recombinant PLVAP protein is 45 kD.

Both KFCC-GY4 and KFCC-GY5 monoclonal antibodies bound recombinant PLVAP protein in ELISA (FIG. 17) and immunoblot (FIGS. 18C and 18D) assays.

Figure 19A:
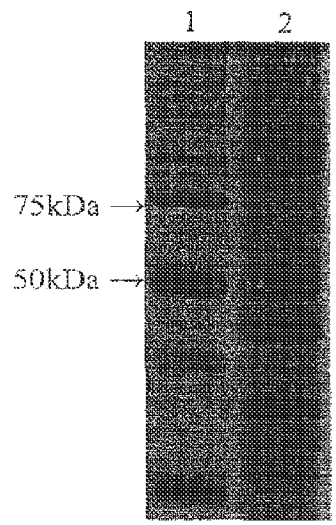
FIGS. 19A and 19C are Coomassie blue-stained SDS acrylamide gels. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.
Figure 19B:
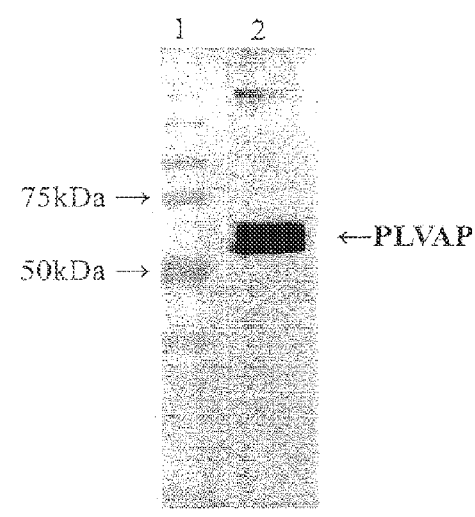
FIG. 19B is an immunoblot wherein the extract shown in Lane 2 of FIG. 19A was probed with KFCC-GY4 monoclonal antibodies. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.
Figure 19C:
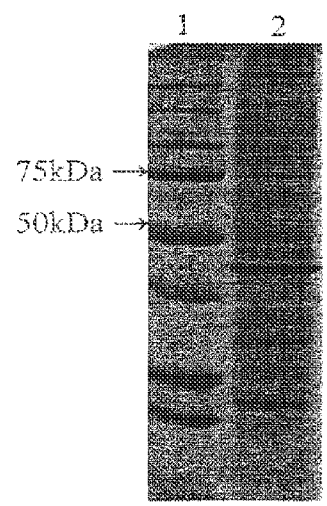
Figure 19D:
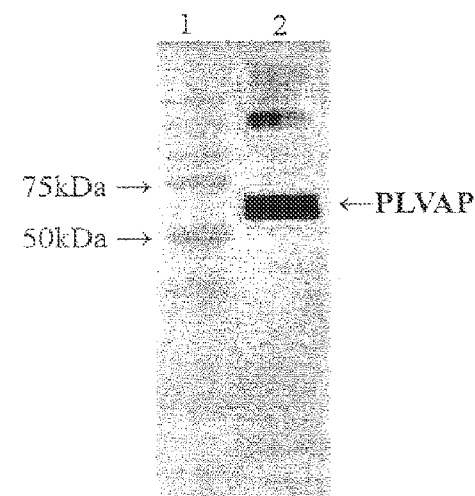
FIG. 19D is an immunoblot wherein the extract shown in Lane 2 of FIG. 19C was probed with KFCC-GY-5 monoclonal antibodies. Lane 1: molecular weight standard; Lane 2: hydrophobic membrane proteins extracted with TX-114 from human umbilical cord vascular endothelial cells that had been stimulated with VEGF (40 ng/ml) for 72 hours before extraction.

These antibodies also specifically reacted with PLVAP protein in extracts from human umbilical cord vascular endothelial cells in an immunoblot assay (FIGS. 19B and 19D). In addition, immunofluorescence staining experiments showed binding of KFCC-GY4 and KFCC-GY5 monoclonal antibodies to PLVAP-expressing human vascular endothelial cells (FIGS. 20C and 20D).

Binding affinities ($K_d$) of the monoclonal antibodies for recombinant PLVAP protein were determined to be $0.41 \times 10^{-7}$ M for KFCC-GY5 mAb and $0.6 \times 10^{-7}$ M for KFCC-GY4 mAb using ANTQ300 quartz crystal microbalance (Lin, et al. *J. Immunol. Methods* 239:121-124, 2000).

Figure 21A:
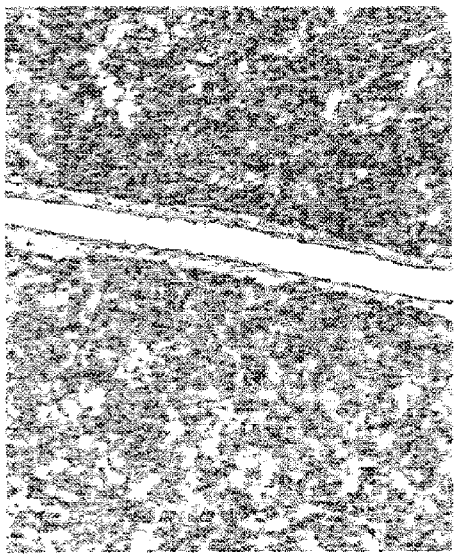
FIG. 21A is a light micrograph of a section of formalin-fixed hepatoma tissue embedded in a paraffin block that was stained with KFCC-GY5 monoclonal anti-PLVAP antibodies. A strong PLVAP signal (dark gray stain) was detected in vascular endothelial cells of hepatoma. Magnification is 100×.
Figure 21B:
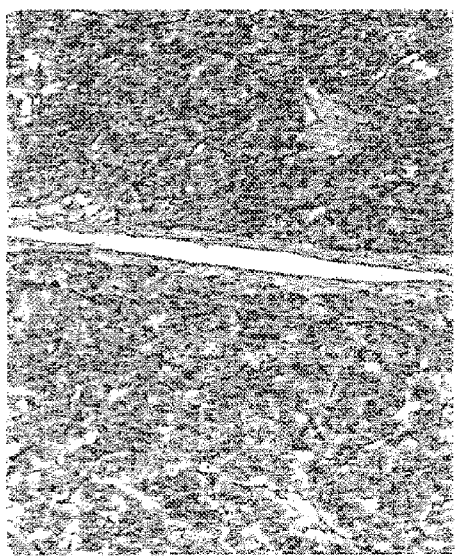
FIG. 21B is a light micrograph of a section of formalin-fixed hepatoma tissue from the same patient as the sample shown in FIG. 21A that was stained with KFCC-GY4 monoclonal anti-PLVAP antibodies. A moderate PLVAP signal (light gray stain) was detected in vascular endothelial cells of hepatoma. Magnification is 100×.
Figure 21C:
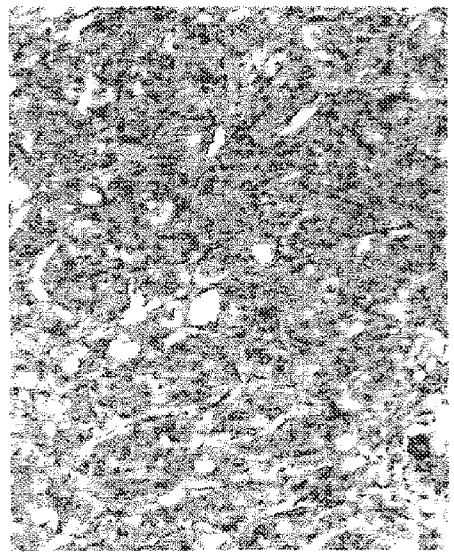
FIG. 21C is a light micrograph of a section of formalin-fixed hepatoma tissue from a different patient than the samples shown in FIGS. 21A and 21B that was stained with KFCC-GY5 monoclonal anti-PLVAP antibodies. A strong PLVAP signal (dark gray stain) was detected in vascular endothelial cells. Magnification is 100×.
Figure 21D:
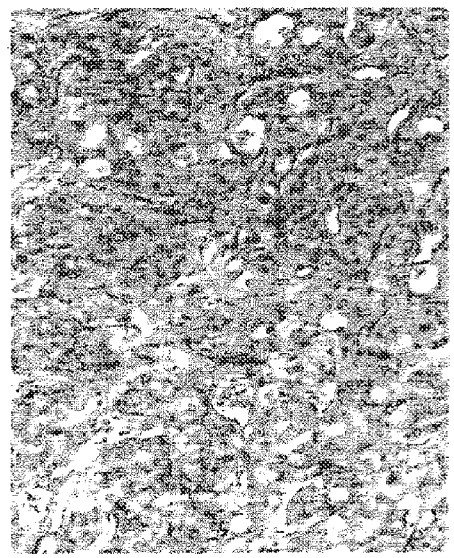
FIG. 21D is a light micrograph of a section of formalin-fixed hepatoma tissue from the same patient as the sample shown in FIG. 21C embedded in a paraffin block that was stained with KFCC-GY4 monoclonal anti-PLVAP antibodies. A moderate PLVAP signal (light gray stain) was detected in vascular endothelial cells, indicating that KFCC-GY4 monoclonal antibodies bind the PLVAP antigen less well than KFCC-GY5 antibodies. Magnification is 100×.
Figure 22A:
Figure 22B:
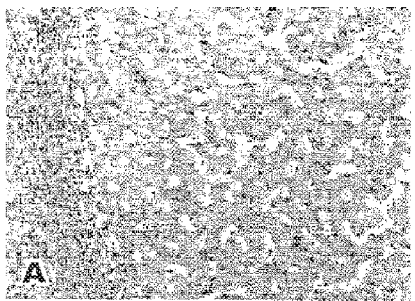
Figure 22C:
Figure 22D:
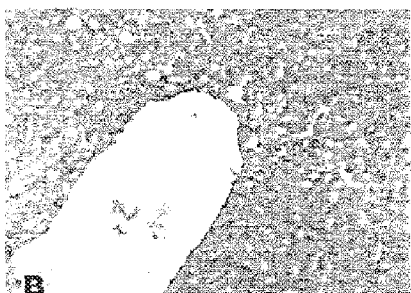
Figure 22E:
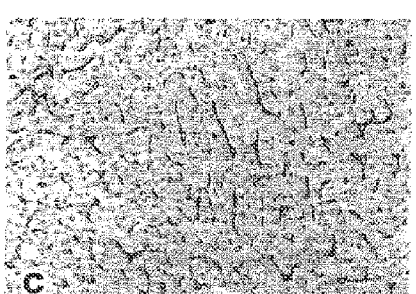
Figure 22F:
Figure 22G:
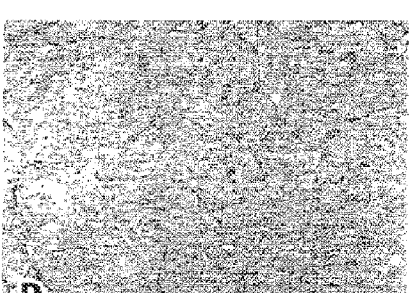
Figure 22H:
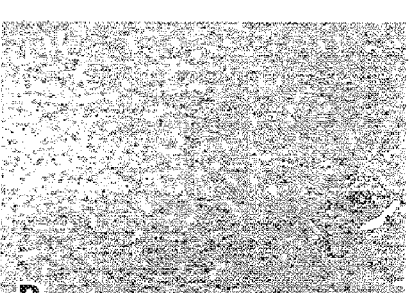

Immunohistochemistry experiments performed on hepatoma sections from the liver of two different hepatoma patients using KFCC-GY4 or KFCC-GY5 monoclonal anti-PLVAP antibodies showed that the KFCC-GY5 monoclonal antibody produced a stronger signal in vascular endothelial cells (FIGS. 21A and 21C) than the KFCC-GY4 monoclonal antibody (FIGS. 21B and 21D).

Immunohistochemistry experiments performed on adjacent hepatoma and non-tumorous liver tissue sections from the liver of the same patient were performed on samples from four different randomly selected hepatoma patients using the KFCC-GY4 monoclonal anti-PLVAP antibody. PLVAP expression was detected in vascular endothelial cells of hepatoma tissues (FIGS. 22A, 22C, 22E and 22G), but not adjacent non-tumorous liver tissues (FIGS. 22B, 22D, 22F and 22H).

Example 4

PLVAP Protein is Expressed on the Surfaces of Vascular Endothelial Cells

Materials and Methods:
Immunofluorescent Microscopy
Reagents:
The reagents used for the following procedure are as described in Example 3, with the following modifications:
 the 1×HBSS wash buffer contained 0.1% sodium azide, which was used to prevent endocytosis of antibodies bound to the cell surface; and
 the KFCC-GY4 and KFCC-GY5 monoclonal anti-PLVAP antibodies were diluted in the 1×HBSS wash buffer with 0.1% sodium azide.
Procedure:
Immunofluorescent staining of human umbilical cord vascular endothelial cells (HUVECs) was performed as described in Example 3, except that the cells were not fixed and permeabilized with methanol. Instead, after incubation with anti-PLVAP monoclonal antibodies, the cells were washed and fixed with 4% paraformaldehyde at room temperature for 10 minutes. Following this incubation, the cells were washed 3 times, then were incubated with FITC-conjugated Goat F(ab')$_2$ anti-mouse IgG. After three additional washes, the cells were processed for immunofluorescent microscopy as described in Example 3.
Results:
Using the approach described above, only PLVAP protein expressed on the cell surface could be detected. The results of these experiments revealed that both KFCC-GY4 and KFCC-GY5 anti-PLVAP monoclonal antibodies bound to the surface of HCC vascular endothelial cells (FIGS. 23B and 23C), indicating that PLVAP protein is expressed on the surfaces of these cells. These findings suggest that antibodies that specifically bind PLVAP with high affinity will be able to bind to the surface of HCC vascular endothelial cells upon injection into the blood vessels of a hepatocellular carcinoma tumor.

Example 5

Anti-Human PLVAP Monoclonal Antibodies Bind to PLVAP Proteins in Non-Human Primate Species Materials and Methods:
Tissue array slides were first prepared according to manufacturer's instructions by baking slides at 60° C. for 2 hours to remove sealing paraffin. Thereafter, the slides were processed for immunohistochemical staining as described in Example 2 (*IHC Detection of PLVAP in Formalin Fixed Tissues*). The only modification was that the slides were incubated with 1 μg/ml KFCC-GY4 and -GY5 monoclonal antibodies for 48 minutes at 37° C.
Results:
In order to determine whether non-human primates can be used to evaluate the pharmacokinetics, pharmacodynamics and toxicity of the KFCC-GY4 and KFCC-GY5 mAbs, as well as other antibodies derived from these mAbs, immunohistochemistry staining of arrays of formalin-fixed normal tissues from human, rhesus monkey and cynomolgus monkey were performed using the KFCC-GY4 and KFCC-GY5 antibodies (FIG. 26). The KFCC-GY4 and KFCC-GY5 anti-human PLVAP monoclonal antibodies bound to both human and monkey (cynomolgus and rhesus) capillary endothelial cells in different tissues with high degree of similarity (FIG. 26). Examples of KFCC-GY5 antibody binding to human and monkey normal adrenal gland, kidney, brain and liver sections are shown in FIGS. 27A-27F2. Anti-human CD34 monoclonal antibody was also used as a positive control on human tissue sections to highlight blood vessels. These results indicate that rhesus and cynomolgus monkeys are suitable for use in pre-clinical trial studies of PLVAP antibodies.

Example 6

KFCC-GY4 and KFCC-GY5 Monoclonal Antibodies Bind to Antigenic Epitopes Between Amino Acids 282 and 482 in the C-Terminal Region of Human PLVAP Protein Materials and Methods:
Molecular Cloning
Plasmids expressing His-tagged N-terminal (amino acids 51-292) or C-terminal (amino acids 282-442) portions of the extracellular domain of human PLVAP (amino acids 51-442) were constructed as follows. pGEM®-T Easy-PLVAP$_{51-442}$ was treated with Eco RV and Stu I, self-ligated and generated the resulting plasmid pGEM®-T Easy-PLVAP$_{51-292}$. For construction of plasmid pET-15b-PLVAP$_{51-292}$, a cDNA fragment representing the amino acid residues 51 to 292 of PLVAP with NdeI/BamHI recognition sequences at the ends was excised from pGEM®-T Easy-PLVAP$_{51-292}$ and inserted into pET-15b (Novagen). To construct pET-15b-PLVAP$_{282-442}$, pET-15b-PLVAP$_{51-442}$ was treated with Nde I and Sac I, followed by blunt-end ligation using T4 DNA polymerase. The expression constructs described above were verified by DNA sequencing and transformed into *Escherichia coli* (Rosetta-Gami™2(DE3)pLysS cells).

Recombinant Protein Expression and Immunoblotting

Expression of His-tagged fusion proteins in *Escherichia coli* Rosetta-Gami™2(DE3)pLysS cells was induced with 1 mM isopropyl-B-D-thiogalactopyranoside for 16 hours at 30° C. Following the induction, the bacterial cells were subjected to lysis by Laemmli sample buffer. The resultant cell lysates were resolved by SDS-PAGE and subjected to Coomassie blue staining and immunoblotting using standard protocols and the following antibodies: primary antibodies: KFCC-GY4, KFCC-GY5, mAb 2A7-6, anti-his mAb (LTK Biotechnology, Taiwan). Immunoblots were developed by alkaline phosphatase-conjugated secondary antibodies against mouse IgG from Chemicon, Inc. using standard procedure.

PCR Amplification and Library Screening

The primers PLVAP Sac I F:

(SEQ ID NO: 36)
5'-CTCCAAGGTGGAGGAGCTGGC-3' and PLVAP Stop Bam HI R:

(SEQ ID NO: 37)
5'-GGATCCTGAGCATATCCCTGCATCCTCC-3' were used to amplify the sequence coding for the C-terminal portion of the PLVAP (amino acids 282-442) extracellular domain. PCR was performed using the following thermal cycle: 94° C. for 5 min, followed by 35 cycles of 94° C. for 30 s, 56° C. for 30 s and 72° C. for 60 s. DNA was purified with the Qiaquick® PCR purification kit (Qiagen, Surrey, UK) and then used in the construction of a PLVAP Novatope® library according to the manufacturer's instructions (Novagen, Merck Biosciences Ltd., Beeston, UK). Briefly, purified PCR product was digested with DNAse I in the presence of $Mn^{2+}$ and fragments between 50-150 base pairs (bp) were gel purified using a gel extraction kit (Qiagen). The DNA fragments were end-filled using T4 DNA polymerase and Tth polymerase to add a single dA residue to each 3' end and then ligated into the pScreen 1b(+)T-vector (Novagen), which is designed to express small inserts as a carboxy-terminal fusion to the T7 bacterial phage gene 10 capsid protein. The library was transformed into NovaBlue (DE3) cells and plated onto Luria-Bertani (LB) media plates containing carbenicillin (50 µg/ml) and tetracycline (12.5 µg/ml). The resulting human PLVAP cDNA library was screened (approximately $10^4$ colonies for each antibody) using the method described in the Novatope® manual: Colonies expressing PLVAP fragments were transferred to nitrocellulose filters by contact with the colony for 1 min. Bacterial colonies on the filters were lysed by incubating in a sealed chloroform vapor chamber for 15 min. Proteins were denatured in colony denaturing solution (20 mM Tris pH 7.9, 6 M Urea, 0.5 M NaCl) for 15 min and the filters were blocked for 30 min in 1% (w/v) gelatin in TBS with 0.05% (v/v) Tween® 20 detergent (TBS-T). Colony debris was removed by wiping with a tissue and then the filters were probed for 1 h with monoclonal antibody KFCC-GY4 and KFCC-GY5 (1 µg/ml) in TBS-T with 0.5% (w/v) gelatin. Blots were washed for 15 min twice in TBS-T with 0.5% (w/v) gelatin and then probed with a 1/5000 dilution of goat-anti mouse immunoglobulin-alkaline phosphatase conjugate (Chemicon) in TBS-T with 0.5% (w/v) gelatin. After washing, blots were developed using bromo-4-chloro-3-indolylphosphate/nitroblue tetrazolium (BCIP: 33 µg/ml; NBT: 66 µg/ml) substrate (Sigma). Positive colonies from each screen were plated onto fresh LB amp/tet plates and then re-probed with monoclonal antibody. Confirmed positives were used in DNA minipreps and the PLVAP gene inserts were sequenced using T7 terminator primer.

ELISA for Study of Binding Interference

Each well of an ELISA plate was coated with 50 µl KFCC-GY5 anti-PLVAP monoclonal antibodies at a concentration of 5 µg/m in PBS overnight. After blocking and washing, 50 µl of recombinant PLVAP protein (0.5 µg/ml) was added to each well. After incubation at room temperature for 60 minutes, the wells were washed and 50 µl of biotinylated KFCC-GY4 antibody at different concentrations was added to each well in duplicates and incubated for 30 minutes. After three washings, the wells were developed with 50 µl of diluted streptavidin-horseradish peroxidase conjugate and substrate. Optical density at 450 nm was measured for each well. Each value was a mean of duplicates.

ELISA for Additive Binding

Each well of an ELISA plate was coated with 50 µl of 0.25 µg/ml recombinant PLVAP protein. The wells were blocked and incubated with 50 µl of each humanized antibody derived from KFCC-GY4 or KFCC-GY5, either separately or together. The final concentration of each antibody was 0.01 µg/ml. The values were an average of duplicates.

Results:

To characterize the KFCC-GY4 and KFCC-GY5 mAbs further, epitope mapping was conducted to determine the antigenic sites in PLVAP that are bound by each of these antibodies. Initial results demonstrated that the antigenic epitopes for both antibodies reside in the C-terminal region of PLVAP protein between amino acids 282 and 482 (FIGS. 28A, 28B and 28C). Both KFCC-GY4 and KFCC-GY5 mAbs reacted positively with PLVAP$_{51-442}$ (lane 1) and PLVAP$_{282-442}$ (lane 2), but did not react with PLVAP51-292 (lane 3) or human CEACAM6 protein unrelated to PLVAP (lane 4). The results indicate that the epitopes for both antibodies reside in the C-terminal end of PLVAP between amino acid residues 292 to 442.

A finer mapping study revealed that the KFCC-GY4 mAb reacted with an *E. coli* clone expressing a peptide encompassing amino acids 431 to 442 of human PLVAP and the KFCC-GY5 mAb reacted with an *E. coli* clone expressing a peptide encompassing amino acids 378 to 404 of human PLVAP. As depicted in Table 5, the epitopes for these two mAbs do not overlap.

TABLE 5

Antigenic epitopes for KFCC-GY4 and
KFCC-GY5 monoclonal antibodies

Amino acid sequence responsible
for antigenic epitope for KFCC-GY5 mAb:
Human 431 SQRPPAGIPVAPSSG       442
(SEQ ID NO: 38)

TABLE 5-continued

Antigenic epitopes for KFCC-GY4 and
KFCC-GY5 monoclonal antibodies

| | | |
|---|---|---|
| Mouse 426 | SQRLPVVNPAAQPSG | 437 |
| (SEQ ID NO: 39) | | |
| Amino acid sequence responsible for antigenic epitope for KFCC-GY4 mAb: | | |
| Human 378 | ELAIRNSALDTCIKTKSQPMMPVSRPM | 404 |
| (SEQ ID NO: 40) | | |
| Mouse 375 | EVDVRISALDTCVKAKSLPAVP-PRVS | 400 |
| (SEQ ID NO: 41) | | |

The KFCC-GY4 and KFCC-GY5 mAbs could each bind to human PLVAP in an enzyme-linked immunoassay (ELISA) without interfering with the binding of the other antibody (FIG. 29). This lack of interference was also observed using fully humanized composite KFCC-GY4 and KFCC-GY5 monoclonal antibodies (FIG. 30), which are described in more detail below.

Example 7

Production and Characterization of Chimeric Antibodies that Specifically Bind PLVAP Materials and Methods:
Abbreviations

| Abbreviation | Description |
|---|---|
| CDR | Complementarity Determining region of an antibody variable region (numbered CDR1-3 for each of the heavy and light chains, as defined by Kabat) |
| Ec (0.1%) | The Absorbance of a 1 mg/ml solution of protein |
| ELISA | Enzyme linked immunosorbent assay |
| FW | Framework region-scaffold region of a variable domain supporting the CDRs |
| HRP | Horse-radish peroxidase |
| IgG | Immunoglobulin G |
| mAb | Monoclonal antibody |
| OD280 nm | Optical density measured at 280 nm |
| P protein | PLVAP protein |
| PBS | Phosphate-buffered saline |
| TMB | 3,3',5,5'-tetramethylbenzidine |
| V-region | Variable region of an antibody chain |

Initial Determination of Variable Region Sequences

Total RNA was extracted using Trizol® reagent (Invitrogen, Carlsbad, Calif.) from 2×10$^7$ cultured hybridoma cells from the cell lines KFCC-GY4 and KFCC-GY5. 5' RACE was carried out using the FirstChoice® RLM-RACE kit (Ambion, Inc., Austin, Tex.) following the manufacturer's instructions to determine the coding sequence of VH and VL domains from KFCC-GY4 and KFCC-GY5. Briefly, 10 μg of extracted RNA was treated with calf intestinal phosphatase (CIP) in a 20 μl total volume reaction mixture containing 2 μl of 10×CIP buffer and 2 μl of CIP for 1 h at 37° C. After extracted with phenol/chloroform, RNA was precipitated with ethanol and resuspended in 11 μl of nuclease-free water. 5 μl of CIP-treated RNA was treated with tobacco acid pyrophosphatase (TAP) in a 10 μl reaction mixture containing 1 μl of 10×TAP buffer and 2 μl of TAP for 1 h at 37° C. 2 μl of the CIP/TAP-treated RNA was then ligated to 300 ng of RNA adaptor by T4 RNA ligase in a 10 μL reaction mixture for 1 h at 37° C. 2 μl of the ligated RNA or control RNA was used as a template to synthesize cDNA with M-MLV reverse transcriptase for 1 h at 42° C. using random decamers. The cDNAs corresponding to variable heavy (VH) and light (VL) chains were then amplified by PCR separately with Takara Ex Taq™ DNA polymerase (Takara Bio Inc., Osaka, Japan) using forward 5' RACE outer primer 5'-GCTGATGGCGAT-GAATGAACACTG-3' (SEQ ID NO:42) and reverse primers complementary to the nucleotide sequences encoding the kappa chain constant region (5'-TCAACGTGAGGGTGCT-GCTCATGC-3' (SEQ ID NO:43)) or the heavy chain CH1 region (5'-TTTCTTGTCCACCTTGGTGCTGCTGG-3' (SEQ ID NO:44)), respectively. The PCR reaction mixtures were incubated for 5 min at 94° C. followed by 35 amplification cycles, comprising denaturation at 94° C. for 30 s, annealing at 57° C. for 30 s and extension at 72° C. for 1 min. The reaction was extended for another 7 min at 72° C. to insure full extension. PCR products were analyzed and purified from the 1.5% agarose gel using the Qiaquick® gel extraction kit (Qiagen, Mississauga, Ontario, Canada). The purified PCR fragments were cloned into the pGEM®-T-easy plasmid vector (Promega, Madison, Wis., USA). A minimum of 5 independent clones for each chain were subjected to nucleotide sequencing analysis. The CDRs were identified according to Kabat definition (FIGS. 15A, 15B, 16A and 16B).

Independent Confirmation of Variable Region Sequences mRNA was successfully extracted (Promega Catalogue No. Z5400) from frozen KFCC-GY4 and KFCC-GY5 cells. RT-PCR was performed using degenerate primer pools for murine signal sequences with a single constant region primer. Heavy chain variable region mRNA was amplified using a set of six degenerate primer pools (HA to HF) and light chain variable region mRNA was amplified using a set of seven degenerate primer pools (kappaA to kappaG)—monoclonal isotyping analysis of the IgGs using Roche Isostrips (Roche Catalogue No. 493027001) revealed them both to be IgG1/kappa isotypes. Amplification products were obtained with heavy chain and kappa light chain primer pools confirming the light chain is from the kappa cluster. Each product was cloned and several clones from each sequenced. For KFCC-GY4 and KFCC-GY5 antibodies, single functional heavy and light chain variable region sequences were identified for each antibody.

Expression of Chimeric Antibodies

The KFCC-GY4 and KFCC-GY5 variable regions were transferred to an expression vector system (Antitope) for IgG4 heavy chain and kappa light chain. NS0 cells were transfected via electroporation and selected using methotrexate. A number of methotrexate resistant colonies were identified and cell lines positive for IgG expression were expanded. Genomic DNA from the lead cell lines was recovered and subjected to PCR and confirmatory sequencing. IgG chimeric KFCC-GY4 and KFCC-GY5 IgG4s were purified from cell culture supernatants on a Protein A-Sepharose® column (GE Healthcare Catalogue No. 110034-93) and quantified by OD280 nm using an extinction coefficient, Ec(0.1%), based on the predicted amino acid sequence—Ec (0.1%) values of 1.484 and 1.334 were used for chimeric KFCC-GY4 and KFCC-GY5, respectively. Greater than 2 mg of antibody was purified and analyzed by SDS-PAGE (FIG. 31). Bands corresponding to the predicted sizes of the heavy and light chains were observed with no evidence of any contamination.

Binding of Chimeric KFCC-GY4 and KFCC-GY5 Antibodies to Recombinant PLVAP

The binding of chimeric KFCC-GY4 and KFCC-GY5 antibodies to recombinant PLVAP protein was assessed in a competition ELISA. Either a dilution series of chimeric or control antibody from 30 μg/ml to 0.014 μg/ml (final concentration) was premixed with a constant concentration of biotinylated murine KFCC-GY4 (0.3 μg/ml, final concentration) or a dilution series of chimeric or control antibody from 10 μg/ml to 0.004 μg/ml (final concentration) was premixed with a constant concentration of biotinylated murine KFCC-GY5 (0.1 μg/ml, final concentration) before incubating for 1 hour at room temperature on a Nunc Immuno™ MaxiSorp® 96 well flat bottom microtitre plate (Fisher Catalogue No. DIS-971-030J) precoated with 1 μg/ml recombinant PLVAP protein diluted in PBS. The binding of the biotinylated mAb was determined by detection with streptavidin-HRP and TMB substrate.

Results:

Variable regions from the KFCC-GY4 and KFCC-GY5 mouse anti-PLVAP monoclonal antibodies were successfully cloned and sequenced. Three complementarity determining regions (CDRs) were identified in each antibody according to Kabat definition. The analysis of the sequences obtained from hybridomas KFCC-GY4 and KFCC-GY5 from the confirmation studies are summarized in Tables 6 and 7. These sequences matched the sequences obtained by the initial characterization (FIGS. 15A, 15B, 16A and 16B), with the exception of a single silent mismatch in the KFCC-GY4 light chain nucleotide sequence. The aberrant transcript (GENBANK® accession number M35669) normally associated with the hybridoma fusion partner SP2/0 was also detected in both cell lines.

TABLE 6

Sequence analysis of KFCC-GY4 monoclonal antibody

|  | H Chain | L Chain |
| --- | --- | --- |
| CDR 1 Length | 5 aa | 16 aa |
| CDR 2 Length | 17 aa | 7 aa |
| CDR 3 Length | 4 aa | 9 aa |
| Closest Human Germline[b] | IGHV1-f*01 (64%) | IGKV2D-30*01 (82%) |
| Closest Human FW1[b] | IGHV1-46*03 (68%) | IGKV2D-29*02 (87%) |
| Closest Human FW2[b] | IGHV7-4-1*03 (71%) | IGKV2D-30*01 (80%) |
| Closest Human FW3[b] | IGHV1-f*01 (70%) | IGKV2D-40*01 (94%) |
| Closest Human J[b] | IGHJ6*01 (91%) | IGKJ4 (90%) |
| Max no. mouse FR residues[c] | 13 (4) | 4 (1) |

TABLE 7

Sequence analysis of KFCC-GY5 monoclonal antibody

|  | H Chain | L Chain |
| --- | --- | --- |
| CDR 1 Length | 5 aa | 16 aa |
| CDR 2 Length | 17 aa | 7 aa |
| CDR 3 Length | 4 aa | 9 aa |
| Closest Human Germline[b] | IGHV1-46*03 (68%) | IGKV2D-29*02 (80%) |
| Closest Human FW1[b] | IGHV7-4-1*02 (76%) | IGKV2D-30*01 (83%) |
| Closest Human FW2[b] | IGHV7-4-1*02 (79%) | IGKV2D-40*01 (93%) |
| Closest Human FW3[b] | IGHV1-69*10 (72%) | IGKV2D-40*01 (91%) |
| Closest Human J[b] | IGHJ6*01 (91%) | IGKJ2 (90%) |
| Max no. mouse FR residues[c] | 9 (3) | 2 (2) |

[a]CDR definitions and sequence numbering according to Kabat
[b]Germline ID(s) indicated followed by % homology
[c]Indicates maximum number of mouse residues that need to be sourced from human sequence segments with number of those potentially critical for affinity indicated in brackets Variable region genes were then combined with human IgG4 heavy chain and kappa light chain constant regions and expressed in NS0 cells to produce chimeric anti-PLVAP antibodies. To accomplish this, plasmid vectors carrying KFCC-GY4 chimeric heavy and light chains and KFCC-GY5 chimeric heavy and light chains were constructed (FIGS. 32A-1 to 32A-4, 32B-1 to 32B-3, 32C-1 to 32C-3, 33A-1 to 33A-4, 33B-1 to 33B-3, 34A-1 to 34A-4, 34B-1 to 34B-3, 34C-1 to 34C-4, 35A-1 to 35A-4 and 35B-1 to 35B-4). These plasmids were used to transfect NSO cells. Stably transfected and chimeric antibody-producing cells were cloned.

The heavy and light chain variable regions for the KFCC-GY4 antibody show good homology to their closest human germline sequences (64% and 80%, respectively, for KFCC-GY4) and the individual framework sequences have close homologues in the human germline database. This therefore reduces the extent of engineering that needs to be undertaken for a successful humanized antibody. The maximum number of mouse framework residues that will need to be sourced from human sequence segments for the KFCC-GY4 heavy chain is 13, with 4 constraining residues probably being crucial for maintenance of binding activity. The maximum number of mouse framework residues that will need to be sourced from human sequence segments for the KFCC-GY4 light chain is 4, with 1 constraining residue thought to be critical for activity (Table 6).

The heavy and light chain variable regions for the KFCC-GY5 antibody also showed good homology to their closest human germline sequences (68% and 80%, respectively, for KFCC-GY5) and the individual framework sequences have close homologues in the human germline database. This therefore reduces the extent of engineering that needs to be undertaken for a successful humanized antibody. The maximum number of mouse framework residues that will need to be sourced from human sequence segments for the heavy chain is 9, with 3 constraining residues probably being crucial for maintenance of binding activity. The maximum number of mouse framework residues that will need to be sourced from human sequence segments for the light chain is 2, with both thought to be critical for activity (Table 7). Composite Human Antibody™ analysis (Antitope; Cambridge, UK) revealed that human framework segments can be found to include all desirable mouse residues, and therefore complete humanized antibodies can be built from both templates.

A competition ELISA assay was used to demonstrate that the binding efficiencies of the chimeric antibodies for PLVAP are similar to that of the respective parent murine antibodies. The chimeric IgG4-GY4 and murine KFCC-GY4 antibodies had very similar binding profiles, with IC50 values of 0.80 μg/m and 0.98 μg/ml, respectively (FIG. 36). Similarly, the chimeric IgG4-GY5 and murine KFCC-GY5 antibodies also had very similar binding profiles, with IC50 values of 0.40 μg/m and 0.49 μg/ml, respectively (FIG. 37). Therefore, the correct variable region sequences for the parent murine monoclonal antibodies were identified and cloned.

Binding affinities were also determined using Biacore™ system Bia T-100. Both chimeric KFCC-GY4 and KFCC-GY5 antibodies were determined to have higher binding affinities for PLVAP than their respective parent mAbs (Table 8). The two chimeric monoclonal antibodies derived from KFCC-GY4 and KFCC-GY5 are also referred to herein as CSR01 and CSR02, respectively.

TABLE 8

Binding affinities of KFCC-GY4, KFCC-GY5, chimeric KFCC-GY4 (CSR01) and chimeric KFCC-GY5 (CSR02) monoclonal antibodies

| Antibody | ka (1/Ms) | kd (1/s) | Kd (M) |
| --- | --- | --- | --- |
| GY4 | $1.51 \times 10^4$ | $7.01 \times 10^{-3}$ | $4.64 \times 10^{-7}$ |
| Chimeric GY4 (CSR01) | $5.21 \times 10^3$ | $2.12 \times 10^{-3}$ | $4.06 \times 10^{-7}$ |
| GY5 | $6.93 \times 10^3$ | $4.14 \times 10^{-4}$ | $5.98 \times 10^{-8}$ |
| Chimeric GY5 (CSR02) | $3.07 \times 10^4$ | $3.01 \times 10^{-5}$ | $9.78 \times 10^{-10}$ | ka: association rate; kd: dissociation rate; Kd: dissociation constant (binding affinity)

Example 8

Production and Characterization of Fully Humanized Antibodies that Specifically Bind PLVAP

Materials and Methods:

Overview

Three different kappa light chains and two different heavy chains were constructed based on the cDNA sequences from chimeric KFCC-GY4 (CSR01) antibody. They were used to transfect NS0 cell line for production of humanized composite antibodies. Five different cell lines were generated for production of five monoclonal antibodies. Similarly, two different kappa light chains and two different heavy chains were constructed based on cDNA sequences from the chimeric KFCC-GY5 (CSR02) antibody. Four cell lines that produce four different monoclonal antibodies were obtained. The nucleotide sequences of the variable domains of these humanized heavy and light chains are summarized in FIGS. 38A-38E and 39A-39D. A flowchart for derivation of chimeric antibodies and fully humanized composite antibodies are outlined in FIG. 40.

Abbreviations

| Abbreviation | Description |
|---|---|
| BLAST CDR | Basic Local Alignment Search Tool Complementarity Determining region of an antibody variable region (numbered CDR1-3 for each of the heavy and light chains, as defined by Kabat) |
| Ec (0.1%) | The absorbance of a 1 mg/ml solution of protein |
| ELISA FW | Enzyme linked immunosorbent assay Framework region-scaffold region of a variable domain supporting the CDRs |
| HRP IgG | Horse-radish Peroxidase Immunoglobulin G |
| mAb | Monoclonal antibody |
| MHC | Major histocompatibility complex |
| OD280 nm | Optical density measured at 280 nm |
| PBS | Phosphate-buffered saline |
| TMB | 3,3',5,5'-tetramethylbenzidine |
| V-region | Variable region of an antibody chain |
| P protein | PLVAP protein |

Design of Human Antibody Variable Region Sequences

Structural models of the mouse KFCC-GY4 and KFCC-GY5 variable (V) regions were produced using Swiss PDB and analysed in order to identify important "constraining" amino acids in the mouse V regions that were likely essential for the binding properties of the antibody. Residues contained within the CDRs (using both Kabat and Chothia definitions), together with a number of framework residues, were considered to be important. Both the VH and VK sequences of KFCC-GY4 and KFCC-GY5 contain typical framework residues. Whereas the CDR 1 and 2 motifs of both antibodies are comparable to many murine antibodies, it was noted that the VH CDR3 for both antibodies are unusually short. From the above analysis, it was considered that composite human sequences of both KFCC-GY4 and KFCC-GY5 could be created with a wide latitude of alternatives outside of CDRs, but with only a narrow menu of possible alternative residues within the CDR sequences. Preliminary analysis indicated that corresponding sequence segments from several human antibodies could be combined to create CDRs similar or identical to those in the mouse sequences. For regions outside of and flanking the CDRs, a wide selection of human sequence segments were identified as possible components of the novel human antibody variable regions.

Epitope Avoidance and Design of Variants

Based upon the above analysis, a large preliminary set of sequence segments that could be used to create both KFCC-GY4 and KFCC-GY5 human antibody variants was selected and analysed using iTope™ technology for analysis of peptide binding to human MEW class II alleles, and using the TCED™ Cell Epitope Database of known antibody sequence-related T cell epitopes (Antitope Ltd.; Cambridge, UK). Sequence segments where significant non-human MEW class II binding peptides were identified, or scored significant hits against the TCED™ database, were discarded. This resulted in a reduced set of segments, and combinations of these were again analysed, as above, to ensure that the junctions between segments did not contain potential T cell epitopes. Selected segments were then combined to produce heavy and light chain variable region sequences for synthesis. For each antibody, five heavy chains and three light chains were constructed with sequences as detailed in FIGS. 41A-41E and 42A-42C (for KFCC-GY5) and FIGS. 43A-43E and 44A-44C (for KFCC-GY4) and sequence alignments as detailed in FIGS. 45 and 46.

Construction, Expression and Purification of Variant Antibodies

Initial variant 1 human antibody VH and VK region genes were synthesized for KFCC-GY4 and KFCC-GY5 using a series of overlapping oligonucleotides that were annealed, ligated and PCR amplified to give full length synthetic V regions. Subsequent human antibody sequence variants were constructed using long overlapping oligonucleotides and PCR, using the initial variant 1 as the template. The assembled variants were then cloned directly into the pANT™ expression vector system (Antitope, Ltd.; Cambridge, UK) for IgG4 heavy chains and kappa light chains. All combinations of composite heavy and light chains (i.e., a total of 15 pairings) were stably transfected into NS0 cells via electroporation and selected using 200 nM methotrexate (Sigma Catalogue No. M8407-500MG). Methotrexate resistant colonies for each construct were tested for IgG expression levels and the best expressing lines were selected and frozen under liquid nitrogen. IgG4 Variants for KFCC-GY4 and KFCC-GY5 were purified from cell culture supernatants on a Protein A-Sepharose® column (GE Healthcare Catalogue No. 110034-93) and quantified by OD280 nm using an extinction coefficient, Ec(0.1%), based on the predicted amino acid sequence (Table 9). Greater than 2 mg of antibody was purified and analysed by SDS-PAGE (FIGS. 47A and 47B). Bands corresponding to the predicted sizes of the heavy and light chains were observed with no evidence of any contamination.

TABLE 9

Ec (0.1%) values for KFCC-GY4 and KFCC-GY5 antibody variants

| | Variant | Ec (0.1%) |
|---|---|---|
| GY4 Chimera | | 1.48 |
| GY4 Variants | (all) | 1.49 |
| GY5 Chimera | | 1.33 |
| GY5 Variants | VH4/VK2 VH5/VK2 | 1.33 |
| GY5 Variants | VH4/VK3 VH5/VK3 | 1.35 |

In addition, CHO-K1 cells were transiently transfected using Lipofectamine® 2000 (Invitrogen #11668-019). 72 hours after transfection, cell media was harvested for antibody purification. Briefly, IgG4 human antibody variants from transient transfections were purified from cell culture supernatants on a Protein A-Sepharose® column (Sigma Catalogue No. P3391-1.5G) and quantified using an Fc capture/kappa chain detection ELISA (Sigma Catalogue No. 16260 and A7164) against a human IgG4/kappa standard (Sigma Catalogue No. 14639). A broad observation was that the number of expressing NS0 clones was significantly lower for KFCC-GY4 lineage clones when compared to KFCC-GY5 lineage clones. Furthermore, it was also noted that both stable and transient yields were lower for KFCC-GY4 lineage clones compared to KFCC-GY5. In some cases, the transient yields from KFCC-GY4 lineages were not sufficient to allow complete characterization of the variants, and so all subsequent analysis was carried out using NS0 purified material from stable cell lines.

Binding of the Variant Antibodies to Recombinant PLVAP Protein

The binding of KFCC-GY4 and KFCC-GY5 human antibody variants to recombinant PLVAP was assessed in a competition ELISA. Either a dilution series of variant or control antibody from 30 µg/ml to 0.014 µg/ml (final concentration) was premixed with a constant concentration of biotinylated murine KFCC-GY4 (0.3 µg/ml, final concentration) or a dilution series of variant or control antibody from 10 µg/ml to 0.004 µg/ml (final concentration) was premixed with a constant concentration of biotinylated murine KFCC-GY5 (0.1 µg/ml, final concentration) before incubating for 1 hour at room temperature on a Nunc Immuno™ MaxiSorp® 96 well flat bottom microtitre plate (Fisher Catalogue No. DIS-971-030J) precoated with 1 µg/ml recombinant "protein P" diluted in PBS. The binding of the biotinylated mAb was determined by detection with streptavidin-HRP and TMB substrate. After stopping the reaction with 3M HCl, absorbance was measured at 450 nm on a Dynex Technologies MRX TC II plate reader and the binding curves of the test antibodies compared against the mouse reference standard.

Titration of PLVAP Binding by Chimeric and Fully Humanized Composite Anti-PLVAP Monoclonal Antibodies Each well of an ELISA plate was coated with 50 µl 2.5 µg/ml recombinant PLVAP protein in PBS. After washing and blocking, each well was incubated with a different concentration of humanized monoclonal antibody (0.5 µg/ml to 0.0025 µg/ml) for 60 minutes at room temperature. The binding of the antibody to PLVAP was measured using alkaline phosphatase conjugate of mouse anti-human IgG4 monoclonal antibody (BD Pharmingen) diluted 1000×.

Results:

The five lead variants of IgG4-GY4 and murine KFCC-GY4 antibodies have very similar binding profiles (FIG. 48). Absolute IC50 values and values relative to the KFCC-GY4 mAb for the five lead variants are shown in Table 10. All of the lead variants shown are within two-fold of the original murine monoclonal antibody.

Similarly, the four lead variants of IgG4-GY5 and murine KFCC-GY5 antibodies have very similar binding profiles (FIG. 49). Absolute IC50 values and values relative to the KFCC-GY5 mAb for the five lead variants are shown in Table 11. All of the lead variants shown are within two-fold of the original murine monoclonal antibody.

TABLE 10

IC50 Values of KFCC-GY4 Composite Human Antibody ™ Variants

| Antibody | IC$_{50}$ (µg/ml) | IC$_{50}$ (ratio compared to GY4 mAb) |
|---|---|---|
| GY4 mAB | 1.82 | 1 |
| VH4/VK2 | 2.53 | 1.39 |
| VH4/VK3 | 2.94 | 1.61 |
| VH5/VK1 | 2.18 | 1.20 |
| VH5/VK2 | 1.91 | 1.05 |
| VH5/VK3 | 2.82 | 1.55 |

GY4 Composite Human Antibody™ variants were purified from NS0 stably transfected supernatant and tested in a competition assay with biotinylated KFCC-GY4 mAb. IC$_{50}$ values are displayed and are also normalized against the binding of the reference KFCC-GY4 mAb.

TABLE 11

IC50 Values of KFCC-GY5 Composite Human Antibody™ Variants

| Antibody | IC50 (µg/ml) | IC50 (ratio compared to GY5 mAb) |
|---|---|---|
| GY5 mAB | 0.38 | 1 |
| VH4/VK2 | 0.56 | 1.47 |
| VH4/VK3 | 0.43 | 1.13 |
| VH5/VK2 | 0.60 | 1.58 |
| VH5/VK3 | 0.41 | 1.08 |

GY5 Composite Human Antibody™ Variants were purified from NS0 stably transfected supernatant and tested in a competition assay with biotinylated KFCC-GY5 mAb. IC$_{50}$ values are displayed and are also normalized against the binding of the reference KFCC-GY5 mAb.

Composite humanized antibodies derived from chimeric KFCC-GY4 and KFCC-GY5 antibodies were able to bind to PLVAP protein (FIG. 50). Fully humanized composite antibodies from chimeric KFCC-GY4 (CSR01) bind less well than chimeric CSR01. In contrast, fully humanized composite antibodies from chimeric KFCC-GY5 (CSR02) bind more or less equally well as chimeric CSR02.

To confirm that the fully humanized antibodies from KFCC-GY4 (CSR01) and KFCC-GY5 (CSR02) can bind to PLVAP without interfering with the binding of each other, an in vitro enzyme linked immunoassay (ELISA) was performed to show that some of the fully humanized composite antibodies from CSR01 and CSR02 are indeed additive in binding to PLVAP (FIG. 30).

Binding of the humanized antibodies to PLVAP proteins expressed on human umbilical cord vascular endothelial cells was assessed by immunofluorescence studies. All humanized antibodies tested in these studies were able to bind to endothelial cells (FIGS. 51A-51C, 52A-52G and 53A-53E). These results indicate that the humanized antibodies that bind these two epitopes can be used as therapeutic or diagnostic agents independently, or used together for their additive effect, if needed.

In summary, the results of the study described in the Examples herein demonstrate that murine monoclonal antibodies can be developed against two different well-defined antigenic epitopes in the extracellular domain of the human PLVAP protein. The amino acid sequences of these two epitopes have been identified. The binding of these antibodies to the two identified epitopes in PLVAP does not cause them to interfere with each other and can be additive. Thus, these antibodies, and antibodies derived from them, can be used as therapeutic or diagnostic agents individually, or used together for their additive effect, if needed. The CDRs responsible for antigen binding have been identified. This information has been successfully utilized to humanize both anti-PLVAP murine monoclonal antibodies for treatment of liver cancer in human subjects and to reduce antigenicity.

Example 9

Development of a Diagnostic Assay for Detecting PLVAP Levels in Serum

Materials and Methods:
PLVAP ELISA
1. Each well of an ELISA plate was coated with 50 µl KFCC-GY4 mAb at 5 µg/m overnight. The antibody was prepared in 1×PBS buffer containing 0.02% sodium azide.

2. After washing each well with 200 ul washing buffer (PBS containing 0.05% Tween-20) three times, each well was blocked with 200 µl blocking buffer (washing buffer containing 2% bovine serum albumin) for 30 minutes at room temperature.
3. Wells were washed three times after blocking.
4. 50 µl PLVAP standards and diluted serum samples were added into designated wells in duplicates and incubated for 60 minutes at room temperature. Standards and serum samples were diluted in blocking buffer.
5. Wells were washed three times and 50 µl of biotinylated KFCC-GY5 mAb were added at 0.25 µg/ml.
6. After incubation for 30 minutes, all wells were washed three times.
7. 50 µl of 2500× diluted Streptavidin-horseradish peroxidase (Pierce, Inc. catalog #: N100) were added to each well and incubated for 30 minutes at room temperature.
8. After three washes, 100 µl OPD substrate prepared according to manufacturer's instruction (Sigma, Inc. catalog #: P-6787) were added and incubated for an optimal duration of time.
9. The incubation was stopped by adding 50 µl of 0.18M $H_2SO_4$.
10. OD measurements were taken at 570 nm.

Results:

Both murine KFCC-GY4 and KFCC-GY5 anti-human PLVAP monoclonal antibodies were used to establish an enzyme-linked immunoassay (ELISA) to measure PLVAP protein concentration in serum. KFCC-GY4 antibody was used to coat an ELISA plate to capture PLVAP protein in serum, and biotinylated KFCC-GY5 antibody was used to detect PLVAP protein captured by the KFCC-GY4 antibody. The recombinant PLVAP protein was used as a reference standard. As shown by the standard curve of the PLVAP ELISA (FIG. 54), the sensitivity for this assay is about 50 ng/ml. When two serum samples from two liver cancer patients were assayed in two dilutions (2× and 4×), both had measurable PLVAP levels (450 ng/ml and 360 ng/nl) and were parallel with the standard curve. No measurable PLVAP was detected in the plasma of two healthy individuals. Therefore, this assay can be used in diagnostic applications to assay PLVAP levels in serum.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

```

What is claimed is:

1. An isolated nucleic acid encoding:
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102;
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108;
   c) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; or
   d) at least one kappa light chain amino acid sequence selected from the group consisting of SEQ ID NO:70, SEQ ID NO:72, SEQ ID NO:88, SEQ ID NO:90, and SEQ ID NO:92.

2. The isolated nucleic acid of claim 1, wherein the isolated nucleic acid encodes:
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108.

3. The isolated nucleic acid of claim 2, wherein the nucleic acid encodes a variable heavy domain comprising an amino acid sequence comprising SEQ ID NO: 68 or 102; and a variable light domain comprising an amino acid sequence comprising SEQ ID NO: 62 or 106.

4. The isolated nucleic acid of claim 1, wherein the isolated nucleic acid encodes:
   a) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; or
   b) at least one kappa light chain amino acid sequence selected from the group consisting of SEQ ID NO:70, SEQ ID NO:72, SEQ ID NO:88, SEQ ID NO:90, and SEQ ID NO:92.

5. The isolated nucleic acid of claim 4, wherein the nucleic acid encodes a variable heavy domain comprising an amino acid sequence comprising SEQ ID NO: 76 or 86; and a variable light domain comprising an amino acid sequence comprising SEQ ID NO: 72 or 92.

6. An isolated cell comprising the nucleic acid of claim 1.
7. An isolated cell comprising the nucleic acid of claim 2.
8. An isolated cell comprising the nucleic acid of claim 3.
9. An isolated cell comprising the nucleic acid of claim 4.
10. An isolated cell comprising the nucleic acid of claim 5.

11. An isolated cell comprising:
i)
   a) a first nucleic acid encoding at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) a second nucleic acid encoding at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108; or
ii)
   a) a first nucleic acid encoding at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; and
   b) a second nucleic acid encoding at least one kappa light chain amino acid sequence selected from the group consisting of SEQ ID NO:70, SEQ ID NO:72, SEQ ID NO:88, SEQ ID NO:90, and SEQ ID NO:92.

12. An isolated protein comprising:
i)
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108; or
ii)
   a) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; and
   b) at least one kappa light chain amino acid sequence selected from the group consisting of SEQ ID NO:70, SEQ ID NO:72, SEQ ID NO:88, SEQ ID NO:90, and SEQ ID NO:92.

13. The protein of claim 12, wherein the protein is bound to a radioactive isotope or a cytotoxic agent.

14. The protein of claim 12, wherein the protein is a monoclonal antibody that specifically binds SEQ ID NO: 23.

15. A composition comprising the protein of claim 12.

16. The composition of claim 15, further comprising at least one chemotherapeutic agent.

17. The composition of claim 16, wherein the chemotherapeutic agent is selected from the group consisting of doxorubicin, cisplatin, mitomycin, 5-fluorouracil, tamoxifen, sorafenib and octreotide.

18. A method of making a protein, comprising culturing the cell of claim 6 under conditions to express the protein and isolating the protein, wherein the protein comprises:

i)
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108; or ii)
   a) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; and
   b) at least one kappa light chain amino acid sequence selected from the group consisting of SEQ ID NO:70, SEQ ID NO:72, SEQ ID NO:88, SEQ ID NO:90, and SEQ ID NO:92.

19. A method of making a protein, comprising culturing the cell of claim 7 under conditions to express the protein and isolating the protein, wherein the protein comprises:

i)
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108; or ii)
   a) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; and
   b) at least one kappa light chain amino acid sequence selected from the group consisting of SEQ ID NO:70, SEQ ID NO:72, SEQ ID NO:88, SEQ ID NO:90, and SEQ ID NO:92.

20. A method of making a protein, comprising culturing the cell of claim 11 under conditions to express the protein and isolating the protein, wherein the protein comprises:

i)
   a) at least one heavy chain amino acid sequence selected from the group consisting of SEQ ID NO:66, SEQ ID NO:68, SEQ ID NO:94, SEQ ID NO:96, SEQ ID NO:98, SEQ ID NO:100, and SEQ ID NO:102; and
   b) at least one kappa light chain amino acid sequence selected from the group consisting of SEQ ID NO:60, SEQ ID NO:62, SEQ ID NO:64, SEQ ID NO:104, SEQ ID NO:106, and SEQ ID NO:108; or ii)
   a) at least one heavy chain amino acid sequence selected from the group consisting of SEQ ID NO:74, SEQ ID NO:76, SEQ ID NO:78, SEQ ID NO:80, SEQ ID NO:82, SEQ ID NO:84, and SEQ ID NO:86; and
   b) at least one kappa light chain amino acid sequence selected from the group consisting of SEQ ID NO:70, SEQ ID NO:72, SEQ ID NO:88, SEQ ID NO:90, and SEQ ID NO:92.

\* \* \* \* \*

SEQUENCE LISTING

<160> NUMBER OF SEQ ID NOS: 108

<210> SEQ ID NO 1
<211> LENGTH: 1322
<212> TYPE: DNA
<213> ORGANISM: Artificial Sequence
<220> FEATURE:
<223> OTHER INFORMATION: Coding sequence for recombinant His-tagged
      human PLVAP amino acids 51-442

<400> SEQUENCE: 1
atgggcagca gccatcatca tcatcatcac agcagcggcc tggtgccgcg cggcagccat        60
atgaacgtgc acgtgagcac agagtccaac ctgcaggcca ccgagcgccg agccgagggc       120
ctatacagtc agctcctagg gctcacggcc tcccagtcca acttgaccaa ggagctcaac       180
ttcaccaccc gcgccaagga tgccatcatg cagatgtggc tgaatgctcg ccgcgacctg       240
gaccgcatca atgccagctt ccgccagtgc cagggtgacc gggtcatcta cacgaacaat       300
cagaggtaca tggctgccat catcttgagt gagaagcaat gcagagatca attcaaggac       360
atgaacaaga gctgcgatgc cttgctcttc atgctgaatc agaaggtgaa gacgctggag       420
gtggagatag ccaaggagaa gaccatttgc actaaggata aggaaagcgt gctgctgaac       480
aaacgcgtgg cggaggaaca gctggttgaa tgcgtgaaaa cccgggagct gcagcaccaa       540
gagcgccagc tggccaagga gcaactgcaa aaggtgcaag ccctctgcct gcccctggac       600
aaggacaagt tgagatgga ccttcgtaac ctgtggaggg actccattat cccacgcagc       660
ctggacaacc tgggttacaa cctctaccat ccctgggct cggaattggc ctccatccgc        720
agagcctgcg accacatgcc cagcctcatg agctccaagg tggaggagct ggcccggagc       780
ctccgggcgg atatcgaacg cgtggcccgc gagaactcag acctccaacg ccagaagctg       840
gaagcccagc agggcctgcg ggccagtcag gaggcgaaac agaaggtgga gaaggaggct       900
caggcccggg aggccaagct ccaagctgaa tgctcccggc agacccagct agcgctggag       960
gagaaggcgg tgctgcggaa ggaacgagac aacctggcca aggagctgga agagaagaag      1020
```

-continued

```
agggaggcgg agcagctcag gatggagctg gccatcagaa actcagccct ggacacctgc   1080
atcaagacca gtcgcagcc gatgatgcca gtgtcaaggc ccatgggccc tgtccccaac    1140
ccccagccca tcgacccagc tagcctggag gagttcaaga ggaagatcct ggagtcccag   1200 aggcccctg caggcatccc tgtagccca tccagtggct gaggaggctc caggcctgag     1260
gaccaaggga tggcccgact cggcggtttg cggaggatgc agggatatgc tcacagggat   1320
tc                                                                 1322
```

<210> SEQ ID NO 2
<211> LENGTH: 413
<212> TYPE: PRT
<213> ORGANISM: Artificial Sequence
<220> FEATURE:
<223> OTHER INFORMATION: Recombinant His-tagged human PLVAP amino acids 51-442

<400> SEQUENCE: 2

```
Met Gly Ser Ser His His His His His Ser Gly Leu Val Pro
 1               5                  10                  15

Arg Gly Ser His Met Asn Val His Val Ser Thr Glu Ser Asn Leu Gln
            20                  25                  30

Ala Thr Glu Arg Arg Ala Glu Gly Leu Tyr Ser Gln Leu Leu Gly Leu
        35                  40                  45

Thr Ala Ser Gln Ser Asn Leu Thr Lys Glu Leu Asn Phe Thr Thr Arg
    50                  55                  60

Ala Lys Asp Ala Ile Met Gln Met Trp Leu Asn Ala Arg Arg Asp Leu
65                  70                  75                  80

Asp Arg Ile Asn Ala Ser Phe Arg Gln Cys Gln Gly Asp Arg Val Ile
                85                  90                  95

Tyr Thr Asn Asn Gln Arg Tyr Met Ala Ala Ile Ile Leu Ser Glu Lys
            100                 105                 110

Gln Cys Arg Asp Gln Phe Lys Asp Met Asn Lys Ser Cys Asp Ala Leu
        115                 120                 125

Leu Phe Met Leu Asn Gln Lys Val Lys Thr Leu Glu Val Glu Ile Ala
    130                 135                 140

Lys Glu Lys Thr Ile Cys Lys Asp Lys Glu Ser Val Leu Leu Asn Lys
145                 150                 155                 160

Arg Val Ala Glu Thr Glu Gln Leu Val Glu Cys Val Lys Thr Arg Glu
                165                 170                 175

Leu Gln His Gln Glu Arg Gln Leu Ala Lys Glu Gln Leu Gln Lys Val
            180                 185                 190

Gln Ala Leu Cys Leu Pro Leu Asp Lys Asp Lys Phe Glu Met Asp Leu
        195                 200                 205

Arg Asn Leu Trp Arg Asp Ser Ile Ile Pro Arg Ser Leu Asp Asn Leu
    210                 215                 220

Gly Tyr Asn Leu Tyr His Pro Leu Gly Ser Glu Leu Ala Ser Ile Arg
225                 230                 235                 240

Arg Ala Cys Asp His Met Pro Ser Leu Met Ser Ser Lys Val Glu Glu
                245                 250                 255

Leu Ala Arg Ser Leu Arg Ala Asp Ile Glu Arg Val Ala Arg Glu Asn
            260                 265                 270

Ser Asp Leu Gln Arg Gln Lys Leu Glu Ala Gln Gly Leu Arg Ala
        275                 280                 285

Ser Gln Glu Ala Lys Gln Lys Val Glu Lys Glu Ala Gln Ala Arg Glu
```

```
            290             295             300
Ala Lys Leu Gln Ala Glu Cys Ser Arg Gln Thr Gln Leu Ala Leu Glu
305                 310                 315                 320

Glu Lys Ala Val Leu Arg Lys Glu Arg Asp Asn Leu Ala Lys Glu Leu
                325                 330                 335

Glu Glu Lys Lys Arg Glu Ala Glu Gln Leu Arg Met Glu Leu Ala Ile
            340                 345                 350

Arg Asn Ser Ala Leu Asp Thr Cys Ile Lys Thr Lys Ser Gln Pro Met
        355                 360                 365

Met Pro Val Ser Arg Pro Met Gly Pro Val Pro Asn Pro Gln Pro Ile
    370                 375                 380

Asp Pro Ala Ser Leu Glu Glu Phe Lys Arg Lys Ile Leu Glu Ser Gln
385                 390                 395                 400

Arg Pro Pro Ala Gly Ile Pro Val Ala Pro Ser Ser Gly
                405                 410
```

<210> SEQ ID NO 3
<211> LENGTH: 342
<212> TYPE: DNA
<213> ORGANISM: Artificial Sequence
<220> FEATURE:
<223> OTHER INFORMATION: KFCC-GY4 VH domain coding sequence

<400> SEQUENCE: 3

```
gaggttcagc tgcagcagtc tggggcagag tttgtgaggt caggggcctc agtcaagttg      60
tcctgcacag cttctggctt caacattaaa gactactata tacactgggt gaagcagagg     120
cctgaacagg gcctggagtg gattggatgg attgatcctg agaatggtga tattgaatat     180
gccccgaagt tccagggcaa ggccactatg actgcagaca catcctccaa tacagcctac     240
ctgcagttca gcagcctgac atctgaggac actgccgtct attactgtct ctaccaagaa     300
ggctcctggg gccaaggcac cactctcaca gtctcctcag cc                        342
```

<210> SEQ ID NO 4
<211> LENGTH: 114
<212> TYPE: PRT
<213> ORGANISM: Artificial Sequence
<220> FEATURE:
<223> OTHER INFORMATION: KFCC-GY4 VH domain

<400> SEQUENCE: 4

```
Glu Val Gln Leu Gln Gln Ser Gly Ala Glu Phe Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Ile Glu Tyr Ala Pro Lys Phe
    50                  55                  60

Gln Gly Lys Ala Thr Met Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Leu Tyr Gln Glu Gly Ser Trp Gly Gln Gly Thr Thr Leu Thr Val Ser
            100                 105                 110

Ser Ala
```

<210> SEQ ID NO 5
<211> LENGTH: 5
<212> TYPE: PRT
<213> ORGANISM: Artificial Sequence
<220> FEATURE:
<223> OTHER INFORMATION: CDR1 sequence

<400> SEQUENCE: 5

Asp Tyr Tyr Ile His
 1               5

<210> SEQ ID NO 6
<211> LENGTH: 17
<212> TYPE: PRT
<213> ORGANISM: Artificial Sequence
<220> FEATURE:
<223> OTHER INFORMATION: CDR2 sequence

<400> SEQUENCE: 6

Trp Ile Asp Pro Glu Asn Gly Asp Ile Glu Tyr Ala Pro Lys Phe Gln
 1               5                  10                  15

Gly

<210> SEQ ID NO 7
<211> LENGTH: 4
<212> TYPE: PRT
<213> ORGANISM: Artificial Sequence
<220> FEATURE:
<223> OTHER INFORMATION: CDR3 sequence

<400> SEQUENCE: 7

Gln Glu Gly Ser
 1

<210> SEQ ID NO 8
<211> LENGTH: 336
<212> TYPE: DNA
<213> ORGANISM: Artificial Sequence
<220> FEATURE:
<223> OTHER INFORMATION: KFCC-GY4 VL domain coding sequence

<400> SEQUENCE: 8

```
gatgttgtga tgacccagac tccactcact tgtcggtta  ccattggaca accagcctcc      60
atctcttgca agtcaagtca gagcctctta aatagtgatg aaagacata  tttgaattgg     120
ttgttacaga ggccaggcca gtctccaaag cgcctaatct atctggtgtc taaattggac    180
tctggagtcc ctgacaggtt cactggcagt ggatcaggga cagatttcac actgaaaatc    240
agcagagtgg aggctgagga tttgggagtt tattattgct ggcaaggtac acattttccg    300
ttcacgttcg gagggggac  caagctggaa ataaaa                              336
```

<210> SEQ ID NO 9
<211> LENGTH: 111
<212> TYPE: PRT
<213> ORGANISM: Artificial Sequence
<220> FEATURE:
<223> OTHER INFORMATION: KFCC-GY4 VL domain

<400> SEQUENCE: 9

Asp Val Val Met Thr Gln Pro Leu Thr Leu Ser Val Thr Ile Gly Gln
 1               5                  10                  15

Pro Ala Ser Ile Ser Cys Lys Ser Ser Gln Ser Leu Leu Asn Ser Asp
                20                  25                  30

Gly Lys Thr Tyr Leu Asn Trp Leu Leu Gln Arg Pro Gly Gln Ser Pro

```
                    35                  40                  45
Lys Arg Leu Ile Tyr Leu Val Ser Lys Leu Asp Ser Gly Val Pro Asp
         50                  55                  60
Arg Phe Thr Gly Ser Gly Ser Gly Thr Asp Phe Thr Leu Lys Ile Ser
 65                  70                  75                  80
Arg Val Glu Ala Glu Asp Leu Gly Val Tyr Tyr Cys Trp Gln Gly Thr
                 85                  90                  95
His Phe Pro Phe Thr Phe Gly Gly Gly Thr Lys Leu Glu Ile Lys
            100                 105                 110
```

<210> SEQ ID NO 10
<211> LENGTH: 16
<212> TYPE: PRT
<213> ORGANISM: Artificial Sequence
<220> FEATURE:
<223> OTHER INFORMATION: CDR1 sequence

<400> SEQUENCE: 10

```
Lys Ser Ser Gln Ser Leu Leu Asn Ser Asp Gly Lys Thr Tyr Leu Asn
 1               5                  10                  15
```

<210> SEQ ID NO 11
<211> LENGTH: 7
<212> TYPE: PRT
<213> ORGANISM: Artificial Sequence
<220> FEATURE:
<223> OTHER INFORMATION: CDR2 sequence

<400> SEQUENCE: 11

```
Leu Val Ser Lys Leu Asp Ser
 1               5
```

<210> SEQ ID NO 12
<211> LENGTH: 9
<212> TYPE: PRT
<213> ORGANISM: Artificial Sequence
<220> FEATURE:
<223> OTHER INFORMATION: CDR3 sequence

<400> SEQUENCE: 12

```
Trp Gln Gly Thr His Phe Pro Phe Thr
 1               5
```

<210> SEQ ID NO 13
<211> LENGTH: 342
<212> TYPE: DNA
<213> ORGANISM: Artificial Sequence
<220> FEATURE:
<223> OTHER INFORMATION: KFCC-GY5 VH domain coding sequence

<400> SEQUENCE: 13

```
caggtccaac tgcagcagcc tggggctgag ctggtgaggc ctggggcttc agtgaagctg      60
tcctgcaagg cttctggcta caccttcacc agcaactaca taaactgggt gaaacagagg     120
cctggacagg gccttgagtg gatcggaaat atttatcctt ctgatggttt tactaactac     180
aatcaaaagt tcaaggacag ggccacattg actgtagaca atcctccag cacagcctac      240 atgcagctca gcagcccgac atctgaggac tctgcggtct attactgtac aagaaacttc     300
gatgtctggg gcgcagggac cacggtcacc gtctcctcag cc                        342
```

<210> SEQ ID NO 14
<211> LENGTH: 114
<212> TYPE: PRT

<213> ORGANISM: Artificial Sequence
<220> FEATURE:
<223> OTHER INFORMATION: KFCC-GY5 VH domain

<400> SEQUENCE: 14

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Asn
            20                  25                  30

Tyr Ile Asn Trp Val Lys Gln Arg Pro Gly Gln Gly Leu Glu Trp Ile
        35                  40                  45

Gly Asn Ile Tyr Pro Ser Asp Gly Phe Thr Asn Tyr Asn Gln Lys Phe
    50                  55                  60

Lys Asp Arg Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Asn Phe Asp Val Trp Gly Ala Gly Thr Thr Val Thr Val Ser
            100                 105                 110

Ser Ala

<210> SEQ ID NO 15
<211> LENGTH: 5
<212> TYPE: PRT
<213> ORGANISM: Artificial Sequence
<220> FEATURE:
<223> OTHER INFORMATION: CDR1 sequence

<400> SEQUENCE: 15

Ser Asn Tyr Ile Asn
1               5

<210> SEQ ID NO 16
<211> LENGTH: 17
<212> TYPE: PRT
<213> ORGANISM: Artificial Sequence
<220> FEATURE:
<223> OTHER INFORMATION: CDR2 sequence

<400> SEQUENCE: 16

Asn Ile Tyr Pro Ser Asp Gly Phe Thr Asn Tyr Asn Gln Lys Phe Lys
1               5                   10                  15

Asp

<210> SEQ ID NO 17
<211> LENGTH: 4
<212> TYPE: PRT
<213> ORGANISM: Artificial Sequence
<220> FEATURE:
<223> OTHER INFORMATION: CDR3 sequence

<400> SEQUENCE: 17

Asn Phe Asp Val
1

<210> SEQ ID NO 18
<211> LENGTH: 336
<212> TYPE: DNA
<213> ORGANISM: Artificial Sequence
<220> FEATURE:
<223> OTHER INFORMATION: KFCC-GY5 VL domain coding sequence

<400> SEQUENCE: 18

```
gatgttgtga tgacccaaac tccactctcc ctgcctgtca gtcttggaga tcaagcctcc    60
atctcttgca gatctagtca gagccttgtc cacagtaatg gaaacaccta tttacagtgg   120
tacctgcaga agccaggcca gtctccaaag ctcctgatct acacagtttc caaccgattt   180
tctggggtcc cagacaggtt cagtggcagt ggatcagggc cagatttcac actcaagatc   240
agcagagtgg aggctgagga tctgggagtt tatttctgct ctcaaagtac acatgttcct   300
ttcacgttcg gctcggggac aaagttggaa ataaaa                             336
```

<210> SEQ ID NO 19
<211> LENGTH: 112
<212> TYPE: PRT
<213> ORGANISM: Artificial Sequence
<220> FEATURE:
<223> OTHER INFORMATION: KFCC-GY5 VL domain

<400> SEQUENCE: 19

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Asn Gly Asn Thr Tyr Leu Gln Trp Tyr Leu Gln Lys Pro Gly Gln Ser
         35                  40                  45

Pro Lys Leu Leu Ile Tyr Thr Val Ser Asn Arg Phe Ser Gly Val Pro
     50                  55                  60

Asp Arg Phe Ser Gly Ser Gly Ser Gly Pro Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110
```

<210> SEQ ID NO 20
<211> LENGTH: 16
<212> TYPE: PRT
<213> ORGANISM: Artificial Sequence
<220> FEATURE:
<223> OTHER INFORMATION: CDR1 sequence

<400> SEQUENCE: 20

```
Arg Ser Ser Gln Ser Leu Val His Ser Asn Gly Asn Thr Tyr Leu Gln
 1               5                  10                  15
```

<210> SEQ ID NO 21
<211> LENGTH: 7
<212> TYPE: PRT
<213> ORGANISM: Artificial Sequence
<220> FEATURE:
<223> OTHER INFORMATION: CDR2 sequence

<400> SEQUENCE: 21

```
Thr Val Ser Asn Arg Phe Ser
 1               5
```

<210> SEQ ID NO 22
<211> LENGTH: 9
<212> TYPE: PRT
<213> ORGANISM: Artificial Sequence
<220> FEATURE:
<223> OTHER INFORMATION: CDR3 sequence

<400> SEQUENCE: 22

Ser Gln Ser Thr His Val Pro Phe Thr
1               5

<210> SEQ ID NO 23
<211> LENGTH: 442
<212> TYPE: PRT
<213> ORGANISM: Homo sapiens

<400> SEQUENCE: 23

Met Gly Leu Ala Met Glu His Gly Gly Ser Tyr Ala Arg Ala Gly Gly
1               5                   10                  15

Ser Ser Arg Gly Cys Trp Tyr Tyr Leu Arg Tyr Phe Phe Leu Phe Val
            20                  25                  30

Ser Leu Ile Gln Phe Leu Ile Ile Leu Gly Leu Val Leu Phe Met Val
        35                  40                  45

Tyr Gly Asn Val His Val Ser Thr Glu Ser Asn Leu Gln Ala Thr Glu
    50                  55                  60

Arg Arg Ala Glu Gly Leu Tyr Ser Gln Leu Leu Gly Leu Thr Ala Ser
65                  70                  75                  80

Gln Ser Asn Leu Thr Lys Glu Leu Asn Phe Thr Thr Arg Ala Lys Asp
                85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
    210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
            260                 265                 270

Asp His Met Pro Ser Leu Met Ser Ser Lys Val Glu Glu Leu Ala Arg
        275                 280                 285

Ser Leu Arg Ala Asp Ile Glu Arg Val Ala Arg Glu Asn Ser Asp Leu
    290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys

```
                  355                 360                 365
Lys Arg Glu Ala Glu Gln Leu Arg Met Glu Leu Ala Ile Arg Asn Ser
    370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
            420                 425                 430

Ala Gly Ile Pro Val Ala Pro Ser Ser Gly
            435                 440

<210> SEQ ID NO 24
<211> LENGTH: 2317
<212> TYPE: DNA
<213> ORGANISM: Homo sapiens

<400> SEQUENCE: 24
cggacgcgtg ggtgagcagg acggtgcac cggacggcgg gatcgagcaa atgggtctgg      60
ccatggagca cggagggtcc tacgctcggg cgggggggcag ctctcgggc tgctggtatt    120 acctgcgcta cttcttcctc ttcgtctccc tcatccaatt cctcatcatc ctggggctcg    180
tgctcttcat ggtctatggc aacgtgcacg tgagcacaga gtccaacctg caggccaccg    240
agcgccgagc cgagggccta cagtcagc tcctagggct cacggcctcc cagtccaact      300
tgaccaagga gctcaacttc accacccgcg ccaaggatgc catcatgcag atgtggctga    360
atgctcgccg cgacctggac cgcatcaatg ccagcttccg ccagtgccag ggtgaccggg    420
tcatctacac gaacaatcag aggtacatgg ctgccatcat cttgagtgag aagcaatgca    480
gagatcaatt caaggacatg aacaagagct gcgatgcctt gctcttcatg ctgaatcaga    540
aggtgaagac gctggaggtg gagatagcca aggagaagac catttgcact aaggataagg    600
aaagcgtgct gctgaacaaa cgcgtggcgg aggaacagct ggttgaatgc gtgaaaaccc    660
gggagctgca gcaccaagag cgccagctgg ccaaggagca actgcaaaag gtgcaagccc    720
tctgcctgcc cctggacaag acaagtttg agatggacct tcgtaacctg tggagggact    780
ccattatccc acgcagcctg acaaacctgg gttacaacct ctaccatccc ctgggctcgg    840
aattggcctc catccgcaga gcctgcgacc acatgcccag cctcatgagc tccaaggtgg    900
aggagctggc ccggagcctc cgggcggata tcgaacgcgt ggcccgcgag aactcagacc    960
tccaacgcca gaagctggaa gcccagcagg cctgcgggc cagtcaggag gcgaaacaga   1020
aggtggagaa ggaggctcag gcccgggagg ccaagctcca agctgaatgc tcccggcaga   1080
cccagctagc gctggaggag aaggcggtgc tgcggaagga acgagacaac ctggccaagg   1140
agctggaaga gaagaagagg gaggcggagc agctcaggat ggagctggcc atcagaaact   1200
cagccctgga cacctgcatc aagaccaagt cgcagccgat gatgccagtg tcaaggccca   1260
tgggccctgt ccccaacccc cagcccatcg acccagctag cctggaggag ttcaagagga   1320
agatcctgga gtcccagagg cccccctgcag gcatccctgt agccccatcc agtggctgag   1380
gaggctccag gcctgaggac caagggatgg cccgactcgg cggtttgcgg aggatgcagg   1440
gatatgctca cagcgcccga cacaaccccc tcccgccgcc cccaaccacc cagggccacc   1500
atcagacaac tccctgcatg caaacccta gtccctctc acaccgcac ccgcctca      1560 cgatccctca cccagagcac acggccgcgg agatgacgtc acgcaagcaa cggcgctgac   1620
```

```
gtcacatatc accgtggtga tggcgtcacg tggccatgta gacgtcacga agagatatag    1680
cgatggcgtc gtgcagatgc agcacgtcgc acacagacat ggggaacttg gcatgacgtc    1740
acaccgagat gcagcaacga cgtcacgggc catgtcgacg tcacacatat taatgtcaca    1800
cagacgcggc gatggcatca cacagacggt gatgatgtca cacacagaca cagtgacaac    1860
acacaccatg acaacgacac ctatagatat ggcaccaaca tcacatgcac gcatgccctt    1920
tcacacacac tttctaccca attctcacct agtgtcacgt tccccgacc ctggcacacg     1980 ggccaaggta cccacaggat cccatcccct cccgcacagc cctgggcccc agcacctccc    2040
ctcctccagc ttcctggcct cccagccact tcctcacccc cagtgcctgg acccggaggt    2100
gagaacagga agccattcac ctccgctcct tgagcgtgag tgtttccagg accccctcgg    2160
ggccctgagc cggggtgag ggtcacctgt tgtcgggagg ggagccactc cttctccccc     2220
aactcccagc cctgcctgtg gcccgttgaa atgttggtgg cacttaataa atattagtaa    2280
atccttaaaa aaaaaaaaaa aaaaaaaaaa aaaaaaa                             2317

<210> SEQ ID NO 25
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 25
cctgcaggca tccctgta                                                  18

<210> SEQ ID NO 26
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 26
cgggccatcc cttggt                                                    16

<210> SEQ ID NO 27
<211> LENGTH: 16
<212> TYPE: DNA
<213> ORGANISM: Artificial Sequence
<220> FEATURE:
<223> OTHER INFORMATION: oligonucleotide probe

<400> SEQUENCE: 27
ccccatccag tggctg                                                    16

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
ccttgagcgt gagtgtttcc a                                              21

<210> SEQ ID NO 29
<211> LENGTH: 25
<212> TYPE: DNA
<213> ORGANISM: Artificial Sequence
<220> FEATURE:
<223> OTHER INFORMATION: oligonucleotide primer
```

<400> SEQUENCE: 29
gtcccccaac ttgagatgta tgaag                                    25

<210> SEQ ID NO 30
<211> LENGTH: 17
<212> TYPE: DNA
<213> ORGANISM: Artificial Sequence
<220> FEATURE:
<223> OTHER INFORMATION: oligonucleotide primer

<400> SEQUENCE: 30
ggcagggctg ggagttg                                             17

<210> SEQ ID NO 31
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 31
gtctcaagtc agtgtacagg taagc                                    25

<210> SEQ ID NO 32
<211> LENGTH: 16
<212> TYPE: DNA
<213> ORGANISM: Artificial Sequence
<220> FEATURE:
<223> OTHER INFORMATION: oligonucleotide probe

<400> SEQUENCE: 32
ctcccaggga gaccaa                                              16

<210> SEQ ID NO 33
<211> LENGTH: 18
<212> TYPE: DNA
<213> ORGANISM: Artificial Sequence
<220> FEATURE:
<223> OTHER INFORMATION: oligonucleotide probe

<400> SEQUENCE: 33
aaggagtggc tccctcc                                             18

<210> SEQ ID NO 34
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 34
catatgaacg tgcacgtgag cacagagtcc                               30

<210> SEQ ID NO 35
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 35
ggatcctgag catatccctg catcctcc                                 28

<210> SEQ ID NO 36

```
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 36
ctccaaggtg gaggagctgg c                                              21

<210> SEQ ID NO 37
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 37
ggatcctgag catatccctg catcctcc                                       28

<210> SEQ ID NO 38
<211> LENGTH: 15
<212> TYPE: PRT
<213> ORGANISM: Homo sapiens

<400> SEQUENCE: 38

Ser Gln Arg Pro Pro Ala Gly Ile Pro Val Ala Pro Ser Ser Gly
 1               5                  10                  15

<210> SEQ ID NO 39
<211> LENGTH: 15
<212> TYPE: PRT
<213> ORGANISM: Mus musculus

<400> SEQUENCE: 39

Ser Gln Arg Leu Pro Val Val Asn Pro Ala Ala Gln Pro Ser Gly
 1               5                  10                  15

<210> SEQ ID NO 40
<211> LENGTH: 27
<212> TYPE: PRT
<213> ORGANISM: Homo sapiens

<400> SEQUENCE: 40

Glu Leu Ala Ile Arg Asn Ser Ala Leu Asp Thr Cys Ile Lys Thr Lys
 1               5                  10                  15

Ser Gln Pro Met Met Pro Val Ser Arg Pro Met
            20                  25

<210> SEQ ID NO 41
<211> LENGTH: 26
<212> TYPE: PRT
<213> ORGANISM: Mus musculus

<400> SEQUENCE: 41

Glu Val Asp Val Arg Ile Ser Ala Leu Asp Thr Cys Val Lys Ala Lys
 1               5                  10                  15

Ser Leu Pro Ala Val Pro Pro Arg Val Ser
            20                  25

<210> SEQ ID NO 42
<211> LENGTH: 24
<212> TYPE: DNA
<213> ORGANISM: Artificial Sequence
<220> FEATURE:
<223> OTHER INFORMATION: oligonucleotide primer
```

<400> SEQUENCE: 42
gctgatggcg atgaatgaac actg 24

<210> SEQ ID NO 43
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 43
tcaacgtgag ggtgctgctc atgc 24

<210> SEQ ID NO 44
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 44
tttcttgtcc accttggtgc tgctgg 26

<210> SEQ ID NO 45
<211> LENGTH: 132
<212> TYPE: PRT
<213> ORGANISM: Artificial Sequence
<220> FEATURE:
<223> OTHER INFORMATION: Signal and GY4 VH sequence

<400> SEQUENCE: 45

Met Gly Trp Ser Leu Ile Leu Leu Phe Leu Val Ala Val Ala Thr Arg
1               5                   10                  15

Val His Ser Glu Val Gln Leu Gln Gln Ser Gly Ala Glu Phe Val Arg
            20                  25                  30

Ser Gly Ala Ser Val Lys Leu Ser Cys Thr Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Trp Ile Asp Pro Glu Asn Gly Asp Ile Glu Tyr Ala
65                  70                  75                  80

Pro Lys Phe Gln Gly Lys Ala Thr Met Thr Ala Asp Thr Ser Ser Asn
                85                  90                  95

Thr Ala Tyr Leu Gln Phe Ser Ser Leu Thr Ser Glu Asp Thr Ala Val
            100                 105                 110

Tyr Tyr Cys Leu Tyr Gln Glu Gly Ser Trp Gly Gln Gly Thr Thr Leu
        115                 120                 125

Thr Val Ser Ser
    130

<210> SEQ ID NO 46
<211> LENGTH: 98
<212> TYPE: PRT
<213> ORGANISM: Artificial Sequence
<220> FEATURE:
<223> OTHER INFORMATION: IgG4 CH1 sequence

<400> SEQUENCE: 46

Ala Ser Thr Lys Gly Pro Ser Val Phe Pro Leu Ala Pro Cys Ser Arg
1               5                   10                  15

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 47
<211> LENGTH: 12
<212> TYPE: PRT
<213> ORGANISM: Artificial Sequence
<220> FEATURE:
<223> OTHER INFORMATION: IgG4 hinge sequence

<400> SEQUENCE: 47

Glu Ser Lys Tyr Gly Pro Pro Cys Pro Ser Cys Pro
1               5                   10

<210> SEQ ID NO 48
<211> LENGTH: 110
<212> TYPE: PRT
<213> ORGANISM: Artificial Sequence
<220> FEATURE:
<223> OTHER INFORMATION: IgG4 CH2 sequence

<400> SEQUENCE: 48

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 49
<211> LENGTH: 107
<212> TYPE: PRT
<213> ORGANISM: Artificial Sequence
<220> FEATURE:
<223> OTHER INFORMATION: IgG4 CH3 sequence

<400> SEQUENCE: 49

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45
```

Asn Asn Tyr Lys Thr Thr Pro Pro Val Leu Asp Ser Asp Gly Ser Phe
            50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 50
<211> LENGTH: 187
<212> TYPE: PRT
<213> ORGANISM: Artificial Sequence
<220> FEATURE:
<223> OTHER INFORMATION: DHFR sequence

<400> SEQUENCE: 50

Met Val Arg Pro Leu Asn Cys Ile Val Ala Val Ser Gln Asn Met Gly
 1               5                  10                  15

Ile Gly Lys Asn Gly Asp Arg Pro Trp Pro Pro Leu Arg Asn Glu Phe
             20                  25                  30

Lys Tyr Phe Gln Arg Met Thr Thr Thr Ser Ser Val Glu Gly Lys Gln
         35                  40                  45

Asn Leu Val Ile Met Gly Arg Lys Thr Trp Phe Ser Ile Pro Glu Lys
     50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala His Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
            180                 185

<210> SEQ ID NO 51
<211> LENGTH: 6322
<212> TYPE: DNA
<213> ORGANISM: Artificial Sequence
<220> FEATURE:
<223> OTHER INFORMATION: KFCC-GY4 VH chimera vector

<400> SEQUENCE: 51
actagttatt aatagtaatc aattacgggg tcattagttc atagcccata tatggagttc     60
cgcgttacat aacttacggt aaatggcccg cctggctgac cgcccaacga ccccgccca    120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300

```
tacatgacct tatgggactt tcctacttgg cagtacatct acgtattagt catcgctatt    360
accatggtga tgcggttttg gcagtacatc aatgggcgtg gatagcggtt tgactcacgg    420
ggatttccaa gtctccaccc cattgacgtc aatgggagtt tgttttggca ccaaaatcaa    480
cgggactttc caaaatgtcg taacaactcc gccccattga cgcaaatggg cggtaggcgt    540
gtacggtggg aggtctatat aagcagagct cgtttagtga accgtcagat ctggcacgag    600
gctggactca caagtctttc tcttcagtga caaacacaga aatagagccg ccaccatggg    660
ttggagcctc atcttgctct tccttgtcgc tgttgctacg cgtgtccact ccgaggttca    720
gctgcagcag tctggggcag agtttgtgag gtcaggggcc tcagtcaagt tgtcctgcac    780
agcttctggc ttcaacatta aagactacta tatacactgg gtgaagcaga ggcctgaaca    840
gggcctggag tggattggat ggattgatcc tgagaatggt gatattgaat atgccccgaa    900
gttccagggc aaggccacta tgactgcaga cacatcctcc aatacagcct acctgcagtt    960
cagcagcctg acatctgagg acactgccgt ctattactgt ctctaccaag aaggctcctg   1020
gggccaaggc accactctca cagtctcctc aggtaagctt tctggggcag gccgggcctg   1080
actttggctg ggggcaggga gggggctaag gtgacgcagg tggcgccagc caggtgcaca   1140
cccaatgccc atgagcccag acactggacc ctgcatggac catcgcggat agacaagaac   1200 cgagggcct ctgcgccctg ggcccagctc tgtcccacac cgcggtcaca tggcaccacc   1260
tctcttgcag cttccaccaa gggcccatcc gtcttccccc tggcgccctg ctccaggagc   1320
acctccgaga gcacagccgc cctgggctgc ctggtcaagg actacttccc cgaaccggtg   1380
acggtgtcgt ggaactcagg cgccctgacc agcggcgtgc acaccttccc ggctgtccta   1440
cagtcctcag gactctactc cctcagcagc gtggtgaccg tgccctccag cagcttgggc   1500
acgaagacct acacctgcaa tgtagatcac aagcccagca acaccaaggt ggacaagaga   1560
gttggtgaga ggccagcaca gggagggagg gtgtctgctg gaagccaggc tcagccctcc   1620
tgcctggacg caccccggct gtgcagcccc agcccagggc agcaaggcag gccccatctg   1680
tctcctcacc tggaggcctc tgaccacccc actcatgctc agggagaggg tcttctggat   1740
ttttccacca ggctccgggc agccacaggc tggatgcccc tacccaggcc ctgcgcata   1800 caggggcagg tgctgcgctc agacctgcca agagccatat ccgggaggac cctgcccctg   1860
acctaagccc accccaaagg ccaaactctc cactccctca gctcagacac cttctctcct   1920
cccagatctg agtaactccc aatcttctct ctgcagagtc caaatatggt ccccatgcc   1980 caccatgccc aggtaagcca acccaggcct cgccctccag ctcaaggcgg gacaggtgcc   2040
ctagagtagc ctgcatccag ggacaggccc cagccgggtg ctgacgcatc cacctccatc   2100
tcttcctcag cacctgagtt cctgggggga ccatcagtct tcctgttccc cccaaaaccc   2160
aaggacactc tcatgatctc ccggacccct gaggtcacgt gcgtggtggt ggacgtgagc   2220
caggaagacc ccgaggtcca gttcaactgg tacgtggatg gcgtggaggt gcataatgcc   2280
aagacaaagc cgcgggagga gcagttcaac agcacgtacc gtgtggtcag cgtcctcacc   2340
gtcctgcacc aggactggct gaacggcaag gagtacaagt gcaaggtctc caacaaaggc   2400
ctcccgtcct ccatcgagaa aaccatctcc aaagccaaag gtgggaccca cggggtgcga   2460
gggccacatg gacagaggtc agctcggccc accctctgcc ctgggagtga ccgctgtgcc   2520
aacctctgtc cctacagggc agccccgaga gccacaggtg tacaccctgc ccccatccca   2580
ggaggagatg accaagaacc aggtcagcct gacctgcctg gtcaaaggct tctacccag   2640 cgacatcgcc gtggagtggg agagcaatgg gcagccggag aacaactaca agaccacgcc   2700
```

```
tcccgtgctg gactccgacg gctccttctt cctctacagc aggctaaccg tggacaagag    2760
caggtggcag gagggggaatg tcttctcatg ctccgtgatg catgaggctc tgcacaacca   2820
ctacacacag aagagcctct ccctgtctct gggtaaatga gtgccagggc cggcaagccc   2880
ccgctccccg ggctctcggg gtcgcgcgag gatgcttggc acgtaccccg tctacatact   2940
tcccaggcac ccagcatgga aataaagcac ccaccactgc cctgggcccc tgtgagactg   3000
tgatggttct ttccacgggt caggccgagt ctgaggcctg agtgacatga gggaggcaga   3060
gcgggtccca ctgtccccac actggcccag gctgtgcagg tgtgcctggg ccacctaggg   3120
tggggctcag ccaggggctg ccctcggcag ggtgggggat tgccagcgt ggccctccct    3180
ccagcagaca tgtgagcaaa aggccagcaa aaggccagga accgtaaaaa ggccgcgttg   3240
ctggcgtttt tccataggct ccgcccccct gacgagcatc acaaaaatcg acgctcaagt   3300
cagaggtggc gaaacccgac aggactataa agataccagg cgtttccccc tggaagctcc   3360
ctcgtgcgct ctcctgttcc gaccctgccg cttaccggat acctgtccgc ctttctccct   3420
tcgggaagcg tggcgctttc tcatagctca cgctgtaggt atctcagttc ggtgtaggtc   3480
gttcgctcca agctgggctg tgtgcacgaa ccccccgttc agcccgaccg ctgcgcctta   3540
tccggtaact atcgtcttga gtccaacccg gtaagacacg acttatcgcc actggcagca   3600
gccactggta acaggattag cagagcgagg tatgtaggcg gtgctacaga gttcttgaag   3660
tggtggccta actacggcta cactagaagg acagtatttg gtatctgcgc tctgctgaag   3720
ccagttacct tcggaaaaag agttggtagc tcttgatccg gcaaacaaac caccgctggt   3780
agcggtggtt ttttgtttg caagcagcag attacgcgca gaaaaaagg atctcaagaa     3840
gatcctttga tcttttctac ggggtctgac gctcagtgga acgaaaactc acgttaaggg   3900
attttggtca tgagattatc aaaaaggatc ttcacctaga tccttttaaa ttaaaaatga   3960
agttttaaat caatctaaag tatatatgag taaacttggt ctgacagtta ccaatgctta   4020
atcagtgagg cacctatctc agcgatctgt ctatttcgtt catccatagt tgcctgactc   4080
cccgtcgtgt agataactac gatacgggag ggcttaccat ctggccccag tgctgcaatg   4140
ataccgcgag acccacgctc accggctcca gatttatcag caataaacca gccagccgga   4200
agggccgagc gcagaagtgg tcctgcaact ttatccgcct ccatccagtc tattaattgt   4260
tgccgggaag ctagagtaag tagttcgcca gttaatagtt tgcgcaacgt tgttgccatt   4320
gctacaggca tcgtggtgtc acgctcgtcg tttggtatgg cttcattcag ctccggttcc   4380
caacgatcaa ggcgagttac atgatccccc atgttgtgca aaaaagcggt tagctccttc   4440
ggtcctccga tcgttgtcag aagtaagttg gccgcagtgt tatcactcat ggttatggca   4500
gcactgcata attctcttac tgtcatgcca tccgtaagat gcttttctgt gactggtgag   4560
tactcaacca agtcattctg agaatagtgt atgcggcgac cgagttgctc ttgcccggcg   4620
tcaatacggg ataataccgc gccacatagc agaactttaa aagtgctcat cattggaaaa   4680
cgttcttcgg ggcgaaaact ctcaaggatc ttaccgctgt tgagatccag ttcgatgtaa   4740
cccactcgtg cacccaactg atcttcagca tcttttactt tcaccagcgt ttctgggtga   4800
gcaaaaacag gaaggcaaaa tgccgcaaaa aagggaataa gggcgacacg gaaatgttga   4860
atactcatac tcttcctttt tcaatattat tgaagcattt atcagggtta ttgtctcatg   4920
agcggataca tatttgaatg tatttagaaa aataaacaaa tagggggttcc gcgcacattt   4980
ccccgaaaag tgccacctga cgtctaagaa accattatta tcatgacatt aacctataaa   5040
```

```
aataggcgta tcacgaggcc ctattgatta ttgactagtg tggaatgtgt gtcagttagg    5100
gtgtggaaag tccccaggct ccccagcagg cagaagtatg caaagcatgc atctcaatta    5160
gtcagcaacc aggtgtggaa agtccccagg ctccccagca ggcagaagta tgcaaagcat    5220
gcatctcaat tagtcagcaa ccatagtccc gccctaact ccgccatcc cgcccctaac     5280 tccgcccagt tccgcccatt ctccgcccca tggctgacta attttttta tttatgcaga    5340 ggccgaggcc gcctcggcct ctgagctatt ccagaagtag tgaggaggct tttttggagg    5400
cctaggcttt tgcaaaaagc tagcttggtg ccctcatggt tcgaccattg aactgcatcg    5460
tcgccgtgtc ccaaaatatg gggattggca agaacggaga ccgaccctgg cctccgctca    5520
ggaacgagtt caagtacttc caaagaatga ccacaacctc ttcagtggaa ggtaaacaga    5580
atctggtgat tatgggtagg aaaacctggt tctccattcc tgagaagaat cgacctttaa    5640
aggacagaat taatatagtt ctcagtagag aactcaaaga accaccacga ggagctcatt    5700
ttcttgccaa aagtttggat gatgccttaa gacttattga acaaccggaa ttggcaagta    5760
aagtagacat ggtttggata gtcggaggca gttctgttta ccaggaagcc atgaatcaac    5820
caggccacct cagactcttt gtgacaagga tcatgcagga atttgaaagt gacacgtttt    5880
tcccagaaat tgatttgggg aaatataaac ttctcccaga atacccaggc gtcctctctg    5940
aggtccagga ggaaaaaggc atcaagtata agtttgaagt ctacgagaag aaagactaac    6000
aggaagatgc tttcaagttc tctgctcccc tcctaaagct atgcattttt ataagaccat    6060 gggactttg ctggctttag atcataatca gccataccac atttgtagag gttttacttg    6120
ctttaaaaaa cctcccacac ctcccctga acctgaaaca taaatgaat gcaattgttg    6180 ttgttaactt gtttattgca gcttctaatg gttacaaata aagcaatagc atcacaaatt    6240
tcacaaataa agcatttttt tcactgcatt ctagttgtgg tttgtccaaa ctcatcaatg    6300
tatcttatca tgtctggatc gg                                             6322
```

<210> SEQ ID NO 52
<211> LENGTH: 133
<212> TYPE: PRT
<213> ORGANISM: Artificial Sequence
<220> FEATURE:
<223> OTHER INFORMATION: Signal and GY4 VK sequence

<400> SEQUENCE: 52

```
Met Arg Val Pro Ala Gln Leu Leu Gln Leu Leu Leu Leu Trp Leu Pro
 1               5                  10                  15

Gly Ala Arg Cys Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asn Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Phe Thr Phe Gly Gly Gly Thr Lys
        115                 120                 125

Leu Glu Ile Lys Arg
    130
```

130

<210> SEQ ID NO 53
<211> LENGTH: 106
<212> TYPE: PRT
<213> ORGANISM: Artificial Sequence
<220> FEATURE:
<223> OTHER INFORMATION: CK sequence

<400> SEQUENCE: 53

```
Thr Val Ala Ala Pro Ser Val Phe Ile Phe Pro Pro Ser Asp Glu Gln
  1               5                  10                  15
Leu Lys Ser Gly Thr Ala Ser Val Val Cys Leu Leu Asn Asn Phe Tyr
             20                  25                  30
Pro Arg Glu Ala Lys Val Gln Trp Lys Val Asp Asn Ala Leu Gln Ser
         35                  40                  45
Gly Asn Ser Gln Glu Ser Val Thr Glu Gln Asp Ser Lys Asp Ser Thr
     50                  55                  60
Tyr Ser Leu Ser Ser Thr Leu Thr Leu Ser Lys Ala Asp Tyr Glu Lys
 65                  70                  75                  80
His Lys Val Tyr Ala Cys Glu Val Thr His Gln Gly Leu Ser Ser Pro
                 85                  90                  95
Val Thr Lys Ser Phe Asn Arg Gly Glu Cys
            100                 105
```

<210> SEQ ID NO 54
<211> LENGTH: 4461
<212> TYPE: DNA
<213> ORGANISM: Artificial Sequence
<220> FEATURE:
<223> OTHER INFORMATION: KFCC-GY4 VK chimera vector

<400> SEQUENCE: 54

```
actagttatt aatagtaatc aattacgggg tcattagttc atagcccata tatggagttc    60
cgcgttacat aacttacggt aaatggcccg cctggctgac cgcccaacga ccccccgccca  120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc cccctattga cgtcaatgac ggtaaatggc ccgcctggca ttatgcccag   300
tacatgacct tatgggactt tcctacttgg cagtacatct acgtattagt catcgctatt   360
accatggtga tgcggttttg gcagtacatc aatgggcgtg gatagcggtt tgactcacgg   420
ggatttccaa gtctccaccc cattgacgtc aatgggagtt gtttttggca ccaaaatcaa   480
cgggactttc caaaatgtcg taacaactcc gccccattga cgcaaatggg cggtaggcgt   540
gtacggtggg aggtctatat aagcagagct cgtttagtga accgtcagat ctggcacgag   600
ggtctcctca ggttgccgcc accatgaggg tccccgctca gctcctgggg ctcctgctgc   660
tctggctccc aggcgcgcga tgtgatgttg tgatgaccca gactccactc actttgtcgg   720
ttaccattgg acaaccagcc tccatctctt gcaagtcaag tcagagcctc ttaaatagtg   780
atggaaagac atatttgaat tggttgttac agaggccagg ccagtctcca aagcgcctaa   840
tctatctggt gtctaaattg gactctggag tccctgacag gttcactggc agtggatcag   900
ggacagattt cacactgaaa atcagcagag tggaggctga ggatttggga gtttattatt   960
gctggcaagg tacacatttt ccgttcacgt tcggaggggg gaccaagctg gaaataaaac  1020
gtgagtagaa tttaaacttt gcttcctcag ttggatcccg caattctaaa ctctgagggg  1080
```

```
gtcggatgac gtggccattc tttgcctaaa gcattgagtt tactgcaagg tcagaaaagc    1140
atgcaaagcc ctcagaatgg ctgcaaagag ctccaacaaa acaatttaga actttattaa    1200
ggaatagggg gaagctagga agaaactcaa aacatcaaga ttttaaatac gcttcttggt    1260
ctccttgcta taattatctg ggataagcat gctgttttct gtctgtccct aacatgccct    1320
gtgattatcc gcaaacaaca cacccaaggg cagaactttg ttacttaaac accatcctgt    1380
ttgcttcttt cctcaggaac tgtggctgca ccatctgtct tcatcttccc gccatctgat    1440
gagcagttga atctggaac tgcctctgtt gtgtgcctgc tgaataactt ctatcccaga    1500
gaggccaaag tacagtggaa ggtggataac gccctccaat cgggtaactc ccaggagagt    1560
gtcacagagc aggacagcaa ggacagcacc tacagcctca gcagcaccct gacgctgagc    1620
aaagcagact acgagaaaca caaagtctac gcctgcgaag tcacccatca gggcctgagc    1680
tcgcccgtca caaagagctt caacagggga gagtgttaga gggagaagtg cccccacctg    1740
ctcctcagtt ccagcctgac cccctcccat cctttggcct ctgaccctt ttccacaggg    1800 gacctacccc tattgcggtc ctccagctca tctttcacct caccccccctc ctcctccttg    1860 gctttaatta tgctaatgtt ggaggagaat gaataaataa agtgaatctt gcacctgtg    1920 gtttctctct ttcctcaatt taataattat tatctgttgt ttaccaacta ctcaatttct    1980
cttataaggg actaaatatg tagtcatcct aaggcgcata accatttata aaaatcatcc    2040
ttcattctat tttaccctat catcctctgc aagacagtcc tccctcaaac ccacaagcct    2100
tctgtcctca cagtcccctg ggccatggta ggagagactt gcttccttgt tttcccctcc    2160
tcagcaagcc ctcatagtcc ttttaaggg tgacaggtct tacggtcata tatcctttga    2220
ttcaattccc tgggaatcaa ccaaggcaaa ttttcaaaa aagaaacct gctataaaga    2280 gaatcattca ttgcaacatg atataaaata acaacacaat aaaagcaatt aaataaacaa    2340
acaataggga aatgtttaag ttcatcatgg tacttagact taatggaatg tcatgcctta    2400
tttacatttt taaacaggta ctgagggact cctgtctgcc aagggccgta ttgagtactt    2460
tccacaacct aatttaatcc acactatact gtgagattaa aaacattcat taaaatgttg    2520
caaaggttct ataaagctga gagacaaata tattctataa ctcagcaatc ccactacatg    2580
tgagcaaaag gccagcaaaa ggccaggaac cgtaaaaagg ccgcgttgct ggcgttttc    2640 cataggctcc gcccccctga cgagcatcac aaaaatcgac gctcaagtca gaggtggcga    2700
aacccgacag gactataaag ataccaggcg tttccccctg gaagctccct cgtgcgctct    2760
cctgttccga ccctgccgct taccggatac ctgtccgcct ttctcccttc gggaagcgtg    2820
gcgctttctc atagctcacg ctgtaggtat ctcagttcgg tgtaggtcgt tcgctccaag    2880
ctgggctgtg tgcacgaacc ccccgttcag cccgaccgct cgccttatc cggtaactat    2940 cgtcttgagt ccaacccggt aagacacgac ttatcgccac tggcagcagc cactggtaac    3000
aggattagca gagcgaggta tgtaggcggt gctacagagt tcttgaagtg gtggcctaac    3060
tacggctaca ctagaaggac agtatttggt atctgcgctc tgctgaagcc agttaccttc    3120
ggaaaaagag ttggtagctc ttgatccggc aaacaaacca ccgctggtag cggtggtttt    3180
tttgtttgca agcagcagat tacgcgcaga aaaaaggat ctcaagaaga tcctttgatc    3240
ttttctacgg ggtctgacgc tcagtggaac gaaaactcac gttaagggat tttggtcatg    3300
agattatcaa aaaggatctt cacctagatc cttttaaatt aaaatgaag ttttaaatca    3360 atctaaagta tatatgagta aacttggtct gacagttacc aatgcttaat cagtgaggca    3420
cctatctcag cgatctgtct atttcgttca tccatagttg cctgactccc cgtcgtgtag    3480
```

```
ataactacga tacgggaggg cttaccatct ggccccagtg ctgcaatgat accgcgagac    3540
ccacgctcac cggctccaga tttatcagca ataaaccagc cagccggaag ggccgagcgc    3600
agaagtggtc ctgcaacttt atccgcctcc atccagtcta ttaattgttg ccgggaagct    3660
agagtaagta gttcgccagt taatagtttg cgcaacgttg ttgccattgc tacaggcatc    3720
gtggtgtcac gctcgtcgtt tggtatggct tcattcagct ccggttccca acgatcaagg    3780
cgagttacat gatcccccat gttgtgcaaa aaagcggtta gctccttcgg tcctccgatc    3840
gttgtcagaa gtaagttggc cgcagtgtta tcactcatgg ttatggcagc actgcataat    3900
tctcttactg tcatgccatc cgtaagatgc ttttctgtga ctggtgagta ctcaaccaag    3960
tcattctgag aatagtgtat gcggcgaccg agttgctctt gcccggcgtc aatacgggat    4020
aataccgcgc cacatagcag aactttaaaa gtgctcatca ttggaaaacg ttcttcgggg    4080
cgaaaactct caaggatctt accgctgttg agatccagtt cgatgtaacc cactcgtgca    4140
cccaactgat cttcagcatc ttttactttc accagcgttt ctgggtgagc aaaaacagga    4200
aggcaaaatg ccgcaaaaaa gggaataagg gcgacacgga aatgttgaat actcatactc    4260
ttcctttttc aatattattg aagcatttat cagggttatt gtctcatgag cggatacata    4320
tttgaatgta tttagaaaaa taaacaaata ggggttccgc gcacatttcc ccgaaaagtg    4380
ccacctgacg tctaagaaac cattattatc atgacattaa cctataaaaa taggcgtatc    4440
acgaggccct attgattatt g                                              4461

<210> SEQ ID NO 55
<211> LENGTH: 132
<212> TYPE: PRT
<213> ORGANISM: Artificial Sequence
<220> FEATURE:
<223> OTHER INFORMATION: Signal and GY5 VH sequence

<400> SEQUENCE: 55

Met Gly Trp Ser Leu Ile Leu Leu Phe Leu Val Ala Val Ala Thr Arg
  1               5                  10                  15

Val His Ser Gln Val Gln Leu Gln Gln Pro Gly Ala Glu Leu Val Arg
             20                  25                  30

Pro Gly Ala Ser Val Lys Leu Ser Cys Lys Ala Ser Gly Tyr Thr Phe
         35                  40                  45

Thr Ser Asn Tyr Ile Asn Trp Val Lys Gln Arg Pro Gly Gln Gly Leu
     50                  55                  60

Glu Trp Ile Gly Asn Ile Tyr Pro Ser Asp Gly Phe Thr Asn Tyr Asn
 65                  70                  75                  80

Gln Lys Phe Lys Asp Arg Ala Thr Leu Thr Val Asp Lys Ser Ser Ser
                 85                  90                  95

Thr Ala Tyr Met Gln Leu Ser Ser Pro Thr Ser Glu Asp Ser Ala Val
            100                 105                 110

Tyr Tyr Cys Thr Arg Asn Phe Asp Val Trp Gly Ala Gly Thr Thr Val
        115                 120                 125

Thr Val Ser Ser
    130

<210> SEQ ID NO 56
<211> LENGTH: 6322
<212> TYPE: DNA
<213> ORGANISM: Artificial Sequence
<220> FEATURE:
<223> OTHER INFORMATION: KFCC-GY5 VH chimera vector
```

<400> SEQUENCE: 56

```
actagttatt aatagtaatc aattacgggg tcattagttc atagcccata tatggagttc    60
cgcgttacat aacttacggt aaatggcccg cctggctgac cgcccaacga cccccgccca   120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc ccctattga cgtcaatgac ggtaaatggc ccgcctggca ttatgcccag   300
tacatgacct tatgggactt tcctacttgg cagtacatct acgtattagt catcgctatt   360
accatggtga tgcggttttg gcagtacatc aatgggcgtg gatagcggtt tgactcacgg   420
ggatttccaa gtctccaccc cattgacgtc aatgggagtt tgttttggca ccaaaatcaa   480
cgggactttc caaaatgtcg taacaactcc gccccattga cgcaaatggg cggtaggcgt   540
gtacggtggg aggtctatat aagcagagct cgtttagtga accgtcagat ctggcacgag   600
gctggactca caagtctttc tcttcagtga caaacacaga aatagagccg ccaccatggg   660
ttggagcctc atcttgctct tccttgtcgc tgttgctacg cgtgtccact cccaggtcca   720
actgcagcag cctggggctg agctggtgag gcctgggggct tcagtgaagc tgtcctgcaa   780
ggcttctggc tacaccttca ccagcaacta cataaactgg gtgaaacaga ggcctggaca   840
gggccttgag tggatcggaa atatttatcc ttctgatggt tttactaact acaatcaaaa   900
gttcaaggac agggccacat tgactgtaga caaatcctcc agcacagcct acatgcagct   960
cagcagcccg acatctgagg actctgcggt ctattactgt acaagaaact tcgatgtctg  1020
gggcgcaggg accacggtca ccgtctcctc aggtaagctt tctggggcag gccgggcctg  1080
actttggctg ggggcaggga gggggctaag gtgacgcagg tggcgccagc caggtgcaca  1140
cccaatgccc atgagcccag acactggacc ctgcatggac catcgcggat agacaagaac  1200
cgaggggcct ctgcgccctg ggcccagctc tgtcccacac cgcggtcaca tggcaccacc  1260
tctcttgcag cttccaccaa gggcccatcc gtcttccccc tggcgccctg ctccaggagc  1320
acctccgaga gcacagccgc cctgggctgc ctggtcaagg actacttccc cgaaccggtg  1380
acggtgtcgt ggaactcagg cgccctgacc agcggcgtgc acaccttccc ggctgtccta  1440
cagtcctcag gactctactc cctcagcagc gtggtgaccg tgccctccag cagcttgggc  1500
acgaagacct acacctgcaa tgtagatcac aagcccagca acaccaaggt ggacaagaga  1560
gttggtgaga ggccagcaca gggagggagg tgtctgctg aagccaggc tcagccctcc  1620
tgcctggacg caccccggct gtgcagcccc agcccagggc agcaaggcag gccccatctg  1680
tctcctcacc tggaggcctc tgaccacccc actcatgctc agggagaggg tcttctggat  1740
ttttccacca ggctccgggc agccacaggc tggatgcccc tacccaggcc ctgcgcata  1800
caggggcagg tgctgcgctc agacctgcca agagccatat ccgggaggac cctgcccctg  1860
acctaagccc acccaaagg ccaaactctc cactccctca gctcagacac cttctctcct  1920
cccagatctg agtaactccc aatcttctct ctgcagagtc caaatatggt cccccatgcc  1980
caccatgccc aggtaagcca acccaggcct cgccctccag ctcaaggcgg gacaggtgcc  2040
ctagagtagc ctgcatccag gacaggccc agccgggtc tgacgcatc cacctccatc  2100
tcttcctcag cacctgagtt cctgggggga ccatcagtct tcctgttccc cccaaaaccc  2160
aaggacactc tcatgatctc ccggacccct gaggtcacgt gcgtggtggt ggacgtgagc  2220
caggaagacc ccgaggtcca gttcaactgg tacgtggatg gcgtggaggt gcataatgcc  2280
```

-continued

| | |
|---|---|
| aagacaaagc cgcgggagga gcagttcaac agcacgtacc gtgtggtcag cgtcctcacc | 2340 |
| gtcctgcacc aggactggct gaacggcaag gagtacaagt gcaaggtctc caacaaaggc | 2400 |
| ctcccgtcct ccatcgagaa aaccatctcc aaagccaaag gtgggaccca cggggtgcga | 2460 |
| gggccacatg gacagaggtc agctcggccc accctctgcc ctgggagtga ccgctgtgcc | 2520 |
| aacctctgtc cctacagggc agccccgaga gccacaggtg tacaccctgc cccatccca | 2580 |
| ggaggagatg accaagaacc aggtcagcct gacctgcctg gtcaaaggct tctaccccag | 2640 |
| cgacatcgcc gtggagtggg agagcaatgg gcagccggag aacaactaca agaccacgcc | 2700 |
| tcccgtgctg gactccgacg gctccttctt cctctacagc aggctaaccg tggacaagag | 2760 |
| caggtggcag gaggggaatg tcttctcatg ctccgtgatg catgaggctc tgcacaacca | 2820 |
| ctacacacag aagagcctct ccctgtctct gggtaaatga gtgccagggc cggcaagccc | 2880 |
| ccgctccccg ggctctcggg gtcgcgcgag gatgcttggc acgtaccccg tctacatact | 2940 |
| tcccaggcac ccagcatgga aataaagcac ccaccactgc cctgggcccc tgtgagactg | 3000 |
| tgatggttct ttccacgggt caggccgagt ctgaggcctg agtgacatga gggaggcaga | 3060 |
| gcgggtccca ctgtcccac actggcccag gctgtgcagg tgtgcctggg ccacctaggg | 3120 |
| tggggctcag ccaggggctg ccctcggcag ggtgggggat ttgccagcgt ggccctccct | 3180 |
| ccagcagaca tgtgagcaaa aggccagcaa aaggccagga accgtaaaaa ggccgcgttg | 3240 |
| ctggcgtttt tccataggct ccgcccccct gacgagcatc acaaaaatcg acgctcaagt | 3300 |
| cagaggtggc gaaacccgac aggactataa agataccagg cgtttccccc tggaagctcc | 3360 |
| ctcgtgcgct ctcctgttcc gaccctgccg cttaccggat acctgtccgc ctttctccct | 3420 |
| tcgggaagcg tggcgctttc tcatagctca cgctgtaggt atctcagttc ggtgtaggtc | 3480 |
| gttcgctcca agctgggctg tgtgcacgaa ccccccgttc agcccgaccg ctgcgcctta | 3540 |
| tccggtaact atcgtcttga gtccaacccg gtaagacacg acttatcgcc actggcagca | 3600 |
| gccactggta acaggattag cagagcgagg tatgtaggcg gtgctacaga gttcttgaag | 3660 |
| tggtggccta actacggcta cactagaagg acagtatttg gtatctgcgc tctgctgaag | 3720 |
| ccagttacct tcggaaaaag agttggtagc tcttgatccg gcaaacaaac caccgctggt | 3780 |
| agcggtggtt tttttgtttg caagcagcag attacgcgca gaaaaaaagg atctcaagaa | 3840 |
| gatcctttga tcttttctac ggggtctgac gctcagtgga acgaaaactc acgttaaggg | 3900 |
| attttggtca tgagattatc aaaaaggatc ttcacctaga tccttttaaa ttaaaaatga | 3960 |
| agttttaaat caatctaaag tatatatgag taaacttggt ctgacagtta ccaatgctta | 4020 |
| atcagtgagg cacctatctc agcgatctgt ctatttcgtt catccatagt tgcctgactc | 4080 |
| cccgtcgtgt agataactac gatacgggag ggcttaccat ctggccccag tgctgcaatg | 4140 |
| ataccgcgag acccacgctc accggctcca gatttatcag caataaacca gccagccgga | 4200 |
| agggccgagc gcagaagtgg tcctgcaact ttatccgcct ccatccagtc tattaattgt | 4260 |
| tgccgggaag ctagagtaag tagttcgcca gttaatagtt tgcgcaacgt tgttgccatt | 4320 |
| gctacaggca tcgtggtgtc acgctcgtcg tttggtatgg cttcattcag ctccggttcc | 4380 |
| caacgatcaa ggcgagttac atgatccccc atgttgtgca aaaaagcggt tagctccttc | 4440 |
| ggtcctccga tcgttgtcag aagtaagttg gccgcagtgt tatcactcat ggttatggca | 4500 |
| gcactgcata attctcttac tgtcatgcca tccgtaagat gcttttctgt gactggtgag | 4560 |
| tactcaacca agtcattctg agaatagtgt atgcggcgac cgagttgctc ttgcccggcg | 4620 |
| tcaatacggg ataataccgc gccacatagc agaactttaa aagtgctcat cattggaaaa | 4680 |

```
cgttcttcgg ggcgaaaact ctcaaggatc ttaccgctgt tgagatccag ttcgatgtaa    4740
cccactcgtg cacccaactg atcttcagca tcttttactt tcaccagcgt ttctgggtga    4800
gcaaaaacag gaaggcaaaa tgccgcaaaa aagggaataa gggcgacacg gaaatgttga    4860
atactcatac tcttcctttt tcaatattat tgaagcattt atcagggtta ttgtctcatg    4920
agcggataca tatttgaatg tatttagaaa aataaacaaa taggggttcc gcgcacattt    4980
ccccgaaaag tgccacctga cgtctaagaa accattatta tcatgacatt aacctataaa    5040
aataggcgta tcacgaggcc ctattgatta ttgactagtg tggaatgtgt gtcagttagg    5100
gtgtggaaag tccccaggct ccccagcagg cagaagtatg caaagcatgc atctcaatta    5160
gtcagcaacc aggtgtggaa agtccccagg ctccccagca ggcagaagta tgcaaagcat    5220
gcatctcaat tagtcagcaa ccatagtccc gcccctaact ccgcccatcc cgcccctaac    5280
tccgcccagt tccgcccatt ctccgcccca tggctgacta attttttttta tttatgcaga    5340 ggccgaggcc gcctcggcct ctgagctatt ccagaagtag tgaggaggct ttttttggagg    5400 cctaggcttt tgcaaaaagc tagcttggtg ccctcatggt tcgaccattg aactgcatcg    5460
tcgccgtgtc ccaaaatatg gggattggca agaacggaga ccgaccctgg cctccgctca    5520
ggaacgagtt caagtacttc caaagaatga ccacaacctc ttcagtggaa ggtaaacaga    5580
atctggtgat tatgggtagg aaaacctggt tctccattcc tgagaagaat cgaccttta    5640 aggacagaat taatatagtt ctcagtagag aactcaaaga accaccacga ggagctcatt    5700
ttcttgccaa aagtttggat gatgccttaa gacttattga acaaccggaa ttggcaagta    5760
aagtagacat ggtttggata gtcggaggca gttctgttta ccaggaagcc atgaatcaac    5820
caggccacct cagactcttt gtgacaagga tcatgcagga atttgaaagt gacacgtttt    5880
tcccagaaat tgatttgggg aaatataaac ttctcccaga atacccaggc gtcctctctg    5940
aggtccagga ggaaaaaggc atcaagtata agtttgaagt ctacgagaag aaagactaac    6000
aggaagatgc tttcaagttc tctgctcccc tcctaaagct atgcattttt ataagaccat    6060 gggactttg ctggctttag atcataatca gccataccac atttgtagag gttttacttg    6120
ctttaaaaaa cctcccacac ctcccctga acctgaaaca taaaatgaat gcaattgttg    6180
ttgttaactt gtttattgca gcttctaatg gttacaaata aagcaatagc atcacaaatt    6240
tcacaaataa agcattttttt tcactgcatt ctagttgtgg tttgtccaaa ctcatcaatg    6300
tatcttatca tgtctggatc gg                                             6322
```

<210> SEQ ID NO 57
<211> LENGTH: 133
<212> TYPE: PRT
<213> ORGANISM: Artificial Sequence
<220> FEATURE:
<223> OTHER INFORMATION: Signal and GY5 VK sequence

<400> SEQUENCE: 57

Met Arg Val Pro Ala Gln Leu Leu Gly Leu Leu Leu Leu Trp Leu Pro
 1               5                  10                  15

Gly Ala Arg Cys Asp Val Val Met Thr Gln Thr Pro Leu Ser Leu Pro
             20                  25                  30

Val Ser Leu Gly Asp Gln Ala Ser Ile Ser Cys Arg Ser Ser Gln Ser
         35                  40                  45

Leu Val His Ser Asn Gly Asn Thr Tyr Leu Gln Trp Tyr Leu Gln Lys
     50                  55                  60

```
Pro Gly Gln Ser Pro Lys Leu Leu Ile Tyr Thr Val Ser Asn Arg Phe
 65                  70                  75                  80

Ser Gly Val Pro Asp Arg Phe Ser Gly Ser Gly Ser Gly Pro Asp Phe
                 85                  90                  95

Thr Leu Lys Ile Ser Arg Val Glu Ala Glu Asp Leu Gly Val Tyr Phe
            100                 105                 110

Cys Ser Gln Ser Thr His Val Pro Phe Thr Phe Gly Ser Gly Thr Lys
        115                 120                 125

Leu Glu Ile Lys Arg
    130

<210> SEQ ID NO 58
<211> LENGTH: 4461
<212> TYPE: DNA
<213> ORGANISM: Artificial Sequence
<220> FEATURE:
<223> OTHER INFORMATION: KFCC-GY5 VK chimera vector

<400> SEQUENCE: 58
actagttatt aatagtaatc aattacgggg tcattagttc atagcccata tatggagttc     60
cgcgttacat aacttacggt aaatggcccg cctggctgac cgcccaacga ccccccgccca   120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtga tgcggttttg gcagtacatc aatgggcgtg gatagcggtt tgactcacgg    420
ggatttccaa gtctccaccc cattgacgtc aatgggagtt tgttttggca ccaaaatcaa    480
cgggactttc caaaatgtcg taacaactcc gccccattga cgcaaatggg cggtaggcgt    540
gtacggtggg aggtctatat aagcagagct cgtttagtga accgtcagat ctggcacgag    600
ggtctcctca ggttgccgcc accatgaggg tccccgctca gctcctgggg ctcctgctgc    660
tctggctccc aggcgcgcga tgtgatgttg tgatgaccca aactccactc tccctgcctg    720
tcagtcttgg agatcaagcc tccatctctt gcagatctag tcagagcctt gtccacagta    780
atggaaacac ctatttacag tggtacctgc agaagccagg ccagtctcca aagctcctga    840
tctacacagt ttccaaccga ttttctgggg tcccagacag gttcagtggc agtggatcag    900
ggccagattt cacactcaag atcagcagag tggaggctga ggatctggga gtttatttct    960
gctctcaaag tacacatgtt cctttcacgt tcggctcggg gacaaagttg gaaataaaac   1020
gtgagtagaa tttaaacttt gcttcctcag ttggatcccg caattctaaa ctctgagggg   1080
gtcggatgac gtggccattc tttgcctaaa gcattgagtt tactgcaagg tcagaaaagc   1140
atgcaaagcc ctcagaatgg ctgcaaagag ctccaacaaa acaatttaga actttattaa   1200
ggaatagggg gaagctagga agaaactcaa aacatcaaga ttttaaatac gcttcttggt   1260
ctccttgcta taattatctg ggataagcat gctgttttct gtctgtccct aacatgccct   1320
gtgattatcc gcaaacaaca cacccaaggg cagaactttg ttacttaaac accatcctgt   1380
ttgcttcttt cctcaggaac tgtggctgca ccatctgtct tcatcttccc gccatctgat   1440
gagcagttga atctggaac tgcctctgtt gtgtgcctgc tgaataactt ctatcccaga   1500
gaggccaaag tacagtggaa ggtggataac gccctccaat cgggtaactc ccaggagagt   1560
gtcacagagc aggacagcaa ggacagcacc tacagcctca gcagcaccct gacgctgagc   1620
```

```
aaagcagact acgagaaaca caaagtctac gcctgcgaag tcacccatca gggcctgagc    1680
tcgcccgtca caaagagctt caacagggga gagtgttaga gggagaagtg ccccacctg    1740 ctcctcagtt ccagcctgac cccctcccat cctttggcct ctgacccttt ttccacaggg    1800
gacctacccc tattgcggtc ctccagctca tctttcacct caccccccct ctcctccttg    1860
gctttaatta tgctaatgtt ggaggagaat gaataaataa agtgaatctt tgcacctgtg    1920
gtttctctct ttcctcaatt taataattat tatctgttgt ttaccaacta ctcaatttct    1980
cttataaggg actaaatatg tagtcatcct aaggcgcata accatttata aaaatcatcc    2040
ttcattctat tttaccctat catcctctgc aagacagtcc tccctcaaac ccacaagcct    2100
tctgtcctca cagtcccctg ggccatggta ggagagactt gcttccttgt tttccctcc    2160 tcagcaagcc ctcatagtcc tttttaaggg tgacaggtct tacggtcata tatccttga    2220 ttcaattccc tgggaatcaa ccaaggcaaa tttttcaaaa gaagaaacct gctataaga    2280 gaatcattca ttgcaacatg atataaaata caacacaat aaaagcaatt aaataaacaa    2340
acaataggga aatgtttaag ttcatcatgg tacttagact taatgaaatg tcatgcctta    2400
tttacatttt taaacaggta ctgagggact cctgtctgcc aagggccgta ttgagtactt    2460
tccacaacct aatttaatcc acactatact gtgagattaa aaacattcat taaaatgttg    2520
caaaggttct ataaagctga gagacaaata tattctataa ctcagcaatc ccactacatg    2580
tgagcaaaag gccagcaaaa ggccaggaac cgtaaaaagg ccgcgttgct ggcgttttc    2640 cataggctcc gcccccctga cgagcatcac aaaaatcgac gctcaagtca gaggtggcga    2700
aacccgacag gactataaag ataccaggcg tttccccctg gaagctccct cgtgcgctct    2760
cctgttccga cctgccgct taccggatac ctgtccgcct ttctcccttc gggaagcgtg    2820
gcgctttctc atagctcacg ctgtaggtat ctcagttcgg tgtaggtcgt tcgctccaag    2880
ctgggctgtg tgcacgaacc ccccgttcag cccgaccgct gcgccttatc cggtaactat    2940
cgtcttgagt ccaacccggt aagacacgac ttatcgccac tggcagcagc cactggtaac    3000
aggattagca gagcgaggta tgtaggcggt gctacagagt tcttgaagtg gtggcctaac    3060
tacggctaca ctagaaggac agtatttggt atctgcgctc tgctgaagcc agttaccttc    3120
ggaaaaagag ttggtagctc ttgatccggc aaacaaacca ccgctggtag cggtggtttt    3180
tttgtttgca agcagcagat tacgcgcaga aaaaaaggat ctcaagaaga tcctttgatc    3240
ttttctacgg ggtctgacgc tcagtggaac gaaaactcac gttaagggat tttggtcatg    3300
agattatcaa aaaggatctt cacctagatc cttttaaatt aaaaatgaag ttttaaatca    3360
atctaaagta tatatgagta aacttggtct gacagttacc aatgcttaat cagtgaggca    3420
cctatctcag cgatctgtct atttcgttca tccatagttg cctgactccc cgtcgtgtag    3480
ataactacga tacgggaggg cttaccatct ggccccagtg ctgcaatgat accgcgagac    3540
ccacgctcac cggctccaga tttatcagca ataaaccagc cagccggaag ggccgagcgc    3600
agaagtggtc ctgcaacttt atccgcctcc atccagtcta ttaattgttg ccgggaagct    3660
agagtaagta gttcgccagt taatagtttg cgcaacgttg ttgccattgc tacaggcatc    3720
gtggtgtcac gctcgtcgtt tggtatggct tcattcagct ccggttccca acgatcaagg    3780
cgagttacat gatccccat gttgtgcaaa aaagcggtta gctccttcgg tcctccgatc    3840
gttgtcagaa gtaagttggc cgcagtgtta tcactcatgg ttatggcagc actgcataat    3900
tctcttactg tcatgccatc cgtaagatgc ttttctgtga ctggtgagta ctcaaccaag    3960
tcattctgag aatagtgtat gcggcgaccg agttgctctt gcccggcgtc aatacgggat    4020
```

```
aataccgcgc cacatagcag aactttaaaa gtgctcatca ttggaaaacg ttcttcgggg   4080
cgaaaactct caaggatctt accgctgttg agatccagtt cgatgtaacc cactcgtgca   4140
cccaactgat cttcagcatc ttttactttc accagcgttt ctgggtgagc aaaaacagga   4200
aggcaaaatg ccgcaaaaaa gggaataagg gcgacacgga aatgttgaat actcatactc   4260 ttccttttc aatattattg aagcatttat cagggttatt gtctcatgag cggatacata    4320
tttgaatgta tttagaaaaa taaacaaata ggggttccgc gcacatttcc ccgaaaagtg   4380
ccacctgacg tctaagaaac cattattatc atgacattaa cctataaaaa taggcgtatc   4440
acgaggccct attgattatt g                                             4461
```

<210> SEQ ID NO 59
<211> LENGTH: 398
<212> TYPE: DNA
<213> ORGANISM: Artificial Sequence
<220> FEATURE:
<223> OTHER INFORMATION: CSR01-VK1 Kappa light chain coding sequence

<400> SEQUENCE: 59

```
atgagggtcc ccgctcagct cctggggctc ctgctgctct ggctcccagg cgcgcgatgt    60
gatgttgtga tgacccagtc tccactcact ttgtcggtta ccctgggaca accagcctcc   120
atctcttgca gtcaagtca gagcctctta aatagtgatg gaaagacata tttgaattgg    180
ttgcagcaga ggccaggcca gtctccaagg cgcctaatct atctggtgtc taaattggac   240
tctggagtcc ctgacaggtt cactggcagt ggatcaggga cagattcaca ctgaaaatca   300
gcagagtgga ggctgaggat gtgggagttt attattgctg gcaaggtaca cattttccgt   360
tcacgttcgg aggggggacc aaggtggaaa taaaacgt                            398
```

<210> SEQ ID NO 60
<211> LENGTH: 133
<212> TYPE: PRT
<213> ORGANISM: Artificial Sequence
<220> FEATURE:
<223> OTHER INFORMATION: CSR01-VK1 Kappa light chain

<400> SEQUENCE: 60

```
Met Arg Val Pro Ala Gln Leu Leu Gly Leu Leu Leu Trp Leu Pro
  1               5                  10                  15

Gly Ala Arg Cys Asp Val Val Met Thr Gln Ser Pro Leu Thr Leu Ser
             20                  25                  30

Val Thr Leu Gly Gln Pro Ala Ser Ile Ser Cys Lys Ser Ser Gln Ser
         35                  40                  45

Leu Leu Asn Ser Asp Gly Lys Thr Tyr Leu Asn Trp Leu Gln Gln Arg
     50                  55                  60

Pro Gly Gln Ser Pro Arg Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Trp Gln Gly Thr His Phe Pro Phe Thr Phe Gly Gly Gly Thr Lys
        115                 120                 125

Val Glu Ile Lys Arg
    130
```

```
<210> SEQ ID NO 61
<211> LENGTH: 399
<212> TYPE: DNA
<213> ORGANISM: Artificial Sequence
<220> FEATURE:
<223> OTHER INFORMATION: CSR01-VK2 Kappa light chain coding sequence

<400> SEQUENCE: 61
atgagggtcc ccgctcagct cctggggctc ctgctgctct ggctcccagg cgcgcgatgt    60
gatgttgtga tgacccagtc tccactcagc ttgcctgtta ccctgggaca accagcctcc   120
atctcttgca agtcaagtca gagcctctta aatagtgatg aaagacata tttgaattgg    180 ttgcagcaga ggccaggcca gtctccaagg cgcctaatct atctggtgtc taaattggac   240
tctggagtcc ctgacaggtt cactggcagt ggatcaggga cagatttcac actgaaaatc   300
agcagagtgg aggctgagga tgtgggagtt tattattgct ggcaaggtac acattttccg   360
ttcacgttcg gaggggggac caaggtggaa ataaaacgt                          399

<210> SEQ ID NO 62
<211> LENGTH: 133
<212> TYPE: PRT
<213> ORGANISM: Artificial Sequence
<220> FEATURE:
<223> OTHER INFORMATION: CSR01-VK2 Kappa light chain

<400> SEQUENCE: 62

Met Arg Val Pro Ala Gln Leu Leu Gly Leu Leu Leu Leu Trp Leu Pro
  1               5                  10                  15

Gly Ala Arg Cys Asp Val Val Met Thr Gln Ser Pro Leu Ser Leu Pro
                 20                  25                  30

Val Thr Leu Gly Gln Pro Ala Ser Ile Ser Cys Lys Ser Ser Gln Ser
             35                  40                  45

Leu Leu Asn Ser Asp Gly Lys Thr Tyr Leu Asn Trp Leu Gln Gln Arg
         50                  55                  60

Pro Gly Gln Ser Pro Arg Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Ser Arg Val Glu Ala Glu Asp Val Gly Val Tyr Tyr
            100                 105                 110

Cys Trp Gln Gly Thr His Phe Pro Phe Thr Phe Gly Gly Gly Thr Lys
            115                 120                 125

Val Glu Ile Lys Arg
        130

<210> SEQ ID NO 63
<211> LENGTH: 399
<212> TYPE: DNA
<213> ORGANISM: Artificial Sequence
<220> FEATURE:
<223> OTHER INFORMATION: CSR01-VK3 Kappa light chain coding sequence

<400> SEQUENCE: 63
atgagggtcc ccgctcagct cctggggctc ctgctgctct ggctcccagg cgcgcgatgt    60
gatgttgtga tgacccagtc tccactcagc ttgcctgtta ccctgggaca accagcctcc   120
atctcttgca agtcaagtca gagcctctta aatagtgatg aaagacata tttgaattgg    180 ttgcagcaga ggccaggcca gtctccaagg cgcctaatct atctggtgtc taaattggac   240
tctggagtcc ctgacaggtt ctctggcagt ggatcaggga cagatttcac actgaaaatc   300
```

-continued agcagagtgg aggctgagga tgtgggagtt tattattgct ggcaaggtac acattttccg        360
ttcacgttcg gagggggggac caaggtggaa ataaaacgt                              399

<210> SEQ ID NO 64
<211> LENGTH: 133
<212> TYPE: PRT
<213> ORGANISM: Artificial Sequence
<220> FEATURE:
<223> OTHER INFORMATION: CSR01-VK3 Kappa light chain

<400> SEQUENCE: 64

Met Arg Val Pro Ala Gln Leu Leu Gly Leu Leu Leu Leu Trp Leu Pro
1               5                   10                  15

Gly Ala Arg Cys Asp Val Val Met Thr Gln Ser Pro Leu Ser Leu Pro
            20                  25                  30

Val Thr Leu Gly Gln Pro Ala Ser Ile Ser Cys Lys Ser Ser Gln Ser
        35                  40                  45

Leu Leu Asn Ser Asp Gly Lys Thr Tyr Leu Asn Trp Leu Gln Gln Arg
    50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Phe Thr Phe Gly Gly Gly Thr Lys
        115                 120                 125

Val Glu Ile Lys Arg
    130

<210> SEQ ID NO 65
<211> LENGTH: 396
<212> TYPE: DNA
<213> ORGANISM: Artificial Sequence
<220> FEATURE:
<223> OTHER INFORMATION: CSR01-VH4 heavy chain coding sequence

<400> SEQUENCE: 65
atgggttgga gcctcatctt gctcttcctt gtcgctgttg ctacgcgtgt ccactccgag        60
gttcagctgg tgcagtctgg ggcagaggtg aagaagccag ggcctcagt caaggtgtcc        120 tgcacagctt ctggcttcaa cattaaagac tactatatac actgggtgag gcaggcccct       180
ggacagggcc tggagtggat ggatggatt gatcctgaga atggtgatat tgaatatgcc        240
ccgaagttcc agggcagggc cactatcact gcagacacat ccaccgatac agcctacatg       300
gagttcagca gcctgagatc tgaggacact gccgtctatt actgtctcta ccaagaaggc       360
tcctggggcc aaggcaccac tgtcacagtc tcctca                                 396

<210> SEQ ID NO 66
<211> LENGTH: 132
<212> TYPE: PRT
<213> ORGANISM: Artificial Sequence
<220> FEATURE:
<223> OTHER INFORMATION: CSR01-VH4 heavy chain

<400> SEQUENCE: 66

Met Gly Trp Ser Leu Ile Leu Leu Phe Leu Val Ala Val Ala Thr Arg
1               5                   10                  15

Val His Ser Glu Val Gln Leu Val Gln Ser Gly Ala Glu Val Lys Lys
            20                  25                  30

Pro Gly Ala Ser Val Lys Val Ser Cys Thr Ala Ser Gly Phe Asn Ile
        35                  40                  45

Lys Asp Tyr Tyr Ile His Trp Val Arg Gln Ala Pro Gly Gln Gly Leu
    50                  55                  60

Glu Trp Ile Gly Trp Ile Asp Pro Glu Asn Gly Asp Ile Glu Tyr Ala
65                  70                  75                  80

Pro Lys Phe Gln Gly Arg Ala Thr Ile Thr Ala Asp Thr Ser Thr Asp
                85                  90                  95

Thr Ala Tyr Met Glu Phe Ser Ser Leu Arg Ser Glu Asp Thr Ala Val
            100                 105                 110

Tyr Tyr Cys Leu Tyr Gln Glu Gly Ser Trp Gly Gln Gly Thr Thr Val
        115                 120                 125

Thr Val Ser Ser
    130

<210> SEQ ID NO 67
<211> LENGTH: 396
<212> TYPE: DNA
<213> ORGANISM: Artificial Sequence
<220> FEATURE:
<223> OTHER INFORMATION: CSR01-VH5 heavy chain coding sequence

<400> SEQUENCE: 67
atgggttgga gcctcatctt gctcttcctt gtcgctgttg ctacgcgtgt ccactccgag      60
gttcagctgg tgcagtctgg ggcagaggtg aagaagccag ggcctcagt caaggtgtcc     120 tgcacagctt ctggcttcaa cattaaagac tactatatac actgggtgag gcaggcccct    180
ggacagggcc tggagtggat tggatggatt gatcctgaga atggtgatat tgaatatgcc    240
ccgaagttcc agggcagggc cactatcact gcagacacat ccaccgatac agcctacatg    300
gagctcagca gcctgagatc tgaggacact gccgtctatt actgtctcta ccaagaaggc    360
tcctggggcc aaggcaccac tgtcacagtc tcctca                              396

<210> SEQ ID NO 68
<211> LENGTH: 132
<212> TYPE: PRT
<213> ORGANISM: Artificial Sequence
<220> FEATURE:
<223> OTHER INFORMATION: CSR01-VH5 heavy chain

<400> SEQUENCE: 68

Met Gly Trp Ser Leu Ile Leu Leu Phe Leu Val Ala Val Ala Thr Arg
1               5                   10                  15

Val His Ser Glu Val Gln Leu Val Gln Ser Gly Ala Glu Val Lys Lys
            20                  25                  30

Pro Gly Ala Ser Val Lys Val Ser Cys Thr Ala Ser Gly Phe Asn Ile
        35                  40                  45

Lys Asp Tyr Tyr Ile His Trp Val Arg Gln Ala Pro Gly Gln Gly Leu
    50                  55                  60

Glu Trp Ile Gly Trp Ile Asp Pro Glu Asn Gly Asp Ile Glu Tyr Ala
65                  70                  75                  80

Pro Lys Phe Gln Gly Arg Ala Thr Ile Thr Ala Asp Thr Ser Thr Asp
                85                  90                  95

Thr Ala Tyr Met Glu Leu Ser Ser Leu Arg Ser Glu Asp Thr Ala Val
            100                 105                 110

```
                Tyr Tyr Cys Leu Tyr Gln Glu Gly Ser Trp Gly Gln Gly Thr Thr Val
                        115                 120                 125

Thr Val Ser Ser
                        130

<210> SEQ ID NO 69
<211> LENGTH: 399
<212> TYPE: DNA
<213> ORGANISM: Artificial Sequence
<220> FEATURE:
<223> OTHER INFORMATION: CSR02-VK2 Kappa light chain coding sequence

<400> SEQUENCE: 69
atgagggtcc ccgctcagct cctggggctc ctgctgctct ggctcccagg cgcgcgatgt      60
gatgttgtga tgacccaatc tccactctcc ctgcctgtca ctcttggaca gccagcctcc     120
atctcttgca gatctagtca gagccttgtc cacagtaatg aaacaccta tttacagtgg      180 tacctgcaga agccaggcca gtctccacag ctcctgatct acacagtttc caaccgattt     240
tctggggtcc cagacaggtt cagtggcagt ggatcaggga ccgatttcac actcaagatc     300
agcagagtgg aggctgagga tgtgggagtt tatttctgct ctcaaagtac acatgttcct     360
ttcacgttcg gccaggggac aaagttggaa ataaaacgt                            399

<210> SEQ ID NO 70
<211> LENGTH: 133
<212> TYPE: PRT
<213> ORGANISM: Artificial Sequence
<220> FEATURE:
<223> OTHER INFORMATION: CSR02-VK2 Kappa light chain

<400> SEQUENCE: 70

Met Arg Val Pro Ala Gln Leu Leu Gly Leu Leu Leu Leu Trp Leu Pro
  1               5                  10                  15

Gly Ala Arg Cys Asp Val Val Met Thr Gln Ser Pro Leu Ser Leu Pro
                 20                  25                  30

Val Thr Leu Gly Gln Pro Ala Ser Ile Ser Cys Arg Ser Ser Gln Ser
             35                  40                  45

Leu Val His Ser Asn Gly Asn Thr Tyr Leu Gln Trp Tyr Leu Gln Lys
         50                  55                  60

Pro Gly Gln Ser Pro Gln Leu Leu Ile Tyr Thr Val Ser Asn Arg Phe
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Phe
                100                 105                 110

Cys Ser Gln Ser Thr His Val Pro Phe Thr Phe Gly Gln Gly Thr Lys
            115                 120                 125

Leu Glu Ile Lys Arg
        130

<210> SEQ ID NO 71
<211> LENGTH: 399
<212> TYPE: DNA
<213> ORGANISM: Artificial Sequence
<220> FEATURE:
<223> OTHER INFORMATION: CSR02-VK3 Kappa light chain coding sequence

<400> SEQUENCE: 71
atgagggtcc ccgctcagct cctggggctc ctgctgctct ggctcccagg cgcgcgatgt      60
```

```
gatgttgtga tgacccaatc tccactctcc ctgcctgtca ctcttggaca gccagcctcc    120
atctcttgca gatctagtca gagccttgtc cacagtaatg aaacaccta tttacagtgg    180 tacctgcaga agccaggcca gtctccacag ctcctgatct acacagtttc caaccgattt    240
tctggggtcc cagacaggtt cagtggcagt ggatcagggc agatttcac actcaagatc    300 agcagagtgg aggctgagga tgtgggagtt tattactgct ctcaaagtac acatgttcct    360
ttcacgttcg gccagggac aaagttggaa ataaaacgt                           399
```

<210> SEQ ID NO 72
<211> LENGTH: 133
<212> TYPE: PRT
<213> ORGANISM: Artificial Sequence
<220> FEATURE:
<223> OTHER INFORMATION: CSR02-VK3 Kappa light chain

<400> SEQUENCE: 72

```
Met Arg Val Pro Ala Gln Leu Leu Gly Leu Leu Leu Leu Trp Leu Pro
  1               5                  10                  15

Gly Ala Arg Cys Asp Val Val Met Thr Gln Ser Pro Leu Ser Leu Pro
             20                  25                  30

Val Thr Leu Gly Gln Pro Ala Ser Ile Ser Cys Arg Ser Ser Gln Ser
         35                  40                  45

Leu Val His Ser Asn Gly Asn Thr Tyr Leu Gln Trp Tyr Leu Gln Lys
     50                  55                  60

Pro Gly Gln Ser Pro Gln Leu Leu Ile Tyr Thr Val Ser Asn Arg Phe
 65                  70                  75                  80

Ser Gly Val Pro Asp Arg Phe Ser Gly Ser Gly Ser Gly Pro Asp Phe
                 85                  90                  95

Thr Leu Lys Ile Ser Arg Val Glu Ala Glu Asp Val Gly Val Tyr Tyr
            100                 105                 110

Cys Ser Gln Ser Thr His Val Pro Phe Thr Phe Gly Gln Gly Thr Lys
        115                 120                 125

Leu Glu Ile Lys Arg
    130
```

<210> SEQ ID NO 73
<211> LENGTH: 396
<212> TYPE: DNA
<213> ORGANISM: Artificial Sequence
<220> FEATURE:
<223> OTHER INFORMATION: CSR02-VH4 heavy chain coding sequence

<400> SEQUENCE: 73

```
atgggttgga gcctcatctt gctcttcctt gtcgctgttg ctacgcgtgt ccactcccag    60
gtccaactgg tgcagtctgg gtctgagctg aagaagcctg ggcttcagt gaaggtgtcc    120 tgcaaggctt ctggctacac cttcaccagc aactacataa actgggtgag acaggcccct    180
ggacagggcc ttgagtggat cggaaatatc tatccttctg atggttttac taactacaat    240
caaaagttca aggacagggt gacaatcact gtagacaaat ccaccagcac agcctacatg    300
gagctcagca gcctgagatc tgaggacacc gcggtctatt actgtacaag aaacttcgat    360
gtctggggcc aagggaccac ggtcaccgtc tcctca                              396
```

<210> SEQ ID NO 74
<211> LENGTH: 132
<212> TYPE: PRT
<213> ORGANISM: Artificial Sequence
<220> FEATURE:

<223> OTHER INFORMATION: CSR02-VH4 heavy chain

<400> SEQUENCE: 74

Met Gly Trp Ser Leu Ile Leu Leu Phe Leu Val Ala Val Ala Thr Arg
1               5                   10                  15

Val His Ser Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Ser Asn Tyr Ile Asn Trp Val Arg Gln Ala Pro Gly Gln Gly Leu
    50                  55                  60

Glu Trp Ile Gly Asn Ile Tyr Pro Ser Asp Gly Phe Thr Asn Tyr Asn
65                  70                  75                  80

Gln Lys Phe Lys Asp Arg Val Thr Ile Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Asn Phe Asp Val Trp Gly Gln Gly Thr Thr Val
        115                 120                 125

Thr Val Ser Ser
    130

<210> SEQ ID NO 75
<211> LENGTH: 396
<212> TYPE: DNA
<213> ORGANISM: Artificial Sequence
<220> FEATURE:
<223> OTHER INFORMATION: CSR02-VH5 heavy chain coding sequence

<400> SEQUENCE: 75
atgggttgga gcctcatctt gctcttcctt gtcgctgttg ctacgcgtgt ccactcccag      60
gtccaactgg tgcagtctgg gtctgagctg aagaagcctg gggcttcagt gaaggtgtcc    120
tgcaaggctt ctggctacac cttcaccagc aactacataa actgggtgag acaggcccct    180
ggacagggcc ttgagtggat gggaaatatc tatccttctg atggttttac taactacaat    240
caaaagttca aggacagggt gacaatcact gtagacaaat ccaccagcac agcctacatg    300
gagctcagca gcctgagatc tgaggacacc gcggtctatt actgtacaag aaacttcgat    360
gtctggggcc aagggaccac ggtcaccgtc tcctca                              396

<210> SEQ ID NO 76
<211> LENGTH: 132
<212> TYPE: PRT
<213> ORGANISM: Artificial Sequence
<220> FEATURE:
<223> OTHER INFORMATION: CSR02-VH5 heavy chain

<400> SEQUENCE: 76

Met Gly Trp Ser Leu Ile Leu Leu Phe Leu Val Ala Val Ala Thr Arg
1               5                   10                  15

Val His Ser Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Ser Asn Tyr Ile Asn Trp Val Arg Gln Ala Pro Gly Gln Gly Leu
    50                  55                  60

Glu Trp Met Gly Asn Ile Tyr Pro Ser Asp Gly Phe Thr Asn Tyr Asn
65                  70                  75                  80

Gln Lys Phe Lys Asp Arg Val Thr Ile Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Asn Phe Asp Val Trp Gly Gln Gly Thr Thr Val
        115                 120                 125

Thr Val Ser Ser
        130

<210> SEQ ID NO 77
<211> LENGTH: 339
<212> TYPE: DNA
<213> ORGANISM: Artificial Sequence
<220> FEATURE:
<223> OTHER INFORMATION: KFCC-GY5 VH Variant 1 coding sequence

<400> SEQUENCE: 77
caggtccaac tggtgcagtc tggggctgag ctgaagaagc ctggggcttc agtgaagctg      60
tcctgcaagg cttctggcta caccttcacc agcaactaca taaactgggt gaaacaggcc     120
cctggacagg gccttgagtg gatcggaaat atctatcctt ctgatggttt tactaactac     180
aatcaaaagt tcaaggacag ggccacattg actgtagaca atccaccag cacagcctac      240 atggagctca gcagcctgag atctgaggac tctgcggtct attactgtac aagaaacttc     300
gatgtctggg gccaagggac cacggtcacc gtctcctca                            339

<210> SEQ ID NO 78
<211> LENGTH: 113
<212> TYPE: PRT
<213> ORGANISM: Artificial Sequence
<220> FEATURE:
<223> OTHER INFORMATION: KFCC-GY5 VH Variant 1

<400> SEQUENCE: 78

Gln Val Gln Leu Val Gln Ser Gly Ala Glu Leu Lys Lys Pro Gly Ala
 1               5                  10                  15

Ser Val Lys Leu Ser Cys Lys Ala Ser Gly Tyr Thr Phe Thr Ser Asn
            20                  25                  30

Tyr Ile Asn Trp Val Lys Gln Ala Pro Gly Gln Gly Leu Glu Trp Ile
        35                  40                  45

Gly Asn Ile Tyr Pro Ser Asp Gly Phe Thr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Ser Ala Val Tyr Tyr Cys
                85                  90                  95

Thr Arg Asn Phe Asp Val Trp Gly Gln Gly Thr Thr Val Thr Val Ser
            100                 105                 110

Ser

<210> SEQ ID NO 79
<211> LENGTH: 339
<212> TYPE: DNA
<213> ORGANISM: Artificial Sequence
<220> FEATURE:
<223> OTHER INFORMATION: KFCC-GY5 VH Variant 2 coding sequence

<400> SEQUENCE: 79
caggtccaac tggtgcagtc tgggtctgag ctgaagaagc ctggggcttc agtgaagctg      60

```
tcctgcaagg cttctggcta ccttcacc agcaactaca taaactgggt gaaacaggcc      120
cctggacagg gccttgagtg gatcggaaat atctatcctt ctgatggttt tactaactac    180
aatcaaaagt tcaaggacag ggccacattg actgtagaca atccaccag cacagcctac     240 atggagctca gcagcctgag atctgaggac accgcggtct attactgtac aagaaacttc    300
gatgtctggg gccaagggac cacggtcacc gtctcctca                           339
```

<210> SEQ ID NO 80
<211> LENGTH: 113
<212> TYPE: PRT
<213> ORGANISM: Artificial Sequence
<220> FEATURE:
<223> OTHER INFORMATION: KFCC-GY5 VH Variant 2

<400> SEQUENCE: 80

```
Gln Val Gln Leu Val Gln Ser Gly Ser Glu Leu Lys Lys Pro Gly Ala
 1               5                  10                  15

Ser Val Lys Leu Ser Cys Lys Ala Ser Gly Tyr Thr Phe Thr Ser Asn
             20                  25                  30

Tyr Ile Asn Trp Val Lys Gln Ala Pro Gly Gln Gly Leu Glu Trp Ile
         35                  40                  45

Gly Asn Ile Tyr Pro Ser Asp Gly Phe Thr Asn Tyr Asn Gln Lys Phe
     50                  55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Asn Phe Asp Val Trp Gly Gln Gly Thr Thr Val Thr Val Ser
            100                 105                 110

Ser
```

<210> SEQ ID NO 81
<211> LENGTH: 339
<212> TYPE: DNA
<213> ORGANISM: Artificial Sequence
<220> FEATURE:
<223> OTHER INFORMATION: KFCC-GY5 VH Variant 3 coding sequence

<400> SEQUENCE: 81

```
caggtccaac tggtgcagtc tgggtctgag ctgaagaagc ctggggcttc agtgaagctg      60
tcctgcaagg cttctggcta ccttcacc agcaactaca taaactgggt gagacaggcc      120
cctggacagg gccttgagtg gatcggaaat atctatcctt ctgatggttt tactaactac    180
aatcaaaagt tcaaggacag ggtgacattg actgtagaca atccaccag cacagcctac     240 atggagctca gcagcctgag atctgaggac accgcggtct attactgtac aagaaacttc    300
gatgtctggg gccaagggac cacggtcacc gtctcctca                           339
```

<210> SEQ ID NO 82
<211> LENGTH: 113
<212> TYPE: PRT
<213> ORGANISM: Artificial Sequence
<220> FEATURE:
<223> OTHER INFORMATION: KFCC-GY5 VH Variant 3

<400> SEQUENCE: 82

```
Gln Val Gln Leu Val Gln Ser Gly Ser Glu Leu Lys Lys Pro Gly Ala
 1               5                  10                  15
```

```
Ser Val Lys Leu Ser Cys Lys Ala Ser Gly Tyr Thr Phe Thr Ser Asn
            20                  25                  30

Tyr Ile Asn Trp Val Arg Gln Ala Pro Gly Gln Gly Leu Glu Trp Ile
            35                  40                  45

Gly Asn Ile Tyr Pro Ser Asp Gly Phe Thr Asn Tyr Asn Gln Lys Phe
 50                      55                  60

Lys Asp Arg Val Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Asn Phe Asp Val Trp Gly Gln Gly Thr Thr Val Thr Val Ser
            100                 105                 110

Ser
```

<210> SEQ ID NO 83
<211> LENGTH: 339
<212> TYPE: DNA
<213> ORGANISM: Artificial Sequence
<220> FEATURE:
<223> OTHER INFORMATION: KFCC-GY5 VH Variant 4 coding sequence

<400> SEQUENCE: 83

```
caggtccaac tggtgcagtc tgggtctgag ctgaagaagc ctggggcttc agtgaaggtg    60
tcctgcaagg cttctggcta caccttcacc agcaactaca taaactgggt gagacaggcc   120
cctggacagg gccttgagtg gatcggaaat atctatcctt ctgatggttt tactaactac   180
aatcaaaagt tcaaggacag ggtgacaatc actgtagaca atccaccagc acagcctac   240
atggagctca gcagcctgag atctgaggac accgcggtct attactgtac aagaaacttc   300
gatgtctggg gccaagggac cacggtcacc gtctcctca                         339
```

<210> SEQ ID NO 84
<211> LENGTH: 113
<212> TYPE: PRT
<213> ORGANISM: Artificial Sequence
<220> FEATURE:
<223> OTHER INFORMATION: KFCC-GY5 VH Variant 4

<400> SEQUENCE: 84

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Asn
            20                  25                  30

Tyr Ile Asn Trp Val Arg Gln Ala Pro Gly Gln Gly Leu Glu Trp Ile
            35                  40                  45

Gly Asn Ile Tyr Pro Ser Asp Gly Phe Thr Asn Tyr Asn Gln Lys Phe
 50                      55                  60

Lys Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Asn Phe Asp Val Trp Gly Gln Gly Thr Thr Val Thr Val Ser
            100                 105                 110

Ser
```

<210> SEQ ID NO 85
<211> LENGTH: 339
<212> TYPE: DNA

<213> ORGANISM: Artificial Sequence
<220> FEATURE:
<223> OTHER INFORMATION: KFCC-GY5 VH Variant 5 coding sequence

<400> SEQUENCE: 85

```
caggtccaac tggtgcagtc tggGtctgag ctgaagaagc ctggggcttc agtgaaggtg      60
tcctgcaagg cttctggcta caccttcacc agcaactaca taaactgggt gagacaggcc    120
cctggacagg gccttgagtg gatgggaaat atctatcctt ctgatggttt tactaactac    180
aatcaaaagt tcaaggacag ggtgacaatc actgtagaca atccaccag cacagcctac     240 atggagctca gcagcctgag atctgaggac accgcggtct attactgtac aagaaacttc    300
gatgtctggg gccaagggac cacggtcacc gtctcctca                           339
```

<210> SEQ ID NO 86
<211> LENGTH: 113
<212> TYPE: PRT
<213> ORGANISM: Artificial Sequence
<220> FEATURE:
<223> OTHER INFORMATION: KFCC-GY5 VH Variant 5

<400> SEQUENCE: 86

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Asn
            20                  25                  30

Tyr Ile Asn Trp Val Arg Gln Ala Pro Gly Gln Gly Leu Glu Trp Met
        35                  40                  45

Gly Asn Ile Tyr Pro Ser Asp Gly Phe Thr Asn Tyr Asn Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Asn Phe Asp Val Trp Gly Gln Gly Thr Thr Val Thr Val Ser
                100                 105                 110

Ser
```

<210> SEQ ID NO 87
<211> LENGTH: 336
<212> TYPE: DNA
<213> ORGANISM: Artificial Sequence
<220> FEATURE:
<223> OTHER INFORMATION: KFCC-GY5 VK Variant 1 coding sequence

<400> SEQUENCE: 87

```
gatgttgtga tgacccaatc tccactctcc ctgcctgtca ctcttggaca gccagcctcc     60
atctcttgca gatctagtca gagccttgtc cacagtaatg aaacaccta tttacagtgg    120 tacctgcaga agccaggcca gtctccacag ctcctgatct acacagtttc caaccgattt    180
tctgggGtcc cagacaggtt cagtggcagt ggatcagggc agatttcac actcaagatc    240 agcagagtgg aggctgagga tgtgggagtt tatttctgct ctcaaagtac acatgttcct    300
ttcacgttcg gccaggggac aaagttggaa ataaaa                              336
```

<210> SEQ ID NO 88
<211> LENGTH: 112
<212> TYPE: PRT
<213> ORGANISM: Artificial Sequence
<220> FEATURE:

<223> OTHER INFORMATION: KFCC-GY5 VK Variant 1

<400> SEQUENCE: 88

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Pro Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gln Gly Thr Lys Leu Glu Ile Lys
            100                 105                 110

<210> SEQ ID NO 89
<211> LENGTH: 336
<212> TYPE: DNA
<213> ORGANISM: Artificial Sequence
<220> FEATURE:
<223> OTHER INFORMATION: KFCC-GY5 VK Variant 2 coding sequence

<400> SEQUENCE: 89

```
gatgttgtga tgacccaatc tccactctcc ctgcctgtca ctcttggaca gccagcctcc      60
atctcttgca gatctagtca gagccttgtc cacagtaatg gaaacaccta tttacagtgg     120
tacctgcaga agccaggcca gtctccacag ctcctgatct acacagtttc caaccgattt     180
tctggggtcc cagacaggtt cagtggcagt ggatcaggga ccgatttcac actcaagatc     240
agcagagtgg aggctgagga tgtgggagtt tatttctgct ctcaaagtac acatgttcct     300
ttcacgttcg gccaggggac aaagttggaa ataaaa                                336
```

<210> SEQ ID NO 90
<211> LENGTH: 112
<212> TYPE: PRT
<213> ORGANISM: Artificial Sequence
<220> FEATURE:
<223> OTHER INFORMATION: KFCC-GY5 VK Variant 2

<400> SEQUENCE: 90

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Phe Thr Phe Gly Gln Gly Thr Lys Leu Glu Ile Lys
            100                 105                 110

<210> SEQ ID NO 91
<211> LENGTH: 336
<212> TYPE: DNA
<213> ORGANISM: Artificial Sequence
<220> FEATURE:
<223> OTHER INFORMATION: KFCC-GY5 VK Variant 3 coding sequence

<400> SEQUENCE: 91

```
gatgttgtga tgacccaatc tccactctcc ctgcctgtca ctcttggaca gccagcctcc      60
atctcttgca gatctagtca gagccttgtc cacagtaatg aaacaccta tttacagtgg     120
tacctgcaga agccaggcca gtctccacag ctcctgatct acacagtttc caaccgattt    180
tctggggtcc cagacaggtt cagtggcagt ggatcaggc cagatttcac actcaagatc     240
agcagagtgg aggctgagga tgtgggagtt tattactgct ctcaaagtac acatgttcct    300
ttcacgttcg gccaggggac aaagttggaa ataaaa                              336
```

<210> SEQ ID NO 92
<211> LENGTH: 112
<212> TYPE: PRT
<213> ORGANISM: Artificial Sequence
<220> FEATURE:
<223> OTHER INFORMATION: KFCC-GY5 VK Variant 3

<400> SEQUENCE: 92

```
Asp Val Val Met Thr Gln Ser Pro Leu Ser Leu Pro Val Thr Leu Gly
  1               5                  10                  15
Gln Pro Ala Ser Ile Ser Cys Arg Ser Ser Gln Ser Leu Val His Ser
             20                  25                  30
Asn Gly Asn Thr Tyr Leu Gln Trp Tyr Leu Gln Lys Pro Gly Gln Ser
         35                  40                  45
Pro Gln Leu Leu Ile Tyr Thr Val Ser Asn Arg Phe Ser Gly Val Pro
     50                  55                  60
Asp Arg Phe Ser Gly Ser Gly Ser Gly Pro Asp Phe Thr Leu Lys Ile
 65                  70                  75                  80
Ser Arg Val Glu Ala Glu Asp Val Gly Val Tyr Tyr Cys Ser Gln Ser
                 85                  90                  95
Thr His Val Pro Phe Thr Phe Gly Gln Gly Thr Lys Leu Glu Ile Lys
            100                 105                 110
```

<210> SEQ ID NO 93
<211> LENGTH: 339
<212> TYPE: DNA
<213> ORGANISM: Artificial Sequence
<220> FEATURE:
<223> OTHER INFORMATION: KFCC-GY4 VH variant 1 coding sequence

<400> SEQUENCE: 93

```
gaggttcagc tggtgcagtc tggggcagag tttaagaagc caggggcctc agtcaagttg     60
tcctgcacag cttctggctt caacattaaa gactactata cactgggt gaagcaggcc      120
cctggacagg gcctggagtg gattggatgg attgatcctg agaatggtga tattgaatat    180
gccccgaagt tccagggcag ggccactatg actgcagaca catccaccaa tacagcctac    240
ctggagttca gcagcctgag atctgaggac actgccgtct attactgtct ctaccaagaa    300
ggctcctggg gccaaggcac cactgtcaca gtctcctca                           339
```

<210> SEQ ID NO 94
<211> LENGTH: 113
<212> TYPE: PRT
<213> ORGANISM: Artificial Sequence
<220> FEATURE:
<223> OTHER INFORMATION: KFCC-GY4 VH variant 1

<400> SEQUENCE: 94

```
Glu Val Gln Leu Val Gln Ser Gly Ala Glu Phe Lys Lys Pro Gly Ala
 1               5                  10                  15

Ser Val Lys Leu Ser Cys Thr Ala Ser Gly Phe Asn Ile Lys Asp Tyr
             20                  25                  30

Tyr Ile His Trp Val Lys Gln Ala Pro Gly Gln Gly Leu Glu Trp Ile
         35                  40                  45

Gly Trp Ile Asp Pro Glu Asn Gly Asp Ile Glu Tyr Ala Pro Lys Phe
 50                  55                  60

Gln Gly Arg Ala Thr Met Thr Ala Asp Thr Ser Asn Thr Ala Tyr
65                  70                  75                  80

Leu Glu Phe Ser Ser Leu Arg Ser Glu Asp Thr Ala Val Tyr Tyr Cys
                 85                  90                  95

Leu Tyr Gln Glu Gly Ser Trp Gly Gln Gly Thr Thr Val Thr Val Ser
            100                 105                 110

Ser
```

<210> SEQ ID NO 95
<211> LENGTH: 339
<212> TYPE: DNA
<213> ORGANISM: Artificial Sequence
<220> FEATURE:
<223> OTHER INFORMATION: KFCC-GY4 VH variant 2 coding sequence

<400> SEQUENCE: 95

```
gaggttcagc tggtgcagtc tggggcagag gtgaagaagc caggggcctc agtcaagttg    60
tcctgcacag cttctggctt caacattaaa gactactata tacactgggt gaggcaggcc   120
cctggacagg gcctggagtg gattggatgg attgatcctg agaatggtga tattgaatat   180
gccccgaagt tccagggcag ggccactatg actgcagaca catccaccaa tacagcctac   240
ctggagttca gcagcctgag atctgaggac actgccgtct attactgtct ctaccaagaa   300
ggctcctggg gccaaggcac cactgtcaca gtctcctca                          339
```

<210> SEQ ID NO 96
<211> LENGTH: 113
<212> TYPE: PRT
<213> ORGANISM: Artificial Sequence
<220> FEATURE:
<223> OTHER INFORMATION: KFCC-GY4 VH variant 2

<400> SEQUENCE: 96

```
Glu Val Gln Leu Val Gln Ser Gly Ala Glu Val Lys Lys Pro Gly Ala
 1               5                  10                  15

Ser Val Lys Leu Ser Cys Thr Ala Ser Gly Phe Asn Ile Lys Asp Tyr
             20                  25                  30

Tyr Ile His Trp Val Arg Gln Ala Pro Gly Gln Gly Leu Glu Trp Ile
         35                  40                  45

Gly Trp Ile Asp Pro Glu Asn Gly Asp Ile Glu Tyr Ala Pro Lys Phe
 50                  55                  60

Gln Gly Arg Ala Thr Met Thr Ala Asp Thr Ser Thr Asn Thr Ala Tyr
65                  70                  75                  80

Leu Glu Phe Ser Ser Leu Arg Ser Glu Asp Thr Ala Val Tyr Tyr Cys
                 85                  90                  95

Leu Tyr Gln Glu Gly Ser Trp Gly Gln Gly Thr Thr Val Thr Val Ser
```

-continued

```
                100                 105                 110
Ser

<210> SEQ ID NO 97
<211> LENGTH: 339
<212> TYPE: DNA
<213> ORGANISM: Artificial Sequence
<220> FEATURE:
<223> OTHER INFORMATION: KFCC-GY4 VH variant 3 coding sequence

<400> SEQUENCE: 97
gaggttcagc tggtgcagtc tggggcagag gtgaagaagc caggggcctc agtcaaggtg      60
tcctgcacag cttctggctt caacattaaa gactactata cactgggt gaggcaggcc      120 cctggacagg gcctggagtg gattggatgg attgatcctg agaatggtga tattgaatat     180
gccccgaagt tccagggcag ggccactatc actgcagaca catccaccaa tacagcctac     240
atggagttca gcagcctgag atctgaggac actgccgtct attactgtct ctaccaagaa     300
ggctcctggg gccaaggcac cactgtcaca gtctcctca                             339

<210> SEQ ID NO 98
<211> LENGTH: 113
<212> TYPE: PRT
<213> ORGANISM: Artificial Sequence
<220> FEATURE:
<223> OTHER INFORMATION: KFCC-GY4 VH variant 3

<400> SEQUENCE: 98

Glu Val Gln Leu Val Gln Ser Gly Ala Glu Val Lys Lys Pro Gly Ala
  1               5                  10                  15

Ser Val Lys Val Ser Cys Thr Ala Ser Gly Phe Asn Ile Lys Asp Tyr
                 20                  25                  30

Tyr Ile His Trp Val Arg Gln Ala Pro Gly Gln Gly Leu Glu Trp Ile
             35                  40                  45

Gly Trp Ile Asp Pro Glu Asn Gly Asp Ile Glu Tyr Ala Pro Lys Phe
         50                  55                  60

Gln Gly Arg Ala Thr Ile Thr Ala Asp Thr Ser Thr Asn Thr Ala Tyr
 65                  70                  75                  80

Met Glu Phe Ser Ser Leu Arg Ser Glu Asp Thr Ala Val Tyr Tyr Cys
                 85                  90                  95

Leu Tyr Gln Glu Gly Ser Trp Gly Gln Gly Thr Thr Val Thr Val Ser
                100                 105                 110

Ser

<210> SEQ ID NO 99
<211> LENGTH: 339
<212> TYPE: DNA
<213> ORGANISM: Artificial Sequence
<220> FEATURE:
<223> OTHER INFORMATION: KFCC-GY4 VH variant 4 coding sequence

<400> SEQUENCE: 99
gaggttcagc tggtgcagtc tggggcagag gtgaagaagc caggggcctc agtcaaggtg      60
tcctgcacag cttctggctt caacattaaa gactactata cactgggt gaggcaggcc      120 cctggacagg gcctggagtg gattggatgg attgatcctg agaatggtga tattgaatat     180
gccccgaagt tccagggcag ggccactatc actgcagaca catccaccga tacagcctac     240
atggagttca gcagcctgag atctgaggac actgccgtct attactgtct ctaccaagaa     300
```

```
ggctcctggg gccaaggcac cactgtcaca gtctcctca                                 339
```

<210> SEQ ID NO 100
<211> LENGTH: 113
<212> TYPE: PRT
<213> ORGANISM: Artificial Sequence
<220> FEATURE:
<223> OTHER INFORMATION: KFCC-GY4 VH variant 4

<400> SEQUENCE: 100

```
Glu Val Gln Leu Val Gln Ser Gly Ala Glu Val Lys Lys Pro Gly Ala
 1               5                  10                  15

Ser Val Lys Val Ser Cys Thr Ala Ser Gly Phe Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Glu Asn Gly Asp Ile Glu Tyr Ala Pro Lys Phe
    50                  55                  60

Gln Gly Arg Ala Thr Ile Thr Ala Asp Thr Ser Thr Asp Thr Ala Tyr
65                  70                  75                  80

Met Glu Phe Ser Ser Leu Arg Ser Glu Asp Thr Ala Val Tyr Tyr Cys
                85                  90                  95

Leu Tyr Gln Glu Gly Ser Trp Gly Gln Gly Thr Thr Val Thr Val Ser
               100                 105                 110

Ser
```

<210> SEQ ID NO 101
<211> LENGTH: 339
<212> TYPE: DNA
<213> ORGANISM: Artificial Sequence
<220> FEATURE:
<223> OTHER INFORMATION: KFCC-GY4 VH variant 5 coding sequence

<400> SEQUENCE: 101

```
gaggttcagc tggtgcagtc tggggcagag gtgaagaagc caggggcctc agtcaaggtg    60
tcctgcacag cttctggctt caacattaaa gactactata cactgggt gaggcaggcc     120 cctggacagg gcctggagtg gattggatgg attgatcctg agaatggtga tattgaatat   180
gccccgaagt tccagggcag ggtgactatc actgcagaca catccaccga tacagcctac   240
atggagctca gcagcctgag atctgaggac actgccgtct attactgtct ctaccaagaa   300
ggctcctggg gccaaggcac cactgtcaca gtctcctca                           339
```

<210> SEQ ID NO 102
<211> LENGTH: 113
<212> TYPE: PRT
<213> ORGANISM: Artificial Sequence
<220> FEATURE:
<223> OTHER INFORMATION: KFCC-GY4 VH variant 5

<400> SEQUENCE: 102

```
Glu Val Gln Leu Val Gln Ser Gly Ala Glu Val Lys Lys Pro Gly Ala
 1               5                  10                  15

Ser Val Lys Val Ser Cys Thr Ala Ser Gly Phe Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Glu Asn Gly Asp Ile Glu Tyr Ala Pro Lys Phe
    50                  55                  60
```

```
Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Leu Tyr Gln Glu Gly Ser Trp Gly Gln Gly Thr Thr Val Thr Val Ser
            100                 105                 110

Ser
```

<210> SEQ ID NO 103
<211> LENGTH: 336
<212> TYPE: DNA
<213> ORGANISM: Artificial Sequence
<220> FEATURE:
<223> OTHER INFORMATION: KFCC-GY4 VK variant 1 coding sequence

<400> SEQUENCE: 103

```
gatgttgtga tgacccagtc tccactcact ttgtcggtta ccctgggaca accagcctcc     60
atctcttgca agtcaagtca gagcctctta aatagtgatg aaagacata tttgaattgg    120
ttgcagcaga ggccaggcca gtctccaagg cgcctaatct atctggtgtc taaattggac   180
tctggagtcc ctgacaggtt cactggcagt ggatcaggga cagatttcac actgaaaatc   240
agcagagtgg aggctgagga tgtgggagtt tattattgct ggcaaggtac acattttccg   300
ttcacgttcg gaggggggac caaggtggaa ataaaa                              336
```

<210> SEQ ID NO 104
<211> LENGTH: 112
<212> TYPE: PRT
<213> ORGANISM: Artificial Sequence
<220> FEATURE:
<223> OTHER INFORMATION: KFCC-GY4 VK variant 1

<400> SEQUENCE: 104

```
Asp Val Val Met Thr Gln Ser Pro Leu Thr Leu Ser Val Thr Leu Gly
  1               5                  10                  15

Gln Pro Ala Ser Ile Ser Cys Lys Ser Ser Gln Ser Leu Leu Asn Ser
             20                  25                  30

Asp Gly Lys Thr Tyr Leu Asn Trp Leu Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Phe Thr Phe Gly Gly Gly Thr Lys Val Glu Ile Lys
            100                 105                 110
```

<210> SEQ ID NO 105
<211> LENGTH: 336
<212> TYPE: DNA
<213> ORGANISM: Artificial Sequence
<220> FEATURE:
<223> OTHER INFORMATION: KFCC-GY4 VK variant 2 coding sequence

<400> SEQUENCE: 105

```
gatgttgtga tgacccagtc tccactcagc ttgcctgtta ccctgggaca accagcctcc     60
atctcttgca agtcaagtca gagcctctta aatagtgatg aaagacata tttgaattgg    120
ttgcagcaga ggccaggcca gtctccaagg cgcctaatct atctggtgtc taaattggac   180
```

```
tctggagtcc ctgacaggtt cactggcagt ggatcaggga cagatttcac actgaaaatc      240
agcagagtgg aggctgagga tgtgggagtt tattattgct ggcaaggtac acattttccg      300
ttcacgttcg agggggggac caaggtggaa ataaaa                                336
```

```
<210> SEQ ID NO 106
<211> LENGTH: 112
<212> TYPE: PRT
<213> ORGANISM: Artificial Sequence
<220> FEATURE:
<223> OTHER INFORMATION: KFCC-GY4 VK variant 2

<400> SEQUENCE: 106
```

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asn Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Phe Thr Phe Gly Gly Gly Thr Lys Val Glu Ile Lys
            100                 105                 110
```

```
<210> SEQ ID NO 107
<211> LENGTH: 336
<212> TYPE: DNA
<213> ORGANISM: Artificial Sequence
<220> FEATURE:
<223> OTHER INFORMATION: KFCC-GY4 VK variant 3 coding sequence

<400> SEQUENCE: 107
```

```
gatgttgtga tgacccagtc tccactcagc ttgcctgtta ccctgggaca accagcctcc       60
atctcttgca agtcaagtca gagcctctta aatagtgatg gaaagacata tttgaattgg      120
ttgcagcaga ggccaggcca gtctccaagg cgcctaatct atctggtgtc taaattggac      180
tctggagtcc ctgacaggtt ctctggcagt ggatcaggga cagatttcac actgaaaatc      240
agcagagtgg aggctgagga tgtgggagtt tattattgct ggcaaggtac acattttccg      300
ttcacgttcg agggggggac caaggtggaa ataaaa                                336
```

```
<210> SEQ ID NO 108
<211> LENGTH: 112
<212> TYPE: PRT
<213> ORGANISM: Artificial Sequence
<220> FEATURE:
<223> OTHER INFORMATION: KFCC-GY4 VK variant 3

<400> SEQUENCE: 108
```

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asn Ser
            20                  25                  30

Asp Gly Lys Thr Tyr Leu Asn Trp Leu Gln Gln Arg Pro Gly Gln Ser
        35                  40                  45
```

-continued

```
Pro Arg Arg Leu Ile Tyr Leu Val Ser Lys Leu Asp Ser Gly Val Pro
    50              55                  60
Asp Arg Phe Ser Gly Ser Gly Thr Asp Phe Thr Leu Lys Ile
65              70                  75                  80
Ser Arg Val Glu Ala Glu Asp Val Gly Val Tyr Tyr Cys Trp Gln Gly
                85                  90                      95
Thr His Phe Pro Phe Thr Phe Gly Gly Gly Thr Lys Val Glu Ile Lys
                100                 105                 110
```